US009321844B2

(12) United States Patent
Kelley et al.

(10) Patent No.: US 9,321,844 B2
(45) Date of Patent: Apr. 26, 2016

(54) ANTI-POLYUBIQUITIN ANTIBODIES

(75) Inventors: Robert F. Kelley, Petaluma, CA (US);
Vishva Dixit, Los Altos, CA (US);
Marissa L. Matsumoto, Foster City, CA (US)

(73) Assignee: Genentech, Inc., South San Francisco, CA (US)

( * ) Notice: Subject to any disclaimer, the term of this patent is extended or adjusted under 35 U.S.C. 154(b) by 818 days.

(21) Appl. No.: 13/567,919

(22) Filed: Aug. 6, 2012

(65) Prior Publication Data
US 2013/0058955 A1 Mar. 7, 2013

Related U.S. Application Data

(60) Provisional application No. 61/515,729, filed on Aug. 5, 2011.

(51) Int. Cl.
*A61K 39/395* (2006.01)
*C07K 16/40* (2006.01)

(52) U.S. Cl.
CPC .............. *C07K 16/40* (2013.01); *C07K 2317/24* (2013.01); *C07K 2317/33* (2013.01); *C07K 2317/55* (2013.01); *C07K 2317/565* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 7,763,245 | B2 | 7/2010 | Gordon et al. |
| 8,133,488 | B2 | 3/2012 | Kelley et al. |
| 8,603,475 | B2 | 12/2013 | Gordon et al. |
| 8,992,919 | B2 | 3/2015 | Dixit et al. |
| 2005/0106667 | A1 | 5/2005 | Fellouse et al. |
| 2005/0119455 | A1 | 6/2005 | Fuh et al. |
| 2007/0166778 | A1 | 7/2007 | Rain et al. |
| 2007/0218069 | A1 | 9/2007 | Gordon et al. |
| 2007/0218079 | A1 | 9/2007 | Patzel |
| 2009/0191209 | A1 | 7/2009 | Kelley et al. |
| 2010/0267050 | A1 | 10/2010 | Gordon et al. |

FOREIGN PATENT DOCUMENTS

| | | |
|---|---|---|
| JP | 07238096 | 9/1995 |
| WO | 2004/003019 A2 | 1/2004 |
| WO | 2007/025216 A2 | 3/2007 |
| WO | 2007/120334 A2 | 10/2007 |
| WO | 2008/121813 A2 | 10/2008 |
| WO | 2009/126350 A2 | 10/2009 |
| WO | 2011/130499 A1 | 10/2011 |
| WO | 2013/022848 A1 | 2/2013 |

OTHER PUBLICATIONS

Kirisako et al. (The EMBO Journal 2006 25:4877-4887).*
Zuin et al. Cells 2014, 3, 690-710.*
Carter (Nat Rev Immunol, 2006; 6:343-357).*
Pascalis et al. (The Journal of Immunology (2002) 169, 3076-3084).*
Padlan et al. (PNAS 1989, 86:5938-5942).*
Lamminmaki et al. (JBC 2001, 276:36687-36694).*
"International Search Report and Written Opinion for International Patent Application No. PCT/US2009/031310".
"Product information sheet for BIOMOL catalogue No. PW8805" pp. 1-2 (Jan. 25, 2004).
Alves-Rodrigues et al. et al., "Ubiquitin, cellular inclusions and their role in neurodegeneration" Trends Neurosci 21(12):516-520 ( 1998).
Beckmann et al. et al., "On ubiquitin ligases and cancer" Hum Mutat 25(6):507-512 ( 2005).
Bodine et al. et al., "Identification of ubiquitin ligases required for skeletal muscle atrophy" Science 294(5547):1704-1708 (Nov. 23, 2001).
Boone, D. L. et al. et al., "The ubiquitin-modifying enzyme A20 is required for termination of toll-like recepetor responses" Nature Immunol 5(10):1052-1060 (Oct. 2004).
Brorson, "Mutational analysis of avidity and fine specificity of anti-levan antibodies" J Immunol (added article title info), 163:6694-6701 (Dec. 1999).
Brummell et al. et al., "Probing the combining site of an anti-carbohydrate antibody by saturation-mutagenesis: role of the heavy-chain CDR3 residues" Biochemistry 32(4):1180-1187 (Feb. 1993).
Burks, E., et al. et al., "In vitro scanning saturation mutagenesis of an antibody binding pocket" P Natl Acad Sci USA 94:412-417 ( 1997).
Cammarata et al. et al., "Ubiquitin-reactive neurites in cerebral cortex of subjects with Huntington's chorea: a pathological correlate of dementia?"Neurosci Lett 156(1-2):96-98 ( 1993).
Campbell, A. Monoclonal Antibody Technology "1"The Netherlands:Elsevier Science Publishers B.V.,:1-32 ( 1984).
Carrion-Vazquez et al. et al., "The mechanical stability of ubiquitin is linkage dependent" Nat Struct Biol (Epub Aug. 17, 2003), 10(9):738-743 (Sep. 2003).
Casset, F. et al., "A peptide mimetic of an anti-CD4 monoclonal antibody by rational design" Biochem Bioph Res Co 307:198-205 ( 2003).
Chau et al., et al., "A multiubiquitin chain in confined to specific lysine in a targeted short-lived protein" Science 243(4898):1576-1583 (Mar. 24, 1989).
Chen et al., "Structural basis for scaffolding-mediated assembly and maturation of a dsDNA virus" Proc Natl Acad Sci U S A. 108(4):1355-60 (Jan. 2011).
Chen, Y. et al., "Selection and analysis of an optimized anti-VEGF antibody: crystal structure of an affinity-matured Fab in complex with antigen" J Mol Biol 293:865-881 ( 1999).
Chung et al. et al., "The role of the ubiquitin-proteasomal pathway in Parkinson's disease and other neurodegenerative disorders" Trends Neurosci 24(11 Suppl Suppl):S7-14 (Nov. 2001).
Ciechanover, "The ubiquitin-proteasome pathway: on protein death and cell life" EMBO J 17(24):7151-7160 ( 1998).
Clark, L. A. et al., "Affinity enhancement of an in vivo matured therapeutic antibody using structure-based computational design" Prot Sci 15:949-960 ( 2006).
Coleman, P.M., "Effects of amino acid sequence changes on antibody-antigen interactions"Res Immunol 145:33-36 ( 1994).
Cook, W. J. et al. et al., "Structure of a diubiquitin conjugate and a model for interaction with ubiquitin conjugating enzyme (E2)" J Biol Chem 267(23):16467-16471 (Aug. 15, 1992).

(Continued)

*Primary Examiner* — Sharon Wen
(74) *Attorney, Agent, or Firm* — McNeill Baur PLLC

(57) ABSTRACT

The invention provides anti-polyubiquitin antibodies and methods of using the same.

17 Claims, 38 Drawing Sheets

(56) References Cited

OTHER PUBLICATIONS

'International Search Report and Written Opinion for International Patent Application No. PCT/US2011/032468'.
International Search Report for PCT/US/2006/062115.
Crosas, B. et al. et al., "Ubiquitin chains are remodeled at the proteasome by opposing ubiquitin ligase and deubiquitinating activities" Cell 127:1401-1413 (Dec. 29, 2006).
De Pascalis et al., J Immunol 169:3076-3084 ( 2002).
Deng et al. et al., "Activation of the IκB kinase complex by TRAF6 requires a dimeric ubiquitin-conjugating enzyme complex and a unique polyubiquitin chain" Cell 103(2):351-361 (Oct. 13, 2000)
Dufner et al., "Harnessing phage and ribosome display for antibody optimisation" Trends Biotechnol 24(11):523-529 ( 2006).
Fellouse et al., "High-throughput generation of synthetic antibodies from highly functional minimalist phage-displayed libraries" J Mol Biol. 373(4):924-40 (Nov. 2007).
Finley: et al. et al., "Inhibition of proteolysis and cell cycle progression in a multiubiquitination-deficient yeast mutant" Mol Cell Biol 14(8):5501-5509 (Aug. 1994).
Flick et al. et al., "Proteolysis-independent regulation of the transcription factor Met4 by a single Lys 48-linked ubiquitin chain" Nat Cell Biol (epub Jun. 20, 2004), 6(7):634-641 (Jul. 2004).
Fujimuro and Yokosawa et al., "Production of antipolyubiquitin monoclonal antibodies and their use for characterization and isolation of polyubiquitinated proteins" Method Enzymol 399:75-86 (Dec. 15, 2005).
Fujimuro et al. et al., "Production and characterization of monoclonal antibodies specific to multi-ubiquitin chains of polyubiquitinated proteins" FEBS Lett 349(2):173-180 ( 1994).
Gallop et al. et al., "Applications of combinatorial technologies to drug discovery. 1. background and peptide combinatorial libraries" J Med Chem 37(9):1233-1251 ( 1994).
Garnett et al., "UBE2S elongates ubiquitin chains on APC/C substrates to promote mitotic exit" Nat Cell Biol. 11(11):1363-9 ( 2009).
Ghosh and Karin, "Missing pieces in the NF-κB puzzle" Cell 109:S81-S96 (Apr. 2002).
Gorman et al., "Transient Production of Proteins Using an Adenovirus Transformed Cell Line" DNA Prot. Eng.Tech. 2(1):3-10 ( 1990).
Guterman and Glickman et al., "Deubiquitinating enzymes are IN/(trinsic to proteasome function)" Curr Protein Pept Sci 5(3):201-211 ( 2004).
Hashizume et al. et al., "The RING heterodimer BRCA1-BARD1 is a ubiquitin ligase inactivated by a breast cancer-derived mutation" J Biol Chem 276(18):14537-14540 (May 4, 2001).
Hicke and Dunn et al. ,"Regulation of membrane protein transport by ubiquitin and ubiquitin-binding proteins" Annu Rev Cell Dev Biol (epub Jun. 20, 2003), 19:141-172 (2003).
Hicke, L., "Protein regulation by monoubiquitin" Nature Reviews Mol Cell Biol 2:195-201 (Mar. 2001).
Hoege et al. et al., "RAD6-dependent DNA repair in linked to modification of PCNA by ubiquitin and SUMO" Nature 419(6903):135-141 (Sep. 12, 2002).
Hofmann and Pickart et al., "In vitro assembly and recognition of Lys-63 polyubiquitin chains" J Biol Chem 276(30):27936-27941 (Jul. 27, 2001).
Hofmann and Pickart et al., "Noncanonical MMS2-encoded ubiquitin-conjugating enzyme functions in assembly of novel polyubiquitin chains for DNA repair" Cell 96(5):645-653 (Mar. 5, 1999).
Holm et al., "Functional mapping and single chain construction of the anti-cytokeratin 8 monoclonal antibody TS1" Mol Immunol 44:1075-1084 ( 2007).
Holmberg et al. et al., "Spinocerebellar ataxia type 7 (SCA7): a neurodegenerative disorder with neuronal intranuclear inclusions" Hum Mol Genet 7(5):913-918 ( 1998).
Jang et al., "The structural basis for DNA binding by an anti-DNA Autoantibody" Mol Immunol. 35(18):1207-17 (Dec. 1998).
Jin et al., "Mechanism of ubiquitin-chain formation by the human anaphase-promoting complex" Cell 133(4):653-65 (May 2008).

Johnson, "Ubiquitin branches out" Nat Cell Biol 4(12):E295-E298 (Dec. 2002).
Kalchaman et al. et. al., "Huntingtin is ubiquitinated and interacts with a specific ubiquitin-conjugating enzyme" J Biol Chem 271(32);19385-19394 (Aug. 9, 1996).
Kim, H. T. et al. et. al., "Certain pairs of ubiquitin-conjugating enzymes (E2s) and ubiquitin-protein ligases (E3s) synthesize non-degradable forked ubiquitin chains containing all possible isopeptide linkages" J Biol Chem 282(24):17375-17386 (Jun. 15, 2007).
Kirkpatrick, D. S. et al. et al., "Quantitative analysis of in vitro ubiquitinated cyclin B1 reveals complex chain topology" Nature Cell Biol 8(7):700-710 (Jul. 2006).
Kishino, T. et al., "UBE3A/E6-AP mutations cause Angelman syndrome" Nature Genetics 15(1):70-73 (Jan. 15, 1997).
Kobayashi, H., et al. et al., "Tryptophan H33 plays an important role in pyrimidin (6-4) pyrimidone photoproduct binding by a high-affinity antibody" Protein Eng 12(10):879-884 ( 1999).
Kumar, Sanjeev et al., "Molecular cloning and expression of the fabs of human autoantibodies in *Escherichia coli*"J Biol Chem 275(45):35129-35136 ( 2000).
Kunkel, "Rapid and Efficient Site-Specific Mutagenesis Whithout Phenotypic Selection" Proc. Natl. Acad. Sci.:488-492 (Jan. 1985).
Kuzuhara et al. et al., "Lewy bodies are ubiquitinated. A light and electron microscopic immunocytochemical study" Acta Neuropathology 75(4):345-353 ( 1988).
Lam et al. et al., "Inhibition of the ubiquitin-proteasome system in Alzheimer's disease" P Natl Acad Sci USA 97(18):9902-9906 (Aug. 29, 2000).
Lee et al., "High-affinity human antibodies from phage-displayed synthetic Fab libraries with a single framework scaffold" J Mol Biol 340(5):1073-1093 ( 2004).
Leigh et al. et al., "New aspects of the pathology of neurodegenerative disorderes ar revealed by ubiquitin antibodies" Acta Neuropathol 79(1):61-72 ( 1989).
Leroy et al. et al., "The ubiquitin pathway in Parkinson's disease" Nature 395(6701):451-452 (Oct. 1, 1998).
Lim et al. et al., "Parkin mediates nonclassical, proteasomal-independent ubiquitination of synphilin-1: implications for Lewy body formation" J Neurosci 25(8):2002-2009 (Feb. 23, 2005).
MacCallum et al., "Antibody-antigen interactions: contact analysis and binding site topography" J Mol Biol 262:732-745 ( 1996).
Majetschak, M. et al., "Extracellular ubiquitin inhibits the TNF-α response to endotoxin in peripheral blood mononuclear cells and regulates endotoxin hyporesponsiveness in critical illness" Blood 101(5):1882-1890 (Mar. 1, 2003).
Matsumoto et al., "K11-linked polyubiquitination in cell cycle control revealed by a K11 linkage-specific antibody" Mol Cell 39(3):477-84 (Aug. 2010).
McNaught et al. et al., "Failure of the ubiquitin-proteasome system in Parkinson's disease" Nat Rev Neurosci 2(8):589-594 (Aug. 2001).
Mitch and Goldberg et al., "Mechanisms of muscle wasting. The role of the ubiquitin-proteasome pathway" New Engl J Med 335(25):1897-1905 (Dec. 19, 1996).
Mori et al., "Ubiquitin is a component of paired helical filaments in Alzheimer's disease" Science 235(4796):1641-1644 (Mar. 27, 1987).
Naze et al., "Mutation analysis and association studies of the ubiquitin carboxy-terminal hydrolase L1 gene in Huntington's disease" Neurosci Lett 328(1):1-4 ( 2002).
Nemes, Z. et al., "Cross-linking of ubiquitin, HSP27, parkin, and α-synuclein by γ-glutamyl-ε-lysine bonds in Alzheimer's neurofibrillary tangles" FASEB J (epub May 7, 2004 (1-25 pgs)), 18:1135-1137 (May 2004).
Newton, K. et al., "Ubiquitin chain editing revealed by polyubiquitin linkage-specific antibodies" Cell 134:668-678 (Aug. 22, 2008).
Palombella, V. J. et al., "The ubiquitin-proteasome pathway is required for processing the NF-κB1 precursor protein and the activation of NF-κB" Cell 78:773-785 ( Sep. 9, 1984).
Peng et al., "A proteomics approach to understanding protein ubiquitination" Nat Biotechnol 21(8):921-926 (Aug. 2003).
Pickart and Fushman, "Polyubiquitin chains: polymeric protein signals" Curr Opin Chem Biol (epub Oct. 28, 2004), 8(6):610-616 (Dec. 2004).

(56) References Cited

OTHER PUBLICATIONS

Pickart, C.M., "Ubiquitin enters the new millennium" Mol. Cell. 8(3):499-504 (Sep. 2001).
Pickart, "Mechanisms underlying ubiquitination" Annu Rev Biochem 70:503-533 (2001).
Rudikoff, S. et al. et al., "Single amino acid substitution altering antigen binding specificity" P Natl Acad Sci USA 79:1979-1983 (Mar. 1982).
Salghetti et al. et al., "Destruction of Myc by ubiquitin-mediated proteolysis: cancer-associated and transforming mutations stabilize Myc" EMBO J 18(3):717-726 (1999).
Seibenhener et al., "Sequestosome 1/p62 is a polyubiquitin chain binding protein involved in ubiquitin proteasome degradation" Mol Cell Biol 24(18):8055-8068 (Sep. 2004).
Shimura et al. et al., "Familial Parkinson disease gene product, parkin, is a ubiquitin-protein ligase" Nat Genet 25(3):302-305 (Jul. 2000).
Smith-Gill, S., et al. et al., "Contributions of immunoglobulin heavy and light chains to antibody specificity for lysozyme and two haptens" J Immunol 139:4135-4144 (1987).
Song, Mi-Kyung, et al. et al., "Light chain of natural antibody plays a dominant role in protein antigen binding" Biochem Bioph Res Co 268:390-394 (2000).
Spataro et al. et al., "The ubiquitin-proteasome pathway in cancer" Brit J Cancer 77(3):448-455 (1998).
Spence et al. et al., "A ubiquitin mutant with specific defects in DNA repair and multiubiquitination" Mol Cell Biol 15(3):1265-1273 (Mar. 1995).
Spence et al. et al., "Cell cycle-regulated modification of the ribosome by a variant multiubiquitin chain" Cell 102(1):67-76 (Jul. 7, 2000).
Staub et al., "Regulation of stability and function of the epithelial Na+ channel (ENaC) by ubiquitination" EMBO J 16(21):6325-6336 (1997).
Stelter and Ulrich et al., "Control of spontaneous and damage-induced mutagenesis by SUMO and ubiquitin conjugation" Nature 425(6954):188-191 (Sep. 11, 2003).
Sun and Chen et al., "The novel functions of ubiquitination in signaling" Curr Opin Cell Biol 16(2):119-126 (2004).
Takada et al., "Serum concentrations of free ubiquitin and multiubiquitin chains" Clin Chem 43(7):1188-1195 (1997).
Tan, J. et al. et al., "Lysine 63-linked ubiquitination promotes the formation and autophagic clearance of protein inclusions associated with neurodegenerative diseases" Human Mol Genetics 17(3):431-439 (Mar. 2008).
Tenno et al., "Structural basis for distinct roles of Lys63- and Lys48-linked polyubiquitin chains" Genes Cells 9(10):865-875 (2004).
Treier, M. et al. et al., "Uniquitin-dependent c-jun degradation in vivo is mediated by the δ domain" Cell 78:787-798 (Sep. 9, 1994).
Ulrich, "Degradation or maintenance: actions of the ubiquitin system on eukaryotic chromatin" Eukaryot Cell 1(1):1-10 (Feb. 2002).
Vajdos, F. F. et al., "Comprehensive functional maps of the antigen-binding site of an anti-ErbB2 antibody obtained with shotgun scanning mutagenesis" J. Mol. Biol. 320:415-428 (2002).
Varadan, R. et al. et al., "Structural properties of polyubiquitin chains in solution" J Mol Biol 324:637-647 (2002).
Ward et al. et al., "Degradation of CFTR by the ubiquitin-proteasome pathway" Cell 83(1):121-127 (Oct. 6, 1995).
Ward et al., "Binding activities of a repertoire of single immunoglobulin variable domains secreted from *Escherichia coli*" Nature 341:544-546 (Oct. 12, 1989).
Wertz, I. E. et al., "De-ubiquitination and ubiquitin ligase domains of A20 downregulte NF-κB signalling" Nature 430:694-699 (Aug. 5, 2004).
Wilkinson, "Ubiquitination and deubiquitination: targeting of proteins for degradation by the proteasome" Semin Cell Dev Biol 11(3):141-148 (2000).
Williamson et al., "Identification of a physiological E2 module for the human anaphase-promoting complex" Proc Natl Acad Sci U S A. 106(43):18213-8 (Oct. 2009).
Wong et al., "Drug discovery in the ubiquitin regulatory pathway" Drug Discov Today 8(16):746-754 (Aug. 2003).
Wu et al., "Humanization of a Murine Monoclonal Antibody by Simultaneous Optimization of Framework and CDR Residues" J Mol Biol 294:151-162 (1999).
Yamin and Miller et al., "The interleukin-1 receptor-associated kinase is degraded by proteasomes following its phosphorylation" J Biol Chem 272(34):21540-21547 (Aug. 22, 1997).
Yedidia et al., "Proteasomes and ubiquitin are involved in the turnover of the wild-type prion protein" EMBO J 20(19):5383-5391 (2001).
Zhang et al., "Parkin functions as an E2-dependent ubiquitin-protein ligase and promotes the degradation of the synaptic vesicle-associated protein, CDCre1-1" P Natl Acad Sci USA 97(24):13354-13359 (Nov. 21, 2000).
Communication of the Extended European Search Report and Opinion, for European Patent Application No. 10188648.9, mailed Apr. 11, 2011 (7 pages).
Communication of the Extended European Search Report and Opinion, for European Patent Application No. 11769579.1, mailed Dec. 3, 2013 (8 pages).
International Search Report and Written Opinion for International Patent Application No. PCT/US2012/049771, mailed Oct. 22, 2012 (11 pages).
Communication of the Extended European Search Report and Opinion, for European Patent Application No. 12822145.4, mailed Jan. 28, 2015 (7 pages).
Behrends et al., "Constructing and decoding unconventional ubiquitin chains," Nat. Structural Mol. Biol. 18(5): 520-528 (2011).
Komander et al., "Molecular discrimination of structurally equivalent Lys 63-linked and linear polyubiquitin chains," EMBO Reports 10(5): 466-473 (2009).
Matsumoto et al., "Engineering and Structural Characterization of a Linear Polyubiquitin-Specific Antibody," J. Mol. Biol. 418: 134-144 (2012).
Newton et al., "Chapter 13: Using Linkage-Specific Monoclonal Antibodies to Analyze Cellular Ubiquitylation," from *Methods in Molecular Biology*, vol. 832 (Clifton, NJ) 185-196 (2012).
Pirim et al., "Production of Anti-polyubiquitin and Anti-ubiquitin Carboxyl Terminal Hydrolsae Antibodies and Immunohistochemically Assessment of Them on Brain Sections of Alzheimer's Disease and Lewy Body Disease," Inter. J. Neuroscience 95: 33-42 (1998).
Tokonaga et al., "Involvement of linear polyubiquitylation of NEMO in NF-κB activation," Nature Cell Biol. 11(2): 123-132 and Supp. Info. pp. 1-17 (2009).

* cited by examiner

| Kabat# | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | A | B | C | D | E | F | 28 | 29 | 30 | 31 | 32 | 33 | 34 | 35 | 36 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|
| | | | | | | | | | | | | | | | | | | | | | | | | | | | | | | | | | | | | | | | | | | |
| 1E3 | D | I | Q | M | T | Q | S | P | S | S | L | S | A | S | V | G | D | R | V | T | I | T | C | R | A | S | Q | - | - | - | - | - | - | D | V | S | T | A | V | A | W | Y |
| 1D8 | D | I | Q | M | T | Q | S | P | S | S | L | S | A | S | V | G | D | R | V | T | I | T | C | R | A | S | Q | - | - | - | - | - | - | D | V | S | T | A | V | A | W | Y |
| 1F4 | D | I | Q | M | T | Q | S | P | S | S | L | S | A | S | V | G | D | R | V | T | I | T | C | R | A | S | Q | - | - | - | - | - | - | S | V | S | S | A | V | A | W | Y |
| 1A10 | D | I | Q | * | | | | | | | | | | | | | | | | | | | | R | A | S | Q | - | - | - | - | - | - | S | V | S | S | A | V | A | W | Y* |

| Kabat# | 37 | 38 | 39 | 40 | 41 | 42 | 43 | 44 | 45 | 46 | 47 | 48 | 49 | 50 | 51 | 52 | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|
| 1E3 | Q | Q | K | P | G | K | A | P | K | L | L | I | Y | S | A | S | F | L | Y | S | G | V | P | S | R | F | S | G | S | G | S | G | T | D | F | T | L | T | I | S | S | L |
| 1D8 | Q | Q | K | P | G | K | A | P | K | L | L | I | Y | S | A | S | F | L | Y | S | G | V | P | S | R | F | S | G | S | G | S | G | T | D | F | T | L | T | I | S | S | L |
| 1F4 | Q | Q | K | P | G | K | A | P | K | L | L | I | Y | S | A | S | S | L | Y | S | G | V | P | S | R | F | S | G | S | G | S | R | S | G | T | D | F | T | L | T | I | S | S | L |
| 1A10 | Q | Q | * | | | | | | | | | | | S | A | S | S | L | Y | S | G | V | P | S | R | F | S | G | S | G | S | R | S | G | T | D | F | * | | | | |

| Kabat# | 79 | 80 | 81 | 82 | 83 | 84 | 85 | 86 | 87 | 88 | 89 | 90 | 91 | 92 | 93 | 94 | 95 | 96 | 97 | 98 | 99 | 100 | 101 | 102 | 103 | 104 | 105 | 106 | 107 |
|---|---|---|---|---|---|---|---|---|---|---|---|---|---|---|---|---|---|---|---|---|---|---|---|---|---|---|---|---|---|
| 1E3 | Q | P | E | D | F | A | T | Y | Y | C | Q | Q | S | Y | T | T | . | P | P | T | F | G | Q | G | T | K | V | E | I | K |
| 1D8 | Q | P | E | D | F | A | T | Y | Y | C | Q | Q | S | Y | T | T | . | P | P | T | F | G | Q | G | T | K | V | E | I | K |
| 1F4 | Q | P | E | D | F | A | T | Y | Y | C | Q | Q | Y | Y | Y | S | P | L | T | F | G | Q | G | T | K | V | E | I | K |
| 1A10 | Q | P | E | D | F | A | T | Y | Y | C | Q | Q | H | Y | T | T | . | P | P | T | F | G | Q | G | T | K | V | E | I | K |

FIGURE 2A

| Kabat# | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 | A | B | 36 | 37 | 38 |
|---|---|---|---|---|---|---|---|---|---|---|---|---|---|---|---|---|---|---|---|---|---|---|---|---|---|---|---|---|---|---|---|---|---|---|---|---|---|---|---|---|
| 1E3 | E | V | Q | L | V | E | S | G | G | G | L | V | Q | P | G | G | S | L | R | L | S | C | A | A | S | G | F | T | F | S | N | T | Y | I | S | - | - | W | V | R |
| 1D8 | E | V | Q | L | V | E | S | G | G | G | L | V | Q | P | G | G | S | L | R | L | S | C | A | A | S | G | F | T | F | T | D | Y | D | I | H | - | - | W | V | R |
| 1F4 | E | V | Q | L | V | E | S | G | G | G | L | V | Q | P | G | G | S | L | R | L | S | C | A | A | S | G | F | N | F | Y | S | Y | Y | M | H | - | - | W | V | R |
| 1A10 | S | E | V | Q | L | V | E | S | G | G | G | L | V | Q | P | G | G | S | L | R | L | S | C | A | A | S | G | F | N | I | Y | S | S | I | H | - | - | W | V | R |

CDR regions indicated: Chothia-CDR H1, Kabat-CDR H1, Contact-CDR H1

| Kabat# | 41 | 42 | 43 | 44 | 45 | 46 | 47 | 48 | 49 | 50 | 51 | 52 | A | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 | 79 |
|---|---|---|---|---|---|---|---|---|---|---|---|---|---|---|---|---|---|---|---|---|---|---|---|---|---|---|---|---|---|---|---|---|---|---|---|---|---|---|---|---|
| 1E3 | P | G | K | G | L | E | W | V | A | S | I | T | P | S | S | G | S | T | D | Y | A | D | S | V | K | G | R | F | T | I | S | A | D | T | S | K | N | T | V | Y |
| 1D8 | P | G | K | G | L | E | W | V | A | G | I | S | P | Y | G | G | Y | T | D | Y | A | D | S | V | K | G | R | F | T | I | S | A | D | T | S | K | N | T | V | Y |
| 1F4 | P | G | K | G | L | E | W | V | A | S | I | Y | S | Y | S | Y | S | Y | Y | Y | A | D | S | V | K | G | R | F | T | I | S | A | D | T | S | K | N | T | A | Y |
| 1A10 | P | G | K | G | L | E | W | V | A | S | I | Y | P | Y | G | Y | S | T | Y | Y | A | D | S | V | K | G | R | F | T | I | S | A | D | T | S | K | N | T | A | Y |

CDR regions indicated: Chothia-CDR H2, Kabat-CDR H2, Contact-CDR H2

| Kabat# | 82 | A | B | C | 83 | 84 | 85 | 86 | 87 | 88 | 89 | 90 | 91 | 92 | 93 | 94 | 95 | 96 | 97 | 98 | 99 | 100 | A | B | C | D | E | 101 | 102 | 103 | 104 | 105 | 106 | 107 | 108 | 109 | 110 | 111 | 112 | ## |
|---|---|---|---|---|---|---|---|---|---|---|---|---|---|---|---|---|---|---|---|---|---|---|---|---|---|---|---|---|---|---|---|---|---|---|---|---|---|---|---|---|
| 1E3 | M | N | S | L | R | A | E | D | T | A | V | Y | Y | Y | C | A | R | T | W | L | L | R | W | V | - | - | - | M | D | Y | W | G | Q | G | T | L | V | T | V | S |
| 1D8 | M | N | S | L | R | A | E | D | T | A | V | Y | Y | Y | C | A | R | E | A | G | S | R | L | L | S | V | - | M | D | Y | W | G | Q | G | T | L | V | T | V | S |
| 1F4 | M | N | S | L | R | A | E | D | T | A | V | Y | Y | Y | C | A | R | G | Y | V | W | K | G | A | . | . | . | M | D | Y | W | G | Q | G | T | L | V | T | V | S |
| 1A10 | M | N | S | L | R | A | E | D | T | A | V | Y | Y | Y | C | A | R | G | Y | S | W | Y | Y | G | S | P | A | F | D | Y | W | G | Q | G | T | L | V | T | V | S |

CDR regions indicated: Chothia-CDR H3, Kabat-CDR H3, Contact-CDR H3

FIGURE 2B

| Kabat# | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | A | B | C | D | E | F | 28 | 29 | 30 | 31 | 32 | 33 | 34 | 35 | 36 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|
| | | | | | | | | | | | | | | | | | | | | | | | | | | | | | | | | | | | | | | | | | | |
| | | | | | | | | | | | | | | | | | | | | | | | | | | | | | | | | | Kabat - CDRL1 | | | | | | | | |
| | | | | | | | | | | | | | | | | | | | | | | | | | | | | | | Chothia - CDRL1 | | | | | | | | | | |
| | | | | | | | | | | | | | | | | | | | | | | | | | | | | | | | | | Contact-CDRL1 | | | | | | | |
| 1D8 | D | I | Q | M | T | Q | S | P | S | S | L | S | A | S | V | G | D | R | V | T | I | T | C | R | A | S | Q | - | - | - | - | - | - | D | V | S | T | A | V | A | W | Y |
| 1D8.3C2 | D | I | Q | M | T | Q | S | P | S | S | L | S | A | S | V | G | D | R | V | T | I | T | C | R | A | S | Q | - | - | - | - | - | - | G | V | D | N | S | V | A | W | Y |
| 1D8.3F8 | D | I | Q | M | T | Q | S | P | S | S | L | S | A | S | V | G | D | R | V | T | I | T | C | R | A | S | Q | - | - | - | - | - | - | D | V | S | T | A | V | A | W | Y |
| 1D8.4F5 | D | I | Q | M | * | | | | | | | | | | | | | | | | | | | | | | | | | | | | | | | | | | | | | * |

| Kabat# | 37 | 38 | 39 | 40 | 41 | 42 | 43 | 44 | 45 | 46 | 47 | 48 | 49 | 50 | 51 | 52 | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|
| | | | | | | | | | | Kabat - CDR L2 | | | | | | | | | | | | | | | | | | | | | | | | | | | | | | | | |
| | | | | | | | | | | | | Chothia - CDR L2 | | | | | | | | | | | | | | | | | | | | | | | | | | | | | | |
| | | | | | | | | Contact - CDR L2 | | | | | | | | | | | | | | | | | | | | | | | | | | | | | | | | | |
| 1D8 | Q | Q | K | P | G | K | A | P | K | L | L | I | Y | S | A | S | F | L | Y | S | G | V | P | S | R | F | S | G | S | G | S | G | T | D | F | T | L | T | I | S | S | L |
| 1D8.3C2 | Q | Q | K | P | G | K | A | P | K | L | L | I | Y | S | A | S | F | L | Y | S | G | V | P | S | R | F | S | G | S | G | S | G | T | D | F | T | L | T | I | S | S | L |
| 1D8.3F8 | Q | Q | K | P | G | K | A | P | K | L | L | I | Y | S | A | S | F | L | Y | S | G | V | P | S | R | F | S | G | S | G | S | G | T | D | F | T | L | T | I | S | S | L |
| 1D8.4F5 | Q | * | | | | | | | | | | | * | | | | | | | * | | | | | | | | | | | | | | | | | | | | | | * |

| Kabat# | 79 | 80 | 81 | 82 | 83 | 84 | 85 | 86 | 87 | 88 | 89 | 90 | 91 | 92 | 93 | 94 | 95 | 96 | 97 | 98 | 99 | 100 | 101 | 102 | 103 | 104 | 105 | 106 | 107 |
|---|---|---|---|---|---|---|---|---|---|---|---|---|---|---|---|---|---|---|---|---|---|---|---|---|---|---|---|---|---|
| | | | | | | | | | | | Kabat - CDR L3 | | | | | | | | | | | | | | | | | | |
| | | | | | | | | | | | | Chothia - CDR L3 | | | | | | | | | | | | | | | | |
| | | | | | | | | | | Contact - CDR L3 | | | | | | | | | | | | | | | | | | |
| 1D8 | Q | P | E | D | F | A | T | Y | Y | C | Q | Q | S | Y | T | T | . | P | P | T | F | G | Q | G | T | K | V | E | I | K |
| 1D8.3C2 | Q | P | E | D | F | A | T | Y | Y | C | Q | Q | S | Y | T | T | . | P | P | T | F | G | Q | G | T | K | V | E | I | K |
| 1D8.3F8 | Q | P | E | D | F | A | T | Y | Y | C | Q | Q | S | Y | A | S | . | P | P | T | F | G | Q | G | T | K | V | E | I | K |
| 1D8.4F5 | Q | P | E | D | F | A | T | Y | Y | C | Q | Q | S | F | T | T | . | P | P | T | F | G | Q | G | T | K | V | E | I | K |

| Kabat# | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | A | B | C | D | E | F | 28 | 29 | 30 | 31 | 32 | 33 | 34 | 35 | 36 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|
| 1E3 | D | I | Q | M | T | Q | S | P | S | S | L | S | A | S | V | G | D | R | V | T | I | T | C | R | A | S | Q | - | - | - | - | - | - | D | V | S | T | A | V | A | W | Y |
| 1F11 | D | I | Q | M | T | Q | S | P | S | S | L | S | A | S | V | G | D | R | V | T | I | T | C | R | A | S | Q | - | - | - | - | - | - | D | V | S | T | A | V | A | W | Y |
| 3F5 | D | I | Q | M | T | Q | S | P | S | S | L | S | A | S | V | G | D | R | V | T | I | T | C | R | A | S | Q | - | - | - | - | - | - | D | V | S | T | A | V | A | W | Y |
| Y102L | D | I | Q | M | T | Q | S | P | S | S | L | S | A | S | V | G | D | R | V | T | I | T | C | R | A | S | Q | - | - | - | - | - | - | D | V | S | T | A | V | A | W | Y |
| 1F11/3F5/Y102L | D | I | Q | M | T | Q | S | P | S | S | L | S | A | S | V | G | D | R | V | T | I | T | C | R | A | S | Q | - | - | - | - | - | - | D | V | S | T | A | V | A | W | Y |

| Kabat# | 37 | 38 | 39 | 40 | 41 | 42 | 43 | 44 | 45 | 46 | 47 | 48 | 49 | 50 | 51 | 52 | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|
| 1E3 | Q | Q | K | P | G | K | A | P | K | L | L | I | Y | S | A | S | F | L | Y | S | G | V | P | S | R | F | S | G | S | G | S | G | T | D | F | T | L | T | I | S | S | L |
| 1F11 | Q | Q | K | P | G | K | A | P | K | L | L | I | Y | S | A | S | F | L | Y | S | G | V | P | S | R | F | S | G | S | G | S | G | T | D | F | T | L | T | I | S | S | L |
| 3F5 | Q | Q | K | P | G | K | A | P | K | L | L | I | Y | S | A | S | F | L | Y | S | G | V | P | S | R | F | S | G | S | G | S | G | T | D | F | T | L | T | I | S | S | L |
| Y102L | Q | Q | K | P | G | K | A | P | K | L | L | I | Y | S | A | K | F | L | Y | S | G | V | P | S | R | F | S | G | S | G | S | G | T | D | F | T | L | T | I | S | S | L |
| 1F11/3F5/Y102L | Q | Q | K | P | G | K | A | P | K | L | L | I | Y | S | A | K | F | L | Y | S | G | V | P | S | R | F | S | G | S | G | S | G | T | D | F | T | L | T | I | S | S | L |

| Kabat# | 79 | 80 | 81 | 82 | 83 | 84 | 85 | 86 | 87 | 88 | 89 | 90 | 91 | 92 | 93 | 94 | 95 | 96 | 97 | 98 | 99 | 100 | 101 | 102 | 103 | 104 | 105 | 106 | 107 |
|---|---|---|---|---|---|---|---|---|---|---|---|---|---|---|---|---|---|---|---|---|---|---|---|---|---|---|---|---|---|
| 1E3 | Q | P | E | D | F | A | T | Y | Y | C | Q | Q | S | Y | T | T | P | P | T | F | G | Q | G | T | K | V | E | I | K |
| 1F11 | Q | P | E | D | F | A | T | Y | Y | C | Q | Q | S | Y | T | T | P | P | T | F | G | Q | G | T | K | V | E | I | K |
| 3F5 | Q | P | E | D | F | A | T | Y | Y | C | Q | Q | S | Y | T | T | P | P | T | F | G | Q | G | T | K | V | E | I | K |
| Y102L | Q | P | E | D | F | A | T | Y | Y | C | Q | Q | S | Y | T | T | . | P | T | F | G | Q | G | T | K | V | E | I | K |
| 1F11/3F5/Y102L | Q | P | E | D | F | A | T | Y | Y | C | Q | Q | S | Y | T | T | . | P | T | F | G | Q | G | T | K | V | E | I | K |

FIGURE 9A

| Kabat# | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 | A | B | 36 | 37 | 38 | 39 | 40 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|
| 1E3 | E | V | Q | L | V | E | S | G | G | G | L | V | Q | P | G | G | S | L | R | L | S | C | A | A | S | G | F | T | F | S | S | N | T | Y | I | - | - | W | V | R | Q | A |
| 1F11 | E | V | Q | L | V | E | S | G | G | G | L | V | Q | P | G | G | S | L | R | L | S | C | A | A | S | G | F | T | F | S | S | N | T | Y | I | - | - | W | V | R | Q | A |
| 3F5 | E | V | Q | L | V | E | S | G | G | G | L | V | Q | P | G | G | S | L | R | L | S | C | A | A | S | G | F | T | F | S | S | N | T | Y | I | - | - | W | V | R | Q | A |
| Y102L | E | V | Q | L | V | E | S | G | G | G | L | V | Q | P | G | G | S | L | R | L | S | C | A | A | S | G | F | T | F | S | S | N | T | Y | I | - | - | W | V | R | Q | A |
| 1F11/3F5/Y102L | E | V | Q | L | V | E | S | G | G | G | L | V | Q | P | G | G | S | L | R | L | S | C | A | A | S | G | F | T | F | S | S | N | T | Y | I | - | - | W | V | R | Q | A |

| Kabat# | 41 | 42 | 43 | 44 | 45 | 46 | 47 | 48 | 49 | 50 | 51 | 52 | A | 53 | 54 | 55 | 56 | 57 | 58 | 59 | 60 | 61 | 62 | 63 | 64 | 65 | 66 | 67 | 68 | 69 | 70 | 71 | 72 | 73 | 74 | 75 | 76 | 77 | 78 | 79 | 80 | 81 |
|---|---|---|---|---|---|---|---|---|---|---|---|---|---|---|---|---|---|---|---|---|---|---|---|---|---|---|---|---|---|---|---|---|---|---|---|---|---|---|---|---|---|---|
| 1E3 | P | G | K | G | L | E | W | V | A | S | I | T | P | S | S | G | S | T | D | Y | A | D | S | V | K | G | R | F | T | I | S | A | D | T | S | K | N | T | A | Y | L | Q |
| 1F11 | P | G | K | G | L | E | W | V | A | S | I | T | P | S | S | G | S | T | D | Y | A | D | S | V | K | G | R | F | T | I | S | A | D | T | S | K | N | T | A | Y | L | Q |
| 3F5 | P | G | K | G | L | E | W | V | A | S | I | T | P | S | S | G | Q | T | D | Y | A | D | S | V | K | G | R | F | T | I | S | A | D | T | S | K | N | T | A | Y | L | Q |
| Y102L | P | G | K | G | L | E | W | V | A | S | I | T | P | S | S | G | S | T | D | Y | A | D | S | V | K | G | R | F | T | I | S | A | D | T | S | K | N | T | A | Y | L | Q |
| 1F11/3F5/Y102L | P | G | K | G | L | E | W | V | A | S | I | T | P | S | S | G | Q | T | D | Y | A | D | S | V | K | G | R | F | T | I | S | A | D | T | S | K | N | T | A | Y | L | Q |

| Kabat# | 82 | A | B | C | 83 | 84 | 85 | 86 | 87 | 88 | 89 | 90 | 91 | 92 | 93 | 94 | 95 | 96 | 97 | 98 | 99 | 100 | A | B | C | D | E | 101 | 102 | 103 | 104 | 105 | 106 | 107 | 108 | 109 | 110 | 111 | 112 |
|---|---|---|---|---|---|---|---|---|---|---|---|---|---|---|---|---|---|---|---|---|---|---|---|---|---|---|---|---|---|---|---|---|---|---|---|---|---|---|---|
| 1E3 | M | N | S | L | R | A | E | D | T | A | V | Y | Y | C | A | R | T | W | L | L | R | W | V | - | - | - | - | M | D | Y | W | G | Q | G | T | L | V | T | V | S | S |
| 1F11 | M | N | S | L | R | A | E | D | T | A | V | Y | Y | C | A | R | T | W | L | L | R | W | V | - | - | - | - | M | D | Y | W | G | Q | G | T | L | V | T | V | S | S |
| 3F5 | M | N | S | L | R | A | E | D | T | A | V | Y | Y | C | A | R | T | W | L | L | R | W | V | - | - | - | - | M | D | Y | W | G | Q | G | T | L | V | T | V | S | S |
| Y102L | M | N | S | L | R | A | E | D | T | A | V | Y | Y | C | A | R | T | W | L | L | R | W | V | - | - | - | - | M | D | L | W | G | Q | G | T | L | V | T | V | S | S |
| 1F11/3F5/Y102L | M | N | S | L | R | A | E | D | T | A | V | Y | Y | C | A | R | T | W | L | L | R | W | V | - | - | - | - | M | D | L | W | G | Q | G | T | L | V | T | V | S | S |

FIGURE 9B

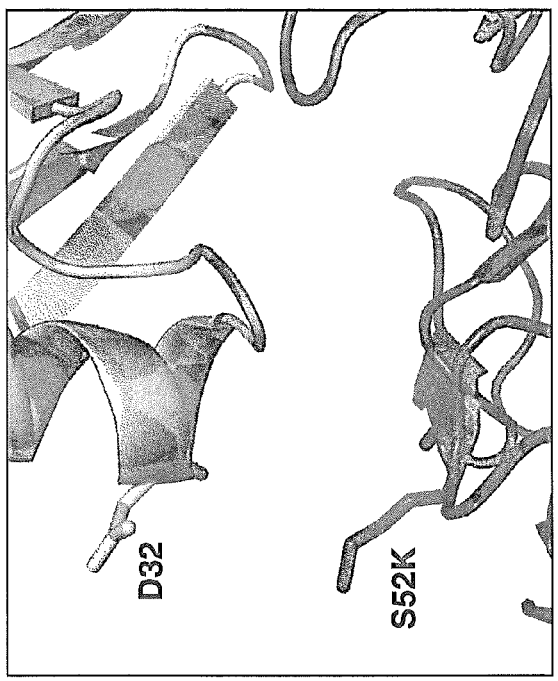
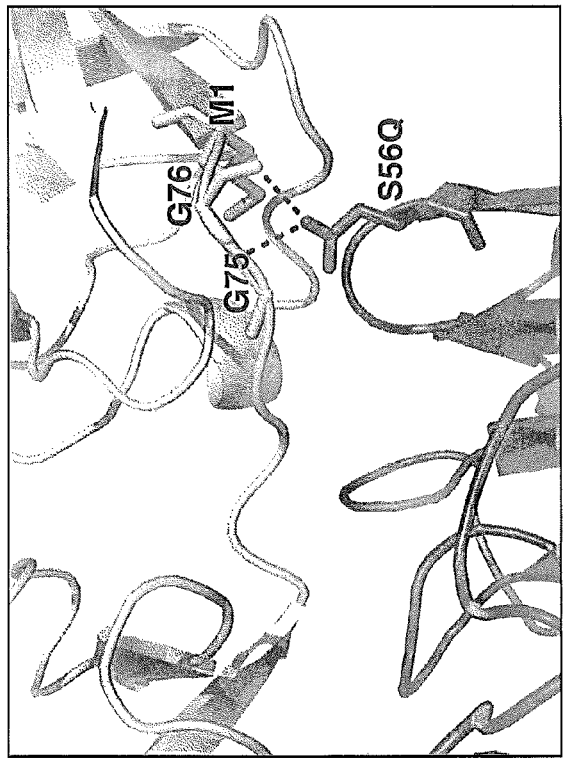
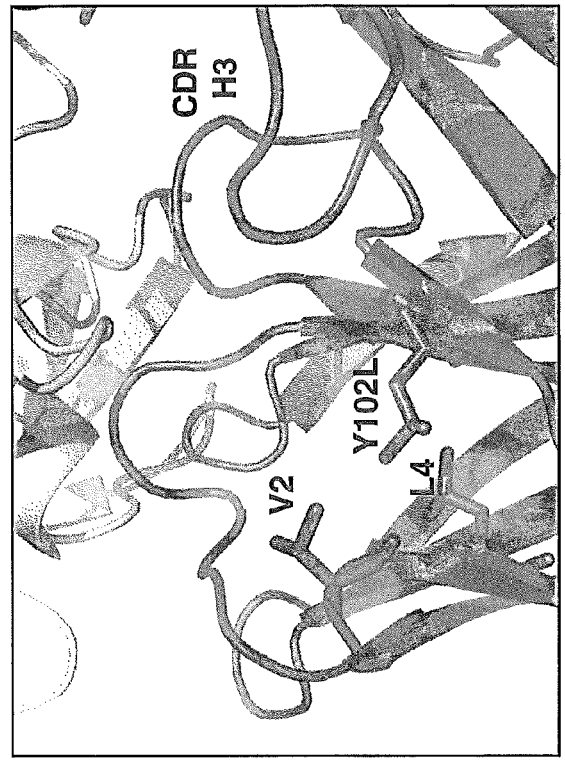
FIGURE 24

US 9,321,844 B2

ANTI-POLYUBIQUITIN ANTIBODIES

RELATED APPLICATIONS

This application claims priority under 35 U.S.C. §119 (e) to U.S. Provisional No. 61/515,729, filed Aug. 5, 2011 which is incorporated by reference herein in its entirety.

SEQUENCE LISTING

The instant application contains a Sequence Listing which has been submitted in ASCII format via EFS-Web and is hereby incorporated by reference in its entirety. Said ASCII copy, created on Aug. 6, 2012, is named P4716R1.txt and is 128,464 bytes in size.

FIELD OF THE INVENTION

The present invention relates to the field of anti-polyubiquitin antibodies, and more particularly to anti-polyubiquitin antibodies that do not specifically bind to monoubiquitin and that are specific for linear polyubiquitin and methods of using the same.

BACKGROUND

Ubiquitin is a small protein that has important regulatory roles in a wide variety of cellular pathways. The best known of these is ubiquitin's role in protein degradation, where covalent attachment of ubiquitin to a target protein enables that targeted protein to be recognized and destroyed by the 26S proteasome (see Wilkinson, *Semin. Cell Devel. Biol.* 11(3): 141-148 (2000)). The covalent attachment of ubiquitin, a 76 amino acid protein, to a target protein is a three-step enzymatic process (Pickart, *Annu. Rev. Biochem.* 70: 503-533 (2001)). First, ubiquitin-activating enzyme E1 forms an ubiquitin-E1 thioester in an ATP-dependent reaction. The ubiquitin is transferred from the ubiquitin-E1 thioester to a member of the ubiquitin-conjugating enzyme (E2) family in the second step. In the third step, with the assistance of a ubiquitin-protein ligase (E3), an isopeptide bond is formed between the carboxyl terminus of ubiquitin and the ε-amino group of a lysine residue on the target protein. Enzymes termed deubiquitinases remove ubiquitin moieties from target proteins (Guterman and Glickman, Curr. Prot. Pep. Sci. 5: 201-210 (2004)).

Ubiquitin contains seven lysine residues (Lys6, Lys11, Lys27, Lys33, Lys29, Lys48, and Lys63), and thus ubiquitin itself may serve as a target protein for ubiquitination (Peng et al., *Nat. Biotechnol.* 21: 921-926 (2003); Pickart and Fushman, *Curr. Opin. Chem. Biol.* 8:610-616 (2004)). The molecule produced upon ubiquitination of a ubiquitin protein is termed a polyubiquitin molecule, and may comprise two or more ubiquitin moieties. Ubiquitination of ubiquitin may theoretically occur at any of the seven lysine residues (Peng et al., *Nat. Biotechnol.* 21: 921-926 (2003)), so that different species of polyubiquitins exist having isopeptide bonds to different lysine residues within ubiquitin. Polyubiquitin chains with internal isopeptide linkages at all seven lysine resides have been reported. Iwai and Tokunaga, *EMBO Reports* 10:706-713 (2009).

Recently it was discovered that linear polyubiquitin chains also form in which the C-terminal glycine of ubiquitin is conjugated to the α-amino group of the N-terminal methionine of another ubiquitin molecule. Iwai and Tokunaga, *EMBO Reports* 10:706-713 (2009). Linear polyubiquitin is formed via the linear ubiquitin chain assembly complex (LUBAC) which is composed of two ring finger proteins, HOIL-1L and HOW. Tokunaga et al., *Nat. Cell Biol.* 11:123-132 (2009). It is believed that genetically encoded, unanchored linear polyubiquitin does not exist in cells as its C-terminus is vulnerable to cleavage by isopeptidase T. Iwai and Tokunaga, *EMBO Reports* 10:706-713 (2009). This observation suggests that linear polyubiquitin is assembled onto a substrate protein post-translationally and that conjugated linear polyubiquitin molecules are potential modulators of protein activity and function. Id. For example, linear polyubiquitination of the NF-kB essential modulator (NEMO) has been shown to play a role in NF-κB activation. Id.

Antibodies which distinguish linear polyubiquitin over polyubiquitin of different lysine linkages would be useful to further examine the role of linear polyubiquitin chains in protein degradation and regulation and to target and modulate linear polyubiquitin in linear polyubiquitin-mediated pathways.

SUMMARY

The invention provides anti-linear polyubiquitin antibodies and methods of using the same. In one embodiment, the invention provides an isolated antibody that specifically binds a first polyubiquitin comprising a C-terminal to N-terminal linkage, wherein the antibody does not specifically bind a second polyubiquitin comprising a lysine linkage. In another embodiment, the invention provides an isolated antibody that specifically binds both a first polyubiquitin comprising a C-terminal to N-terminal linkage and a second polyubiquitin comprising a lysine linkage, wherein the antibody does not specifically bind monoubiquitin, and wherein the antibody binds the second polyubiquitin with a substantially reduced binding affinity as compared to the binding affinity of the antibody for the first polyubiquitin.

In another embodiment the invention provides an isolated antibody that specifically binds C- to N-terminal linked polyubiquitin, wherein the antibody does not specifically bind monoubiquitin. In one aspect, the antibody comprises at least one hypervariable (HVR) sequence selected from HVR-L1, HVR-L2, HVR-L3, HVR-H1, HVR-H2, and HVR-H3 of any of SEQ ID NOs: 1, 4, 19 and 50-57; SEQ ID NOs: 2 and 58-63; SEQ ID NOs: 3, 5, 6, 20, 21 and 64-72; SEQ ID NOs: 7, 10, 13, 16, 22 and 73-81; SEQ ID NOs: 8, 11, 14, 17, 23, 24 and 82-86; and SEQ ID NOs: 9, 12, 15, 18 and 87-93, respectively.

In another aspect, the antibody comprises at least one sequence selected from HVR-L1, HVR-L2 and HVR-L3, wherein HVR-L1 comprises the amino acid sequence RASQX$_1$VX$_2$X$_3$X$_4$VA (SEQ ID NO: 39), wherein amino acid X$_1$ is selected from amino acid D, S and G, amino acid X$_2$ is selected from S and D, amino acid X$_3$ is selected from S, T and N and amino acid X$_4$ is selected from A and S; wherein HVR-L2 comprises the amino acid sequence of SEQ ID NO: 2; and wherein HVR-L3 comprises the amino acid sequence QQX$_5$X$_6$X$_7$X$_8$X$_9$PX$_{10}$T (SEQ ID NO: 40), wherein amino acid X$_5$ is selected from S, Y and H, amino acid X$_6$ is selected from Y and F, amino acid X$_7$ is selected from T, Y and A, amino acid X$_8$ is selected from T, Y and S, amino acid X$_9$ is optional and if present is serine, and amino acid X$_{10}$ is selected from P and L.

In another aspect, the antibody comprises at least one hypervariable (HVR) sequence selected from HVR-H1, HVR-H2, and HVR-H3 wherein HVR-H1 comprises the amino acid sequence X$_{11}$X$_{12}$X$_{13}$X$_{14}$X$_{15}$X$_{16}$X$_{17}$X$_{18}$ (SEQ ID NO: 41), wherein amino acid X$_{11}$ is selected from T and N, amino acid X$_{12}$ is selected from F and I, amino acid X$_{13}$ is selected from S, T and Y, amino acid $X_{14}$ is selected from N, D, S and Y, amino acid $X_{15}$ is selected from T, Y, S and D, amino acid $X_{16}$ is selected from Y, D and S, amino acid $X_{17}$ is selected from I and M, and amino acid $X_{18}$ is selected from S and H; and wherein HVR-H2 comprises the amino acid sequence $AX_{19}IX_{20}X_{21}X_{22}X_{23}X_{24}X_{25}TX_{26}$ (SEQ ID NO: 42), wherein amino acid $X_{19}$ is selected from S, G, W and E, amino acid $X_{20}$ is selected from T, S and Y, amino acid $X_{21}$ is selected from P and S, amino acid $X_{22}$ is selected from S and Y, amino acid $X_{23}$ is selected from G, S and Y, amino acid $X_{24}$ is selected from G and S, amino acid $X_{25}$ is selected from S and Y, and amino acid $X_{26}$ is selected from D and S, and HVR-H3 comprises the amino acid sequence $RX_{27}X_{28}X_{29}X_{30}X_{31}X_{32}X_{33}X_{34}X_{35}X_{36}X_{37}D$ (SEQ ID NO: 43) wherein amino acid $X_{27}$ is selected from T, E and G, amino acid $X_{28}$ is selected from W, A and Y, amino acid $X_{29}$ is selected from L, G, V and S, amino acid $X_{30}$ is selected from L, S and W, amino acid $X_{31}$ is selected from R, K and Y, amino acid $X_{32}$ is selected from W, L, G and Y, amino acid $X_{33}$ is selected from V, L, A and G, amino acid $X_{37}$ is selected from M and F, and wherein amino acids $X_{34}$, $X_{35}$, and $X_{36}$ are optionally present and if present, amino acid $X_{34}$ is S, amino acid $X_{35}$ is selected from V and P, and amino acid $X_{36}$ is A.

In another aspect, the antibody comprises at least one hypervariable (HVR) sequence selected from HVR-L1, HVR-L2, and HVR-L3, wherein HVR-L1 comprises the amino acid sequence RASQ $X_{38}X_{39}X_{40}X_{41}X_{42}X_{43}A$ (SEQ ID NO: 44), wherein amino acid $X_{38}$ is selected from D, A, E, G, L, N, S, T and V, amino acid $X_{39}$ is selected from V, A, L and S, amino acid $X_{40}$ is selected from S, F, G, L, R and V, amino acid $X_{41}$ is selected from T, G, I, N, S and V, amino acid $X_{42}$ is selected from A, H, Q, R, S, and Y, and amino acid $X_{43}$ is selected from V and L, and wherein HVR-L2 comprises the amino acid sequence $SX_{44}X_{45}X_{46}X_{47}YX_{48}$ (SEQ ID NO: 45), wherein amino acid $X_{44}$ is selected from A and R, amino acid $X_{45}$ is selected from S, K, Q, and R, amino acid $X_{46}$ is selected from F and Y, amino acid $X_{47}$ is selected from L, A, F, G, H, I, K, M, N, P, R, S, V and Y, and amino acid $X_{48}$ is selected from S, A, D, F, G, H, V, W and Y and wherein HVR-L3 comprises the sequence QQ $X_{49}X_{50}X_{51}X_{52}$PPT (SEQ ID NO: 46), wherein amino acid $X_{49}$ is selected from H and S, amino acid $X_{50}$ is selected from Y, K, N, Q, R, S, V, and W, amino acid $X_{51}$ is selected from T, I, Q, R, S and V, and amino acid $X_{52}$ is selected from T, A, D, F, G, K, N, P, Q, R, S and V.

In another aspect, the antibody comprises at least one hypervariable (HVR) sequence selected from HVR-H1, HVR-H2 and HVR-H3, wherein HVR-H1 comprises the amino acid sequence $X_{53}X_{54}X_{55}YX_{56}S$ (SEQ ID NO: 47), wherein amino acid $X_{53}$ is selected from A, F, K, M, Q, R and S, amino acid $X_{54}$ is selected from N and W, amino acid $X_{55}$ is selected from T, A, I, L, M, and V, and amino acid $X_{56}$ is selected from I, M and V, and wherein HVR-L2 comprises the amino acid sequence $AX_{57}X_{58}TPX_{59}SGX_{60}TX_{61}$ (SEQ ID NO:48), wherein amino acid $X_{57}$ is selected from T and S, amino acid $X_{58}$ is selected from I, S and V, amino acid $X_{59}$ is selected from S and A, amino acid $X_{60}$ is selected from S, H, I, L, M and Q, amino acid $X_{61}$ is selected from D and N, and wherein HVR-H3 comprises the amino acid sequence $X_{62}WX_{63}X_{64}RWVX_{65}D$ (SEQ ID NO:49) wherein amino acid $X_{62}$ is selected from S and T, amino acid $X_{63}$ is selected from L and Y, amino acid $X_{64}$ is selected from L, I and V, amino acid $X_{65}$ is selected from M and F.

In another aspect, the antibody comprises an HVR-L1 sequence of SEQ ID NO: 1 or 4, an HVR-L2 sequence of SEQ ID NO: 2, and an HVR-L3 sequence selected from SEQ ID NO: 3, 5 and 6, respectively. In another aspect, the antibody comprises an HVR-H1 sequence selected from SEQ ID NO: 7, 10, 13 and 16, an HVR-H2 sequence selected from SEQ ID NO: 11, 23 and 24, and an HVR-H3 sequence of SEQ ID NO: 12, respectively. In another aspect, the antibody comprises an HVR-L1 sequence selected from SEQ ID NO: 1 and 50-56, an HVR-L2 sequence selected from SEQ ID NO: 2 and 57-62 and an HVR-L3 sequence selected from SEQ ID NO: 3 and 63-71, respectively. In another aspect, the antibody comprises an HVR-H1 sequence selected from SEQ ID NO: 7 and 72-80, an HVR-H2 sequence selected from SEQ ID NO: 8 and 81-85, and an HVR-H3 sequence selected from SEQ ID NO: 9 and 86-92, respectively.

In another aspect, the antibody comprises HVR-L1, HVR-L2, and HVR-L3 sequences corresponding to those set forth for clones 1E2, 1D8, 1F4 or 1A10 in FIG. 1A. In another aspect, the antibody comprises HVR-H1, HVR-H2, and HVR-H3 sequences corresponding to those set forth for clones 1E2, 1D8, 1F4 or 1A10 in FIG. 1B. In another aspect, the antibody comprises HVR-L1, HVR-L2, and HVR-L3 sequences corresponding to those set forth for clones 1D8.3C2, 1D8.3F8 or 1D8.4F5 in FIG. 4A. In another aspect, the antibody comprises HVR-H1, HVR-H2, and HVR-H3 sequences corresponding to those set forth for clones 1D8.3C2, 1D8.3F8 or 1D8.4F5 in FIG. 4B.

In another aspect, the antibody comprises the HVR-L1 sequence of SEQ ID NO: 1, the HVR-L2 sequence of SEQ ID NO: 2, the HVR-L3 sequence of SEQ ID NO: 3, the HVR-H1 sequence of SEQ ID NO: 10, the HVR-H2 sequence of SEQ ID NO: 11 and the HVR-H3 sequence of SEQ ID NO: 12. In another aspect, the antibody comprises the HVR-L1 sequence of SEQ ID NO: 19, the HVR-L2 sequence of SEQ ID NO: 2, the HVR-L3 sequence of SEQ ID NO: 3, the HVR-H1 sequence of SEQ ID NO: 10, the HVR-H2 sequence of SEQ ID NO: 23 and the HVR-H3 sequence of SEQ ID NO: 12. In another aspect, the antibody comprises the HVR-L1 sequence of SEQ ID NO: 1, the HVR-L2 sequence of SEQ ID NO: 2, the HVR-L3 sequence of SEQ ID NO: 20, the HVR-H1 sequence of SEQ ID NO: 10, the HVR-H2 sequence of SEQ ID NO: 11 and the HVR-H3 sequence of SEQ ID NO: 12. In another aspect, the antibody comprises the HVR-L1 sequence of SEQ ID NO: 1, the HVR-L2 sequence of SEQ ID NO: 2, the HVR-L3 sequence of SEQ ID NO: 20, the HVR-H1 sequence of SEQ ID NO: 10, the HVR-H2 sequence of SEQ ID NO: 11 and the HVR-H3 sequence of SEQ ID NO: 12. In another aspect, the antibody comprises the HVR-L1 sequence of SEQ ID NO: 1, the HVR-L2 sequence of SEQ ID NO: 2, the HVR-L3 sequence of SEQ ID NO: 3, the HVR-H1 sequence of SEQ ID NO: 7, the HVR-H2 sequence of SEQ ID NO: 8 and the HVR-H3 sequence of SEQ ID NO: 9. In another aspect, the antibody comprises the HVR-L1 sequence of SEQ ID NO: 1, the HVR-L2 sequence selected from SEQ ID NO: 2, 57 and 59, the HVR-L3 sequence selected from SEQ ID NO: 3, 64 and 71, the HVR-H1 sequence of SEQ ID NO: 7 or 79, the HVR-H2 sequence of SEQ ID NO: 8 or 81, and the HVR-L3 sequence selected from SEQ ID NO: 9, 86, 88 or 89. In another aspect, the antibody comprises the HVR-L1 sequence of SEQ ID NO: 1, the HVR-L2 sequence of SEQ ID NO: 57, the HVR-L3 sequence of SEQ ID NO: 3, the HVR-H1 sequence of SEQ ID NO: 7, the HVR-H2 sequence of SEQ ID NO: 8 and the HVR-H3 sequence of SEQ ID NO: 9. In another aspect, the antibody comprises the HVR-L1 sequence of SEQ ID NO: 1, the HVR-L2 sequence of SEQ ID NO: 2, the HVR-L3 sequence of SEQ ID NO: 3, the HVR-H1 sequence of SEQ ID NO: 7, the HVR-H2 sequence of SEQ ID NO: 81 and the HVR-H3 sequence of SEQ ID NO: 9. In another aspect, the antibody comprises the HVR-L1 sequence of SEQ ID NO: 1, the HVR-L2 sequence of SEQ ID NO: 57, the HVR-L3 sequence of SEQ ID NO: 3, the HVR-H1 sequence of SEQ ID NO: 7, the HVR-H2 sequence of SEQ ID NO: 81 and the HVR-H3 sequence of SEQ ID NO: 9. In certain aspects any of the antibodies described herein may include a leucine as the first amino acid after the C-terminal end of HVR-H3 (e.g., the amino acid immediately adjacent to the C-terminal end of a HVR-H3, such as 1E3, -TWLLRVMDL (SEQ ID NO:96).

In another aspect, the antibody comprises a light chain amino acid sequence selected from SEQ ID NOs: 25-28, 33-35, 94 and 193-195. In another aspect, the antibody comprises a heavy chain amino acid sequence selected from SEQ ID NOs: 29-31, 36-38, 95 and 196-198.

In another aspect, the antibody comprises light chain and heavy chain amino acid sequences with at least 95% sequence identity to the amino acid sequences of one of the following combinations of sequences: SEQ ID NOs 25 and 29; SEQ ID NOs: 26 and 30; SEQ ID NOs: 27 and 31; SEQ ID NOs: 28 and 32; SEQ ID NOs: 33 and 36; SEQ ID NOs: 34 and 37; SEQ ID NOs: 35 and 38; SEQ ID NOs: 95 and 95; SEQ ID NOs: 193 and 196; SEQ ID NOs: 194 and 197; and SEQ ID NOs: 195 and 198.

In another embodiment, the invention provides an isolated antibody, wherein the antibody binds to the same antigenic determinant on C- to N-terminal-linked polyubiquitin as any one of the foregoing antibodies, and wherein the antibody does not specifically bind to monoubiquitin. In another embodiment, the invention provides an isolated antibody that competes with any one of the foregoing antibodies for binding to C- to N-terminal-linked polyubiquitin, wherein the antibody does not specifically bind to monoubiquitin. In another embodiment, the invention provides any of the foregoing isolated antibodies, wherein the antibody specifically binds to a C- to N-terminal-linked polyubiquitinated protein. In another embodiment, the invention provides any of the foregoing isolated antibodies, wherein the antibody modulates at least one polyubiquitin-mediated signaling pathway.

In one general aspect, any of the foregoing antibodies is a monoclonal antibody. In another general aspect, any of the foregoing antibodies is a human antibody. In another general aspect, any of the foregoing antibodies is a humanized antibody. In another general aspect, any of the foregoing antibodies is a chimeric antibody. In another general aspect, any of the foregoing antibodies is an antibody fragment that binds C- to N-terminal-linked polyubiquitin.

In another embodiment, the invention provides an isolated nucleic acid encoding any of the foregoing antibodies. In another embodiment, the invention provides a vector comprising an isolated nucleic acid encoding any of the foregoing antibodies. In another embodiment, the invention provides a host cell comprising an isolated nucleic acid encoding any of the foregoing antibodies. In another embodiment, the invention provides a host cell comprising a vector comprising an isolated nucleic acid encoding any of the foregoing antibodies.

In another embodiment, the invention provides a method of producing any of the foregoing antibodies, comprising culturing the above-recited host cell under conditions wherein the antibody is produced. In one aspect, the method further comprises recovering the antibody from the host cell. In another aspect, the method further comprises purification of the antibody.

In another embodiment, the invention provides an immunoconjugate comprising any of the foregoing antibodies and a cytotoxic agent. In another embodiment, the invention provides a pharmaceutical formulation comprising any of the foregoing antibodies and a pharmaceutically acceptable carrier. In one aspect, the pharmaceutical formulation further comprises an additional therapeutic agent. In one such aspect, the additional therapeutic agent is a chemotherapeutic agent.

In another embodiment, the invention provides any of the foregoing antibodies for use as a medicament. In another embodiment, the invention provides any of the foregoing antibodies for use in treating a cell-cycle-related disease or disorder. In one aspect, the cell-cycle-related disease or disorder is selected from a disease or disorder associated with aberrantly increased cell cycle progression and a disease or disorder associated with aberrantly decreased cell cycle progression. In one such aspect, the disease or disorder associated with aberrantly increased cell cycle progression is cancer. In another such aspect, the disease or disorder associated with aberrantly decreased cell cycle progression is selected from a degenerative muscle disorder and a degenerative nerve disorder.

In another embodiment, the invention provides the use of any of the foregoing antibodies in the manufacture of a medicament. In one aspect, the medicament is for a disease or disorder selected from cancer, a degenerative muscle disorder, and a degenerative nerve disorder. In another embodiment, the invention provides a method of treating an individual having a disease or disorder selected from cancer, a degenerative muscle disorder, and a degenerative nerve disorder, comprising administering to the individual an effective amount of any of the foregoing antibodies.

In another embodiment, the invention provides a method of determining the presence of a polyubiquitin or polyubiquitinated protein in a sample suspected of containing a polyubiquitin or polyubiquitinated protein, comprising exposing the same to at least one of the foregoing antibodies and determining the binding of the at least one antibody to a polyubiquitin or polyubiquitinated protein in the sample. In another embodiment, the invention provides a method of separating C— to N-terminal-linked polyubiquitinated protein from non-C- to N-terminal-linked polyubiquitinated protein in a sample, comprising contacting the sample with at least one of the foregoing antibodies. In another embodiment, the invention provides a method of determining the function and/or activity of C- to N-terminal-linked polyubiquitin in a cell or sample comprising contacting the cell or sample with at least one of the foregoing antibodies and assessing the effect of said contacting step on the cell or sample.

BRIEF DESCRIPTION OF THE FIGURES

FIGS. 2A and 2B depict the light and heavy chain amino acid sequences of the Fabs obtained in Example 1. FIG. 2A depicts the light chain sequence of clones 1E3, 1D8, 1F4 and 1A10 (SEQ ID NOs: 25-28, respectively). FIG. 2B depicts the heavy chain sequence alignment of clones 1E3, 1D8, 1F4 and 1A10 (SEQ ID NOs: 29-32, respectively). In both FIGS. 2A and 2B, the HVR sequences for each clone are indicated by the boxed regions, with the first box indicating HVR-L1 (FIG. 2A) or HVR-H1 (FIG. 2B), the second box indicating HVR-L2 (FIG. 2A) or HVR-H2 (FIG. 2B), and the third box indicating HVR-L3 (FIG. 2A) or HVR-H3 (FIG. 2B).

FIGS. 5A and 5B depict the light and heavy chain amino acid sequences of the affinity matured clones obtained in Example 2 from the 1D8 affinity maturation library sorts.

FIG. 5A depicts the light chain sequences of the affinity matured clones 1D8.3C2, 1D8.3F8 and 1D8.4F5 (SEQ ID NOs: 33-35, respectively). FIG. 5A discloses the 1D8 sequence as SEQ ID NO: 26.

FIG. 5B depicts the heavy chain sequence alignment of the affinity matured clones 1D8.3C2, 1D8.3F8 and 1D8.4F5 (SEQ ID NOs: 36-38, respectively). FIG. 5B discloses the 1D8 sequence as SEQ ID NO: 30. In both FIGS. 5A and 5B, the HVR sequences for each clone are indicated by the boxed regions, with the first box indicating HVR-L1 (FIG. 5A) or HVR-H1 (FIG. 5B), the second box indicating HVR-L2 (FIG. 5A) or HVR-H2 (FIG. 5B), and the third box indicating HVR-L3 (FIG. 5A) or HVR-H3 (FIG. 5B). Amino acid changes relative to the 1D8 parental sequence are highlighted in gray.

FIGS. 9A and 9B depict the light and heavy chain amino acid sequences of the 1E3 Fab, affinity matured clones obtained in Example 3 from the second 1E3 affinity maturation library sorts (1F11 and 3F5), the Y102L mutation observed in clone 4E4 and the triple mutant Fab incorporating the amino acid changes from clones 1F11 and 3F5 and the Y102L mutation as described in Example 3P. FIG. 9A depicts the light chain sequences of the affinity matured clones for 1E3, 1F11, 3F5, Y102L and 1F11/3F5/Y102L (SEQ ID NOs: 25, 193, 194, 195 and 94, respectively). FIG. 9B depicts the heavy chain sequence alignment of the affinity matured clones for 1E3, 1F11, 3F5, Y102L and 1F11/3F5/Y102L (SEQ ID NOs: 29, 196, 197, 198 and 95, respectively). In both FIGS. 9A and 9B, the Kabat positions targeted for amino acid variation in the second affinity maturation libraries for 1E3 are indicated by the boxed regions. Amino acid changes relative to the 1E3 parental sequence are highlighted in gray.

FIG. 18A shows the results of IP experiments in 0M, 2M, 4M and 6M urea.

FIG. 23B discloses residues 31-37, 70-76 and 60-63 as SEQ ID NOS 379-381, respectively. C) The paratope on 1F11/3F5/Y102L Fab is shown in dark gray on the surface of the Fab that interacts with diubiquitin. Residues which have at least 25% of their solvent accessible surface area buried at the interface of 1F11/3F5/Y102L and diubiquitin and/or are within 4.5 Å of the diubiquitin are indicated by single letter amino acid code and residue number. FIG. 23C discloses residues 95-99 and 52-56 as SEQ ID NOS 378 and 377, respectively.

FIG. 24 shows additional close up views of the co-crystal structure of the complex formed between the 1F11/3F5/Y102L Fab fragment and linear diubiquitin. A) Close up showing the hydrogen bonds formed between the side chain of Gln56 of the heavy chain and the main chain carbonyl groups of Gly75 and Gly76. Diubiquitin is shown in light gray and the Fab in dark grey. B) Potential electrostatic interaction between Lys52 of the light chain and Asp32 and dipole from the carboxy-terminal end of the alpha helix of diubiquitin. Diubiquitin is shown in light gray and the Fab in dark gray. C) Hydrophobic interactions between Leu102 of the heavy chain and Val2 and Leu4 of framework 1 of the heavy chain. Leu102 is at the carboxyl-terminal end of CDR H3. Diubiquitin is shown in light gray and the Fab in dark gray.

DETAILED DESCRIPTION OF EMBODIMENTS OF THE INVENTION

I. Definitions

Figure 1:
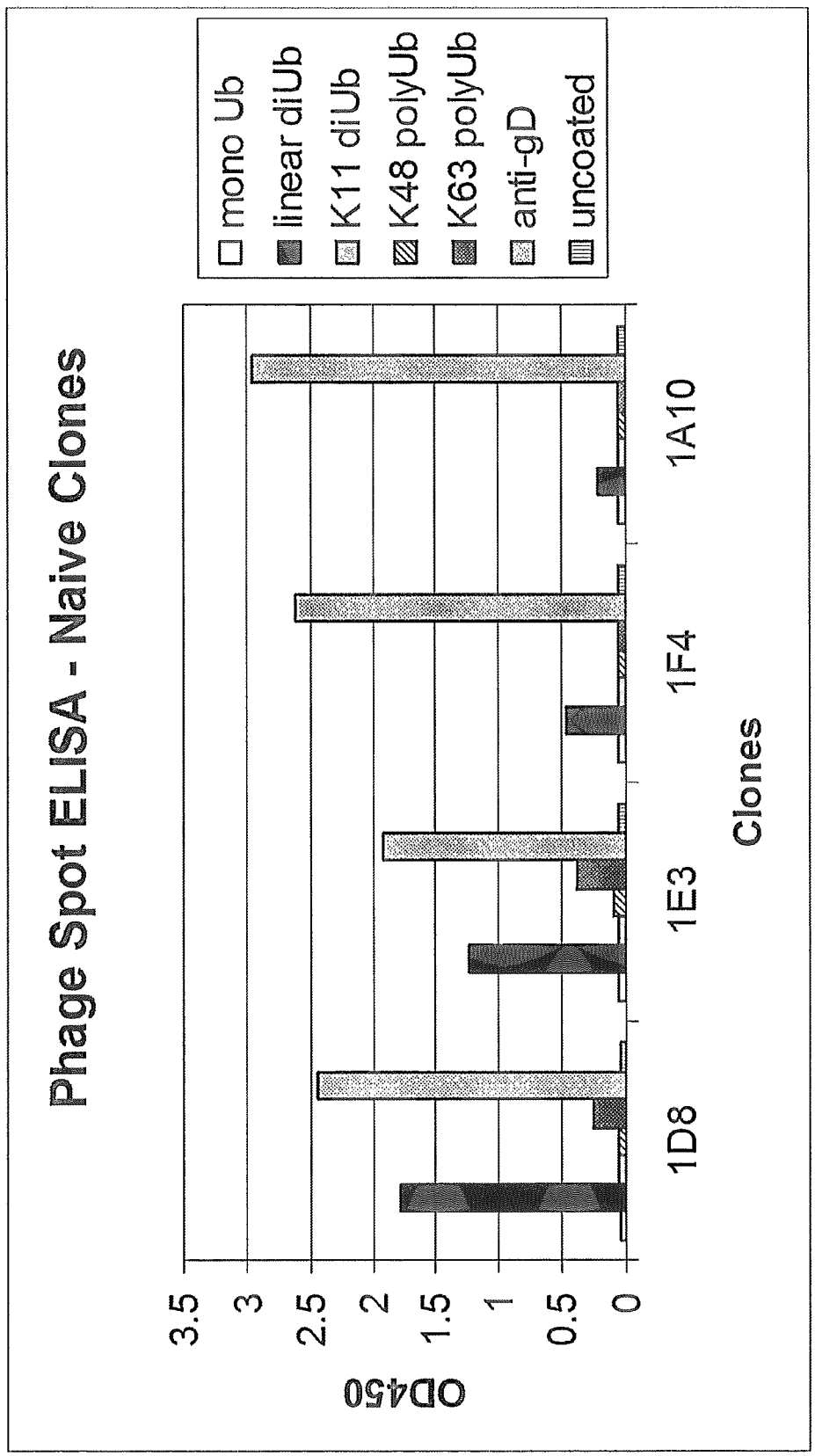
FIG. 1 shows the results of a phage spot ELISA demonstrating the relative binding signals at a wavelength of 450 nm for clones 1D8, 1E3, 1F4 and 1A10 to a panel of ubiquitin proteins, as described in Example 1B. The Fab library clones each contained a gD tag and display of the Fab on phage was assessed by binding to an anti-gD antibody. An uncoated well was used as a negative control.

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Specific illustrative and exemplary embodiments for measuring binding affinity are described in the following.

An "affinity matured" antibody refers to an antibody with one or more alterations in one or more hypervariable regions (HVRs), compared to a parent antibody which does not possess such alterations, such alterations resulting in an improvement in the affinity of the antibody for antigen.

An "agonist antibody" as used herein is an antibody which mimics at least one of the functional activities of a polypeptide of interest.

An "antagonist antibody" or a "blocking antibody" is an antibody which inhibits or reduces biological activity of the antigen to which it specifically binds. Certain blocking antibodies or antagonist antibodies substantially or completely inhibit the biological activity of the antigen.

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies; linear antibodies; single-chain antibody molecules (e.g. scFv); and multispecific antibodies formed from antibody fragments.

An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more. An exemplary competition assay is provided herein.

The terms "anti-linear linked polyubiquitin antibody" and "an antibody that binds to linear linked polyubiquitin" refer to an antibody that is capable of binding linear linked polyubiquitin with sufficient affinity such that the antibody is useful as a diagnostic and/or therapeutic agent in targeting linear linked polyubiquitin. In one embodiment, the extent of binding of an anti-linear linked polyubiquitin antibody to an unrelated, non-linear linked polyubiquitin protein is less than about 10% of the binding of the antibody to linear linked polyubiquitin as measured, e.g., by a radioimmunoassay (RIA). In certain embodiments, an antibody that binds to linear linked polyubiquitin has a dissociation constant (Kd) of $\leq 1$ µM, $\leq 100$ nM, $\leq 10$ nM, $\leq 1$ nM, $\leq 0.1$ nM, $\leq 0.01$ nM, or $\leq 0.001$ nM (e.g. $10^{-8}$ M or less, e.g. from $10^{-8}$ M to $10^{-13}$ M, e.g., from $10^{-9}$ M to $10^{-13}$ M). In certain embodiments, an anti-linear linked polyubiquitin antibody binds to an epitope of linear linked polyubiquitin that is conserved among linear linked polyubiquitin from different species.

As used herein, the term "anti-polyubiquitin antibody" refers to an antibody that is capable of specifically binding to a polyubiquitin molecule.

As used herein, the terms "anti-ubiquitin antibody" and "anti-monoubiquitin antibody" are used interchangeably, and refer to an antibody that is capable of specifically binding to a ubiquitin molecule.

The term "chimeric" antibody refers to an antibody in which a portion of the heavy and/or light chain is derived from a particular source or species, while the remainder of the heavy and/or light chain is derived from a different source or species.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., IgG$_1$, IgG$_2$, IgG$_3$, IgG$_4$, IgA$_1$, and IgA$_2$. The heavy chain constant domains that correspond to the different classes of immunoglobulins are called α, δ, ε, γ, and µ, respectively.

The term "cytotoxic agent" as used herein refers to a substance that inhibits or prevents a cellular function and/or causes cell death or destruction. Cytotoxic agents include, but are not limited to, radioactive isotopes (e.g., At$^{211}$, I$^{131}$, I$^{125}$, Y$^{90}$, Re$^{186}$, Re$^{188}$, Sm$^{153}$, Bi$^{212}$, P$^{32}$, Pb$^{212}$ and radioactive isotopes of Lu); chemotherapeutic agents or drugs (e.g., methotrexate, adriamicin, vinca alkaloids (vincristine, vinblastine, etoposide), doxorubicin, melphalan, mitomycin C, chlorambucil, daunorubicin or other intercalating agents); growth inhibitory agents; enzymes and fragments thereof such as nucleolytic enzymes; antibiotics; toxins such as small molecule toxins or enzymatically active toxins of bacterial, fungal, plant or animal origin, including fragments and/or variants thereof; and the various antitumor or anticancer agents disclosed below.

A "disorder" is any condition that would benefit from treatment with an antibody of the invention. This includes chronic and acute disorders or diseases including those pathological conditions which predispose the mammal to the disorder in question. Non-limiting examples of disorders to be treated herein include cancer, and hypotrophy disorders including, but not limited to, degenerative muscle disorders and degenerative nerve disorders.

"Effector functions" refer to those biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation.

An "effective amount" of an agent, e.g., a pharmaceutical formulation, refers to an amount effective, at dosages and for periods of time necessary, to achieve the desired therapeutic or prophylactic result.

The term "Fc region" herein is used to define a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., *Sequences of Proteins of Immunological Interest*, 5th Ed. Public Health Service, National Institutes of Health, Bethesda, Md., 1991.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

The terms "full length antibody," "intact antibody," and "whole antibody" are used herein interchangeably to refer to an antibody having a structure substantially similar to a native antibody structure or having heavy chains that contain an Fc region as defined herein.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., *Sequences of Proteins of Immunological Interest*, Fifth Edition, NIH Publication 91-3242, Bethesda Md. (1991), vols. 1-3. In one embodiment, for the VL, the subgroup is subgroup kappa I as in Kabat et al., supra. In one embodiment, for the VH, the subgroup is subgroup III as in Kabat et al., supra.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "hypervariable region" or "HVR," as used herein, refers to each of the regions of an antibody variable domain which are hypervariable in sequence and/or form structurally defined loops ("hypervariable loops"). Generally, native four-chain antibodies comprise six HVRs; three in the VH (H1, H2, H3), and three in the VL (L1, L2, L3). HVRs generally comprise amino acid residues from the hypervariable loops and/or from the "complementarity determining regions" (CDRs), the latter being of highest sequence variability and/or involved in antigen recognition. Exemplary hypervariable loops occur at amino acid residues 26-32 (L1), 50-52 (L2), 91-96 (L3), 26-32 (H1), 53-55 (H2), and 96-101 (H3). (Chothia and Lesk, *J. Mol. Biol.* 196:901-917 (1987).) Exemplary CDRs (CDR-L1, CDR-L2, CDR-L3, CDR-H1, CDR-H2, and CDR-H3) occur at amino acid residues 24-34 of L1, 50-56 of L2, 89-97 of L3, 31-35B of H1, 50-65 of H2, and 95-102 of H3. (Kabat et al., *Sequences of Proteins of Immunological Interest*, 5th Ed. Public Health Service, National Institutes of Health, Bethesda, Md. (1991).) With the exception of CDR1 in VH, CDRs generally comprise the amino acid residues that form the hypervariable loops. CDRs also comprise "specificity determining residues," or "SDRs," which are residues that contact antigen. SDRs are contained within regions of the CDRs called abbreviated-CDRs, or a-CDRs. Exemplary a-CDRs (a-CDR-L1, a-CDR-L2, a-CDR-L3, a-CDR-H1, a-CDR-H2, and a-CDR-H3) occur at amino acid residues 31-34 of L1, 50-55 of L2, 89-96 of L3, 31-35B of H1, 50-58 of H2, and 95-102 of H3. (See Almagro and Fransson, *Front. Biosci.* 13:1619-1633 (2008).) Unless otherwise indicated, HVR residues and other residues in the variable domain (e.g., FR residues) are numbered herein according to Kabat et al., supra.

An "immunoconjugate" is an antibody conjugated to one or more heterologous molecule(s), including but not limited to a cytotoxic agent.

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

An "isolated" antibody is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman et al., *J. Chromatogr. B* 848:79-87 (2007).

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

"Isolated nucleic acid encoding an anti-linear linked polyubiquitin antibody" refers to one or more nucleic acid molecules encoding antibody heavy and light chains (or fragments thereof), including such nucleic acid molecule(s) in a single vector or separate vectors, and such nucleic acid molecule(s) present at one or more locations in a host cell.

As used herein, the terms "linear linked polyubiquitin" and "C-terminal to N-terminal linked polyubiquitin" are interchangeable, and refer to a polyubiquitin molecule comprising at least one isopeptide bond between the C-terminus (e.g., the C-terminal glycine) of one ubiquitin moiety and the N-terminal α-amino group (e.g., the N-terminal methionine) of another ubiquitin moiety.

As used herein, "lysine linkage" indicates a linkage between one ubiquitin moiety and another ubiquitin moiety which involves a lysine residue (e.g., K6, K11, K27, K29, K33, K48, and/or K63).

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

A "naked antibody" refers to an antibody that is not conjugated to a heterologous moiety (e.g., a cytotoxic moiety) or radiolabel. The naked antibody may be present in a pharmaceutical formulation.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (λ), based on the amino acid sequence of its constant domain.

The term "package insert" is used to refer to instructions customarily included in commercial packages of therapeutic products, that contain information about the indications, usage, dosage, administration, combination therapy, contraindications and/or warnings concerning the use of such therapeutic products.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

$$100 \text{ times the fraction } X/Y$$

where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

As used herein, the term "polyubiquitin" is defined as all species of native human and synthetic polymeric chains of ubiquitin which fall within human and synthetic classes of different polymeric linkages of ubiquitin, including, but not limited to, linear polyubiquitin, K6-linked polyubiquitin, K11-linked polyubiquitin, K27-linked polyubiquitin, K29-linked polyubiquitin, K33-linked polyubiquitin, K48-linked polyubiquitin and K63-linked polyubiquitin. Polyubiquitin may be of any length, and includes at least two ubiquitin moieties.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or to slow the progression of a disease.

As used herein, the terms "ubiquitin" and "monoubiquitin" are used interchangeably, and refer to any native ubiquitin from any vertebrate source, including mammals such as primates (e.g. humans) and rodents (e.g., mice and rats), unless otherwise indicated. The term encompasses "full-length," unprocessed ubiquitin as well as any shortened or posttranslationally modified form of ubiquitin that results from processing in the cell, excepting molecules comprised of multiple ubiquitin moieties. The term also encompasses naturally occurring variants of ubiquitin, e.g., splice variants or allelic variants. The amino acid sequence of an exemplary human ubiquitin is shown in SEQ ID NO:97: MQIFVKTLTGKTI-TLEVEPSDTIENVKAKIQDKEGIPPDQQRLIFA GKQLEDGRTLSDYNIQKESTLHLVLRLRGG (SEQ ID NO: 97). Ubiquitin has at least one lysine residue at amino acid 6, amino acid 11, amino acid 27, amino acid 29, amino acid 33, amino acid 48, and/or amino acid 63 (marked in bold in SEQ ID NO: 97, above).

As used herein, the term "ubiquitin pathway" refers to a biochemical pathway in a cell or reconstituted in vitro that includes ubiquitin and/or polyubiquitin.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt et al. *Kuby Immunology*, 6$^{th}$ ed., W.H. Freeman and Co., page 91 (2007).) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., *J. Immunol.* 150:880-887 (1993); Clarkson et al., *Nature* 352:624-628 (1991).

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

II. Compositions and Methods

In one aspect, the invention is based, in part, on the creation of antibodies that are capable of specifically recognizing a first polyubiquitin molecule containing a first polyubiquitin linkage but not specifically binding to a second polyubiquitin molecule containing a second polyubiquitin linkage. In certain embodiments, antibodies that specifically bind to linear polyubiquitin or C-terminal to N-terminal-linked polyubiquitin are provided. Antibodies of the invention are useful both in research and, e.g., for the diagnosis or treatment, e.g., of diseases and disorders relating to aberrant cell cycle progression.

The unique properties of the anti-linear polyubiquitin antibodies of the invention make them particularly useful for distinguishing between different linked forms of polyubiquitin in a cellular system without resorting to cumbersome and expensive genetic manipulation or biophysical methods such as mass spectrometry. The anti-linear linked polyubiquitin antibodies of the invention can be used to characterize the function(s) and activities of specific linear polyubiquitins both in vitro and in vivo. The anti-linear linked polyubiquitin antibodies of the invention can also be used to determine the role of specific linear polyubiquitins in the development and pathogenesis of disease. The anti-linear linked polyubiquitin antibodies of the invention can further be used to treat diseases in which one or more specific linear polyubiquitins are aberrantly regulated or aberrantly functioning without interfering with the normal activity of polyubiquitins for which the anti-polyubiquitin antibodies are not specific.

The involvement of the ubiquitin system in the NFκ-B pathway has been described. Karin et al., *Nature Rev. Immunol.* 5:749-759 (2005) and Chen, Z. J., *Nature Cel Biol.* 7:758-765 (2005). Stimulation of cells with proinflammatory cytokines has been shown to result in K63-linked polyubiquitination of RIP1 and NEMO proteins which result in activation of IκB kinase (IKK). Tokunaga et al., *Nature Cell Biol.* 11:123-132 (2009). IKK is then polyubiquitinated with K48-linked polyubiquitin and subsequently degraded, leading to activation of NFκ-B. Id. Recently it was also shown that LUBAC activates the NFκ-B pathway but not the JNK pathway via linear polyubiquitination of NFκ-B. Id. NF-κB also plays a role in cell proliferation and the cell cycle. Many cancers display aberrant activation of NF-κB and suppression of NF-κB suppresses cancer cell proliferation. Garg and Aggarwal, *Leukemia* 16: 1053-68 (2002). The presence of linear-linked polyubiquitin on proteins such as NF-κB plays an important role in modulation of NF-κB activity and cell cycle progression. Thus, the antibodies and Fabs of the invention provide a useful therapeutic means for modulation of disorders and disease states in which cell cycle regulation is aberrant. In one embodiment, the anti-linear polyubiquitin antibodies of the invention are used to treat diseases and disorders where cell cycle progression is aberrantly upregulated, resulting in too much cell division, such as cancer. In another embodiment, the anti-linear-linked polyubiquitin antibodies of the invention are used to treat diseases and disorders where cell cycle progression is aberrantly downregulated, resulting in too little cell division and concomitant wasting or destruction of tissue. Examples of such diseases include, but are not limited to, degenerative muscle disorders and degenerative nerve disorders (including, but not limited to, Charcot Marie Tooth syndrome, poliomyelitis, amyotrophic lateral sclerosis, and Guillain-Barre syndrome).

As used herein, the terms "cell proliferative disorder" and "proliferative disorder" refer to disorders that are associated with some degree of abnormal cell proliferation. In one embodiment, the cell proliferative disorder is cancer.

The terms "cancer" and "cancerous" refer to or describe the physiological condition in mammals that is typically characterized by unregulated cell growth/proliferation. Examples of cancer include, but are not limited to, carcinoma, lymphoma (e.g., Hodgkin's and non-Hodgkin's lymphoma), blastoma, sarcoma, and leukemia. More particular examples of such cancers include squamous cell cancer, small-cell lung cancer, non-small cell lung cancer, adenocarcinoma of the lung, squamous carcinoma of the lung, cancer of the peritoneum, hepatocellular cancer, gastrointestinal cancer, appendiceal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma, leukemia and other lymphoproliferative disorders, and various types of head and neck cancer.

The term "tumor" as used herein refers to all neoplastic cell growth and proliferation, whether malignant or benign, and all pre-cancerous and cancerous cells and tissues. The terms "cancer," "cancerous," "cell proliferative disorder," "proliferative disorder" and "tumor" are not mutually exclusive as referred to herein.

The term "degenerative muscle disorder" refers to or describes the physiological condition in muscle-containing animals that is typically characterized by deterioration or weakening of skeletal and/or smooth muscle such that normal muscular function is reduced. Examples of degenerative muscular disorders include, but are not limited to, muscular dystrophy, myotonic dystrophy, myotonia congenita, cachexia, sarcopenia, multiple sclerosis, amyotrophic lateral sclerosis, Isaac's syndrome, stiff-person syndrome, familiar periodic paralyses, myopathy, myotonia, rhabdomyolyses, muscle atrophy, and various types of muscle weakness and muscle rigidity.

The term "degenerative nerve disorder" refers to or describes the physiological condition in nerve-containing animals that is typically characterized by deterioration of nervous tissue or deterioration of communication between cells in nervous tissue. Examples of degenerative nerve disorders include, but are not limited to, neurodegenerative diseases (including, but not limited to, Lewy body disease, post-poliomyelitis syndrome, Shy-Draeger syndrome, olivopontocerebellar atrophy, Parkinson's disease, multiple system atrophy, amyotrophic lateral sclerosis, Guillian-Barre syndrome, Carcot Marie Tooth syndrome, striatonigral degeneration, and nervous cell/tissue destruction caused by or associated with tauopathies, prion diseases, bulbar palsy, motor neuron disease, dementia, and nervous system heterodegenerative disorders (including, but not limited to, Canavan disease, Huntington's disease, neuronal ceroidlipofuscinosis, Alexander's disease, Tourette's syndrome, Menkes kinky hair syndrome, Cockayne syndrome, Halervorden-Spatz syndrome, lafora disease, Rett syndrome, hepatolenticular degeneration, Lesch-Nyhan syndrome, and Unverricht-Lundborg syndrome).

In another aspect, the anti-linear linked polyubiquitin antibodies of the invention find utility as reagents for detection and isolation of linear linked polyubiquitin, such as detection of polyubiquitin in various cell types and tissues, including the determination of polyubiquitin density and distribution in cell populations and within a given cell, and cell sorting based on the presence or amount of polyubiquitin. In yet another aspect, the present anti-linear linked polyubiquitin antibodies are useful for the development of polyubiquitin antagonists with blocking activity patterns similar to those of the subject antibodies of the invention. As a further example, anti-linear linked polyubiquitin antibodies of the invention can be used to identify other anti-polyubiquitin antibodies that bind substantially the same antigenic determinant(s) of polyubiquitin as the antibodies exemplified herein, including linear and conformational epitopes.

The anti-linear linked polyubiquitin antibodies of the invention can be used in assays based on the physiological pathways in which polyubiquitin is involved to screen for small molecule antagonists of linear linked polyubiquitin function. For example, since linear linked polyubiquitin chains are known to be necessary for NFκB activation, (Tokunaga et al., *Nature Cell Biol.* 11:123-132 (2009)), the activity of anti-linear linked polyubiquitin antibodies to modulate (up- or down-regulate) NFκ13 activation in treated cells or tissues may be compared to the activity of one or more potential small molecule antagonists of linear linked polyubiquitin in modulating NFκ13 activation.

A. Exemplary Anti-Linear Linked Polyubiquitin Antibodies

In one aspect, the invention provides isolated antibodies that bind to linear or C-terminal to N-terminal-linked polyubiquitin. In certain embodiments, an anti-linear linked polyubiquitin antibody specifically binds to C-terminal to N-terminal-linked polyubiquitin but does not specifically bind to monoubiquitin. In certain embodiments, an anti-linear linked polyubiquitin antibody specifically binds to C-terminal to N-terminal-linked polyubiquitin but does not specifically bind to polyubiquitin having a lysine linkage (i.e., K6-, K11-, K27-, K29-, K33-, K48-, and/or K63-linkages).

In one aspect, the invention provides an anti-linear linked polyubiquitin antibody comprising an HVR-H1 region comprising the sequence of at least one of SEQ ID NOs: 7, 10, 13, 16, 22 and 73-81. In one aspect, the invention provides an antibody comprising an HVR-H2 region comprising the sequence of at least one of SEQ ID NOs: 8, 11, 14, 17, 23, 24 and 82-86. In one aspect, the invention provides an antibody comprising an HVR-H3 region comprising the sequence of at least one of SEQ ID NOs: 9, 12, 15, 18 and 87-93.

In one aspect, the invention provides an antibody comprising an HVR-H1 region comprising the sequence of at least one of SEQ ID NOs: 7, 10, 13, 16, 22 and 73-81, and, an HVR-H2 region comprising the sequence of at least one of SEQ ID NOs: 8, 11, 14, 17, 23, 24 and 82-86. In one aspect, the invention provides an antibody comprising an HVR-H1 region comprising the sequence of at least one of SEQ ID NOs: 7, 10, 13, 16, 22 and 73-81, and an HVR-H3 region comprising the sequence of at least one of SEQ ID NOs: 9, 12, 15, 18 and 87-93. In one aspect, the invention provides an antibody comprising an HVR-H2 region comprising the sequence of at least one of SEQ ID NOs: 8, 11, 14, 17, 23, 24 and 81-85 and an HVR-H3 region comprising the sequence of at least one of SEQ ID NOs: 9, 12, 15, 18 and 86-92.

In one aspect, the invention provides an antibody comprising an HVR-L1 region comprising the sequence of at least one of SEQ ID NOs: 1, 4, 19 and 50-57. In one aspect, the invention provides an antibody comprising an HVR-L2 region comprising the sequence of at least one of SEQ ID NOs: 2 and 58-62. In one aspect, the invention provides an antibody comprising an HVR-L3 region comprising the sequence of at least one of SEQ ID NOs: 3, 5, 6, 20, 21 and 64-72.

In one aspect, the invention provides an antibody comprising an HVR-L1 region comprising the sequence of at least one of SEQ ID NOs: 1, 4, 19 and 50-57 and an HVR-L2 region comprising the sequence of at least one of SEQ ID NOs: 2 and 58-63. In one aspect, the invention provides an antibody comprising an HVR-L1 region comprising the sequence of at least one of SEQ ID NOs: 1, 4, 19 and 50-57 and an HVR-L3 region comprising the sequence of at least one of SEQ ID NOs: 3, 5, 6, 20, 21 and 64-72. In one aspect, the invention provides an antibody comprising an HVR-L2 region comprising the sequence of at least one of SEQ ID NOs: 2 and 58-63 and an HVR-L3 region comprising the sequence of at least one of SEQ ID NOs: 3, 5, 6, 20, 21 and 64-72.

In one aspect, the invention provides an antibody comprising at least one, at least two, at least three, at least four, at least five or all six of the following:
  (i) an HVR-H1 sequence comprising at least one sequence of SEQ ID NOs: 7, 10, 13, 16, 22 and 73-81;
  (ii) an HVR-H2 sequence comprising at least one sequence of SEQ ID NOs: 8, 11, 14, 17, 23, 24 and 82-86;
  (iii) an HVR-H3 sequence comprising at least one sequence of SEQ ID NOs: 9, 12, 15, 18 and 87-93;

(iv) an HVR-L1 sequence comprising at least one sequence of SEQ ID NOs: 1, 4, 19 and 50-57;
(v) an HVR-L2 sequence comprising at least one sequence of SEQ ID NOs: 2 and 58-63; and
(vi) an HVR-L3 sequence comprising at least one sequence of SEQ ID NO: 3, 5, 6, 20, 21 and 64-72.

Some embodiments of antibodies of the invention comprise a light chain variable domain of humanized 4D5 antibody (huMAb4D5-8) (HERCEPTIN®, Genentech, Inc., South San Francisco, Calif., USA) (also referred to in U.S. Pat. No. 6,407,213 and Lee et al., J. Mol. Biol. (2004), 340 (5):1073-93) as depicted in SEQ ID NO: 98 below.

```
                                                        (SEQ ID NO: 98)
1 Asp Be Gln Met Thr Gln Ser Pro Ser Ser Leu Ser Ala Ser Val Gly Asp

Arg Val Thr Be Thr Cys Arg Ala Ser Gln Asp Val Asn Thr Ala Val Ala Trp

Tyr Gln Gln Lys Pro Gly Lys Ala Pro Lys Leu Leu Be Tyr Ser Ser Ala Ser Phe

Leu Tyr Ser Gly Val Pro Ser Arg Phe Ser Gly Ser Arg Ser Gly Thr Asp Phe

Thr Leu Thr Be Ser Ser Leu Gln Pro Glu Asp Phe Ala Thr Tyr Tyr Cys Gln

Gln His Tyr Thr Thr Pro Pro Thr Phe Gly Gln Gly Thr Lys Val Glu Ile Lys 107
(HVR residues are underlined)
```

In one aspect, the invention provides an antibody that specifically binds linear linked polyubiquitin with high affinity but binds polyubiquitin some other lysine linkage with substantially reduced affinity, comprising at least one, at least two, at least three, at least four, at least five or all six of the following:
(i) an HVR-H1 sequence comprising at least one sequence of SEQ ID NOs: 7, 10, 13, 16, 22 and 73-81;
(ii) an HVR-H2 sequence comprising at least one sequence of SEQ ID NOs: 8, 11, 14, 17, 23, 24 and 82-86;

In one embodiment, the huMAb4D5-8 light chain variable domain sequence is modified at one or more of positions 28, 30, 31, 53, 66, and 91 (Asp, Asn, Thr, Phe, Arg, and His as indicated in bold/italics above, respectively). In one embodiment, the modified huMAb4D5-8 sequence comprises Ser in position 28, Ser in position 30, Ser in position 31, Ser in position 53, Gly in position 66, and/or Ser in position 91. Accordingly, in one embodiment, an antibody of the invention comprises a light chain variable domain comprising the sequence depicted in SEQ ID NO: 99 below:

```
                                                        (SEQ ID NO: 99)
1 Asp Be Gln Met Thr Gln Ser Pro Ser Ser Leu Ser Ala Ser Val Gly Asp

Arg Val Thr Be Thr Cys Arg Ala Ser Gln Ser Val Ser Ser Ala Val Ala Trp

Tyr Gln Gln Lys Pro Gly Lys Ala Pro Lys Leu Leu Be Tyr Ser Ala Ser Ser

Leu Tyr Ser Gly Val Pro Ser Arg Phe Ser Gly Ser Gly Ser Gly Thr Asp Phe

Thr Leu Thr Be Ser Ser Leu Gln Pro Glu Asp Phe Ala Thr Tyr Tyr Cys Gln

Gln Ser Tyr Thr Thr Pro Pro Thr Phe Gly Gln Gly Thr Lys Val Glu Be Lys 107
(HVR residues are underlined)
```

(iii) an HVR-H3 sequence comprising at least one sequence of SEQ ID NOs: 9, 12, 15, 18 and 87-93;
(iv) an HVR-L1 sequence comprising at least one sequence of SEQ ID NOs: 1, 4, 19 and 50-57;
(v) an HVR-L2 sequence comprising at least one sequence of SEQ ID NOs: 2 and 58-63; and
(vi) an HVR-L3 sequence comprising at least one sequence of SEQ ID NO: 3, 5, 6, 20, 21 and 64-72.

Figure 5B:
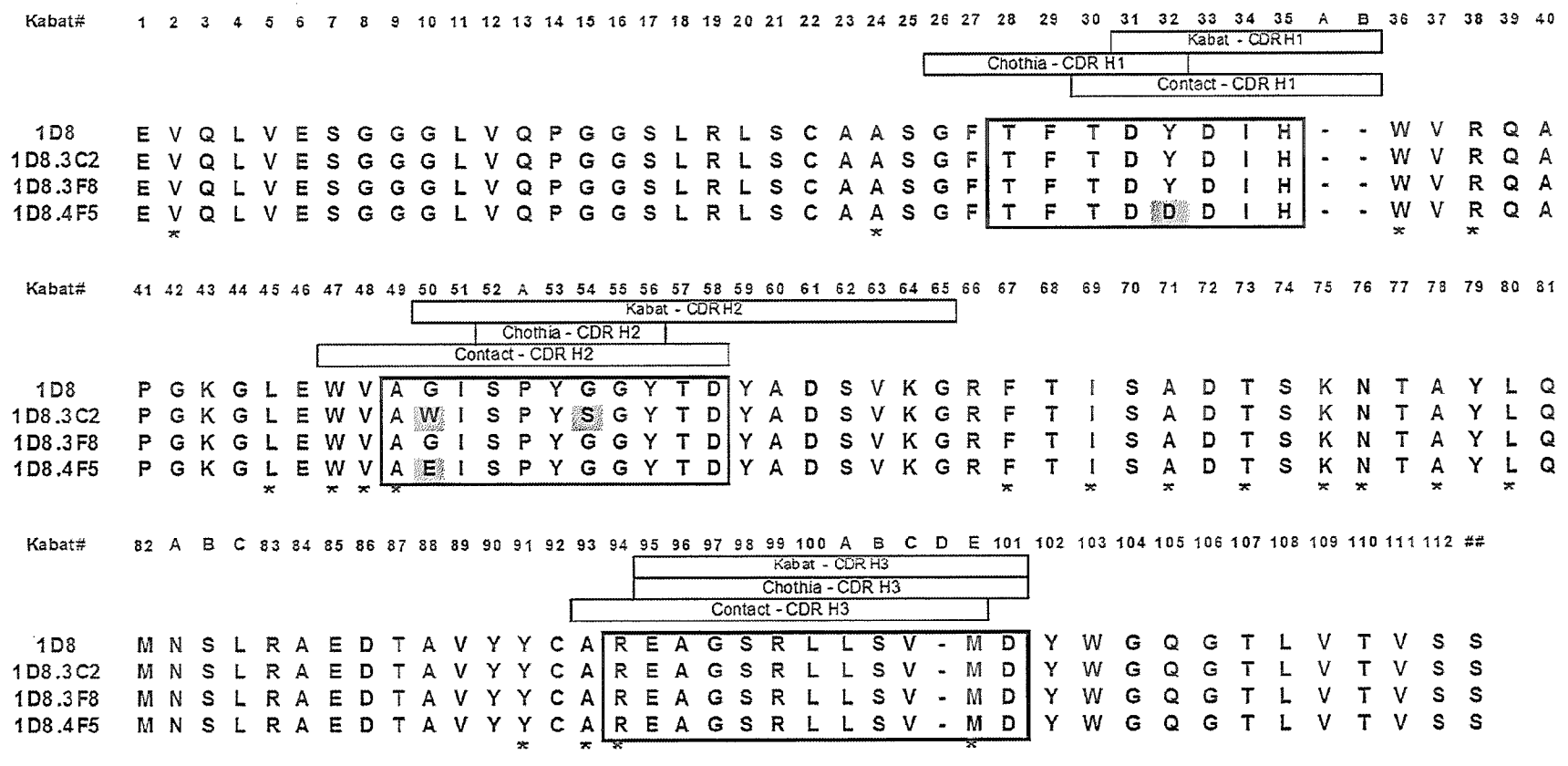

In one aspect, the invention provides antibodies comprising heavy chain HVR sequences as depicted in FIG. 2B, 5B, or 9B. In one embodiment, the antibodies comprise light chain HVR sequences as depicted in FIG. 2A, 5A, or 9A. In one embodiment, the antibodies comprise heavy chain HVR sequences as depicted in FIG. 2B, 5B, or 9B and light chain HVR sequences as depicted in FIG. 2A, 5A, or 9A. In one embodiment, the antibodies comprise light chain HVR sequences as depicted in Tables 5 and 7. In one embodiment, the invention provides antibodies comprising heavy chain HVR sequences as depicted in Tables 5 and 7. In one embodiment, the antibodies comprise heavy chain HVR sequences as depicted in Tables 5 and 7 and light chain HVR sequences as depicted in Tables 5 and 7.

Substituted residues with respect to huMAb4D5-8 are indicated in bold/italics above.

Antibodies of the invention can comprise any suitable framework variable domain sequence, provided binding activity to linear linked polyubiquitin is substantially retained. For example, in some embodiments, antibodies of the invention comprise a human subgroup III heavy chain framework consensus sequence. In one embodiment of these antibodies, the framework consensus sequence comprises substitution at position 71, 73, 78 and/or 102. In some embodiments of these antibodies, position 71 is A, 73 is T 78 is A and/or 102 is L. In one embodiment, these antibodies comprise heavy chain variable domain framework sequences of huMAb4D5-8 (HERCEPTIN®, Genentech, Inc., South San Francisco, Calif., USA) (also referred to in U.S. Pat. Nos. 6,407,213 & 5,821,337, and Lee et al., J. Mol. Biol. (2004), 340(5):1073-93). In one embodiment, these antibodies further comprise a human id light chain framework consensus sequence. In one embodiment, these antibodies comprise at least one, two or all of the light chain HVR sequences of SEQ ID NOs: 1-6, 19-21 and 50-72. In one embodiment, these antibodies comprise light chain HVR sequences of huMAb4D5-8 as described in U.S. Pat. Nos. 6,407,213 &

5,821,337.) In one embodiment, these antibodies comprise light chain variable domain sequences of huMAb4D5-8 (SEQ ID NO: 98 and 99) (HERCEPTIN®, Genentech, Inc., South San Francisco, Calif., USA) (also referred to in U.S. Pat. Nos. 6,407,213 & 5,821,337, and Lee et al., *J. Mol. Biol.* (2004), 340(5):1073-93).

In one embodiment, an antibody of the invention is affinity matured to obtain the target binding affinity desired. In one example, an affinity matured antibody of the invention which specifically binds to linear linked polyubiquitin with high affinity but binds to polyubiquitin having a lysine linkage with substantially reduced affinity comprises substitution at HVR-H1 amino acid position 32. In another example, an affinity matured antibody of the invention which specifically binds to linear linked polyubiquitin having a lysine linkage with substantially reduced affinity comprises substitution at HVR-H2 amino acid positions 50, 54 and/or 56. In another example, an affinity matured antibody of the invention which specifically binds to linear linked polyubiquitin having a lysine linkage with substantially reduced affinity comprises substitution at HVR-H3 amino acid position 103. In another example, an affinity matured antibody of the invention which specifically binds to linear linked polyubiquitin with high affinity but binds to polyubiquitin having other lysine linkages with substantially reduced affinity comprises substitution at HVR-L1 amino acid positions 28, 30, 31 and/or 32. In another example, an affinity matured antibody of the invention which specifically binds to linear linked polyubiquitin with high affinity but binds to polyubiquitin having other lysine linkages with substantially reduced affinity comprises substitution at HVR-L3 amino acid positions 92, 93 and/or 94. In another example, an affinity matured antibody of the invention which specifically binds to linear linked polyubiquitin with high affinity but binds to polyubiquitin having other lysine linkages with substantially reduced affinity comprises substitution at HVR-L2 amino acid position 52.

In one embodiment, an antibody of the invention comprises at least one heavy chain variable domain sequence of SEQ ID NOs: 29-32, 36-38, 95 and 196-198. In one embodiment, an antibody of the invention comprises at least one light chain variable domain of SEQ ID NOs: 25-28, 33-35, 94 and 193-195. In one embodiment, an antibody of the invention comprises a heavy chain variable domain comprising at least one sequence of SEQ ID NOs: 29-32, 36-38, 95 and 196-198 and also comprises a light chain variable domain comprising at least one sequence of SEQ ID NOs: 25-28, 33-35, 94 and 193-195. In other embodiments, an antibody of the invention corresponding to a particular clone number comprises a heavy chain variable domain comprising an HVR-H1, HVR-H2, and HVR-H3 sequence as set forth in FIG. 2B, 5B or 9B for that clone number. In other embodiments, an antibody of the invention corresponding to a particular clone number comprises a light chain variable domain comprising an HVR-L1, HVR-L2 and HVR-L3 sequence as set forth in FIGS. 2A, 5A and 9A for that clone number. In other embodiments, an antibody of the invention corresponding to a particular clone number comprises a heavy chain variable domain comprising an HVR-H1, HVR-H2, and HVR-H3 sequence as set forth in FIG. 2B, 5B or 9B for that clone number and also comprises a light chain variable domain comprising an HVR-L1, HVR-L2 and HVR-L3 sequence as set forth in FIGS. 2A, 5A and 9A for that clone number.

In one aspect, the invention provides an antibody that competes with any of the above-mentioned antibodies for binding to linear linked polyubiquitin. In one aspect, the invention provides an antibody that binds to the same antigenic determinant on linear linked polyubiquitin as any of the above-mentioned antibodies.

As shown herein, the antibodies of the invention specifically bind to an isolated polyubiquitin having a C-terminal to N-terminal linkage. As shown herein, the antibodies of the invention also specifically bind to polyubiquitin having a linear C-terminal to N-terminal linkage when that polyubiquitin is attached to a heterologous protein.

In any of the above embodiments, an anti-linear linked polyubiquitin antibody is humanized. In one embodiment, an anti-linear linked polyubiquitin antibody comprises HVRs as in any of the above embodiments, and further comprises an acceptor human framework, e.g. a human immunoglobulin framework or a human consensus framework. In another embodiment, an anti-linear linked polyubiquitin antibody comprises HVRs as in any of the above embodiments, and further comprises a VH comprising an FR1, FR2, FR3, or FR4 sequence of any of SEQ ID NOs: 29-32, 36-38 and 95. In another embodiment, an anti-linear linked polyubiquitin antibody comprises HVRs as in any of the above embodiments, and further comprises a VL comprising an FR1, FR2, FR3, or FR4 sequence of any of SEQ ID NOs: 25-28, 33-35, 94 and 193-195.

In another aspect, an anti-linear linked polyubiquitin antibody comprises a heavy chain variable domain (VH) sequence having at least 90%, 91%, 92%, 93%, 94%, 95%, 96%, 97%, 98%, 99%, or 100% sequence identity to the amino acid sequence of any of SEQ ID NOs: 29-32, 26-38, 95 and 196-198. In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-linear linked polyubiquitin antibody comprising that sequence retains the ability to bind to linear linked polyubiquitin. In certain embodiments, a total of 1 to 10 amino acids have been substituted, inserted and/or deleted in any one of SEQ ID NOs: 29-32, 36-38, 95 and 196-198. In certain embodiments, substitutions, insertions, or deletions occur in regions outside the HVRs (i.e., in the FRs). Optionally, the anti-linear linked polyubiquitin antibody comprises the VH sequence of any of SEQ ID NOs: 29-32, 36-38, 95 and 196-198, including post-translational modifications of that sequence.

In another aspect, an anti-linear linked polyubiquitin antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence of any of SEQ ID NOs: 25-28, 33-35, 94 and 193-195. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-linear linked polyubiquitin antibody comprising that sequence retains the ability to bind to linear-linked polyubiquitin. In certain embodiments, a total of 1 to 10 amino acids have been substituted, inserted and/or deleted in any of SEQ ID NOs: 25-28, 33-35, 94 and 193-195. In certain embodiments, the substitutions, insertions, or deletions occur in regions outside the HVRs (i.e., in the FRs). Optionally, the anti-linear linked polyubiquitin antibody comprises the VL sequence in any of SEQ ID NOs: 25-28, 33-35, 94 and 193-195, including post-translational modifications of that sequence.

In another aspect, an anti-linear linked polyubiquitin antibody is provided, wherein the antibody comprises a VH as in any of the embodiments provided above, and a VL as in any of the embodiments provided above. In one embodiment, the antibody comprises the VH and VL sequences in any of SEQ ID NOs: 29-32, 36-38, 95 and 196-198 and SEQ ID NOs: 25-28, 33-35, 94 and 193-195, respectively, including post-translational modifications of those sequences.

In a further aspect of the invention, an anti-linear linked polyubiquitin antibody according to any of the above embodiments is a monoclonal antibody, including a chimeric, humanized or human antibody. In one embodiment, an anti-linear linked polyubiquitin antibody is an antibody fragment, e.g., a Fv, Fab, Fab', scFv, diabody, or F(ab')$_2$ fragment. In another embodiment, the antibody is a full length antibody, e.g., an intact IgG1 antibody or other antibody class or isotype as defined herein.

Compositions comprising at least one anti-linear linked polyubiquitin antibody or at least one polynucleotide comprising sequences encoding an anti-linear linked polyubiquitin antibody are provided. In certain embodiments, a composition may be a pharmaceutical composition. As used herein, compositions comprise one or more antibodies that bind to one or more polyubiquitin and/or one or more polynucleotides comprising sequences encoding one or more antibodies that bind to one or more polyubiquitin. These compositions may further comprise suitable carriers, such as pharmaceutically acceptable excipients including buffers, which are well known in the art.

In a further aspect, an anti-linear linked polyubiquitin antibody according to any of the above embodiments may incorporate any of the features, singly or in combination, as described in Sections 1-7 below:

I. Antibody Affinity

In certain embodiments, an antibody provided herein has a dissociation constant (Kd) of ≤100 nM, ≤10 nM, ≤1 nM, ≤0.1 nM, ≤0.01 nM, or ≤0.001 nM (e.g. $10^{-8}$ M or less, e.g. from $10^{-8}$ M to $10^{-13}$ M, e.g., from $10^{-9}$ M to $10^{-13}$ M).

In one embodiment, Kd is measured by a radiolabeled antigen binding assay (RIA) performed with the Fab version of an antibody of interest and its antigen as described by the following assay. Solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen et al., *J. Mol. Biol.* 293:865-881 (1999)). To establish conditions for the assay, MICROTITER® multi-well plates (Thermo Scientific) are coated overnight with 5 µg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 µM or 26 µM [$^{125}$I]-antigen are mixed with serial dilutions of a Fab of interest (e.g., consistent with assessment of the anti-VEGF antibody, Fab-12, in Presta et al., *Cancer Res.* 57:4593-4599 (1997)). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN-20®) in PBS. When the plates have dried, 150 µl/well of scintillant (MICROSCINT-20™; Packard) is added, and the plates are counted on a TOPCOUNT™ gamma counter (Packard) for ten minutes. Concentrations of each Fab that give less than or equal to 20% of maximal binding are chosen for use in competitive binding assays.

According to another embodiment, Kd is measured using a surface plasmon resonance assays using a BIACORE®-2000 or a BIACORE®-3000 (BIAcore, Inc., Piscataway, N.J.) at 25° C. with, e.g., immobilized antigen CM5 chips at ~10 response units (RU). Briefly, carboxymethylated dextran biosensor chips (CM5, BIACORE, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 µg/ml (~0.2 µM) before injection at a flow rate of 5 µl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20™) surfactant (PBST) at 25° C. at a flow rate of approximately 25 µl/min. Association rates ($k_{on}$) and dissociation rates ($k_{off}$) are calculated using a simple one-to-one Langmuir binding model (BIACORE® Evaluation Software version 3.2) by simultaneously fitting the association and dissociation sensorgrams. The equilibrium dissociation constant (Kd) is calculated as the ratio $k_{off}/k_{on}$. See, e.g., Chen et al., *J. Mol. Biol.* 293:865-881 (1999). If the on-rate exceeds $10^6$ $M^{-1}$ $s^{-1}$ by the surface plasmon resonance assay above, then the on-rate can be determined by using a fluorescent quenching technique that measures the increase or decrease in fluorescence emission intensity (excitation=295 nm; emission=340 nm, 16 nm bandpass) at 25° C. of a 20 nM anti-antigen antibody (Fab form) in PBS, pH 7.2, in the presence of increasing concentrations of antigen as measured in a spectrometer, such as a stop-flow equipped spectrophometer (Aviv Instruments) or a 8000-series SLM-AMINCO™ spectrophotometer (ThermoSpectronic) with a stirred cuvette. Other coupling chemistries for the target antigen to the chip surface (e.g., streptavidin/biotin, hydrophobic interaction, or disulfide chemistry) are also readily available instead of the amine coupling methodology (CM5 chip) described above, as will be understood by one of ordinary skill in the art.

2. Antibody Fragments

In certain embodiments, an antibody provided herein is an antibody fragment. Antibody fragments include, but are not limited to, Fab, Fab', Fab'-SH, F(ab')$_2$, Fv, and scFv fragments, and other fragments described below. For a review of certain antibody fragments, see Hudson et al. *Nat. Med.* 9:129-134 (2003). For a review of scFv fragments, see, e.g., Pluckthün, in *The Pharmacology of Monoclonal Antibodies*, vol. 113, Rosenburg and Moore eds., (Springer-Verlag, New York), pp. 269-315 (1994); see also WO 93/16185; and U.S. Pat. Nos. 5,571,894 and 5,587,458. For discussion of Fab and F(ab')$_2$ fragments comprising salvage receptor binding epitope residues and having increased in vivo half-life, see U.S. Pat. No. 5,869,046.

Diabodies are antibody fragments with two antigen-binding sites that may be bivalent or bispecific. See, for example, EP 404,097; WO 1993/01161; Hudson et al., *Nat. Med.* 9:129-134 (2003); and Hollinger et al., *Proc. Natl. Acad. Sci. USA* 90: 6444-6448 (1993). Triabodies and tetrabodies are also described in Hudson et al., *Nat. Med.* 9:129-134 (2003).

Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, Mass.; see, e.g., U.S. Pat. No. 6,248,516 B1).

Antibody fragments can be made by various techniques, including but not limited to proteolytic digestion of an intact antibody as well as production by recombinant host cells (e.g. *E. coli* or phage), as described herein.

3. Chimeric and Humanized Antibodies

In certain embodiments, an antibody provided herein is a chimeric antibody. Certain chimeric antibodies are described, e.g., in U.S. Pat. No. 4,816,567; and Morrison et al., *Proc. Natl. Acad. Sci. USA*, 81:6851-6855 (1984)). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro and Fransson, *Front. Biosci.* 13:1619-1633 (2008), and are further described, e.g., in Riechmann et al., *Nature* 332:323-329 (1988); Queen et al., *Proc. Nat'l Acad. Sci. USA* 86:10029-10033 (1989); U.S. Pat. Nos. 5,821,337, 7,527,791, 6,982,321, and 7,087,409; Kashmiri et al., *Methods* 36:25-34 (2005) (describing SDR (a-CDR) grafting); Padlan, *Mol. Immunol.* 28:489-498 (1991) (describing "resurfacing"); Dall'Acqua et al., *Methods* 36:43-60 (2005) (describing "FR shuffling"); and Osbourn et al., *Methods* 36:61-68 (2005) and Klimka et al., *Br. J. Cancer,* 83:252-260 (2000) (describing the "guided selection" approach to FR shuffling).

Human framework regions that may be used for humanization include but are not limited to: framework regions selected using the "best-fit" method (see, e.g., Sims et al. *J. Immunol.* 151:2296 (1993)); framework regions derived from the consensus sequence of human antibodies of a particular subgroup of light or heavy chain variable regions (see, e.g., Carter et al. *Proc. Natl. Acad. Sci. USA,* 89:4285 (1992); and Presta et al. *J. Immunol.,* 151:2623 (1993)); human mature (somatically mutated) framework regions or human germline framework regions (see, e.g., Almagro and Fransson, *Front. Biosci.* 13:1619-1633 (2008)); and framework regions derived from screening FR libraries (see, e.g., Baca et al., *J. Biol. Chem.* 272:10678-10684 (1997) and Rosok et al., *J. Biol. Chem.* 271:22611-22618 (1996)).

4. Human Antibodies

In certain embodiments, an antibody provided herein is a human antibody. Human antibodies can be produced using various techniques known in the art. Human antibodies are described generally in van Dijk and van de Winkel, *Curr. Opin. Pharmacol.* 5: 368-74 (2001) and Lonberg, *Curr. Opin. Immunol.* 20:450-459 (2008).

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, *Nat. Biotech.* 23:1117-1125 (2005). See also, e.g., U.S. Pat. Nos. 6,075,181 and 6,150,584 describing XENOMOUSE™ technology; U.S. Pat. No. 5,770,429 describing HuMab® technology; U.S. Pat. No. 7,041,870 describing K-M MOUSE® technology, and U.S. Patent Application Publication No. US 2007/0061900, describing VelociMouse® technology). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor *J. Immunol.,* 133: 3001 (1984); Brodeur et al., *Monoclonal Antibody Production Techniques and Applications,* pp. 51-63 (Marcel Dekker, Inc., New York, 1987); and Boerner et al., *J. Immunol.,* 147: 86 (1991).) Human antibodies generated via human B-cell hybridoma technology are also described in Li et al., *Proc. Natl. Acad. Sci. USA,* 103:3557-3562 (2006). Additional methods include those described, for example, in U.S. Pat. No. 7,189,826 (describing production of monoclonal human IgM antibodies from hybridoma cell lines) and Ni, *Xiandai Mianyixue,* 26(4):265-268 (2006) (describing human-human hybridomas). Human hybridoma technology (Trioma technology) is also described in Vollmers and Brandlein, *Histology and Histopathology,* 20(3):927-937 (2005) and Vollmers and Brandlein, *Methods and Findings in Experimental and Clinical Pharmacology,* 27(3):185-91 (2005).

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

5. Library-Derived Antibodies

Antibodies of the invention may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom et al. in *Methods in Molecular Biology* 178:1-37 (O'Brien et al., ed., Human Press, Totowa, N.J., 2001) and further described, e.g., in the McCafferty et al., *Nature* 348: 552-554; Clackson et al., *Nature* 352: 624-628 (1991); Marks et al., *J. Mol. Biol.* 222: 581-597 (1992); Marks and Bradbury, in *Methods in Molecular Biology* 248:161-175 (Lo, ed., Human Press, Totowa, N.J., 2003); Sidhu et al., *J. Mol. Biol.* 338(2): 299-310 (2004); Lee et al., *J. Mol. Biol.* 340(5):

1073-1093 (2004); Fellouse, *Proc. Natl. Acad. Sci. USA* 101 (34): 12467-12472 (2004); and Lee et al., *J. Immunol. Methods* 284(1-2): 119-132 (2004).

In certain phage display methods, repertoires of VH and VL genes are separately cloned by polymerase chain reaction (PCR) and recombined randomly in phage libraries, which can then be screened for antigen-binding phage as described in Winter et al., *Ann. Rev. Immunol.*, 12: 433-455 (1994). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self antigens without any immunization as described by Griffiths et al., *EMBO J*, 12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, *J. Mol. Biol.*, 227: 381-388 (1992). Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

Antibodies or antibody fragments isolated from human antibody libraries are considered human antibodies or human antibody fragments herein.

6. Multispecific Antibodies

In certain embodiments, an antibody provided herein is a multispecific antibody, e.g. a bispecific antibody. Multispecific antibodies are monoclonal antibodies that have binding specificities for at least two different sites. In certain embodiments, one of the binding specificities is for linear linked polyubiquitin and the other is for any other antigen. In certain embodiments, bispecific antibodies may bind to two different epitopes of linear linked polyubiquitin. Bispecific antibodies may also be used to localize cytotoxic agents to cells which express linear linked polyubiquitin. Bispecific antibodies can be prepared as full length antibodies or antibody fragments.

Techniques for making multispecific antibodies include, but are not limited to, recombinant co-expression of two immunoglobulin heavy chain-light chain pairs having different specificities (see Milstein and Cuello, *Nature* 305: 537 (1983)), WO 93/08829, and Traunecker et al., *EMBO J.* 10: 3655 (1991)), and "knob-in-hole" engineering (see, e.g., U.S. Pat. No. 5,731,168). Multi-specific antibodies may also be made by engineering electrostatic steering effects for making antibody Fc-heterodimeric molecules (WO 2009/089004A1); cross-linking two or more antibodies or fragments (see, e.g., U.S. Pat. No. 4,676,980, and Brennan et al., *Science*, 229: 81 (1985)); using leucine zippers to produce bi-specific antibodies (see, e.g., Kostelny et al., *J. Immunol.*, 148(5):1547-1553 (1992)); using "diabody" technology for making bispecific antibody fragments (see, e.g., Hollinger et al., *Proc. Natl. Acad. Sci. USA*, 90:6444-6448 (1993)); and using single-chain Fv (sFv) dimers (see, e.g. Gruber et al., *J. Immunol.*, 152:5368 (1994)); and preparing trispecific antibodies as described, e.g., in Tutt et al. *J. Immunol.* 147: 60 (1991).

Engineered antibodies with three or more functional antigen binding sites, including "Octopus antibodies," are also included herein (see, e.g. US 2006/0025576A1).

The antibody or fragment herein also includes a "Dual Acting FAb" or "DAF" comprising an antigen binding site that binds to linear linked polyubiquitin as well as another, different antigen (see, US 2008/0069820, for example).

7. Antibody Variants

In certain embodiments, amino acid sequence variants of the antibodies provided herein are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

a) Substitution, Insertion, and Deletion Variants

In certain embodiments, antibody variants having one or more amino acid substitutions are provided. Sites of interest for substitutional mutagenesis include the HVRs and FRs. Conservative substitutions are shown in Table 1 under the heading of "conservative substitutions." More substantial changes are provided in Table 1 under the heading of "exemplary substitutions," and as further described below in reference to amino acid side chain classes. Amino acid substitutions may be introduced into an antibody of interest and the products screened for a desired activity, e.g., retained/improved antigen binding, decreased immunogenicity, or improved ADCC or CDC.

TABLE 1

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:
  (1) hydrophobic: Norleucine, Met, Ala, Val, Leu, Ile;
  (2) neutral hydrophilic: Cys, Ser, Thr, Asn, Gln;
  (3) acidic: Asp, Glu;
  (4) basic: His, Lys, Arg;
  (5) residues that influence chain orientation: Gly, Pro;
  (6) aromatic: Trp, Tyr, Phe.

Non-conservative substitutions will entail exchanging a member of one of these classes for another class.

One type of substitutional variant involves substituting one or more hypervariable region residues of a parent antibody (e.g. a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g. binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, *Methods Mol. Biol.* 207:179-196 (2008)), and/or SDRs (a-CDRs), with the resulting variant VH or VL being tested for binding affinity. Affinity maturation by constructing and reselecting from secondary libraries has been described, e.g., in Hoogenboom et al. in *Methods in Molecular Biology* 178:1-37 (O'Brien et al., ed., Human Press, Totowa, N.J., (2001).) In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may be outside of HVR "hotspots" or SDRs. In certain embodiments of the variant VH and VL sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham and Wells (1989) *Science,* 244:1081-1085. In this method, a residue or group of target residues (e.g., charged residues such as arg, asp, his, lys, and glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g. for ADEPT) or a polypeptide which increases the serum half-life of the antibody.

b) Glycosylation Variants

In certain embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. *TIBTECH* 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibody variants with certain improved properties.

In one embodiment, antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e.g. complex, hybrid and high mannose structures) as measured by MALDI-TOF mass spectrometry, as described in WO 2008/077546, for example. Asn297 refers to the asparagine residue located at about position 297 in the Fc region (Eu numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. *J. Mol. Biol.* 336:1239-1249 (2004); Yamane-Ohnuki et al. *Biotech. Bioeng.* 87: 614 (2004). Examples of cell lines capable of producing defucosylated antibodies include Lec13 CHO cells deficient in protein fucosylation (Ripka et al. *Arch. Biochem. Biophys.* 249:533-545 (1986); US Pat Appl No US 2003/0157108 A1, Presta, L; and WO 2004/056312 A1, Adams et al., especially at Example 11), and knockout cell lines, such as alpha-1,6-fucosyltransferase gene, FUT8, knockout CHO cells (see, e.g., Yamane-Ohnuki et al. *Biotech. Bioeng.* 87: 614 (2004); Kanda, Y. et al., *Biotechnol. Bioeng.*, 94(4):680-688 (2006); and WO2003/085107).

Antibodies variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878 (Jean-Mairet et al.); U.S. Pat. No. 6,602,684 (Umana et al.); and US 2005/0123546 (Umana et al.). Antibody variants with at least one galactose residue in the oligosaccharide attached to the Fc region are also provided. Such antibody variants may have improved CDC function. Such antibody variants are described, e.g., in WO 1997/30087 (Patel et al.); WO 1998/58964 (Raju, S.); and WO 1999/22764 (Raju, S.).

c) Fc Region Variants

In certain embodiments, one or more amino acid modifications may be introduced into the Fc region of an antibody provided herein, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

In certain embodiments, the invention contemplates an antibody variant that possesses some but not all effector functions, which make it a desirable candidate for applications in which the half life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, *Annu. Rev. Immunol.* 9:457-492 (1991). Non-limiting examples of in vitro assays to assess ADCC activity of a molecule of interest is described in U.S. Pat. No. 5,500,362 (see, e.g. Hellstrom, I. et al. *Proc. Nat'l Acad. Sci. USA* 83:7059-7063 (1986)) and Hellstrom, I et al., *Proc. Nat'l Acad. Sci. USA* 82:1499-1502 (1985); U.S. Pat. No. 5,821,337 (see Bruggemann, M. et al., *J. Exp. Med.* 166:1351-1361 (1987)). Alternatively, non-radioactive assays methods may be employed (see, for example, ACTI™ non-radioactive cytotoxicity assay for flow cytometry (CellTechnology, Inc. Mountain View, Calif.; and CytoTox 96® non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. *Proc. Nat'l Acad. Sci. USA* 95:652-656 (1998). C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al., *J. Immunol. Methods* 202:163 (1996); Cragg, M. S. et al., *Blood* 101:1045-1052 (2003); and Cragg, M. S. and M. J. Glennie, *Blood* 103:2738-2743 (2004)). FcRn binding and in vivo clearance/half life determinations can also be performed using methods known in the art (see, e.g., Petkova, S. B. et al., *Int'l. Immunol.* 18(12):1759-1769 (2006)).

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody variants with improved or diminished binding to FcRs are described. (See, e.g., U.S. Pat. No. 6,737,056; WO 2004/056312, and Shields et al., *J. Biol. Chem.* 9(2): 6591-6604 (2001).)

In certain embodiments, an antibody variant comprises an Fc region with one or more amino acid substitutions which improve ADCC, e.g., substitutions at positions 298, 333, and/or 334 of the Fc region (EU numbering of residues).

In some embodiments, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie et al. *J. Immunol.* 164: 4178-4184 (2000).

Antibodies with increased half lives and improved binding to the neonatal Fc receptor (FcRn), which is responsible for the transfer of maternal IgGs to the fetus (Guyer et al., *J. Immunol.* 117:587 (1976) and Kim et al., *J. Immunol.* 24:249 (1994)), are described in US2005/0014934A1 (Hinton et al.). Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826).

See also Duncan & Winter, *Nature* 322:738-40 (1988); U.S. Pat. No. 5,648,260; U.S. Pat. No. 5,624,821; and WO 94/29351 concerning other examples of Fc region variants.

d) Cysteine Engineered Antibody Variants

In certain embodiments, it may be desirable to create cysteine engineered antibodies, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain embodiments, any one or more of the following residues may be substituted with cysteine: V205 (Kabat numbering) of the light chain; A118 (EU numbering) of the heavy chain; and S400 (EU numbering) of the heavy chain Fc region. Cysteine engineered antibodies may be generated as described, e.g., in U.S. Pat. No. 7,521,541.

e) Antibody Derivatives

In certain embodiments, an antibody provided herein may be further modified to contain additional nonproteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer is attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and nonproteinaceous moiety that may be selectively heated by exposure to radiation are provided. In one embodiment, the nonproteinaceous moiety is a carbon nanotube (Kam et al., *Proc. Natl. Acad. Sci. USA* 102: 11600-11605 (2005)). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

B. Recombinant Methods and Compositions

Antibodies may be produced using recombinant methods and compositions, e.g., as described in U.S. Pat. No. 4,816,567. In one embodiment, isolated nucleic acid encoding an anti-linear linked polyubiquitin antibody described herein is provided. Such nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic, e.g. a Chinese Hamster Ovary (CHO) cell or lymphoid cell (e.g., Y0, NS0, Sp20 cell). In one embodiment, a method of making an anti-linear linked polyubiquitin antibody is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of an anti-linear linked polyubiquitin antibody, nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, *Methods in Molecular Biology*, Vol. 248 (B. K. C. Lo, ed., Humana Press, Totowa, N.J., 2003), pp. 245-254, describing expression of antibody fragments in *E. coli*.) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross, *Nat. Biotech.* 22:1409-1414 (2004), and Li et al., *Nat. Biotech.* 24:210-215 (2006).

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., *J. Gen Virol.* 36:59 (1977)); baby hamster kidney cells (BHK); mouse sertoli cells (TM4 cells as described, e.g., in Mather, *Biol. Reprod.* 23:243-251 (1980)); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al., *Annals N.Y. Acad. Sci.* 383: 44-68 (1982); MRC 5 cells; and FS4 cells. Other useful mammalian host cell lines include Chinese hamster ovary (CHO) cells, including DHFR− CHO cells (Urlaub et al., *Proc. Natl. Acad. Sci. USA* 77:4216 (1980)); and myeloma cell lines such as Y0, NS0 and Sp2/0. For a review of certain mammalian host cell lines suitable for antibody production, see, e.g., Yazaki and Wu, *Methods in Molecular Biology*, Vol. 248 (B. K. C. Lo, ed., Humana Press, Totowa, N.J.), pp. 255-268 (2003).

C. Assays

Anti-linear linked polyubiquitin antibodies provided herein may be identified, screened for, or characterized for their physical/chemical properties and/or biological activities by various assays known in the art.

1. Binding Assays and Other Assays

In one aspect, an antibody of the invention is tested for its antigen binding activity, e.g., by known methods such as ELISA, Western blot, etc.

In another aspect, competition assays may be used to identify an antibody that competes with, e.g., any of Fabs or antibodies described herein such as 1E3, 1D8, 1F4, 1A10, 1D8.3C2, 1D8.3F8, 1D8.4F5, 1F11, 2A2, 2C11, 2H5, 3E4, 4C9, 4E4, 4G7, 3F5, 3A7 and 4C10 or hybrid antibodies as described herein, for example 4E4/T110A, 4C9/T110A, 4G7/Y102G, 1F11/3F5, 1F11/3E4, 1F11/4G7, 2C11/3E4, 2C11/3F5, 2C11/4G7, 2H5/3E4, 2H5/3F5, 2H5/4G7, 1F11/3F5/Y102L for binding to linear linked polyubiquitin. In certain embodiments, such a competing antibody binds to the same epitope (e.g., a linear or a conformational epitope) that is bound by any of Fabs or antibodies described herein such as 1E3, 1D8, 1F4, 1A10, 1D8.3C2, 1D8.3F8, 1D8.4F5, 1F11, 2A2, 2C11, 2H5, 3E4, 4C9, 4E4, 4G7, 3F5, 3A7 and 4C10 or hybrid antibodies as described herein, for example 4E4/T110A, 4C9/T110A, 4G7/Y102G, 1F11/3F5, 1F11/3E4, 1F11/4G7, 2C11/3E4, 2C11/3F5, 2C11/4G7, 2H5/3E4, 2H5/3F5, 2H5/4G7, 1F11/3F5/Y102L for binding to linear linked polyubiquitin. Detailed exemplary methods for mapping an epitope to which an antibody binds are provided in Morris (1996) "Epitope Mapping Protocols," in *Methods in Molecular Biology* vol. 66 (Humana Press, Totowa, N.J.).

In an exemplary competition assay, immobilized linear linked polyubiquitin is incubated in a solution comprising a first labeled antibody that binds to linear linked polyubiquitin (e.g., antibodies 1E3, 1D8, 1F4, 1A10, 1D8.3C2, 1D8.3F8, 1D8.4F5, 1F11, 2A2, 2C11, 2H5, 3E4, 4C9, 4E4, 4G7, 3F5, 3A7 and 4C10 or hybrid antibodies 4E4/T110A, 4C9/T110A, 4G7/Y102G, 1F11/3F5, 1F11/3E4, 1F11/4G7, 2C11/3E4, 2C11/3F5, 2C11/4G7, 2H5/3E4, 2H5/3F5, 2H5/4G7, 1F11/3F5/Y102L for binding to linear linked polyubiquitin and a second unlabeled antibody that is being tested for its ability to compete with the first antibody for binding to linear linked polyubiquitin. The second antibody may be present in a hybridoma supernatant. As a control, immobilized linear linked polyubiquitin is incubated in a solution comprising the first labeled antibody but not the second unlabeled antibody. After incubation under conditions permissive for binding of the first antibody to linear linked polyubiquitin, excess unbound antibody is removed, and the amount of label associated with immobilized linear linked polyubiquitin is measured. If the amount of label associated with immobilized linear linked polyubiquitin is substantially reduced in the test sample relative to the control sample, then that indicates that the second antibody is competing with the first antibody for binding to linear linked polyubiquitin. See Harlow and Lane (1988) *Antibodies: A Laboratory Manual* ch. 14 (Cold Spring Harbor Laboratory, Cold Spring Harbor, N.Y.).

2. Activity Assays

In one aspect, assays are provided for identifying anti-linear linked polyubiquitin antibodies thereof having biological activity. Biological activity may include, e.g., modulating the rate of degradation of linear linked polyubiquitinated proteins in a cell or tissue, and modulating the rate of cell cycle progression of a cell. Antibodies having such biological activity in vivo and/or in vitro are also provided.

In certain embodiments, an antibody of the invention is tested for such biological activity.

D. Immunoconjugates

The invention also provides immunoconjugates comprising an anti-linear linked polyubiquitin antibody herein conjugated to one or more cytotoxic agents, such as chemotherapeutic agents or drugs, growth inhibitory agents, toxins (e.g., protein toxins, enzymatically active toxins of bacterial, fungal, plant, or animal origin, or fragments thereof), or radioactive isotopes.

In one embodiment, an immunoconjugate is an antibody-drug conjugate (ADC) in which an antibody is conjugated to one or more drugs, including but not limited to a maytansinoid (see U.S. Pat. Nos. 5,208,020, 5,416,064 and European Patent EP 0 425 235 B1); an auristatin such as monomethyl-lauristatin drug moieties DE and DF (MMAE and MMAF) (see U.S. Pat. Nos. 5,635,483 and 5,780,588, and 7,498,298); a dolastatin; a calicheamicin or derivative thereof (see U.S. Pat. Nos. 5,712,374, 5,714,586, 5,739,116, 5,767,285, 5,770, 701, 5,770,710, 5,773,001, and 5,877,296; Hinman et al., *Cancer Res.* 53:3336-3342 (1993); and Lode et al., *Cancer Res.* 58:2925-2928 (1998)); an anthracycline such as daunomycin or doxorubicin (see Kratz et al., *Current Med. Chem.* 13:477-523 (2006); Jeffrey et al., *Bioorganic & Med. Chem. Letters* 16:358-362 (2006); Torgov et al., *Bioconj. Chem.* 16:717-721 (2005); Nagy et al., *Proc. Natl. Acad. Sci. USA* 97:829-834 (2000); Dubowchik et al., *Bioorg. & Med. Chem. Letters* 12:1529-1532 (2002); King et al., *J. Med. Chem.* 45:4336-4343 (2002); and U.S. Pat. No. 6,630,579); methotrexate; vindesine; a taxane such as docetaxel, paclitaxel, larotaxel, tesetaxel, and ortataxel; a trichothecene; and CC1065.

In another embodiment, an immunoconjugate comprises an antibody as described herein conjugated to an enzymatically active toxin or fragment thereof, including but not limited to diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, sapaonaria officinalis inhibitor, gelonin, mitogellin, restrictocin, phenomycin, enomycin, and the tricothecenes.

In another embodiment, an immunoconjugate comprises an antibody as described herein conjugated to a radioactive atom to form a radioconjugate. A variety of radioactive isotopes are available for the production of radioconjugates. Examples include $At^{211}$, $I^{131}$, $I^{125}$, $Y^{90}$, $Re^{186}$, $Re^{188}$, $sm^{153}$, $Bi^{212}$, $P^{32}$, $Pb^{212}$ and radioactive isotopes of Lu. When the radioconjugate is used for detection, it may comprise a radioactive atom for scintigraphic studies, for example tc99m or 1123, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese or iron.

Conjugates of an antibody and cytotoxic agent may be made using a variety of bifunctional protein coupling agents such as N-succinimidyl-3-(2-pyridyldithio) propionate (SPDP), succinimidyl-4-(N-maleimidomethyl)cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis(p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., *Science* 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of a cytotoxic drug in the cell. For example, an acid-labile linker, peptidase-sensitive linker, photolabile linker, dimethyl linker or disulfide-containing linker (Chari et al., *Cancer Res.* 52:127-131 (1992); U.S. Pat. No. 5,208,020) may be used.

The immunoconjugates or ADCs herein expressly contemplate, but are not limited to such conjugates prepared with cross-linker reagents including, but not limited to, BMPS, EMCS, GMBS, HBVS, LC-SMCC, MBS, MPBH, SBAP, SIA, STAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinyl-sulfone)benzoate) which are commercially available (e.g., from Pierce Biotechnology, Inc., Rockford, Ill., U.S.A).

E. Methods and Compositions for Diagnostics and Detection

In certain embodiments, any of the anti-linear linked polyubiquitin antibodies provided herein is useful for detecting the presence of linear linked polyubiquitin in a biological sample. The term "detecting" as used herein encompasses quantitative or qualitative detection. In certain embodiments, a biological sample comprises a cell or tissue, such as, but not limited to, a tumor cell, a muscle cell or a nerve cell.

In one embodiment, an anti-linear linked polyubiquitin antibody for use in a method of diagnosis or detection is provided. In a further aspect, a method of detecting the presence of linear linked polyubiquitin in a biological sample is provided. In certain embodiments, the method comprises contacting the biological sample with an anti-linear linked polyubiquitin antibody as described herein under conditions permissive for binding of the anti-linear linked polyubiquitin antibody to a polyubiquitin or polyubiquitinated protein, and detecting whether a complex is formed between the anti-linear linked polyubiquitin antibody and the polyubiquitin or polyubiquitinated protein. Such method may be an in vitro or in vivo method. In one embodiment, an anti-linear linked polyubiquitin antibody is used to select subjects eligible for therapy with an anti-linear linked polyubiquitin antibody, e.g. where linear linked polyubiquitin is a biomarker for selection of patients.

Exemplary disorders that may be diagnosed using an antibody of the invention include cell-cycle-related diseases or disorders, which may be a disease or disorder associated with aberrantly increased cell cycle progression or a disease or disorder associated with aberrantly decreased cell cycle progression. In one aspect, a disease or disorder associated with aberrantly increased cell cycle progression is cancer. In another aspect, a disease or disorder associated with aberrantly decreased cell cycle progression is, e.g., a degenerative muscle disorder or a degenerative nerve disorder.

In certain embodiments, labeled anti-linear linked polyubiquitin antibodies are provided. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}$P, $^{14}$C, $^{125}$I, $^{3}$H, and $^{131}$I, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

F. Pharmaceutical Formulations

Pharmaceutical formulations of an anti-linear linked polyubiquitin antibody as described herein are prepared by mixing such antibody having the desired degree of purity with one or more optional pharmaceutically acceptable carriers (*Remington's Pharmaceutical Sciences* 16th edition, Osol, A. Ed. (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Exemplary pharmaceutically acceptable carriers herein further include interstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases.

Exemplary lyophilized antibody formulations are described in U.S. Pat. No. 6,267,958. Aqueous antibody formulations include those described in U.S. Pat. No. 6,171,586 and WO2006/044908, the latter formulations including a histidine-acetate buffer.

The formulation herein may also contain more than one active ingredients as necessary for the particular indication being treated, preferably those with complementary activities that do not adversely affect each other. For example, it may be desirable to further provide one or more chemotherapeutic agents. Such active ingredients are suitably present in combination in amounts that are effective for the purpose intended.

Active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

Sustained-release preparations may be prepared. Suitable examples of sustained-release preparations include semipermeable matrices of solid hydrophobic polymers containing the antibody, which matrices are in the form of shaped articles, e.g. films, or microcapsules.

The formulations to be used for in vivo administration are generally sterile. Sterility may be readily accomplished, e.g., by filtration through sterile filtration membranes.

G. Therapeutic Methods and Compositions

Any of the anti-linear linked polyubiquitin antibodies provided herein may be used in therapeutic methods.

In one aspect, an anti-linear linked polyubiquitin antibody for use as a medicament is provided. In further aspects, an anti-linear linked polyubiquitin antibody for use in treating disorders associated with aberrant cell cycle regulation (including, but not limited to, proliferation disorders such as cancer and hypotrophy disorders including, but not limited to, degenerative muscle disorders and degenerative nerve disorders) is provided. In certain embodiments, an anti-linear linked polyubiquitin antibody for use in a method of treatment is provided. In certain embodiments, the invention provides an anti-linear linked polyubiquitin antibody for use in a method of treating an individual having a disorder associated with aberrant cell cycle regulation, comprising administering to the individual an effective amount of the anti-linear linked polyubiquitin antibody. In one such embodiment, the method further comprises administering to the individual an effective amount of at least one additional therapeutic agent, e.g., as described below. In further embodiments, the invention provides an anti-linear linked polyubiquitin antibody for use in modulating cell cycle regulation such that the rate of cell cycle progression is adjusted. In certain embodiments, the invention provides an anti-linear linked polyubiquitin antibody for use in a method of modulating the rate of cell cycle progression in an individual comprising administering to the individual an effective of the anti-linear linked polyubiquitin antibody to modulate cell cycle progression and thereby adjust the rate of cell division. An "individual" according to any of the above embodiments is preferably a human.

In a further aspect, the invention provides for the use of an anti-linear linked polyubiquitin antibody in the manufacture or preparation of a medicament. In one embodiment, the medicament is for treatment of disorders associated with aberrant cell cycle regulation (including, but not limited to, proliferation disorders such as cancer and hypotrophy disorders including, but not limited to, degenerative muscle disorders and degenerative nerve disorders). In a further embodiment, the medicament is for use in a method of treating a disorder associated with aberrant cell cycle regulation comprising administering to an individual having such a disorder an effective amount of the medicament. In one such embodiment, the method further comprises administering to the individual an effective amount of at least one additional therapeutic agent, e.g., as described below. In a further embodiment, the medicament is for modulating the rate of cell cycle progression. In a further embodiment, the medicament is for use in a method of modulating the rate of cell cycle progression in an individual comprising administering to the individual an amount effective of the medicament to adjust the rate of cellular division. An "individual" according to any of the above embodiments may be a human.

In a further aspect, the invention provides a method for treating a disorder associated with aberrant cell cycle regulation. In one embodiment, the method comprises administering to an individual having such a disorder associated with aberrant cell cycle regulation an effective amount of an anti-linear linked polyubiquitin antibody. In one such embodiment, the method further comprises administering to the individual an effective amount of at least one additional therapeutic agent, as described below. An "individual" according to any of the above embodiments may be a human.

In a further aspect, the invention provides pharmaceutical formulations comprising any of the anti-linear linked polyubiquitin antibodies provided herein, e.g., for use in any of the above therapeutic methods. In one embodiment, a pharmaceutical formulation comprises any of the anti-linear linked polyubiquitin antibodies provided herein and a pharmaceutically acceptable carrier. In another embodiment, a pharmaceutical formulation comprises any of the anti-linear linked polyubiquitin antibodies provided herein and at least one additional therapeutic agent, e.g., as described below.

Antibodies of the invention can be used either alone or in combination with other agents in a therapy. For instance, an antibody of the invention may be co-administered with at least one additional therapeutic agent. In certain embodiments, an additional therapeutic agent is a chemotherapeutic agent.

A "chemotherapeutic agent" is a chemical compound useful in the treatment of cancer. Examples of chemotherapeutic agents include alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammaII and calicheamicin omegaII (see, e.g., Agnew, Chem. Intl. Ed. Engl., 33: 183-186 (1994)); dynemicin, including dynemicin A; an esperamicin; as well as neocarzinostatin chromophore and related chromoprotein enediyne antiobiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); thiotepa; taxoids, e.g., TAXOL® paclitaxel (Bristol-Myers Squibb Oncology, Princeton, N.J.), ABRAXANE™ Cremophor-free, albumin-engineered nanoparticle formulation of paclitaxel (American Pharmaceutical Partners, Schaumberg, Ill.), and TAXOTERE® doxetaxel (Rhône-Poulenc Rorer, Antony, France); chloranbucil; gemcitabine (GEMZAR®); 6-thioguanine; mercaptopurine; methotrexate; platinum analogs such as cisplatin and carboplatin; vinblastine (VELBAN®); platinum; etoposide (VP-16); ifosfamide; mitoxantrone; vincristine (ONCOVIN®); oxaliplatin; leucovovin; vinorelbine (NAVELBINE®); novantrone; edatrexate; daunomycin; aminopterin; ibandronate; topoisomerase inhibitor RFS 2000; difluoromethylomithine (DMFO); retinoids such as retinoic acid; capecitabine (XELODA®); pharmaceutically acceptable salts, acids or derivatives of any of the above; as well as combinations of two or more of the above such as CHOP, an abbreviation for a combined therapy of cyclophosphamide, doxorubicin, vincristine, and prednisolone, and FOLFOX, an abbreviation for a treatment regimen with oxaliplatin (ELOXATIN™) combined with 5-FU and leucovovin.

Also included in this definition are anti-hormonal agents that act to regulate, reduce, block, or inhibit the effects of hormones that can promote the growth of cancer, and are often in the form of systemic, or whole-body treatment. They may be hormones themselves. Examples include anti-estrogens and selective estrogen receptor modulators (SERMs), including, for example, tamoxifen (including NOLVADEX® tamoxifen), EVISTA® raloxifene, droloxifene, 4-hydroxytamoxifen, trioxifene, keoxifene, LY117018, onapristone, and FARESTON® toremifene; anti-progesterones; estrogen receptor down-regulators (ERDs); agents that function to suppress or shut down the ovaries, for example, leutinizing hormone-releasing hormone (LHRH) agonists such as LUPRON® and ELIGARD® leuprolide acetate, goserelin acetate, buserelin acetate and tripterelin; other anti-androgens such as flutamide, nilutamide and bicalutamide; and aromatase inhibitors that inhibit the enzyme aromatase, which regulates estrogen production in the adrenal glands, such as, for example, 4(5)-imidazoles, aminoglutethimide, MEGASE® megestrol acetate, AROMASIN® exemestane, formestanie, fadrozole, RIVISOR® vorozole, FEMARA® letrozole, and ARIMIDEX® anastrozole. In addition, such definition of chemotherapeutic agents includes bisphosphonates such as clodronate (for example, BONEFOS® or OSTAC®), DIDROCAL® etidronate, NE-58095, ZOMETA® zoledronic acid/zoledronate, FOSAMAX® alendronate, AREDIA® pamidronate, SKELID® tiludronate, or ACTONEL® risedronate; as well as troxacitabine (a 1,3-dioxolane nucleoside cytosine analog); antisense oligonucleotides, particularly those that inhibit expression of genes in signaling pathways implicated in abherant cell proliferation, such as, for example, PKC-alpha, Raf, H-Ras, and epidermal growth factor receptor (EGF-R); vaccines such as THERATOPE® vaccine and gene therapy vaccines, for example, ALLOVECTIN® vaccine, LEUVECTIN® vaccine, and VAXID® vaccine; LURTOTECAN® topoisomerase 1 inhibitor; ABARELIX® rmRH; lapatinib ditosylate (an ErbB-2 and EGFR dual tyrosine kinase small-molecule inhibitor also known as GW572016); and pharmaceutically acceptable salts, acids or derivatives of any of the above.

Such combination therapies noted above encompass combined administration (where two or more therapeutic agents are included in the same or separate formulations), and separate administration, in which case, administration of the antibody of the invention can occur prior to, simultaneously, and/or following, administration of the additional therapeutic agent and/or adjuvant. Antibodies of the invention can also be used in combination with radiation therapy.

An antibody of the invention (and any additional therapeutic agent) can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic. Various dosing schedules including but not limited to single or multiple administrations over various time-points, bolus administration, and pulse infusion are contemplated herein.

Antibodies of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody need not be, but is optionally formulated with one or more agents currently used to prevent or treat the disorder in question. The effective amount of such other agents depends on the amount of antibody present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

The location of the binding target of an antibody of the invention may be taken into consideration in preparation and administration of the antibody. When the binding target is an intracellular molecule, certain embodiments of the invention provide for the antibody or antigen-binding fragment thereof to be introduced into the cell where the binding target is located. In one embodiment, an antibody of the invention can be expressed intracellularly as an intrabody. The term "intrabody," as used herein, refers to an antibody or antigen-binding portion thereof that is expressed intracellularly and that is capable of selectively binding to a target molecule, as described in Marasco, Gene Therapy 4: 11-15 (1997); Kontermann, Methods 34: 163-170 (2004); U.S. Pat. Nos. 6,004,940 and 6,329,173; U.S. Patent Application Publication No. 2003/0104402, and PCT Publication No. WO2003/077945.

Intracellular expression of an intrabody is effected by introducing a nucleic acid encoding the desired antibody or antigen-binding portion thereof (lacking the wild-type leader sequence and secretory signals normally associated with the gene encoding that antibody of antigen-binding fragment) into a target cell. Any standard method of introducing nucleic acids into a cell may be used, including, but not limited to, microinjection, ballistic injection, electroporation, calcium phosphate precipitation, liposomes, and transfection with retroviral, adenoviral, adeno-associated viral and vaccinia vectors carrying the nucleic acid of interest. One or more nucleic acids encoding all or a portion of an anti-polyubiquitin antibody of the invention can be delivered to a target cell, such that one or more intrabodies are expressed which are capable of intracellular binding to a polyubiquitin and modulation of one or more polyubiquitin-mediated cellular pathways.

In another embodiment, internalizing antibodies are provided. Antibodies can possess certain characteristics that enhance delivery of antibodies into cells, or can be modified to possess such characteristics. Techniques for achieving this are known in the art. For example, cationization of an antibody is known to facilitate its uptake into cells (see, e.g., U.S. Pat. No. 6,703,019). Lipofections or liposomes can also be used to deliver the antibody into cells. Where antibody fragments are used, the smallest inhibitory fragment that specifically binds to the binding domain of the target protein is generally advantageous. For example, based upon the variable-region sequences of an antibody, peptide molecules can be designed that retain the ability to bind the target protein sequence. Such peptides can be synthesized chemically and/or produced by recombinant DNA technology. See, e.g., Marasco et al., Proc. Natl. Acad. Sci. USA 90: 7889-7893 (1993).

Entry of modulator polypeptides into target cells can be enhanced by methods known in the art. For example, certain sequences, such as those derived from HIV Tat or the Antennapedia homeodomain protein are able to direct efficient uptake of heterologous proteins across cell membranes. See, e.g., Chen et al., Proc. Natl. Acad. Sci. USA 96: 4325-4329 (1999).

When the binding target is located in the brain, certain embodiments of the invention provide for the antibody or antigen-binding fragment thereof to traverse the blood-brain barrier. Certain neurodegenerative diseases are associated with an increase in permeability of the blood-brain barrier, such that the antibody or antigen-binding fragment can be readily introduced to the brain. When the blood-brain barrier remains intact, several art-known approaches exist for transporting molecules across it, including, but not limited to, physical methods, lipid-based methods, and receptor and channel-based methods.

Physical methods of transporting the antibody or antigen-binding fragment across the blood-brain barrier include, but are not limited to, circumventing the blood-brain barrier entirely, or by creating openings in the blood-brain barrier. Circumvention methods include, but are not limited to, direct injection into the brain (see, e.g., Papanastassiou et al., Gene Therapy 9: 398-406 (2002); interstitial infusion/convection-enhanced delivery (see, e.g., Bobo et al., Proc. Natl. Acad. Sci. USA 91: 2076-2080 (1994)), and implanting a delivery device in the brain (see, e.g., Gill et al., Nature Med. 9: 589-595 (2003); and Gliadel Wafers™, Guildford Pharmaceutical). Methods of creating openings in the barrier include, but are not limited to, ultrasound (see, e.g., U.S. Patent Publication No. 2002/0038086), osmotic pressure (e.g., by administration of hypertonic mannitol (Neuwelt, E. A., Implication of the Blood-Brain Barrier and its Manipulation, vols. 1 & 2, Plenum Press, N.Y. (1989))), permeabilization by, e.g., bradykinin or permeabilizer A-7 (see, e.g., U.S. Pat. Nos. 5,112,596, 5,268,164, 5,506,206, and 5,686,416), and transfection of neurons that straddle the blood-brain barrier with vectors containing genes encoding the antibody or antigen-binding fragment (see, e.g., U.S. Patent Publication No. 2003/0083299).

Lipid-based methods of transporting the antibody or antigen-binding fragment across the blood-brain barrier include, but are not limited to, encapsulating the antibody or antigen-binding fragment in liposomes that are coupled to antibody binding fragments that bind to receptors on the vascular endothelium of the blood-brain barrier (see, e.g., U.S. Patent Application Publication No. 20020025313), and coating the antibody or antigen-binding fragment in low-density lipoprotein particles (see, e.g., U.S. Patent Application Publication No. 20040204354) or apolipoprotein E (see, e.g., U.S. Patent Application Publication No. 20040131692).

Receptor and channel-based methods of transporting the antibody or antigen-binding fragment across the blood-brain barrier include, but are not limited to, using glucocorticoid blockers to increase permeability of the blood-brain barrier (see, e.g., U.S. Patent Application Publication Nos. 2002/0065259, 2003/0162695, and 2005/0124533); activating potassium channels (see, e.g., U.S. Patent Application Publication No. 2005/0089473); inhibiting ABC drug transporters (see, e.g., U.S. Patent Application Publication No. 2003/0073713); coating antibodies with a transferrin and modulating activity of the one or more transferrin receptors (see, e.g., U.S. Patent Application Publication No. 2003/0129186), and cationizing the antibodies (see, e.g., U.S. Pat. No. 5,004,697).

For the prevention or treatment of disease, the appropriate dosage of an antibody of the invention (when used alone or in combination with one or more other additional therapeutic agents) will depend on the type of disease to be treated, the type of antibody, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments. Depending on the type and severity of the disease, about 1 µg/kg to 15 mg/kg (e.g. 0.1 mg/kg-10 mg/kg) of antibody can be an initial candidate dosage for administration to the patient, whether, for example, by one or more separate administrations, or by continuous infusion. One typical daily dosage might range from about 1 µg/kg to 100 mg/kg or more, depending on the factors mentioned above. For repeated administrations over several days or longer, depending on the condition, the treatment would generally be sustained until a desired suppression of disease symptoms occurs. One exemplary dosage of the antibody would be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g. every week or every three weeks (e.g. such that the patient receives from about two to about twenty, or e.g. about six doses of the antibody). An initial higher loading dose, followed by one or more lower doses may be administered. However, other dosage regimens may be useful. The progress of this therapy is easily monitored by conventional techniques and assays.

It is understood that any of the above formulations or therapeutic methods may be carried out using an immunoconjugate of the invention in place of or in addition to an anti-linear linked polyubiquitin antibody.

H. Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is an antibody of the invention. The label or package insert indicates that the composition is used for treating the condition of choice. Moreover, the article of manufacture may comprise (a) a first container with a composition contained therein, wherein the composition comprises an antibody of the invention; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

It is understood that any of the above articles of manufacture may include an immunoconjugate of the invention in place of or in addition to an anti-linear linked polyubiquitin antibody.

III. Examples

The following are examples of methods and compositions of the invention. It is understood that various other embodiments may be practiced, given the general description provided above.

Example 1

Isolation and Characterization of Anti-Linear Polyubiquitin Antibodies

A) Antigen Generation

The antigen used for sorting the phage display libraries was linear diubiquitin (Boston Biochem). Linear diubiquitin is a head to tail fusion of two ubiquitins through a peptide bond between the carboxy terminus of the first ubiquitin and the amino terminus of the second ubiquitin.

B) Naïve Library Sorting

The naïve YSGX Fab phage display library was subjected to four rounds of sorting against linear diubiquitin. No enrichment was observed after four rounds of sorting (see Table 2). The YSGX Fab phage display library contains randomized amino acids in all three heavy chain CDRs and light chain CDR L3 (see U.S. Published Patent Application No. 2005-0106667 and Fellouse F. et al. *JMB* 373:924-40 (2007)), and is based on a humanized antibody 4D5.

The naïve common light chain YSGX Fab phage display library was subjected to four rounds of sorting against linear diubiquitin. Twenty-five-fold enrichment was observed after four rounds of sorting (see Table 2). The common light chain YSGX Fab phage display library contains randomized amino acids in all three heavy chain CDRs as described for the YSGX library (see U.S. Published Patent Application No. 2005-0106667 and Fellouse F. et al. *JMB* 373:924-40 (2007)), however the light chain sequence is fixed as a modified version of humanized antibody 4D5.

The naïve VH Fab phage display library was subjected to four rounds of sorting against linear diubiquitin. Eight hundred-fold enrichment was observed after four rounds of sorting (see Table 1). The VH Fab phage display library contains randomized amino acids in all three heavy chain CDRs (see U.S. Published Patent Application No. 2005/0119455 and Lee C. W. et al. *JMB* 340:1073-93 (2004)), and is based on a humanized antibody 4D5.

Linear diubiquitin (Boston Biochem) was immobilized on a 96-well Maxisorb immunoplate (NUNC). Plates were coated overnight at 4° C. with 5 μg/mL linear diubiquitin in 50 mM sodium carbonate buffer, pH 9.6. The coated plates were blocked with 200 μL/well of 2.5% milk in phosphate buffered saline (PBS) containing 0.05% Tween 20 (PBST) for one hour at 25° C. with shaking. The naïve phage libraries were precipitated from glycerol stocks with ⅕ volume of 20% polyethylene glycol (PEG)/2.5M NaCl, resuspended in 2.5% milk/PBST, and incubated at 25° C. for one hour while the plate was blocking. After one hour, the blocking buffer was dumped off of the plate and 100 μL/well of phage in 2.5% milk/PBST was added and incubated at 25° C. for four hours with shaking. After binding, the plate was washed ten times with PBST by manually filling the wells and dumping off the buffer between washes. Phage were eluted with 150 μL/well of 50 mM HCl/500 mM KCl for 30 minutes at 25° C. with shaking. The elution was neutralized with 150 μL/well of 1 M Tris, pH 7.5 and subsequently propagated in XL1-Blue (Agilent) *Escherichia coli* (*E. coli*) with the addition of M13K07 helper phage.

Amplified phage were used for additional rounds of selection against linear diubiquitin as described above. In rounds two through four, soluble ubiquitin of different forms were added to the phage for counterselection. In the second round, 10 μg/mL of soluble monoubiquitin (Boston Biochem) was used. In the third and fourth rounds, 10 μg/mL each of soluble monoubiquitin (Boston Biochem), K11-linked diubiquitin (Genentech), K48-linked polyubiquitin 2-7 (Boston Biochem), and K63-linked polyubiquitin 2-7 chains (Boston Biochem) were used. Enrichment was calculated for rounds two through four by comparing the number of phage recovered with linear diubiquitin compared to an uncoated well. Enrichment was observed in rounds two through four for the common light chain library and the VH library, but not the YSGX library (see Table 2).

TABLE 2

| Library | Round 2 | Round 3 | Round 4 |
|---|---|---|---|
| Common light chain YSGX | 2X | 2X | 25X |
| YSGX | 0X | 0X | 0X |
| VH | 3X | 120X | 800X |

Ninety-six individual clones from the second round of sorting of the VH library, 192 clones from the third round of sorting of the VH library, 96 clones from the fourth round of sorting of the VH library, and 192 clones from the fourth round of sorting of the common light chain library were screened. Since no enrichment was seen for the YSGX library, no clones were screened from this library. Individual clones were grown up in a 96-well format in 1 mL of 2YT broth containing 50 μg/mL carbenicillin and 1×10$^{10}$ phage/mL M13K07 helper phage at 37° C. overnight with shaking. Cells were pelleted by spinning at 3000 rpm for ten minutes. Supernatants from those cultures were used in high-throughput phage spot enzyme linked immunosorbant assays (ELISAs) for binding to linear diubiquitin (Boston Biochem), monoubiquitin (Boston Biochem), K11-linked diubiquitin (Genentech), K48-linked polyubiquitin 2-7 (Boston Biochem), K63-linked polyubiquitin 2-7 (Boston Biochem), an anti-gD antibody (Genentech), or an uncoated well. All of the Fab libraries contain a carboxy-terminal gD tag on the light chain which allows for assessment of display level by anti-gD antibody binding. The panel of ubiquitin proteins was immobilized on 384-well Maxisorb immunoplates (NUNC). Plates were coated at 4° C. overnight with 2 μg/mL of each protein in 50 mM sodium carbonate buffer, pH 9.6. The coated plates were blocked with 60 μL/well of 2.5% milk in PBST for one hour at 25° C. with shaking. After one hour, the blocking buffer was dumped off of the plate and 20 μL/well of PBST and 10 μL/well of phage supernatant were added. Plates were incubated at 25° C. for one hour with shaking. The plate was then washed six times with PBST by manually filling the wells and dumping off the wash buffer. A 1:5,000 dilution of an anti-M13 horseradish peroxidase (HRP)-conjugated secondary antibody (GE Healthcare) in PBST was used for detection of phage binding. 30 μL/well of the secondary dilution was added and the plate was incubated at 25° C. for 30 minutes with shaking. The plate was then washed six times with PBST and twice with PBS, both manually. Bound secondary antibody was detected using a TMB substrate (KPL) followed by quenching with an equal volume of 1 M phosphoric acid. The absorbance was read at 450 nm.

From the common light chain library, several weak linear diubiquitin-specific binders were identified (see FIG. 1). The light and heavy chain variable domains of these clones were sequenced. Two unique sequences (1F4 (SEQ ID NOs:27 and 31) and 1A10 (SEQ ID NOs:28 and 31)) were identified, however, based on the light chain sequence it was determined that one of these clones (1F4) was actually from the YSGX library that does not contain a fixed light chain (see FIG. 2A). From the VH library several clones showing strong linear diubiquitin binding with weaker binding to K63-linked polyubiquitin were identified (see FIG. 1). The heavy chain variable domains of these VH library clones were sequenced. The CDR H1, CDR H2, and CDR H3 sequences are expected to be clone-specific, whereas, the heavy chain framework sequences should be identical, based on the VH library design. The entire light chain sequence (both framework and CDRs) is expected to be invariant due to the library design. The CDR L1 sequence is RASQDVSTAVA (SEQ ID NO:1), the CDR L2 sequence is SASFLYS (SEQ ID NO:2), and the CDR L3 sequence is QQSYTTPPT (SEQ ID NO:3). Two unique heavy chain sequences were identified (1D8 (SEQ ID NO:30) and 1E3 (SEQ ID NO:29)) (see FIG. 2B).

C) Conversion of the Phagemids to Monovalent Fab Display

The 1D8 and 1E3 phagemid clones from the VH library were converted from bivalent Fab-zip format to monovalent Fab display for affinity maturation purposes. The leucine zipper between the end of the CH1 constant domain and the start of gene III (gpIII) was removed using Kunkel mutagenesis (see Kunkel, *Proc. Natl. Acad. Sci. USA* 82:488 (1985)). Mutagenic oligonucleotide F220-delzip (TCTTGTGA-CAAAACTCACAGTGGCGGTGGCTCTGGT) (SEQ ID NO:100) was combined with 1 μg of 1D8 or 1E3 phagemid Kunkel DNA.

The 1A10 and 1F4 clones from the common light chain library and the YSGX library, respectively, were converted from bivalent Fab-C format to monovalent Fab display for affinity maturation purposes. The cysteine between the end of the CH1 constant domain and gpIII was removed using Kunkel mutagenesis. Mutagenic oligonucleotide F1120-delCGRP (TGTGACAAAACTCACCTCAGTGGCGGTG-GCTCTGGTTCCGGTGATTTTGATTATGAAAAG) (SEQ ID NO:101) was combined with 1 μg of 1A10 or 1F4 phagemid Kunkel DNA. The resulting monovalent Fab phagemids were used to produce phage for IC$_{50}$ ELISAs.

D) Phage IC$_{50}$ ELISAs

Figure 3:
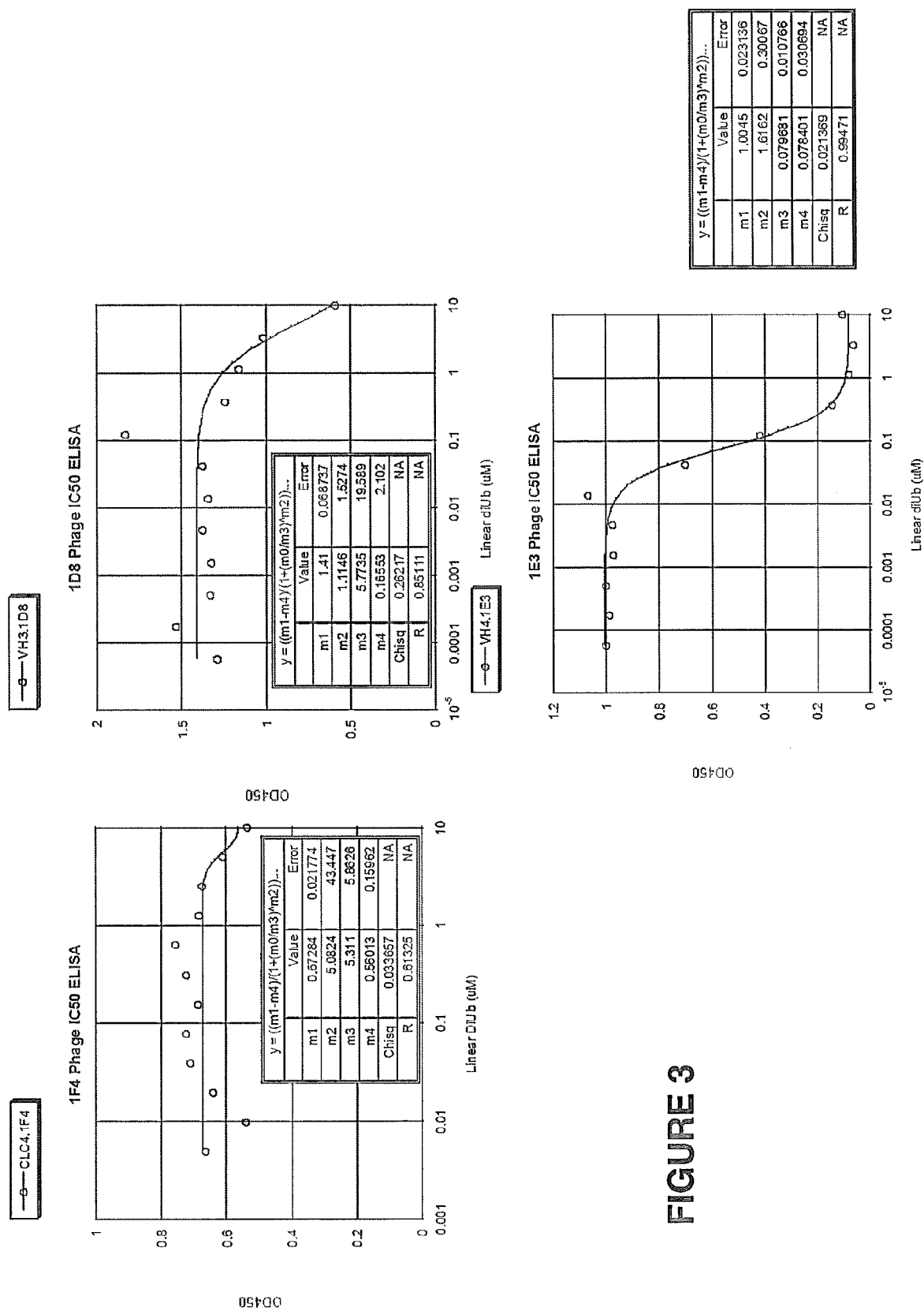
FIG. 3 depicts the results of a phage IC$_{50}$ competition ELISA to measure the affinity of the purified 1F4, 1D8 and 1E3 Fabs for linear diubiquitin.

Phage displaying monovalent Fab for 1D8, 1E3, 1A10, and 1F4 were tested in an IC$_{50}$ ELISA to get an estimate of relative affinity for linear diubiquitin. An initial titer ELISA was done to determine the amount of phage at which a signal of OD$_{450}$=0.5 would be achieved. Linear diubiquitin (Boston Biochem) was immobilized on 96-well Maxisorb immunoplates (NUNC). Linear diubiquitin was coated overnight at 4° C. at 1 μg/mL in 50 mM sodium carbonate buffer, pH 9.6. The coated plates were blocked with 200 μL/well of 2.5% milk in PBST for one hour at 25° C. with shaking. Twelve two-fold serial dilutions of the phage were made in 2.5% milk in PBST from OD$_{268}$=4.0 to OD$_{268}$=0.002. After one hour, the blocking buffer was dumped off of the plate and 100 μL/well of each phage dilution was added and incubated at 25° C. for 15 minutes with shaking. The plate was then washed six times with PBST using a plate washer. A 1:5000 dilution of an anti-M13 phage-HRP-conjugated secondary antibody (GE Healthcare) in PBST was used for detection of phage binding. 100 μL/well of the secondary dilution was added and the plate was incubated at 25° C. for 30 minutes with shaking. The plate was then washed 12 times with PBST using a plate washer and twice with PBS manually. Bound secondary antibody was detected using a TMB substrate (KPL) followed by quenching with an equal volume of 1 M phosphoric acid. The absorbance was read at 450 nm. The concentration of phage at which an OD$_{450}$=0.5 was OD$_{268}$=1.0 of phage for clone 1F4, an OD$_{268}$=0.125 for clone 1D8, and an OD$_{268}$=0.5 for clone 1E3. For clone 1A10, even at phage OD$_{268}$=4.0 the OD$_{450}$ was only 0.376. This binding is quite weak and therefore clone 1A10 was not pursued further. Two-fold serial dilutions of soluble linear diubiquitin from 10 μM to 5 nM for clone 1F4 and three-fold serial dilutions of soluble linear diubiquitin from 10 μM to 56 μM for clones 1D8 and 1E3 plus the selected phage concentrations in 2.5% milk in PBST were incubated at 25° C. for one hour with shaking. The amount of unbound phage at each linear diubiquitin concentration was then measured by incubating the mixtures with a 96-well Maxisorb immunoplate that had been coated with 1 μg/mL linear diubiquitin and blocked with 2.5% milk in PBST. The phage/linear diubiquitin mixture was incubated on the plate for 15 minutes at 25° C. with shaking. The plate was then washed six times with PBST using a plate washer. A 1:5000 dilution of an anti-M13 phage-HRP-conjugated secondary antibody (GE Healthcare) in PBST was used for detection of phage binding. 100 μL/well of the secondary dilution was added and the plate was incubated at 25° C. for 30 minutes with shaking. The plate was then washed 12 times with PBST using a plate washer and twice with PBS manually. Bound secondary antibody was detected using a TMB substrate (KPL) followed by quenching with an equal volume of 1 M phosphoric acid. The absorbance was read at 450 nm. The absorbance was plotted against soluble linear diubiquitin concentration and shows that for 1F4 the $IC_{50}$ is greater than 10 μM (see FIG. 3), for 1D8 the $IC_{50}$ is near 5 μM (see FIG. 3), and for 1E3 the $IC_{50}$ is 80 nM (see FIG. 3).

E) Fab Production

Clones derived from the Fab phage display libraries are expressed under the control of the *E. coli* alkaline phosphatase (PhoA) promoter. Both the light chain and the heavy chain contain an amino-terminal bacterial stII signal sequence to allow secretion in *E. coli* and are expressed from a single phagemid vector. The heavy chain carboxyl terminus is fused in-frame to the C-terminus of gene product III (gpIII) of the M13 bacteriophage, allowing for display of a monovalent Fab fragment on phage. In order to express soluble Fab, a stop codon was introduced into the 1D8 and 1E3 monovalent phagemids between the end of the CH1 constant domain of the Fab and the start of gpIII. Mutagenic oligonucleotides:
5'-FabdelzipTAA (CCCAAATCTTGTGACAAAACTCA-CACATAAAGTGGCGGTGG CTCTGGTTCCGGTG) (SEQ ID NO:102) and
3'-FabdelzipTAA (CACCGGAACCAGAGCCACCGC-CACTTTATGTGTGAGTT TTGTCACAAGATTTGGG) (SEQ ID NO:103) were used to insert the stop codon using the QuikChange® Lightning Site-Directed Mutagenesis kit (Agilent). The resulting soluble Fab expression plasmids were transformed into the *E. coli* strain 62A7 (Genentech) and plated on solid agar containing carbenicillin. Single colonies were used to inoculate 25 mL of 2YT broth containing 50 μg/mL carbenicillin. The culture was grown overnight at 37° C. and 5 mL were used to inoculate 500 mL of complete C.R.A.P. media (3.57 g (NH4)2SO4, 0.71 g sodium citrate 2H2O, 1.07 g KCl, 5.36 g yeast extract (certified), 5.36 g Hycase SF (Sheffield), pH adjusted to 7.3 by addition of KOH and volume adjusted to 872 mL with ultrapure water, autoclaved, cooled to 55° C., to which was added (per L) 110 mL 1M MOPS pH 7.3, 11 mL 50% glucose, and 7 mL 1M MgSO4) with 50 μg/mL carbenicillin. The cultures were grown at 30° C. for 24 hours with shaking. Cells were harvested by centrifugation and pellets were stored at −20° C. The Fab was purified by resuspending the cell pellet in 35 mL of cold wash buffer (Phosphate Buffered Saline (PBS)+150 mM NaCl) containing 10 μg/mL DNaseI (Invitrogen), 0.2 mg/mL lysozyme (USB), and 1 mM phenylmethylsulphonylfluoride (PMSF) (Calbiochem). The pellet was resuspended by vortexing rapidly. To allow complete lysis the cells were incubated for 15 minutes at 25° C. Cell debris was pelleted by centrifugation and lysate was loaded on 1 mL protein A-sepharose (GE Healthcare) column preequilibrated with cold wash buffer. The column was washed with 50 mL of cold wash buffer, eluted with 3 mL of 0.1 M acetic acid, and neutralized with 150 μL of 1 M Tris, pH 11.0. The Fab was concentrated using Amicon Ultra-15 centrifugal filter units (10 kDa cut-off, Millipore). The resulting Fab concentration was determined spectrophotometrically (1 $OD_{280}$=1.5 mg/mL).

F) Fab Western Blot

Figure 4:
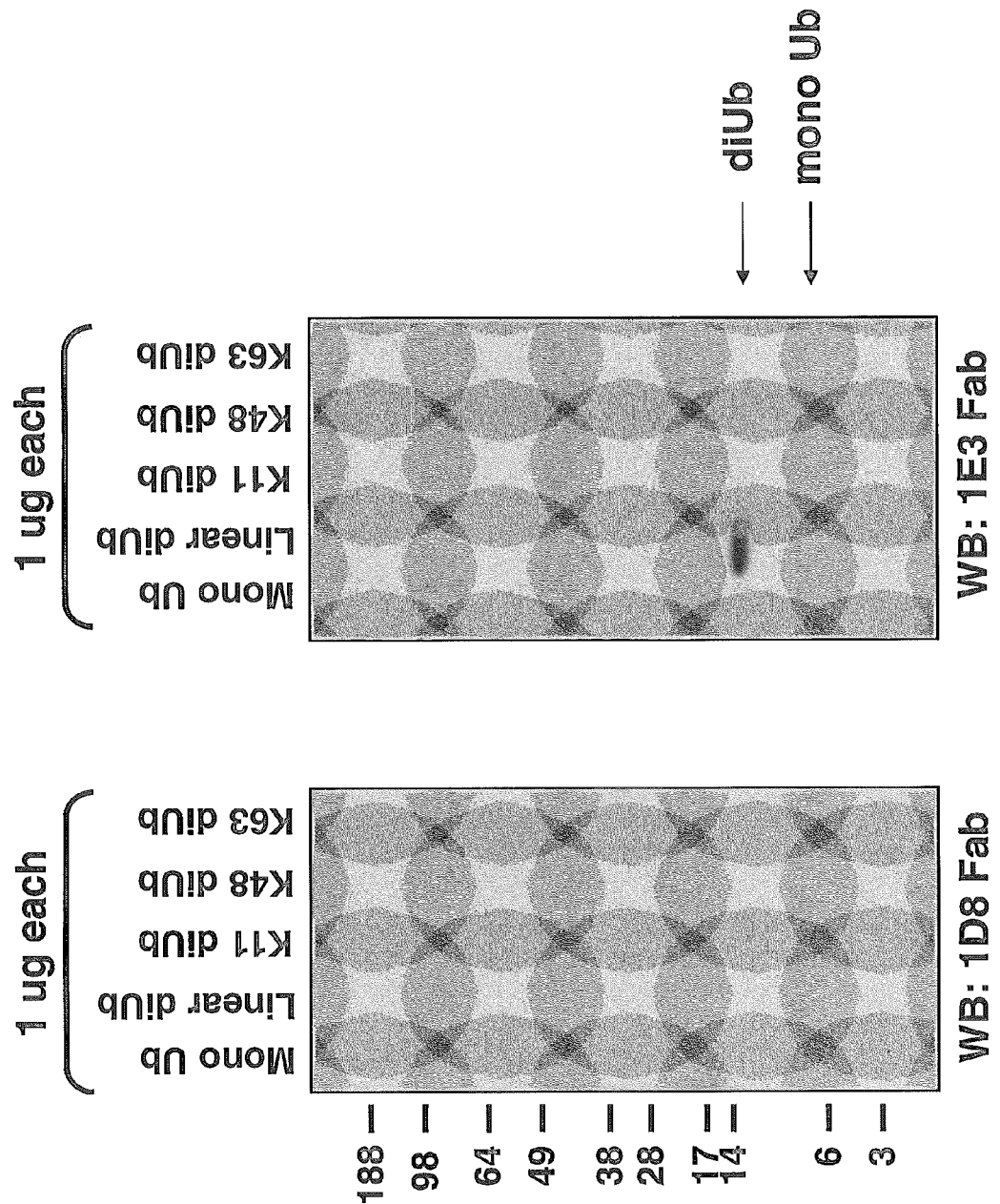
FIG. 4 shows the results of a western blot analysis to determine the ability of the 1D8 and 1E3 Fabs to specifically recognize a panel of diubiquitin proteins in an immobilized context.

The 1D8 and 1E3 Fabs (from Example 1E) were tested for binding to linear diubiquitin (Boston Biochem), monoubiquitin (Boston Biochem), K1'-linked diubiquitin (Genentech), K48-linked diubiquitin (Boston Biochem), and K63-linked diubiquitin (Boston Biochem) in a western blot. 1 μg of each protein in 1×LDS buffer (Invitrogen) with reducing agent was heated at 70° C. for ten minutes and run on 4-12% NuPAGE Bis Tris 1.0 mm gels in MES buffer (Invitrogen) in duplicate. Gels were transferred at 30 V constant for 1.5 hours by wet transfer in 10% methanol and 1× NuPAGE transfer buffer (Invitrogen) to 0.2 μm nitrocellulose (Invitrogen). Non-specific binding sites on the membranes were blocked by incubation in 5% milk in PBST for 1.5 hours at 25° C. with shaking. The membranes were then incubated in 5 μg/mL of 1D8 or 1E3 Fab in 5% milk in PBST for one hour at 25° C. with shaking. The membrane was washed three times in PBST with shaking. The Fabs were detected by incubating the membrane in a 1:10000 dilution of a goat anti-human Fab fragment-specific HRP-conjugated secondary antibody (Sigma Aldrich) in 5% milk in PBST for one hour at 25° C. with shaking. The membranes were then washed three times in PBST followed by one wash in PBS. The secondary antibody was detected using Super Signal West Pico chemiluminescent substrate (Thermo Scientific) followed by exposure of the blots to film. The 1E3 Fab detects only the linear diubiquitin but not monoubiquitin, K11-linked diubiquitin, K48-linked diubiquitin, or K63-linked diubiquitin (see FIG. 4). The 1D8 Fab did not detect any forms of ubiquitin by western blot (see FIG. 4).

G) Affinity Analysis of Isolated 1D8 and 1E3 Fabs

The affinity of the 1D8 and 1E3 Fabs (from Example 1E) was analyzed by surface plasmon resonance (SPR) using a BIACORE™ 3000 (GE Healthcare). Approximately 120 resonance units (RUs) of linear diubiquitin (Boston Biochem), K48-linked diubiquitin (Boston Biochem), and K63-linked diubiquitin (Boston Biochem) were immobilized on flow cell two, flow cell three, and flow cell four, respectively, of a CM5 chip using the amine coupling protocol supplied by the manufacturer. Flow cell one was activated and ethanolamine blocked without immobilizing protein, to be used for reference subtraction. Two-fold serial dilutions (0.5-500 nM) of 1E3 Fab in 10 mM Hepes, pH 7.2, 150 mM NaCl, and 0.01% Tween 20 (HBST) were injected (60 μL total at a flow rate of 30 μL/minute) over each flow cell using HBST as the running buffer. The signal for each flow cell was recorded and the reference signal was subtracted. Different regeneration conditions were scouted. Even with 10 mM HCl the chip surface could not be completely regenerated back to baseline. When 10 mM glycine, pH 1.7 was tested this altered the chip surface and decreased the binding capacity.

An alternative approach was tested using a Fab capture method on a BIACORE™ 3000 (GE Healthcare). Approximately 11,000 resonance units (RUs) of an anti-human Fab capture antibody (GE Healthcare) were immobilized on flow cells one and two of a CM5 chip using the amine coupling protocol supplied by the manufacturer. 10 μL of 10 μg/mL Fab in 10 mM Hepes, pH 7.2, 150 mM NaCl, and 0.01% Tween 20 (HBST) was injected at a flow rate of 10 μL/minute over flow cell two, resulting in capture of approximately 430 RUs of Fab. Flow cell one had only the capture antibody on it to serve as a reference subtraction. Two-fold serial dilutions (1-1000 nM) of linear diubiquitin (Boston Biochem) or K63-linked diubiquitin (Boston Biochem) in HBST were injected (60 μL total at a flow rate of 30 μL/minute) over flow cells one and two. The signal for each flow cell was recorded and the reference signal was subtracted. Following a dissociation period of four minutes, the chip surface was regenerated with two injections of 30 μL of 10 mM glycine, pH 2.1 at a flow rate of 30 μL/minute. Data were difficult to fit to any binding model because the diubiquitin did not fully dissociate from the chip. In addition the association rates were very fast and binding did not reach a plateau even at the highest concentration of diubiquitin used. Therefore it is difficult to estimate a $K_D$ for these Fabs.

Example 2

Affinity Maturation of 1F4, 1D8, and 1E3

A) Stop Template Generation

A TAA stop codon was inserted separately into either CDR L1, CDR L2, CDR L3, CDR H3, or both CDRs L3 and H3 (resulting in L1, L2, L3, H3, and L3/H3 stop templates, respectively) for library synthesis using Kunkel mutagenesis. Stop codons force diversity within a particular CDR loop by requiring repair of the stop in order to get full length Fab expression and display on phage. The stop codon mutagenic oligonucleotides listed below were combined with 1 μg of the corresponding monovalent phagemid Kunkel DNA. The resulting monovalent Fab phagemid stop templates were used for affinity maturation library generation.

For clones 1D8 and 1E3 the CDR L1 stop mutagenic oligonucleotide used to insert a TAA stop codon at position 24 (Kabat numbering) within CDR L1 of the light chain was 4D5LC1.stop (GTCACCATCACCTGCTAAGCCAGT-CAGGATGTG) (SEQ ID NO:104). For clones 1D8 and 1E3 the CDR L2 stop mutagenic oligonucleotide used to insert a TAA stop codon at position 50 (Kabat numbering) within CDR L2 of the light chain was 4D5LC2.stop (GAAGCTTCT-GATTTACTAAGCATCCTTCCTCTAC) (SEQ ID NO:105). For clones 1D8 and 1E3 the CDR L3 stop mutagenic oligonucleotide used to insert a TAA stop codon at position 89 (Kabat numbering) within CDR L3 of the light chain was 4D5LC3.stop (GCAACTTATTACTGTTAACAATCT-TATACTACTC) (SEQ ID NO:106). The CDR H3 stop mutagenic oligonucleotide used to insert a TAA stop codon at position 95 (Kabat numbering) within CDR H3 of the heavy chain of clone 1D8 was VH3.1D8.H3stop (GCCGTCTAT-TATTGTGCTCGTTAAGCCGGGTCCCGCT-TGTTGTCG) (SEQ ID NO:107). The CDR H3 stop mutagenic oligonucleotide used to insert a TAA stop codon at position 98 (Kabat numbering) within CDR H3 of the heavy chain of clone 1E3 was 413Vh5SRo6 (GAGGACACTGC-CGTCTATTATTGTGCTCGTGAGGCCTCG-TAACTGCCCCCCTACGTTA TGGACTACTGGGGT-CAAGGAACACTAGTC) (SEQ ID NO:108).

For clone 1F4 the CDR L1 stop mutagenic oligonucleotide used to insert a TAA stop codon at position 27 (Kabat numbering) within CDR L1 of the light chain was CLC.L1stop (CATCACCTGCCGTGCCAGTTAATCCGT-GTCCAGCGCTGTAG) (SEQ ID NO:109). For clone 1F4 the CDR L2 stop mutagenic oligonucleotide used to insert a TAA stop codon at position 52 (Kabat numbering) within CDR L2 of the light chain was CLC.L2stop (CTTCTGATT-TACTCGGCATAAAGCCTCTACTCTGGAGTC) (SEQ ID NO:110). For clone 1F4 the CDR L3 stop mutagenic oligonucleotide used to insert a TAA stop codon at position 90 (Kabat numbering) within CDR L3 of the light chain was CLC4.1F4.L3stop (GCAACTTATTACTGTCAGTAATAT-TATTATTATTCTCCG) (SEQ ID NO:111). The CDR H3 stop mutagenic oligonucleotide used to insert a TAA stop codon at position 94 (Kabat numbering) within CDR H3 of the heavy chain of clone 1F4 was CLC4.1F4.H3stop (GC-CGTCTATTATTGTGCTTAAGGT-TACGTTTGGAAAGGTG) (SEQ ID NO:112).

B) Affinity Maturation Library Generation

A total of ten affinity maturation libraries were generated for each clone (1F4, 1D8, and 1E3). All libraries were generated by Kunkel mutagenesis (see Kunkel, *Proc. Natl. Acad. Sci. USA* 82:488 (1985)). In the case of soft randomization, degenerate oligonucleotides were synthesized such that the wild-type residue would be retained 50% of the time and 50% of the time one of the remaining 19 amino acids would be encoded. To achieve soft randomization, oligonucleotides were designed such that certain nucleotide positions were occupied 70% of the time with the indicated base and 10% of the time occupied by one of the three other bases (Gallop et al., *J. Med. Chem.* 37:1233 (1994)). For those oligonucleotides that follow where such soft randomization was included at a particular base, the presence of soft randomization is indicated by the presence of a number at that base position. The number "5" indicates that the base adenine is present 70% of the time at that position, while the bases guanine, cytosine, and thymine are each present 10% of the time. Similarly, the number "6" refers to guanine, "7" to cytosine, and "8" to thymine, where in each case, each of the other three bases is present only 10% of the time. In the case of hard randomization, degenerate oligonucleotides were synthesized such that amino acid diversity found at certain positions within natural human antibodies would be allowed. In this case degenerate codons were used where the letter "R" encodes for guanine or adenine, "Y" encodes for thymine or cytosine, "M" encodes for adenine or cytosine, "K" encodes for guanine or thymine, "S" encodes for guanine or cytosine, "W" encodes for adenine or thymine, "H" encodes for adenine, cytosine, or thymine, "B" encodes for guanine, thymine, or cytosine, "V" encodes for guanine, cytosine, or adenine, "D" encodes for guanine, adenine, or thymine, and "N" encodes for guanine, adenine, cytosine, or thymine.

Ten libraries were generated for 1F4 and designated L1, L2, L3, L1/L2/L3, H3, L3/H3, L1/H2, L2/H1, H2/H3, and L3/H1/H2. The 1F4 L1 library had positions 28-33 (Kabat numbering) of the light chain hard randomized to allow for amino acid diversity found at these positions within natural human antibodies. The L1 mutagenic oligonucleotides F111-L1 (ACCTGCCGTGCCAGTCAGRDTRK-TRVWANWTHTGTAGCCTGGTATCAACAGAAAC) (SEQ ID NO:113) and F202-L1 (ACCTGCCGTGCCAGT-CAGRDTRKTRVWANWT HTCTGGCCTGGTATCAA-CAGAAAC) (SEQ ID NO:114) were mixed at a 1:2 ratio resulting in the "L1 oligo mix" and combined with 20 μg of Kunkel DNA of the 1F4 L1 stop template (described in Example 2A) to generate the library by Kunkel mutagenesis.

The 1F4 L2 library had positions 50, 53, and 55 (Kabat numbering) of the light chain hard randomized to allow for amino acid diversity found at these positions within natural human antibodies. The L2 mutagenic oligonucleotides F201-L2 (CCGAAGCTTCTGATTTA CKBGGCATCCAVCCTC-TACTCTGGAGTCCCT) (SEQ ID NO:115) and F203-L2 (CCGAAGCTTCTGATTTACKBGGCATC-CAVCCTCGMATCTGGAGTCCCTTCTCGC) (SEQ ID NO:116) were mixed at a 1:1 ratio resulting in the "L2 oligo mix" and combined with 20 μg of Kunkel DNA of the 1F4 L2 stop template (described in Example 2A) to generate the library by Kunkel mutagenesis.

The 1F4 L3 library had positions 91-96 (Kabat numbering) of the light chain either hard randomized to allow for amino acid diversity found at these positions within natural human antibodies or soft randomized. The mutagenic oligonucleotides F133a (GCAACTTA TTACTGTCAGCAATMTDM-CRVTNHTCCTYKGACGTTCGGACAGGGTACC) (SEQ ID NO:117), F133b (GCAACTTATTACTGTCAGCAAT-MTDMCRVTNHTC CTTWTACGTTCGGACAGGG-TACC) (SEQ ID NO:118), F133c (GCAACTTATT ACTGT-CAGCAASRTDMCRVTNHTCCTYKGACGTTCGGACA-GGGTACC) (SEQ ID NO:119), F133d (GCAACTTAT-TACTGTCAGCAASRTDMCRVTNHTCCTT WTACGT-TCGGACAGGGTACC) (SEQ ID NO:120) were mixed at a 1:1:1:1 ratio resulting in the "L3 hard oligo mix". The mutagenic oligonucleotides F563-L3soft1 (ACTTATTACTGTCAGCAA878857577577CCT777ACG-TTCGGACAGGGTACC) (SEQ ID NO:121), F564-L3soft2 (ACTTATTACTGTCAGCAA878857577577CCTTWTACGT TCGGACAGGGTACC) (SEQ ID NO:122), and F565-L3soft3 (ACTTATTACTGTCAGCAA 878857577577CCTYKGACGTTCGGACAGGGTACC) (SEQ ID NO:123) were mixed at a 1:0.5:1 ratio resulting in the "L3 soft oligo mix". The "L3 hard oligo mix", the "L3 soft oligo mix", and the mutagenic oligonucleotide 1F4.L3 soft (GCAACTTATTACTGTCAG CAA857857857-857878CCG788ACGTTCGGACAGGGTACCAAG) (SEQ ID NO:124) were then mixed at a 1:1:1 ratio resulting in the "L3 total oligo mix" and combined with 20 μg of Kunkel DNA of the 1F4 L3 stop template (described in Example 2A) to generate the library by Kunkel mutagenesis.

The 1F4 H3 library had positions 95, 97, 99, 100, and 100a (Kabat numbering) of the heavy chain soft randomized. Mutagenic oligonucleotide CLC.1F4.H3soft (GACACTGCCGTCTATTATTGTGCTCGC668TAC688T-GG555668678ATGGACTACTGGGG TCAAGGAACC) (SEQ ID NO:125) was combined with 20 μg of Kunkel DNA of the 1F4 H3 stop template (described in Example 2A) to generate the library by Kunkel mutagenesis.

The 1F4 L3/H3 library had positions 91-96 (Kabat numbering) of the light chain either hard randomized to allow for amino acid diversity found at these positions within natural human antibodies or soft randomized. It also had positions 95, 97, 99, 100, and 100a (Kabat numbering) of the heavy chain soft randomized. The "L3 total oligo mix" and the mutagenic oligonucleotide CLC.1F4.H3soft (SEQ ID NO:126) described above were mixed at a 1:1 ratio and combined with 20 μg of Kunkel DNA of the 1F4 L3/H3 stop template (described in Example 2A) to generate the library by Kunkel mutagenesis.

The 1F4 L1/H2 library had positions 28-33 (Kabat numbering) of the light chain hard randomized to allow for amino acid diversity found at these positions within natural human antibodies. It also had positions 50, 52, 53, 54, and 58 (Kabat numbering) of the heavy chain soft randomized. The "L1 oligo mix" described above and the mutagenic oligonucleotide CLC.1F4.H2soft (GGTAAGGGCCT-GGAATGGGTTGCA878ATT857TCT857857AG CTATACT878TATGCCGATAGCGTCAAGGGCCG) (SEQ ID NO:126) were mixed at a 1:1 ratio and combined with 20 μg of Kunkel DNA of the 1F4 L1 stop template (described in Example 2A) to generate the library by Kunkel mutagenesis.

The 1F4 L2/H1 library had positions 50, 53, and 55 (Kabat numbering) of the light chain hard randomized to allow for amino acid diversity found at these positions within natural human antibodies. It also had positions 30-33 (Kabat numbering) of the heavy chain soft randomized. The "L2 oligo mix" described above and the mutagenic oligonucleotide CLC4.1F4.H1soft (GCAGCTTCTGGCTTCAACTTT-857878857857ATGCACTGGGTGCGTCAGGCC) (SEQ ID NO:127) were mixed at a 1:1 ratio and combined with 20 μg of Kunkel DNA of the 1F4 L2 stop template (described in Example 2A) to generate the library by Kunkel mutagenesis.

The 1F4 H2/H3 library had positions 50, 52, 53, 54, 58, 95, 97, 99, 100, and 100a (Kabat numbering) of the heavy chain soft randomized. Mutagenic oligonucleotides CLC4.1F4.H2soft (SEQ ID NO:126) and CLC4.1F4.H3soft (SEQ ID NO:125) described above were mixed at a 1:1 ratio and combined with 20 μg of Kunkel DNA of the 1F4 H3 stop template (described in Example 2A) to generate the library by Kunkel mutagenesis.

The 1F4 L1/L2/L3 library had positions 28-33, 50, 53, and 55 (Kabat numbering) of the light chain hard randomized to allow for amino acid diversity found at these positions within natural human antibodies. It also had positions 91-96 (Kabat numbering) of the light chain either hard randomized to allow for amino acid diversity found at these positions within natural human antibodies or soft randomized. The "L1 oligo mix", the "L2 oligo mix", and the "L3 total oligo mix" were mixed at a 1:1:1 ratio and combined with 20 μg of Kunkel DNA of the 1F4 L3 stop template (described in Example 2A) to generate the library by Kunkel mutagenesis.

The 1F4 L3/H1/H2 library had positions 91-96 (Kabat numbering) of the light chain either hard randomized to allow for amino acid diversity found at these positions within natural human antibodies or soft randomized. It also had positions 30-33, 50, 52, 53, 54, and 58 (Kabat numbering) of the heavy chain soft randomized. The "L3 total oligo mix", CLC4.1F4.H1soft (SEQ ID NO:127) and CLC4.1F4.H2soft (SEQ ID NO:126) described above were mixed at a 1:1:1 ratio and combined with 20 μg of Kunkel DNA of the 1F4 L3 stop template (described in Example 2A) to generate the library by Kunkel mutagenesis.

Ten libraries were generated for 1D8 and designated L1, L2, L3, L1/L2/L3, H3, L3/H3, L1/H2, L2/H1, H2/H3, and L3/H1/H2. The 1D8 μl library had positions 28-33 (Kabat numbering) of the light chain hard randomized to allow for amino acid diversity found at these positions within natural human antibodies. The L1 mutagenic oligonucleotides F111-L1 (SEQ ID NO:113) and F202-L1 (SEQ ID NO:114) described above were mixed at a 1:2 ratio resulting in the "L1 oligo mix" and combined with 20 μg of Kunkel DNA of the 1D8 μl stop template (described in Example 2A) to generate the library by Kunkel mutagenesis.

The 1D8 L2 library had positions 50, 53, and 55 (Kabat numbering) of the light chain hard randomized to allow for amino acid diversity found at these positions within natural human antibodies. The L2 mutagenic oligonucleotides F201-L2 (SEQ ID NO:115) and F203-L2 (SEQ ID NO:116) described above were mixed at a 1:1 ratio resulting in the "L2 oligo mix" and combined with 20 μg of Kunkel DNA of the 1D8 L2 stop template (described in Example 2A) to generate the library by Kunkel mutagenesis.

The 1D8 L3 library had positions 91-94 and 96 (Kabat numbering) of the light chain either hard randomized to allow for amino acid diversity found at these positions within natural human antibodies or soft randomized. The mutagenic oligonucleotides F133a (SEQ ID NO:117), F133b (SEQ ID NO:118), F133c (SEQ ID NO:119), and F133d (SEQ ID NO:120) described above were mixed at a 1:1:1:1 ratio resulting in the "L3 hard oligo mix". The mutagenic oligonucleotides F563-L3soft1 (SEQ ID NO:121), F564-L3soft2 (SEQ ID NO:122), and F565-L3soft3 (SEQ ID NO:123) described above were mixed at a 1:0.5:1 ratio resulting in the "L3 soft oligo mix". The "L3 hard oligo mix" and the "L3 soft oligo mix" were then mixed at a 1:1 ratio and combined with 20 μg of Kunkel DNA of the 1D8 L3 stop template (described in Example 2A) to generate the library by Kunkel mutagenesis.

The 1D8 H3 library had positions 96-100c (Kabat numbering) of the heavy chain soft randomized. Mutagenic oligonucleotide VH3.1D8.H3soft (GCCGTCTATTATTGT-GCTCG TGAG6786688785657887888878688ATGGAC-TACTGGGGTCAAGGAACC) (SEQ ID NO:128) was combined with 20 μg of Kunkel DNA of the 1D8 H3 stop template (described in Example 2A) to generate the library by Kunkel mutagenesis.

The 1D8 L3/H3 library had positions 91-94 and 96 (Kabat numbering) of the light chain either hard randomized to allow for amino acid diversity found at these positions within natural human antibodies or soft randomized. It also had positions 96-100c (Kabat numbering) of the heavy chain soft randomized. The "L3 soft oligo mix", the "L3 hard oligo mix", and the mutagenic oligonucleotide VH3.1D8.H3soft (SEQ ID NO:128) described above were mixed at a 0.5:0.5:1 ratio and combined with 20 µg of Kunkel DNA of the 1D8 L3/H3 stop template (described in Example 2A) to generate the library by Kunkel mutagenesis.

The 1D8 L1/H2 library had positions 28-33 (Kabat numbering) of the light chain hard randomized to allow for amino acid diversity found at these positions within natural human antibodies. It also had positions 50, 52, 53, 54, and 58 (Kabat numbering) of the heavy chain soft randomized. The "L1 oligo mix" described above and the mutagenic oligonucleotide VH3.1D8.H2soft (GGTAAGGGCCTGGAATGGGT-TGCT668ATT878CCT857668 GGTTATACT-657TATGCCGATAGCGTCAAGGGCCG) (SEQ ID NO:129) were mixed at a 1:1 ratio and combined with 20 µg of Kunkel DNA of the 1D8 L1 stop template (described in Example 2A) to generate the library by Kunkel mutagenesis.

The 1D8 L2/H1 library had positions 50, 53, and 55 (Kabat numbering) of the light chain hard randomized to allow for amino acid diversity found at these positions within natural human antibodies. It also had positions 30-33 (Kabat numbering) of the heavy chain soft randomized. The "L2 oligo mix" described above and the mutagenic oligonucleotide VH3.1D8.H1soft (GCAGCTTCTGGCTTCACCTTC-577657857657ATTCACTGGGTGCGTCAGGCC) (SEQ ID NO:130) were mixed at a 1:1 ratio and combined with 20 µg of Kunkel DNA of the 1D8 L2 stop template (described in Example 2A) to generate the library by Kunkel mutagenesis.

The 1D8 H2/H3 library had positions 50, 52, 53, 54, 58, and 96-100c (Kabat numbering) of the heavy chain soft randomized. Mutagenic oligonucleotides VH3.1D8.H2soft (SEQ ID NO:129) and VH3.1D8.H3soft (SEQ ID NO:128) described above were mixed at a 1:1 ratio and combined with 20 µg of Kunkel DNA of the 1D8 H3 stop template (described in Example 2A) to generate the library by Kunkel mutagenesis.

The 1D8 L1/L2/L3 library had positions 28-33, 50, 53, and 55 (Kabat numbering) of the light chain hard randomized to allow for amino acid diversity found at these positions within natural human antibodies. It also had positions 91-94 and 96 (Kabat numbering) of the light chain either hard randomized to allow for amino acid diversity found at these positions within natural human antibodies or soft randomized. The "L1 oligo mix", the "L2 oligo mix", the "L3 hard oligo mix", and the "L3 soft oligo mix" were mixed at a 1:1:0.5:0.5 ratio and combined with 20 µg of Kunkel DNA of the 1D8 L3 stop template (described in Example 2A) to generate the library by Kunkel mutagenesis.

The 1D8 L3/H1/H2 library had positions 91-94 and 96 (Kabat numbering) of the light chain either hard randomized to allow for amino acid diversity found at these positions within natural human antibodies or soft randomized. It also had positions 30-33, 50, 52, 53, 54, and 58 (Kabat numbering) of the heavy chain soft randomized. The "L3 hard oligo mix", the "L3 soft oligo mix", VH3.1D8.H1soft (SEQ ID NO:130) and VH3.1D8.H2soft (SEQ ID NO:129) described above were mixed at a 0.5:0.5:1:1 ratio and combined with 20 µg of Kunkel DNA of the 1D8 L3 stop template (described in Example 2A) to generate the library by Kunkel mutagenesis.

Ten libraries were generated for 1E3 and designated L1, L2, L3, L1/L2/L3, H3, L3/H3, L1/H2, L2/H1, H2/1-13, and L3/H1/H2. The 1E3 µl library had positions 28-33 (Kabat numbering) of the light chain hard randomized to allow for amino acid diversity found at these positions within natural human antibodies. The L1 mutagenic oligonucleotides F111-L1 (SEQ ID NO:113) and F202-L1 (SEQ ID NO:114) described above were mixed at a 1:2 ratio resulting in the "L1 oligo mix" and combined with 20 µg of Kunkel DNA of the 1E3 L1 stop template (described in Example 2A) to generate the library by Kunkel mutagenesis.

The 1E3 L2 library had positions 50, 53, and 55 (Kabat numbering) of the light chain hard randomized to allow for amino acid diversity found at these positions within natural human antibodies. The L2 mutagenic oligonucleotides F201-L2 (SEQ ID NO:115) and F203-L2 (SEQ ID NO:116) described above were mixed at a 1:1 ratio resulting in the "L2 oligo mix" and combined with 20 µg of Kunkel DNA of the 1E3 L2 stop template (described in Example 2A) to generate the library by Kunkel mutagenesis.

The 1E3 L3 library had positions 91-94 and 96 (Kabat numbering) of the light chain either hard randomized to allow for amino acid diversity found at these positions within natural human antibodies or soft randomized. The mutagenic oligonucleotides F133a (SEQ ID NO:117), F133b (SEQ ID NO:118), F133c (SEQ ID NO:119), and F133d (SEQ ID NO:120) described above were mixed at a 1:1:1:1 ratio resulting in the "L3 hard oligo mix". The mutagenic oligonucleotides F563-L3soft1 (SEQ ID NO:121), F564-L3soft2 (SEQ ID NO:122), and F565-L3soft3 (SEQ ID NO:123) described above were mixed at a 1:0.5:1 ratio resulting in the "L3 soft oligo mix". The "L3 hard oligo mix" and the "L3 soft oligo mix" were then mixed at a 1:1 ratio and combined with 20 µg of Kunkel DNA of the 1E3 L3 stop template (described in Example 2A) to generate the library by Kunkel mutagenesis.

The 1E3 H3 library had positions 95, 97, 98, 99, and 100a (Kabat numbering) of the heavy chain soft randomized. Mutagenic oligonucleotide VH4.1E3.H3soft (GACACTGCCGTCTATTATTGTGCTCGT577TGG7887-88565TGG688ATGGACTACTGGGG TCAAGGAAC-CCTG) (SEQ ID NO:131) was combined with 20 µg of Kunkel DNA of the 1E3 H3 stop template (described in Example 2A) to generate the library by Kunkel mutagenesis.

The 1E3 L3/H3 library had positions 91-94 and 96 (Kabat numbering) of the light chain either hard randomized to allow for amino acid diversity found at these positions within natural human antibodies or soft randomized. It also had positions 95, 97, 98, 99, and 100a (Kabat numbering) of the heavy chain soft randomized. The "L3 soft oligo mix", the "L3 hard oligo mix", and the mutagenic oligonucleotide VH4.1E3.H3soft (SEQ ID NO:131) described above were mixed at a 0.5:0.5:1 ratio and combined with 20 µg of Kunkel DNA of the 1E3 L3/H3 stop template (described in Example 2A) to generate the library by Kunkel mutagenesis.

The 1E3 L1/H2 library had positions 28-33 (Kabat numbering) of the light chain hard randomized to allow for amino acid diversity found at these positions within natural human antibodies. It also had positions 50, 52, 53, 54, and 58 (Kabat numbering) of the heavy chain soft randomized. The "L1 oligo mix" described above and the mutagenic oligonucleotide VH4.1E3.H2soft (GGTAAGGGCCTGGAATGGGTT-GCT878ATT577CCT878878GGTTCTA CT657TATGCCGATAGCGTCAAGGGCCG) (SEQ ID NO:132) were mixed at a 1:1 ratio and combined with 20 µg of Kunkel DNA of the 1E3 µl stop template (described in Example 2A) to generate the library by Kunkel mutagenesis.

The 1E3 L2/H1 library had positions 50, 53, and 55 (Kabat numbering) of the light chain hard randomized to allow for amino acid diversity found at these positions within natural human antibodies. It also had positions 30-33 (Kabat numbering) of the heavy chain soft randomized. The "L2 oligo mix" described above and the mutagenic oligonucleotide VH4.1E3.H1soft (GCAGCTTCTGGCTTCACCTTC87855-8577857ATTAGCTGGGTGCGTCAGGCC) (SEQ ID NO:133) were mixed at a 1:1 ratio and combined with 20 μg of Kunkel DNA of the 1E3 L2 stop template (described in Example 2A) to generate the library by Kunkel mutagenesis.

The 1E3 H2/H3 library had positions 50, 52, 53, 54, 58, 95, 97, 98, 99, and 100a (Kabat numbering) of the heavy chain soft randomized. Mutagenic oligonucleotides VH4.1E3.H2soft (SEQ ID NO:132) and VH4.1E3.H3soft (SEQ ID NO:133) described above were mixed at a 1:1 ratio and combined with 20 μg of Kunkel DNA of the 1E3 H3 stop template (described in Example 2A) to generate the library by Kunkel mutagenesis.

The 1E3 L1/L2/L3 library had positions 28-33, 50, 53, and 55 (Kabat numbering) of the light chain hard randomized to allow for amino acid diversity found at these positions within natural human antibodies. It also had positions 91-94 and 96 (Kabat numbering) of the light chain either hard randomized to allow for amino acid diversity found at these positions within natural human antibodies or soft randomized. The "L1 oligo mix", the "L2 oligo mix", the "L3 hard oligo mix", and the "L3 soft oligo mix" were mixed at a 1:1:0.5:0.5 ratio and combined with 20 μg of Kunkel DNA of the 1E3 L3 stop template (described in Example 2A) to generate the library by Kunkel mutagenesis.

The 1E3 L3/H1/H2 library had positions 91-94 and 96 (Kabat numbering) of the light chain either hard randomized to allow for amino acid diversity found at these positions within natural human antibodies or soft randomized. It also had positions 30-33, 50, 52, 53, 54, and 58 (Kabat numbering) of the heavy chain soft randomized. The "L3 hard oligo mix", the "L3 soft oligo mix", VH4.1E3.H1soft (SEQ ID NO:133) and VH4.1E3.H2soft (SEQ ID NO:132) described above were mixed at a 0.5:0.5:1:1 ratio and combined with 20 μg of Kunkel DNA of the 1E3 L3 stop template (described in Example 2A) to generate the library by Kunkel mutagenesis.

The mutagenesis reactions were electroporated into electrocompetent XL1-Blue (Agilent) *E. coli* and recovered in 25 mL of SOC medium for 45 minutes at 37° C. with shaking. Twenty microliters were removed and ten-fold serial dilutions were plated onto solid agar plates containing carbenicillin and grown overnight at 37° C. to determine the library size. The remaining culture was transferred to 500 mL of 2YT broth containing 50 μg/mL carbenicillin and 1×10$^{10}$ phage/mL M13K07 helper phage. The cells were infected at 37° C. for one hour with shaking. 50 μg/mL of kanamycin was added and the cultures were grown for another seven hours at 37° C. with shaking. The temperature was then shifted to 30° C. and the cultures were grown for another 22 hours. The libraries each contained at least ~9.5×10$^9$ colony forming units (CFUs). The phage were purified from the culture supernatant by two rounds of precipitation with ⅕ volume of 20% polyethylene glycol (PEG)/2.5M NaCl.

C) Affinity Maturation Library Sorting

The 1F4, 1D8, and 1E3 affinity maturation libraries underwent four rounds of sorting. Each of the ten sub-libraries were sorted in parallel for the first round and then pooled for sorts two through four. The first round was plate-based sorting with linear diubiquitin immobilized on a 96-well Maxisorb immunoplate (NUNC). Plates were coated overnight at 4° C. with 5 μg/mL linear diubiquitin (Boston Biochem) in 50 mM sodium carbonate buffer, pH 9.6. The coated plates were blocked with 200 μL/well of 2.5% milk in PBS containing 0.05% Tween 20 (PBST) for one hour at 25° C. with shaking. The phage libraries were diluted to an OD=2.0 in 2.5% milk in PBST and 30 μg/mL of K63-linked polyubiquitin 2-7 (Boston Biochem) was added for counterselection. After one hour, the blocking buffer was dumped off of the plate and 100 μL/well of the phage was added and incubated at 25° C. for three hours with shaking. After binding, the plate was washed 20 times with PBST by manually filling the wells and dumping off the buffer between washes. Phage were eluted with 150 μL/well of 50 mM HCl/500 mM KCl for 30 minutes at 25° C. with shaking. The elution was neutralized with 150 μL/well of 1 M Tris, pH 7.5 and subsequently propagated in XL1-Blue (Agilent) *E. coli* with the addition of M13K07 helper phage.

Amplified phage were used for additional rounds of selection against linear diubiquitin in plate-based sorting. Solution-based sorting was not possible because biotinylation of linear diubiquitin interfered with Fab binding. Stringency of the later sorts was increased in three ways: by adding 30 μg/mL soluble monoubiquitin, K11-linked polyubiquitin, K48-linked polyubiquitin 2-7, and K63-linked polyubiquitin 2-7 to the phage for counterselection; by increasing the number and duration of plate washes; and by decreasing the amount of phage used and the duration of phage binding. The second sort was done exactly as the first sort, except that the soluble ubiquitins added was expanded to include the above listed chains, the amount of phage used was OD$_{268}$=1.0, the duration of phage binding was decreased to 2 hours, and the number of plate washes was increased to 30. The third sort was done exactly as the second sort, except that the duration of phage binding was reduced to 1.5 hours and the number of plate washes was increased to 40 followed by four additional washes of 15 minutes each with shaking at 25° C. with five quick washes in between each 15 minute wash. The fourth sort was done exactly as the third sort, except that the amount of phage used was reduced to OD$_{268}$=0.5, the duration of phage binding was reduced to 1 hour, and the washes included 40 quick washes followed by four 15 minute washes with shaking at 37° C. Enrichment was calculated for rounds two through four by comparing the number of phage recovered with linear diubiquitin compared to an uncoated well. Enrichment was observed in rounds two through four for all three libraries (see Table 3).

TABLE 3

| Library | Round 2 | Round 3 | Round 4 |
|---|---|---|---|
| 1F4 AM | 143X | 500X | 5000X |
| 1D8 AM | 850X | 1400X | 5500X |
| 1E3 AM | 45X | 167X | 60X |

Figure 6:
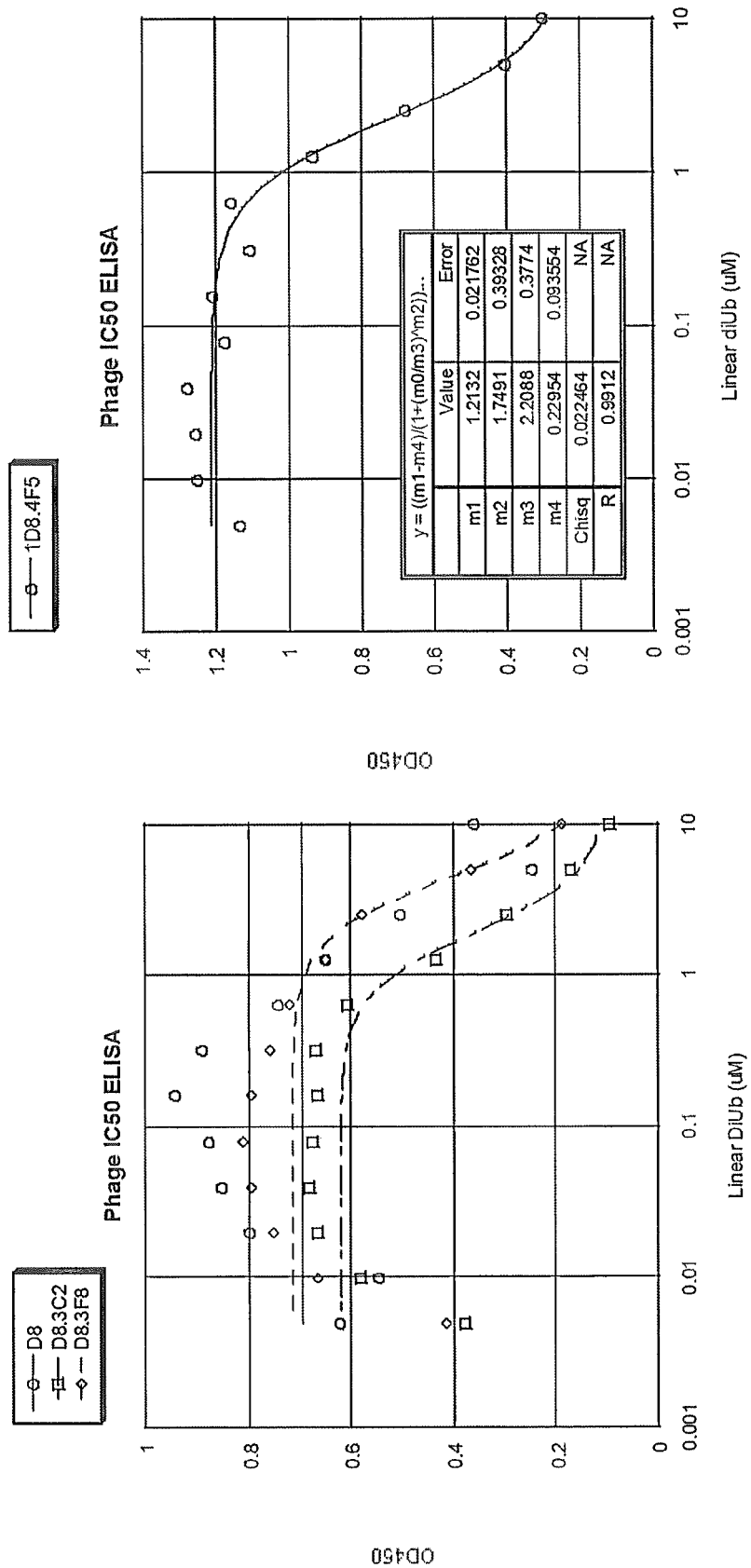
FIG. 6 depicts the results of a phage IC$_{50}$ competition ELISA to measure the affinity of the 1D8, 1D8.3C2, 1D8.3F8 and 1D8.4F5 Fabs for linear diubiquitin.

After four rounds of sorting 96 individual clones were picked from the 1F4 third round sort, 1D8 second round sort, 1D8 third round sort, 1D8 fourth round sort, and 1E3 third round sort and grown up in 96-well format in 1 mL of 2YT broth containing 50 μg/mL carbenicillin and 1×10$^{10}$ phage/mL M13K07 helper phage. Supernatants from those cultures were used in high-throughput phage spot ELISAs for binding to linear diubiquitin (Boston Biochem), monoubiquitin (Boston Biochem), K11-linked diubiquitin (Genentech), K48-linked diubiquitin (Boston Biochem), K63-linked diubiquitin (Boston Biochem), an anti-gD antibody (Genentech), or an uncoated well (as described in Example 1B). From the 1F4 third round sort all clones were very weak linear diubiquitin binders showing OD$_{450}$ of less than 0.4 and therefore were not pursued. From the 1D8 second round sort 93 of the clones were linear diubiquitin-specific, but sequencing revealed that all were the parental wild-type 1D8 sequence. From the 1D8 third round sort 48 of the clones were linear diubiquitin-specific, but sequencing revealed that all but two were the parental wild-type 1D8 sequence. The two non-parental clones 1D8.3C2 (SEQ ID NOs: 33 and 36) and 1D8.3F8 (SEQ ID NOs: 34 and 37) (see FIGS. 5A and 5B) were tested by phage IC$_{50}$ ELISA as in example 1D and demonstrated to have IC$_{50}$s in the low µM range for linear diubiquitin, only slightly improved over 1D8 (see FIG. 6). From the 1D8 fourth round sort 94 of the clones showed strong binding to both linear diubiquitin and K63-linked diubiquitin (OD$_{450}$ greater than 1.0 for linear, OD$_{450}$ greater than 0.5 for K63) and therefore were not pursued. Only one clone, 1D8.4F5 (SEQ ID NOs: 35 and 38) (see FIGS. 5A and 5B) showed strong linear diubiquitin binding with little K63-linked diubiquitin binding (OD$_{450}$-1.3, OD$_{450}$-0.1 for K63). The phage IC$_{50}$ for 1D8.4F5 was also measured by ELISA as in example 1D and determined to be ~2 µM, only slightly better than the parental clone 1D8 (see FIG. 6). From the 1E3 third round sort 33 of the clones were linear diubiquitin-specific, however they were all very weak binders (OD$_{450}$ of less than 0.5) and therefore were not pursued. An additional 27 clones showed stronger binding to linear diubiquitin (OD$_{450}$ of greater than 0.5 but less than 1.0) however they also showed increased binding to K63-linked diubiquitin (OD$_{450}$ of greater than 0.1) and therefore were not pursued.

Example 3

Second Affinity Maturation of 1E3

A) Stop Template Generation

A TAA stop codon was inserted separately into either CDR L1, CDR L2, CDR L3, CDR H1, CDR H2, and CDR H3 (resulting in L1, L2, L3, H1, H2, and H3 stop templates, respectively) for library synthesis using Kunkel mutagenesis. Stop codons force diversity within a particular CDR loop by requiring repair of the stop in order to get full length Fab expression and display on phage. The stop codon mutagenic oligonucleotides listed below were combined with 1 µg of 1E3 monovalent phagemid Kunkel DNA. The resulting monovalent Fab phagemid stop templates were used for affinity maturation library generation.

The mutagenic oligonucleotide used to insert a TAA stop codon at position 31 (Kabat numbering) within CDR L1 of the 1E3 light chain was E3.L1 stop (GCCAGTCAGGAT-GTG TCCTAAGCTGTAGCCTGGTATCAAC) (SEQ ID NO:134). The mutagenic oligonucleotide used to insert a TAA stop codon at position 53 (Kabat numbering) within CDR L2 of the 1E3 light chain was E3.L2stop (CTGATT-TACTCGGCATCCTAACTCTACTCTGGAGTCCCTTC) (SEQ ID NO:135). The mutagenic oligonucleotide used to insert a TAA stop codon at position 93 (Kabat numbering) within CDR L3 of the 1E3 light chain was E3.L3stop (CT-TATTACT GTCAGCAATCTTATTAAACTCCTC-CCACGTTCGGACAG) (SEQ ID NO:136). The mutagenic oligonucleotide used to insert a TAA stop codon at position 32 (Kabat numbering) within CDR H1 of the 1E3 light chain was E3.H1stop (GGCTTCACCTTC AGTAATTAATATATT-AGCTGGGTGCGTC) (SEQ ID NO:137). The mutagenic oligonucleotide used to insert a TAA stop codon at position 54 (Kabat numbering) within CDR H2 of the 1E3 light chain was E3.H2stop (GTTGCTTCTATTACTCCTTAAAGCGGT-TCTACTGACTATG) (SEQ ID NO:138). The mutagenic oligonucleotide used to insert a TAA stop codon at position 99 (Kabat numbering) within CDR H3 of the 1E3 light chain was E3.H3stop (GCTCGTACCTGGTTGCTCTAATGGGT-TATGGACTACTGG) (SEQ ID NO:139).

B) Single Position NNK Library Generation

Since the first attempt at affinity maturation of 1F4 and 1D8 resulted in only modest improvements in affinity with IC$_{50}$s still in the low µM range, clone 1E3 which had a starting IC$_{50}$ of 80 nM was focused on. The first attempt at 1E3 affinity maturation produced many clones that showed strong binding to both linear and K63-linked diubiquitin. Therefore a different approach was taken to minimize K63-linked diubiquitin binding by limiting the number of mutations incorporated into single clones. Single position NNK randomization was used to incorporate a single amino acid change into one CDR at a time. Six single CDR libraries designated L1, L2, L3, H1, H2, and H3 were generated where a single residue in any one clone was allowed to retain the wild-type residue or to change to any one of the other 19 amino acids.

The L1 library had positions 28-34 (Kabat numbering) of the light chain hard randomized individually using the NNK codon to allow for all 20 amino acids. The L1 mutagenic oligonucleotides
E3.L1.1 (CATCACCTGCCGTGCCAGTCAGNNKGT-GTCCACTGCTG TAGCCTGGTATCAACAGAAAC-CAGG) (SEQ ID NO:140),
E3.L1.2 (CATCACCTGCCGTGCCAGTCAGGATNNK-TCCACTGCTGTAGCCTGGTATC AACAGAAACCAGG) (SEQ ID NO:141),
E3.L1.3 (CATCACCTGCCGTGCCAGTCAGGATGT-GNNKACTGCTGTAGCCTGGTATCA ACAGAAAC-CAGG) (SEQ ID NO:142),
E3.L1.4 (CATCACCTGCCGTGCCAGTCAGGATGT-GTCCNNKGCTGTAGCCTGGTATCAA CAGAAAC-CAGG) (SEQ ID NO:143),
E3.L1.5 (CATCACCTGCCGTGCCAGTCAGGATGT-GTCCACTNNKGTAGCCTGGTATCA ACAGAAAC-CAGG) (SEQ ID NO:144),
E3.L1.6 (CATCACCTGCCGTGCCAGTCAGGATGT-GTCCACTGCTNNKGCCTGGTATCAA CAGAAAC-CAGG) (SEQ ID NO:145), and
E3.L1.7 (CATCACCTGCCGTGCCAGTCAGGATGT-GTCCACTGCTGTANNKTGGTATCAA CAGAAAC-CAGG) (SEQ ID NO:146) were mixed at a 1:1:1:1:1:1:1 ratio and combined with 20 µg of Kunkel DNA of the 1E3 µl stop template (described in Example 3A) to generate the library by Kunkel mutagenesis.

The L2 library had positions 50-56 (Kabat numbering) of the light chain hard randomized individually using the NNK codon to allow for all 20 amino acids. The L2 mutagenic oligonucleotides
E3.L2.1 (GCTCCGAAGCTTCTGATTTACNNKG-CATCCTTCCTCTACTCTG GAGTCCCTTCTCGCT-TCTCTG) (SEQ ID NO:147),
E3.L2.2 (GCTCCGAAGCTTCTGATTTACTCGNNK-TCCTTCCTCTACTCTGGAGTCCCTT CTCGCT-TCTCTG) (SEQ ID NO:148),
E3.L2.3 (GCTCCGAAGCTTCTGATTTACTCG-GCANNKTTCCTCTACTCTGGAGTCCCTT CTCGCT-TCTCTG) (SEQ ID NO:149),
E3.L2.4 (GCTCCGAAGCTTCTGATTTACTCG-GCATCCNNKCTCTACTCTGGAGTCCCTT CTCGCT-TCTCTG) (SEQ ID NO:150),
E3.L2.5 (GCTCCGAAGCTTCTGATTTACTCG-GCATCCTTCNNKTACTCTGGAGTCCCTT CTCGCT-TCTCTG) (SEQ ID NO:151),
E3.L2.6 (GCTCCGAAGCTTCTGATTTACTCG-GCATCCTTCCTCNNKTCTGGAGTCCCTT CTCGCT-TCTCTG) (SEQ ID NO:152), and
E3.L2.7 (GCTCCGAAGCTTCTGATTTACTCG-GCATCCTTCCTCTACNNKGGAGTCCCTT CTCGCT- TCTCTG) (SEQ ID NO:153) were mixed at a 1:1:1:1:1:1 ratio and combined with 20 of Kunkel DNA of the 1E3 L2 stop template (described in Example 3A) to generate the library by Kunkel mutagenesis.

The L3 library had positions 91-96 (Kabat numbering) of the light chain hard randomized individually using the NNK codon to allow for all 20 amino acids. The L3 mutagenic oligonucleotides
E3.L3.1 (GCAACTTATTACTGTCAGCAANNK-TATACTACTCCTCCCACG TTCGGACAGGGTAC-CAAG) (SEQ ID NO:154),
E3.L3.2 (GCAACTTATTACTGTCAGCAATCTNN-KACTACTCCTCCCACGTTCGGACA GGGTACCAAG) (SEQ ID NO:155),
E3.L3.3 (GCAACTTATTACTGTCAGCAATCTTAT-NNKACTCCTCCCACGTTCGGACA GGGTACCAAG) (SEQ ID NO:156),
E3.L3.4 (GCAACTTATTACTGTCAGCAATCT-TATACTNNKCCTCCCACGTTCGGACA GGGTAC-CAAG) (SEQ ID NO:157),
E3.L3.5 (GCAACTTATTACTGTCAGCAATCT-TATACTACTNNKCCCACGTTCGGACA GGGTAC-CAAG) (SEQ ID NO:158), and
E3.L3.6 (GCAACTTATTACTGTCAGCAATCT-TATACTACTCCTNNKACGTTCGGACA GGGTAC-CAAG) (SEQ ID NO:159) were mixed at a 1:1:1:1:1:1 ratio and combined with 20 µg of Kunkel DNA of the 1E3 L3 stop template (described in Example 3A) to generate the library by Kunkel mutagenesis.

The H1 library had positions 30-35 (Kabat numbering) of the heavy chain hard randomized individually using the NNK codon to allow for all 20 amino acids. The H1 mutagenic oligonucleotides
E3.H1.1 (GCAGCTTCTGGCTTCACCTTCNN-KAATACTTATATTAGCT GGGTGCGTCAGGCCCCG) (SEQ ID NO:160),
E3.H1.2 (GCAGCTTCTGGCTTCACCTTCAGTNN-KACTTATATTAGCTGGGTGCG TCAGGCCCCG) (SEQ ID NO:161),
E3.H1.3 (GCAGCTTCTGGCTTCACCTTCAGTAAT-NNKTATATTAGCTGGGTGCG TCAGGCCCCG) (SEQ ID NO:162),
E3.H1.4 (GCAGCTTCTGGCTTCACCTTCAG-TAATACTNNKATTAGCTGGGTGCG TCAGGCCCCG) (SEQ ID NO:163),
E3.H1.5 (GCAGCTTCTGGCTTCACCTTCAG-TAATACTTATNNKAGCTGGGTGCG TCAGGCCCCG) (SEQ ID NO:164), and
E3.H1.6 (GCAGCTTCTGGCTTCACCTTCAG-TAATACTTATATTNNKTGGGTGCG TCAGGCCCCG) (SEQ ID NO:165) were mixed at a 1:1:1:1:1:1 ratio and combined with 20 µg of Kunkel DNA of the 1E3 H1 stop template (described in Example 3A) to generate the library by Kunkel mutagenesis.

The H2 library had positions 49-58 (Kabat numbering) of the heavy chain hard randomized individually using the NNK codon to allow for all 20 amino acids. The H2 mutagenic oligonucleotides
E3.H2.1 (GGTAAGGGCCTGGAATGGGTTNNKTC-TATTACTCCTTCAGCGGTTCTACTG ACTATGCCGAT-AGCGTCAAGGGC) (SEQ ID NO:166),
E3.H2.2 (GGTAAGGGCCTGGAATGGGTTGCTNN-KATTACTCCTTCAGCGGTTCTACTG ACTATGC-CGATAGCGTCAAGGGC) (SEQ ID NO:167),
E3.H2.3 (GGTAAGGGCCTGGAATGGGTTGCTTCT-NNKACTCCTTCAGCGGTTCTACTG ACTATGCCGAT-AGCGTCAAGGGC) (SEQ ID NO:168),
E3.H2.4 (GGTAAGGGCCTGGAATGGGTTGCTTC-TATTNNKCCTTCTAGCGGTTCTACTG ACTATGC-CGATAGCGTCAAGGGC) (SEQ ID NO:169),
E3.H2.5 (GGTAAGGGCCTGGAATGGGTTGCTTC-TATTACTNNKTCTAGCGGTTCTACTG ACTATGC-CGATAGCGTCAAGGGC) (SEQ ID NO:170),
E3.H2.6 (GGTAAGGGCCTGGAATGGGTTGCTTC-TATTACTCCTNNKAGCGGTTCTACTG ACTATGC-CGATAGCGTCAAGGGC) (SEQ ID NO:171),
E3.H2.7 (GGTAAGGGCCTGGAATGGGTTGCTTC-TATTACTCCTTCTNNKGGTTCTACTG ACTATGC-CGATAGCGTCAAGGGC) (SEQ ID NO:172),
E3.H2.8 (GGTAAGGGCCTGGAATGGGTTGCTTC-TATTACTCCTTCTAGCNNKTCTACTG ACTATGC-CGATAGCGTCAAGGGC) (SEQ ID NO:173),
E3.H2.9 (GGTAAGGGCCTGGAATGGGTTGCTTC-TATTACTCCTTCTAGCGGTNNKACTG ACTATGC-CGATAGCGTCAAGGGC) (SEQ ID NO:174),
E3.H2.10 (GGTAAGGGCCTGGAATGGGTTGCTTC-TATTACTCCTTCTAGCGGTTCTNNKG ACTATGC-CGATAGCGTCAAGGGC) (SEQ ID NO:175), and
E3.H2.11 (GGTAAGGGCCTGGAATGGGTTGCTTC-TATTACTCCTTCTAGCGGTTCTACT NNKTATGC-CGATAGCGTCAAGGGC) (SEQ ID NO:176) were mixed at a 1:1:1:1:1:1:1:1:1:1:1 ratio and combined with 20 µg of Kunkel DNA of the 1E3 H2 stop template (described in Example 3A) to generate the library by Kunkel mutagenesis.

The H3 library had positions 95-102 (Kabat numbering) of the heavy chain hard randomized individually using the NNK codon to allow for all 20 amino acids. The H3 mutagenic oligonucleotides
E3.H3.1 (GCCGTCTATTATTGTGCTCGTNNKTGGT-TGCTCCGGTGGGTTATGGACTAC TGGGGTCAAG-GAACCCTGGTC) (SEQ ID NO:177),
E3.H3.2 (GCCGTCTATTATTGTGCTCGTACCNNKT-TGCTCCGGTGGGTTATGGACTAC TGGGGTCAAG-GAACCCTGGTC) (SEQ ID NO:178),
E3.H3.3 (GCCGTCTATTATTGTGCTCGTACCTG-GNNKCTCCGGTGGGTTATGGACTAC TGGGGT-CAAGGAACCCTGGTC) (SEQ ID NO:179),
E3.H3.4 (GCCGTCTATTATTGTGCTCGTACCTGGT-TGNNKCGGTGGGTTATGGACTAC TGGGGTCAAG-GAACCCTGGTC) (SEQ ID NO:180),
E3.H3.5 (GCCGTCTATTATTGTGCTCGTACCTGGT-TGCTCNNKTGGGTTATGGACTAC TGGGGTCAAG-GAACCCTGGTC) (SEQ ID NO:181),
E3.H3.6 (GCCGTCTATTATTGTGCTCGTACCTGGT-TGCTCCGGNNKGTTATGGACTAC TGGGGTCAAG-GAACCCTGGTC) (SEQ ID NO:182),
E3.H3.7 (GCCGTCTATTATTGTGCTCGTACCTGGT-TGCTCCGGTGGNNKATGGACTAC TGGGGTCAAG-GAACCCTGGTC) (SEQ ID NO:183),
E3.H3.8 (GCCGTCTATTATTGTGCTCGTACCTGGT-TGCTCCGGTGGGTTNNKGACTAC TGGGGTCAAG-GAACCCTGGTC) (SEQ ID NO:184),
E3.H3.9 (GCCGTCTATTATTGTGCTCGTACCTGGT-TGCTCCGGTGGGTTATGNNKTAC TGGGGTCAAG-GAACCCTGGTC) (SEQ ID NO:185), and
E3.H3.10 (GCCGTCTATTATTGTGCTCGTACCTGGT-TGCTCCGGTGGGTTATGGACNNKT GGGGTCAAG-GAACCCTGGTC) (SEQ ID NO:186) were mixed at a 1:1:1:1:1:1:1:1:1:1 ratio and combined with 20 µg of Kunkel DNA of the 1E3 H3 stop template (described in Example 3A) to generate the library by Kunkel mutagenesis.

The mutagenesis reactions were electroporated into electrocompetent XL1-Blue (Agilent) *E. coli* and recovered in 25 mL of SOC medium for 45 minutes at 37° C. with shaking.

Twenty microliters were removed and ten-fold serial dilutions were plated onto solid agar plates containing carbenicillin and grown overnight at 37° C. to determine the library size. The remaining culture was transferred to 500 mL of 2YT broth containing 50 µg/mL carbenicillin and 1×10$^{10}$ phage/mL M13K07 helper phage. The cells were infected at 37° C. for one hour with shaking. 50 µg/mL of kanamycin was added and the cultures were grown for another seven hours at 37° C. with shaking. The temperature was then shifted to 30° C. and the cultures were grown for another 22 hours. The libraries each contained at least ~1.5×10$^{10}$ colony forming units (CFUs). The phage were purified from the culture supernatant by two rounds of precipitation with ⅕ volume of 20% polyethylene glycol (PEG)/2.5M NaCl.

Sixty-four individual clones from each of the six libraries were sequenced to make sure the amino acid diversity in the library accurately reflected the design. The libraries all were as designed.

C) Affinity Maturation Library Sorting

The six CDR NNK affinity maturation libraries underwent three rounds of sorting in parallel against either linear diubiquitin or K63-linked diubiquitin. Plates were coated overnight at 4° C. with 5 µg/mL linear diubiquitin (Boston Biochem) or K63-linked diubiquitin (Boston Biochem) in 50 mM sodium carbonate buffer, pH 9.6. The coated plates were blocked with 200 µL/well of 2.5% milk in PBS containing 0.05% Tween 20 (PBST) for one hour at 25° C. with shaking. The phage libraries were diluted to an OD=1.0 in 2.5% milk in PBST. After one hour, the blocking buffer was dumped off of the plate and 100 µL/well of the phage was added and incubated at 25° C. for 1.5 hours with shaking. After binding, the plate was washed 10 times with PBST by manually filling the wells and dumping off the buffer between washes. Phage were eluted with 100 µL/well of 50 mM HCl/500 mM KCl for 30 minutes at 25° C. with shaking. The elution was neutralized with 100 µL/well of 1 M Tris, pH 7.5 and subsequently propagated in XL1-Blue (Agilent) *E. coli* with the addition of M13K07 helper phage.

Amplified phage were used for additional rounds of selection against linear diubiquitin or K63-linked diubiquitin in plate-based sorting. Solution-based sorting was not possible because biotinylation of linear diubiquitin interfered with 1E3 Fab binding. Stringency of the later sorts was increased in two ways: by increasing the number and duration of plate washes; and by decreasing the amount of phage used and the duration of phage binding. The second sort was done exactly as the first sort, except that the amount of phage used was OD$_{268}$=0.5 and the number of plate washes were increased to 21 with the last wash incubating at 25° C. with shaking for 5 minutes. The third sort was done exactly as the second sort, except that the duration of phage binding was reduced to one hour and the number of plate washes was increased to 30. For the linear diubiquitin sort this was followed by four additional washes of 15 minutes each with shaking at 25° C., with five quick washes in between each 15 minute wash. Then a one hour wash with shaking at 25° C. was performed followed by five quick washes. Enrichment was calculated for rounds two and three by comparing the number of phage recovered with linear diubiquitin or K63-linked diubiquitin compared to an uncoated well. Strong enrichment was observed in rounds two and three for all six libraries sorted against linear diubiquitin with only modest enrichment seen for K63-linked diubiquitin (see Table 4).

TABLE 4

| Library | Linear diUb Round 2 | Linear diUb Round 3 | K63 diUb Round 2 | K63 diUb Round 3 |
|---|---|---|---|---|
| L1 | 10,000X | 1,000X | 0X | 3-5X |
| L2 | 10,000X | 1,000X | 0X | 3-5X |
| L3 | 10,000X | 1,000X | 0X | 3-5X |
| H1 | 10,000X | 1,000X | 0X | 3-5X |
| H2 | 10,000X | 1,000X | 0X | 10X |
| H3 | 10,000X | 1,000X | 0X | 10X |

After three rounds of sorting 64 individual clones were picked for each of the six libraries from the linear diubiquitin second round sort, the linear diubiquitin third round sort, and the K63-linked diubiquitin third round sort and grown up in 96-well format in 1 mL of 2YT broth containing 50 µg/mL carbenicillin and 1×10$^{10}$ phage/mL M13K07 helper phage. Supernatants from those cultures were used in high-throughput phage spot ELISAs for binding to 1 µg/mL coated linear diubiquitin (Boston Biochem), K63-linked diubiquitin (Boston Biochem), an anti-gD antibody (Genentech), or an uncoated well as previously described (Example 1B). The variable domains of these clones were also sequenced (see Table 5—linear diubiquitin and Table 6—K63-linked diubiquitin). Sequencing of H3 clones revealed that a T110A mutation was present in some clones outside of the region targeted for randomization in the library design in addition to the intended mutation. This is likely due to an oligonucleotide synthesis error or a mutagenesis error.

D) Single Spot Competition Phage ELISA

Single spot competition phage ELISAs were done to determine which clones had the biggest improvement in affinity for linear diubiquitin compared to the parental 1E3 clone. The phage supernatants from the phage spot ELISAs (Example 3C) were used. The competition ELISA was done as described for the IC$_{50}$ ELISA (Example 1D) except phage supernatants were used instead of purified phage and only a single concentration (25 nM) of soluble linear diubiquitin (Boston Biochem) was used. The competition was also done for each clone without addition of any soluble linear diubiquitin to determine the phage binding signal in the absence of any competing antigen. The percent inhibition in binding in the presence of 25 nM linear diubiquitin was calculated as [1−(OD$_{450}$ for 25 nM linear/OD$_{450}$ for no linear)]×100%. The 1E3 parental clone showed variable percent inhibition of binding ranging from 20% to 75% inhibition in the presence of 25 nM linear diubiquitin (see Table 5). This was due to variability in the OD$_{450}$ for binding linear diubiquitin in the absence of any competing soluble linear diubiquitin. Clones showing 60 percent inhibition or greater or those which were isolated many times in the linear diubiquitin sort were selected for further analysis by phage IC$_{50}$ ELISA.

Table 5 below shows CDR L1, L2, L3, H1, H2 and H3 sequences from clones isolated from the sorting of the 1E3 L1, L2, L3, H1, H2 and H3 NNK libraries, respectively against linear diubiquitin. Also shown are the OD$_{450}$ signals from the competition spot ELISA in the absence and presence of 25 nM soluble linear diubiquitin. The percent inhibition in binding in the presence of 25 nM linear diubiquitin was calculated as [1−(OD$_{450}$ for 25 nM linear/OD$_{450}$ for no linear)]×100%. Table 6 below shows CDR L1, L2, L3, H1, H2 and H3 sequences from clones isolated from the sorting of the 1E3 L1, L2, L3, H1, H2 and H3 NNK libraries, respectively, against K63-linked diubiquitin.

Table 5 discloses the CDR L1 sequences as SEQ ID NOS 1, 56, 199, 200, 200, 57, 201, 202, 202, 203, 204, 204-207, 207, 208, 50, 50, 50, 50, 50, 50, 209, 209, 54, 54, 54, 54, 210, 55, 55, 53, 211, 212, 212, 212-214, 52, 52, 215, 215, 215, 216, 216, 217, 217, 217, 218, 1, 1, 1, 1, 1, 1, 1, 1, 1, 1, 1, 1, 1, 1 and 1, respectively, in order of appearance. Table 5 discloses the CDR L2 sequences as SEQ ID NOS 2, 59, 59, 58, 58, 58, 219, 60, 60, 60, 60, 60, 60, 60, 60, 60, 60, 220, 220, 220, 220, 221, 221-223, 223-226, 226, 226, 62, 227, 228, 228, 229, 61, 61, 230-233, 233-237, 237, 238, 238, 238, 239, 239, 239, 2, 2, 2, 2, 2, 2, 2, 2, 2, 2, 2 and 2, respectively, in order of appearance. Table 5 discloses the CDR L3 sequences as SEQ ID NOS 3, 6, 6, 240, 240, 240-242, 66, 66, 66, 66, 243, 68, 244, 244-247, 247, 248, 248, 248, 70, 64, 64, 64, 64, 249, 250, 250, 71, 71, 251, 72, 72, 72, 72, 72, 72, 72, 69, 65, 65, 65, 252, 252, 252, 252, 252, 67, 67, 67, 67, 67, 67, 67, 67, 253, 3, 3, 3, 3 and 254, respectively, in order of appearance. Table 5 discloses the CDR H1 sequences as SEQ ID NOS 255, 256, 73, 79, 79, 257, 257, 75, 75, 75, 75, 77, 77, 77, 77, 77, 77, 77, 258, 258, 259, 81, 74, 74, 74, 74, 74, 74, 74, 74, 74, 74, 74, 74, 74, 74, 78, 76, 76, 76, 76, 76, 76, 76, 76, 76, 76, 80, 80, 80, 260, 260, 255, 255, 255, 255, 255, 255, 255, 255, 255, 255, 255, 255 and 255, respectively, in order of appearance. Table 5 discloses the CDR H2 sequences as SEQ ID NOS 8, 17, 84, 261, 261, 261, 261, 261-263, 85, 83, 83, 264, 82, 82, 82, 82, 82, 82, 82, 82, 82, 82, 82, 86, 8, 8, 8, 8, 8, 8, 8, 8, 8, 8, 8, 8, 8, 8, 8, 8, 8, 8, 8, 8, 8, 8, 8, 8, 8, 8, 8, 8, 8, 8, 8, 8, 8, 8, 8 and 8, respectively, in order of appearance. Table 5 discloses the CDR H3 sequences as SEQ ID NOS 265-269, 269, 270-273, 273, 273, 273, 273, 273, 273, 273, 273, 273, 273, 273, 273, 273, 273, 273, 273, 273, 273, 273, 273, 273, 273, 273, 273, 273, 273, 274, 274, 274, 274, 274-278, 278, 278, 278-281, 281, 282, 282, 282, 282, 265, 265, 265, 265, 265, 265 and 265, respectively, in order of appearance.

TABLE 5

| | | | | | | | | | | | CDR L1 | | | | | | | |
| | | | | | | | | | | 24 | | | | | | 34 | |
| | | no diUb | 25 nM | % inhibition | R | A | S | Q | D | V | S | T | A | V | A | well |
|---|---|---|---|---|---|---|---|---|---|---|---|---|---|---|---|---|
| 46.ABI46747 | 0.933 | 0.304 | 67.42 | R | A | S | Q | A | V | S | T | A | V | A | 1D10 |
| 32.ABI46747 | 1.267 | 0.567 | 55.25 | R | A | S | Q | E | V | S | T | A | V | A | |
| 26.ABI46747 | 0.251 | 0.135 | 46.22 | R | A | S | Q | G | V | S | T | A | V | A | |
| 47.ABI46747 | 0.316 | 0.17 | 46.20 | R | A | S | Q | G | V | S | T | A | V | A | |
| 56.ABI46747 | 0.595 | 0.23 | 61.34 | R | A | S | Q | L | V | S | T | A | V | A | 1E8 |
| 36.ABI46747 | 0.282 | 0.151 | 46.45 | R | A | S | Q | N | V | S | T | A | V | A | |
| 23.ABI46747 | 0.237 | 0.117 | 50.63 | R | A | S | Q | S | V | S | T | A | V | A | |
| 49.ABI46747 | 0.439 | 0.188 | 57.18 | R | A | S | Q | S | V | S | T | A | V | A | |
| 41.ABI46747 | 0.291 | 0.207 | 28.87 | R | A | S | Q | T | V | S | T | A | V | A | |
| 06.ABI46747 | 0.633 | 0.349 | 44.87 | R | A | S | Q | V | V | S | T | A | V | A | |
| 11.ABI46747 | 0.247 | 0.15 | 39.27 | R | A | S | Q | V | V | S | T | A | V | A | |
| 61.ABI46747 | 0.266 | 0.118 | 55.64 | R | A | S | Q | D | A | S | T | A | V | A | |
| 25.ABI46747 | 0.225 | 0.155 | 31.11 | R | A | S | Q | D | L | S | T | A | V | A | |
| 37.ABI46747 | 0.264 | 0.176 | 33.33 | R | A | S | Q | D | S | S | T | A | V | A | |
| 48.ABI46747 | 0.118 | 0.091 | 22.88 | R | A | S | Q | D | S | S | T | A | V | A | |
| 02.ABI46747 | 0.204 | 0.088 | 56.86 | R | A | S | Q | D | V | F | T | A | V | A | |
| 05.ABI46747 | 0.272 | 0.155 | 43.01 | R | A | S | Q | D | V | G | T | A | V | A | 1A5 |
| 10.ABI46747 | 0.263 | 0.14 | 46.77 | R | A | S | Q | D | V | G | T | A | V | A | |
| 19.ABI46747 | 0.386 | 0.211 | 45.34 | R | A | S | Q | D | V | G | T | A | V | A | |
| 21.ABI46747 | 0.104 | 0.093 | 10.58 | R | A | S | Q | D | V | G | T | A | V | A | |
| 28.ABI46747 | 0.16 | 0.109 | 31.88 | R | A | S | Q | D | V | G | T | A | V | A | |
| 35.ABI46747 | 0.214 | 0.095 | 55.61 | R | A | S | Q | D | V | G | T | A | V | A | |
| 03.ABI46747 | 0.236 | 0.133 | 43.64 | R | A | S | Q | D | V | L | T | A | V | A | |
| 13.ABI46747 | 0.195 | 0.137 | 29.74 | R | A | S | Q | D | V | L | T | A | V | A | |
| 18.ABI46747 | 0.187 | 0.146 | 21.93 | R | A | S | Q | D | V | R | T | A | V | A | |
| 39.ABI46747 | 0.778 | 0.219 | 71.85 | R | A | S | Q | D | V | R | T | A | V | A | 1D3 |
| 50.ABI46747 | 0.3 | 0.158 | 47.33 | R | A | S | Q | D | V | R | T | A | V | A | |
| 58.ABI46747 | 0.262 | 0.12 | 54.20 | R | A | S | Q | D | V | R | T | A | V | A | |
| 24.ABI46747 | 0.085 | 0.059 | 30.59 | R | A | S | Q | D | V | V | T | A | V | A | |
| 20.ABI46747 | 0.281 | 0.182 | 35.23 | R | A | S | Q | D | V | S | G | A | V | A | |
| 43.ABI46747 | 0.63 | 0.142 | 77.46 | R | A | S | Q | D | V | S | G | A | V | A | 1D7 |
| 15.ABI46747 | 0.661 | 0.208 | 68.53 | R | A | S | Q | D | V | S | I | A | V | A | 1B3 |
| 42.ABI46747 | 0.441 | 0.254 | 42.40 | R | A | S | Q | D | V | S | N | A | V | A | |
| 33.ABI46747 | 0.433 | 0.202 | 53.35 | R | A | S | Q | D | V | S | S | A | V | A | |
| 51.ABI46747 | 0.174 | 0.111 | 36.21 | R | A | S | Q | D | V | S | S | A | V | A | |
| 54.ABI46747 | 1.823 | 1.62 | 11.14 | R | A | S | Q | D | V | S | S | A | V | A | |
| 52.ABI46747 | 0.194 | 0.133 | 31.44 | R | A | S | Q | D | V | S | V | A | V | A | |
| 09.ABI46747 | 0.131 | 0.122 | 6.87 | R | A | S | Q | D | V | S | T | H | V | A | |
| 08.ABI46747 | 0.287 | 0.111 | 61.32 | R | A | S | Q | D | V | S | T | Q | V | A | 1A8 |
| 45.ABI46747 | 0.197 | 0.119 | 39.59 | R | A | S | Q | D | V | S | T | Q | V | A | |
| 27.ABI46747 | 0.267 | 0.172 | 35.58 | R | A | S | Q | D | V | S | T | R | V | A | |
| 53.ABI46747 | 0.184 | 0.112 | 39.13 | R | A | S | Q | D | V | S | T | R | V | A | |
| 57.ABI46747 | 0.324 | 0.138 | 57.41 | R | A | S | Q | D | V | S | T | R | V | A | |
| 14.ABI46747 | 0.215 | 0.112 | 47.91 | R | A | S | Q | D | V | S | T | S | V | A | |
| 16.ABI46747 | 0.278 | 0.144 | 48.20 | R | A | S | Q | D | V | S | T | S | V | A | |
| 07.ABI46747 | 0.276 | 0.103 | 62.68 | R | A | S | Q | D | V | S | T | Y | V | A | 1A7 |
| 12.ABI46747 | 1.119 | 0.661 | 40.93 | R | A | S | Q | D | V | S | T | Y | V | A | |
| 30.ABI46747 | 0.204 | 0.098 | 51.96 | R | A | S | Q | D | V | S | T | Y | V | A | |
| 40.ABI46747 | 0.243 | 0.146 | 39.92 | R | A | S | Q | D | V | S | T | A | L | A | |

TABLE 5-continued

| | no diUb | 25 nM | % inhibition | | | | | | | | | | |
|---|---|---|---|---|---|---|---|---|---|---|---|---|---|
| 01.ABI46747 | 0.376 | 0.186 | 50.53 | R | A | S | Q | D | V | S | T | A | V A |
| 04.ABI46747 | 0.143 | 0.091 | 36.36 | R | A | S | Q | D | V | S | T | A | V A |
| 17.ABI46747 | 0.203 | 0.103 | 49.26 | R | A | S | Q | D | V | S | T | A | V A |
| 22.ABI46747 | 0.188 | 0.12 | 36.17 | R | A | S | Q | D | V | S | T | A | V A |
| 29.ABI46747 | 0.148 | 0.12 | 18.92 | R | A | S | Q | D | V | S | T | A | V A |
| 31.ABI46747 | 0.646 | 0.201 | 68.89 | R | A | S | Q | D | V | S | T | A | V A |
| 34.ABI46747 | 0.208 | 0.121 | 41.83 | R | A | S | Q | D | V | S | T | A | V A |
| 38.ABI46747 | 0.377 | 0.15 | 60.21 | R | A | S | Q | D | V | S | T | A | V A |
| 44.ABI46747 | 0.294 | 0.169 | 42.52 | R | A | S | Q | D | V | S | T | A | V A |
| 55.ABI46747 | 0.788 | 0.266 | 66.24 | R | A | S | Q | D | V | S | T | A | V A |
| 59.ABI46747 | 0.232 | 0.14 | 39.66 | R | A | S | Q | D | V | S | T | A | V A |
| 60.ABI46747 | 0.258 | 0.127 | 50.78 | R | A | S | Q | D | V | S | T | A | V A |
| 62.ABI46747 | 1.155 | 0.253 | 78.10 | R | A | S | Q | D | V | S | T | A | V A |
| 63.ABI46747 | 0.189 | 0.112 | 40.74 | R | A | S | Q | D | V | S | T | A | V A |
| 64.ABI46747 | 0.201 | 0.121 | 39.80 | R | A | S | Q | D | V | S | T | A | V A |

L2 NNK 3rd sort linear diUb selected clones

| | no diUb | 25 nM | % inhibition | CDR L2 50 S A S F L Y S 56 | Well |
|---|---|---|---|---|---|
| 89.ABI46747 | 0.806 | 0.306 | 62.03 | S R S F L Y S | 1H5 |
| 23.ABI46748 | 0.24 | 0.104 | 56.67 | S R S F L Y S | |
| 71.ABI46747 | 0.311 | 0.159 | 48.87 | S A K F L Y S | 1F11 |
| 91.ABI46747 | 0.32 | 0.171 | 46.56 | S A K F L Y S | |
| 07.ABI46748 | 0.198 | 0.093 | 53.03 | S A K F L Y S | |
| 10.ABI46748 | 0.181 | 0.091 | 49.72 | S A Q F L Y S | |
| 67.ABI46747 | 0.981 | 0.635 | 35.27 | S A R F L Y S | |
| 74.ABI46747 | 0.229 | 0.113 | 50.66 | S A R F L Y S | |
| 76.ABI46747 | 0.312 | 0.167 | 46.47 | S A R F L Y S | |
| 77.ABI46747 | 0.314 | 0.189 | 39.81 | S A R F L Y S | |
| 79.ABI46747 | 1.021 | 0.79 | 22.62 | S A R F L Y S | |
| 94.ABI46747 | 0.153 | 0.099 | 35.29 | S A R F L Y S | |
| 96.ABI46747 | 0.415 | 0.25 | 39.76 | S A R F L Y S | |
| 02.ABI46748 | 0.332 | 0.109 | 67.17 | S A R F L Y S | 2A2 |
| 12.ABI46748 | 0.26 | 0.114 | 56.15 | S A R F L Y S | |
| 24.ABI46748 | 0.108 | 0.094 | 12.96 | S A R F L Y S | |
| 65.ABI46747 | 0.162 | 0.115 | 29.01 | S A S Y L Y S | |
| 69.ABI46747 | 0.246 | 0.113 | 54.04 | S A S Y L Y S | |
| 81.ABI46747 | 0.176 | 0.167 | 5.11 | S A S Y L Y S | |
| 88.ABI46747 | 0.222 | 0.102 | 54.05 | S A S Y L Y S | |
| 80.ABI46747 | 2.066 | 1.417 | 31.41 | S A S F A Y S | |
| 26.ABI46748 | 0.408 | 0.166 | 59.31 | S A S F A Y S | |
| 86.ABI46747 | 0.759 | 0.309 | 59.29 | S A S F F Y S | |
| 82.ABI46747 | 0.31 | 0.163 | 47.42 | S A S F G Y S | |
| 11.ABI46748 | 0.187 | 0.104 | 44.39 | S A S F G Y S | |
| 85.ABI46747 | 0.234 | 0.161 | 31.20 | S A S F H Y S | |
| 15.ABI46748 | 0.129 | 0.08 | 37.98 | S A S F I Y S | |
| 93.ABI46747 | 0.266 | 0.135 | 49.25 | S A S F K Y S | |
| 13.ABI46748 | 0.062 | 0.063 | -1.61 | S A S F K Y S | |
| 30.ABI46748 | 0.092 | 0.062 | 32.61 | S A S F K Y S | |
| 25.ABI46748 | 0.364 | 0.132 | 63.74 | S A S F M Y S | 2C1 |
| 28.ABI46748 | 0.217 | 0.078 | 64.06 | S A S F N Y S | 2C4 |
| 04.ABI46748 | 0.139 | 0.087 | 37.41 | S A S F P Y S | |
| 05.ABI46748 | 0.168 | 0.117 | 30.36 | S A S F P Y S | |
| 87.ABI46747 | 0.197 | 0.136 | 30.96 | S A S F R Y S | |
| 09.ABI46748 | 0.573 | 0.219 | 61.78 | S A S F S Y S | 2A9 |
| 20.ABI46748 | 0.328 | 0.16 | 51.22 | S A S F S Y S | |
| 17.ABI46748 | 0.312 | 0.146 | 53.21 | S A S F V Y S | |
| 19.ABI46748 | 0.2 | 0.133 | 33.50 | S A S F Y Y S | |

TABLE 5-continued

| | no diUb | 25 nM | % inhibition | CDR L3 | |
|---|---|---|---|---|---|
| 95.ABI46747 | 0.251 | 0.134 | 46.61 | S A S F L Y A | |
| 06.ABI46748 | 0.122 | 0.065 | 46.72 | S A S F L Y D | |
| 27.ABI46748 | 0.087 | 0.08 | 8.05 | S A S F L Y D | |
| 73.ABI46747 | 0.381 | 0.178 | 53.28 | S A S F L Y F | |
| 72.ABI46747 | 0.311 | 0.177 | 43.09 | S A S F L Y G | |
| 75.ABI46747 | 0.269 | 0.142 | 47.21 | S A S F L Y H | |
| 78.ABI46747 | 0.232 | 0.113 | 51.29 | S A S F L Y V | |
| 03.ABI46748 | 1.115 | 0.789 | 29.24 | S A S F L Y V | |
| 66.ABI46747 | 0.349 | 0.177 | 49.28 | S A S F L Y W | |
| 68.ABI46747 | 0.367 | 0.153 | 58.31 | S A S F L Y W | |
| 22.ABI46748 | 0.098 | 0.062 | 36.73 | S A S F L Y W | |
| 16.ABI46748 | 0.128 | 0.087 | 32.03 | S A S F L Y Y | |
| 21.ABI46748 | 0.094 | 0.077 | 18.09 | S A S F L Y Y | |
| 29.ABI46748 | 0.845 | 0.59 | 30.18 | S A S F L Y Y | |
| 01.ABI46747 | 0.376 | 0.186 | 50.53 | S A S F L Y S | |
| 70.ABI46747 | 0.238 | 0.151 | 36.55 | S A S F L Y S | |
| 83.ABI46747 | 0.394 | 0.184 | 53.30 | S A S F L Y S | |
| 84.ABI46747 | 0.366 | 0.185 | 49.45 | S A S F L Y S | |
| 90.ABI46747 | 0.116 | 0.066 | 43.10 | S A S F L Y S | |
| 92.ABI46747 | 0.138 | 0.093 | 32.61 | S A S F L Y S | |
| 01.ABI46748 | 0.14 | 0.114 | 18.57 | S A S F L Y S | |
| 08.ABI46748 | 0.12 | 0.068 | 43.33 | S A S F L Y S | |
| 14.ABI46748 | 0.112 | 0.071 | 36.61 | S A S F L Y S | |
| 18.ABI46748 | 0.838 | 0.698 | 16.71 | S A S F L Y S | |
| 31.ABI46748 | 0.145 | 0.091 | 37.24 | S A S F L Y S | |
| 32.ABI46748 | 0.153 | 0.097 | 36.60 | S A S F L Y S | |

L3 NNK 3rd sort linear diUb selected clones

| | no diUb | 25 nM | % inhibition | CDR L3<br>89          97<br>Q Q S Y T T P P T | Well |
|---|---|---|---|---|---|
| 55.ABI46748 | 0.146 | 0.117 | 19.86 | Q Q H Y T T P P T | |
| 64.ABI46748 | 0.147 | 0.069 | 53.06 | Q Q H Y T T P P T | |
| 43.ABI46748 | 0.289 | 0.183 | 36.68 | Q Q S K T T P P T | |
| 60.ABI46748 | 0.046 | 0.045 | 2.17 | Q Q S K T T P P T | |
| 88.ABI46748 | 0.207 | 0.202 | 2.42 | Q Q S K T T P P T | |
| 48.ABI46748 | 0.259 | 0.123 | 52.51 | Q Q S N T T P P T | |
| 54.ABI46748 | 0.118 | 0.1 | 15.25 | Q Q S Q T T P P T | |
| 38.ABI46748 | 0.79 | 0.563 | 28.73 | Q Q S R T T P P T | 2D2 |
| 47.ABI46748 | 0.282 | 0.105 | 62.77 | Q Q S R T T P P T | |
| 82.ABI46748 | 0.316 | 0.093 | 70.57 | Q Q S R T T P P T | |
| 96.ABI46748 | 0.198 | 0.094 | 52.53 | Q Q S R T T P P T | |
| 72.ABI46748 | 0.161 | 0.079 | 50.93 | Q Q S S T T P P T | |
| 50.ABI46748 | 0.451 | 0.128 | 71.62 | Q Q S V T T P P T | 2E2 |
| 57.ABI46748 | 0.117 | 0.085 | 27.35 | Q Q S W T T P P T | |
| 58.ABI46748 | 0.168 | 0.083 | 50.60 | Q Q S W T T P P T | |
| 63.ABI46748 | 0.422 | 0.172 | 59.24 | Q Q S Y I T P P T | |
| 51.ABI46748 | 0.142 | 0.117 | 17.61 | Q Q S Y Q T P P T | |
| 36.ABI46748 | 1.852 | 1.157 | 37.53 | Q Q S Y R T P P T | |
| 61.ABI46748 | 0.292 | 0.157 | 46.23 | Q Q S Y R T P P T | |
| 52.ABI46748 | 0.268 | 0.142 | 47.01 | Q Q S Y S T P P T | |
| 62.ABI46748 | 0.267 | 0.121 | 54.68 | Q Q S Y S T P P T | |
| 65.ABI46748 | 0.17 | 0.09 | 47.06 | Q Q S Y S T P P T | |
| 70.ABI46748 | 0.373 | 0.115 | 69.17 | Q Q S Y V T P P T | 2F10 |

TABLE 5-continued

| | no diUb | 25 nM | % inhibition | CDR L3 | Well |
|---|---|---|---|---|---|
| 33.ABI46748 | 1.414 | 0.93 | 34.23 | Q Q S Y T A P P T | 2C9 |
| 59.ABI46748 | 0.162 | 0.106 | 34.57 | Q Q S Y T A P P T | |
| 74.ABI46748 | 0.897 | 0.316 | 64.77 | Q Q S Y T A P P T | |
| 76.ABI46748 | 0.312 | 0.128 | 58.97 | Q Q S Y T A P P T | |
| 46.ABI46748 | 0.176 | 0.089 | 49.43 | Q Q S Y T D P P T | |
| 81.ABI46748 | 0.475 | 0.416 | 12.42 | Q Q S Y T F P P T | |
| 86.ABI46748 | 0.303 | 0.124 | 59.08 | Q Q S Y T F P P T | |
| 83.ABI46748 | 0.33 | 0.13 | 60.61 | Q Q S Y T G P P T | 2G11 |
| 91.ABI46748 | 0.212 | 0.094 | 55.66 | Q Q S Y T G P P T | |
| 80.ABI46748 | 0.236 | 0.122 | 48.31 | Q Q S Y T K P P T | |
| 34.ABI46748 | 0.136 | 0.088 | 35.29 | Q Q S Y T N P P T | |
| 40.ABI46748 | 0.216 | 0.109 | 49.54 | Q Q S Y T N P P T | |
| 71.ABI46748 | 0.128 | 0.081 | 36.72 | Q Q S Y T N P P T | |
| 75.ABI46748 | 0.353 | 0.134 | 62.04 | Q Q S Y T N P P T | |
| 77.ABI46748 | 0.175 | 0.078 | 55.43 | Q Q S Y T N P P T | |
| 89.ABI46748 | 0.54 | 0.122 | 77.41 | Q Q S Y T N P P T | 2H5 |
| 90.ABI46748 | 0.646 | 0.173 | 73.22 | Q Q S Y T N P P T | |
| 68.ABI46748 | 0.341 | 0.115 | 66.28 | Q Q S Y T P P P T | 2F8 |
| 35.ABI46748 | 0.527 | 0.146 | 72.30 | Q Q S Y T Q P P T | 2C11 |
| 45.ABI46748 | 0.166 | 0.077 | 53.61 | Q Q S Y T Q P P T | |
| 73.ABI46748 | 0.157 | 0.074 | 52.87 | Q Q S Y T Q P P T | |
| 41.ABI46748 | 0.156 | 0.107 | 31.41 | Q Q S Y T R P P T | |
| 53.ABI46748 | 0.137 | 0.089 | 35.04 | Q Q S Y T R P P T | |
| 69.ABI46748 | 0.154 | 0.096 | 37.66 | Q Q S Y T R P P T | |
| 78.ABI46748 | 0.104 | 0.071 | 31.73 | Q Q S Y T R P P T | |
| 95.ABI46748 | 0.261 | 0.103 | 60.54 | Q Q S Y T R P P T | |
| 39.ABI46748 | 0.265 | 0.103 | 61.13 | Q Q S Y T S P P T | |
| 42.ABI46748 | 0.148 | 0.587 | 48.87 | Q Q S Y T S P P T | |
| 49.ABI46748 | 0.439 | 0.128 | 70.84 | Q Q S Y T S P P T | 2E1 |
| 56.ABI46748 | 0.119 | 0.092 | 22.69 | Q Q S Y T S P P T | |
| 84.ABI46748 | 0.294 | 0.177 | 39.80 | Q Q S Y T S P P T | |
| 92.ABI46748 | 0.118 | 0.067 | 43.22 | Q Q S Y T S P P T | |
| 93.ABI46748 | 0.26 | 0.159 | 38.85 | Q Q S Y T S P P T | |
| 94.ABI46748 | 0.165 | 0.089 | 46.06 | Q Q S Y T S P P T | |
| 66.ABI46748 | 0.266 | 0.134 | 49.62 | Q Q S Y T V P P T | |
| 01.ABI46748 | 0.14 | 0.114 | 18.57 | Q Q S Y T T P P T | |
| 67.ABI46748 | 1.324 | 0.488 | 63.14 | Q Q S Y T T P P T | |
| 79.ABI46748 | 0.208 | 0.117 | 43.75 | Q Q S Y T T P P T | |
| 85.ABI46748 | 0.285 | 0.129 | 54.74 | Q Q S Y T T P P T | |
| 87.ABI46748 | 0.134 | 0.07 | 47.76 | Q Q S Y T T P P T | |

| H1 NNK 3rd sort linear diUb selected clones | | | | | |
|---|---|---|---|---|---|
| | | | | CDR H1 30 35 | |
| | no diUb | 25 nM | % inhibition | S N T Y I S | Well |
| 39.ABI46749 | 0.139 | 0.067 | 51.80 | A N T Y I S | |
| 05.ABI46749 | 0.372 | 0.115 | 69.09 | F N T Y I S | 3A5 |
| 04.ABI46749 | 0.21 | 0.149 | 29.05 | K N T Y I S | |
| 42.ABI46749 | 0.397 | 0.126 | 68.26 | K N T Y I S | 3D6 |
| 03.ABI46749 | 0.178 | 0.09 | 49.44 | M N T Y I S | |
| 20.ABI46749 | 0.161 | 0.096 | 40.37 | M N T Y I S | |
| 09.ABI46749 | 0.144 | 0.089 | 38.19 | Q N T Y I S | |
| 11.ABI46749 | 0.259 | 0.137 | 47.10 | Q N T Y I S | |
| 19.ABI46749 | 0.365 | 0.117 | 67.95 | Q N T Y I S | 3B7 |
| 63.ABI46749 | 0.121 | 0.088 | 27.27 | Q N T Y I S | |
| 08.ABI46749 | 0.194 | 0.093 | 52.06 | R N T Y I S | |
| 25.ABI46749 | 0.233 | 0.093 | 60.09 | R N T Y I S | |
| 26.ABI46749 | 0.112 | 0.082 | 26.79 | R N T Y I S | |
| 33.ABI46749 | 0.414 | 0.14 | 66.18 | R N T Y I S | 3C9 |
| 37.ABI46749 | 0.336 | 0.118 | 64.88 | R N T Y I S | |
| 50.ABI46749 | 0.332 | 0.126 | 62.05 | R N T Y I S | |
| 64.ABI46749 | 0.332 | 0.13 | 60.84 | R N T Y I S | |
| 12.ABI46749 | 0.183 | 0.095 | 48.09 | S W T Y I S | |
| 55.ABI46749 | 0.173 | 0.092 | 46.82 | S W T Y I S | |

TABLE 5-continued

| | no diUb | 25 nM | % inhibition | CDR H2 (91-96) S N X Y X S | Well |
|---|---|---|---|---|---|
| 31.ABI46749 | 0.131 | 0.089 | 32.06 | S N A Y I S | |
| 61.ABI46749 | 0.237 | 0.091 | 61.60 | S N I Y I S | 3F1 |
| 07.ABI46749 | 0.429 | 0.129 | 69.93 | S N L Y I S | 3A7 |
| 14.ABI46749 | 0.392 | 0.092 | 76.53 | S N L Y I S | |
| 15.ABI46749 | 0.177 | 0.09 | 49.15 | S N L Y I S | |
| 17.ABI46749 | 0.167 | 0.097 | 41.92 | S N L Y I S | |
| 18.ABI46749 | 1.717 | 0.636 | 62.96 | S N L Y I S | |
| 27.ABI46749 | 0.413 | 0.111 | 73.12 | S N L Y I S | |
| 28.ABI46749 | 0.228 | 0.092 | 59.65 | S N L Y I S | |
| 29.ABI46749 | 0.131 | 0.082 | 37.40 | S N L Y I S | |
| 43.ABI46749 | 0.217 | 0.096 | 55.76 | S N L Y I S | |
| 49.ABI46749 | 0.363 | 0.1 | 72.45 | S N L Y I S | |
| 53.ABI46749 | 0.121 | 0.066 | 45.45 | S N L Y I S | |
| 54.ABI46749 | 0.153 | 0.083 | 45.75 | S N L Y I S | |
| 56.ABI46749 | 0.137 | 0.096 | 29.93 | S N L Y I S | |
| 62.ABI46749 | 0.13 | 0.084 | 35.38 | S N L Y I S | |
| 38.ABI46749 | 0.391 | 0.118 | 69.82 | S N M Y I S | 3D2 |
| 21.ABI46749 | 0.135 | 0.101 | 25.19 | S N V Y I S | |
| 23.ABI46749 | 0.252 | 0.098 | 61.11 | S N V Y I S | 3B11 |
| 24.ABI46749 | 0.112 | 0.084 | 25.00 | S N V Y I S | |
| 30.ABI46749 | 0.118 | 0.086 | 27.12 | S N V Y I S | |
| 34.ABI46749 | 0.33 | 0.1 | 69.70 | S N V Y I S | |
| 36.ABI46749 | 0.16 | 0.099 | 38.13 | S N V Y I S | |
| 40.ABI46749 | 0.132 | 0.073 | 44.70 | S N V Y I S | |
| 44.ABI46749 | 0.136 | 0.098 | 27.94 | S N V Y I S | |
| 45.ABI46749 | 0.287 | 0.093 | 67.60 | S N V Y I S | |
| 60.ABI46749 | 1.114 | 0.484 | 56.55 | S N V Y I S | |
| 22.ABI46749 | 0.246 | 0.108 | 56.10 | S N T Y M S | |
| 52.ABI46749 | 0.435 | 0.12 | 72.41 | S N T Y M S | 3E4 |
| 57.ABI46749 | 0.163 | 0.097 | 40.49 | S N T Y M S | |
| 02.ABI46749 | 0.161 | 0.107 | 33.54 | S N T Y V S | |
| 41.ABI46749 | 0.145 | 0.102 | 29.66 | S N T Y V S | |
| 01.ABI46749 | 0.227 | 0.106 | 53.30 | S N T Y I S | |
| 06.ABI46749 | 0.117 | 0.065 | 44.44 | S N T Y I S | |
| 10.ABI46749 | 0.299 | 0.105 | 64.88 | S N T Y I S | |
| 13.ABI46749 | 0.154 | 0.097 | 37.01 | S N T Y I S | |
| 16.ABI46749 | 0.118 | 0.081 | 31.36 | S N T Y I S | |
| 32.ABI46749 | 0.127 | 0.082 | 35.43 | S N T Y I S | |
| 35.ABI46749 | 0.448 | 0.114 | 74.55 | S N T Y I S | |
| 46.ABI46749 | 0.103 | 0.062 | 39.81 | S N T Y I S | |
| 47.ABI46749 | 0.138 | 0.07 | 49.28 | S N T Y I S | |
| 48.ABI46749 | 0.276 | 0.144 | 47.83 | S N T Y I S | |
| 51.ABI46749 | 0.062 | 0.056 | 9.68 | S N T Y I S | |
| 58.ABI46749 | 0.059 | 0.356 | 39.66 | S N T Y I S | |
| 59.ABI46749 | 0.056 | 0.049 | 12.50 | S N T Y I S | |

H2 NNK 3rd sort linear diUb selected clones

| | no diUb | 25 nM | % inhibition | CDR H2 (49-58) A S I T P S S G S T D | Well |
|---|---|---|---|---|---|
| 84.ABI46749 | 0.108 | 0.081 | 25.00 | A T I T P S S G S T D | |
| 94.ABI46749 | 0.373 | 0.122 | 67.29 | A S S T P S S G S T D | 3H10 |
| 69.ABI46749 | 0.146 | 0.083 | 43.15 | A S V T P S S G S T D | |
| 74.ABI46749 | 0.168 | 0.097 | 42.26 | A S V T P S S G S T D | |
| 02.ABI46750 | 0.367 | 0.167 | 54.50 | A S V T P S S G S T D | |
| 07.ABI46750 | 0.346 | 0.168 | 51.45 | A S V T P S S G S T D | |
| 16.ABI46750 | 0.235 | 0.1515 | 35.74 | A S V T P S S G S T D | |
| 70.ABI46749 | 0.047 | 0.044 | 6.38 | A S I T P A S G S T D | |

TABLE 5-continued

| | no diUb | 25 nM | % inhibition | | | | | | | | | | | Well |
|---|---|---|---|---|---|---|---|---|---|---|---|---|---|---|
| 75.ABI46749 | 0.207 | 0.093 | 55.07 | A | S | I | T | P | S | S | G | H | T D | |
| 14.ABI46750 | 0.236 | 0.093 | 60.59 | A | S | I | T | P | S | S | G | H | T D | 4B2 |
| 93.ABI46749 | 0.236 | 0.091 | 61.44 | A | S | I | T | P | S | S | G | I | T D | 3H9 |
| 22.ABI46750 | 0.252 | 0.094 | 62.70 | A | S | I | T | P | S | S | G | L | T D | |
| 66.ABI46749 | 0.183 | 0.074 | 59.56 | A | S | I | T | P | S | S | G | L | T D | |
| 65.ABI46749 | 0.186 | 0.131 | 29.57 | A | S | I | T | P | S | S | G | M | T D | 3F5 |
| 72.ABI46749 | 0.102 | 0.089 | 12.75 | A | S | I | T | P | S | S | G | Q | T D | |
| 73.ABI46749 | 0.126 | 0.083 | 34.13 | A | S | I | T | P | S | S | G | Q | T D | |
| 81.ABI46749 | 0.261 | 0.11 | 57.85 | A | S | I | T | P | S | S | G | Q | T D | |
| 90.ABI46749 | 0.243 | 0.099 | 59.26 | A | S | I | T | P | S | S | G | Q | T D | |
| 92.ABI46749 | 0.144 | 0.084 | 41.67 | A | S | I | T | P | S | S | G | Q | T D | |
| 95.ABI46749 | 0.213 | 0.094 | 55.87 | A | S | I | T | P | S | S | G | Q | T D | |
| 96.ABI46749 | 0.243 | 0.154 | 36.63 | A | S | I | T | P | S | S | G | Q | T D | |
| 11.ABI46750 | 0.29 | 0.161 | 44.45 | A | S | I | T | P | S | S | G | Q | T D | |
| 19.ABI46750 | 0.34 | 0.191 | 43.82 | A | S | I | T | P | S | S | G | Q | T D | |
| 23.ABI46750 | 0.24 | 0.126 | 47.50 | A | S | I | T | P | S | S | G | Q | T D | |
| 29.ABI46750 | 0.47 | 0.162 | 65.53 | A | S | I | T | P | S | S | G | S | T N | 4C5 |
| 01.ABI46749 | 0.227 | 0.106 | 53.30 | A | S | I | T | P | S | S | G | S | T D | |
| 67.ABI46749 | 0.173 | 0.106 | 38.73 | A | S | I | T | P | S | S | G | S | T D | |
| 68.ABI46749 | 0.222 | 0.089 | 59.91 | A | S | I | T | P | S | S | G | S | T D | |
| 71.ABI46749 | 0.373 | 0.097 | 73.99 | A | S | I | T | P | S | S | G | S | T D | |
| 76.ABI46749 | 0.114 | 0.071 | 37.72 | A | S | I | T | P | S | S | G | S | T D | |
| 77.ABI46749 | 0.108 | 0.067 | 37.96 | A | S | I | T | P | S | S | G | S | T D | |
| 78.ABI46749 | 0.355 | 0.22 | 38.03 | A | S | I | T | P | S | S | G | S | T D | |
| 79.ABI46749 | 0.118 | 0.085 | 27.97 | A | S | I | T | P | S | S | G | S | T D | |
| 80.ABI46749 | 0.223 | 0.139 | 37.67 | A | S | I | T | P | S | S | G | S | T D | |
| 82.ABI46749 | 0.201 | 0.086 | 57.21 | A | S | I | T | P | S | S | G | S | T D | |
| 83.ABI46749 | 0.15 | 0.077 | 48.67 | A | S | I | T | P | S | S | G | S | T D | |
| 85.ABI46749 | 0.136 | 0.085 | 37.50 | A | S | I | T | P | S | S | G | S | T D | |
| 86.ABI46749 | 0.136 | 0.078 | 42.65 | A | S | I | T | P | S | S | G | S | T D | |
| 87.ABI46749 | 0.142 | 0.078 | 45.07 | A | S | I | T | P | S | S | G | S | T D | |
| 88.ABI46749 | 0.343 | 0.147 | 57.14 | A | S | I | T | P | S | S | G | S | T D | |
| 89.ABI46749 | 0.104 | 0.06 | 42.31 | A | S | I | T | P | S | S | G | S | T D | |
| 91.ABI46749 | 0.281 | 0.09 | 67.97 | A | S | I | T | P | S | S | G | S | T D | |
| 01.ABI46750 | 0.475 | 0.315 | 33.68 | A | S | I | T | P | S | S | G | S | T D | |
| 05.ABI46750 | 1.492 | 1.206 | 19.17 | A | S | I | T | P | S | S | G | S | T D | |
| 06.ABI46750 | 0.27 | 0.145 | 46.30 | A | S | I | T | P | S | S | G | S | T D | |
| 09.ABI46750 | 0.399 | 0.239 | 40.10 | A | S | I | T | P | S | S | G | S | T D | |
| 10.ABI46750 | 0.327 | 0.178 | 45.57 | A | S | I | T | P | S | S | G | S | T D | |
| 12.ABI46750 | 0.302 | 0.17 | 43.71 | A | S | I | T | P | S | S | G | S | T D | |
| 13.ABI46750 | 0.078 | 0.063 | 19.23 | A | S | I | T | P | S | S | G | S | T D | |
| 15.ABI46750 | 0.226 | 0.099 | 56.19 | A | S | I | T | P | S | S | G | S | T D | |
| 17.ABI46750 | 0.82 | 0.356 | 56.59 | A | S | I | T | P | S | S | G | S | T D | |
| 18.ABI46750 | 0.359 | 0.178 | 50.42 | A | S | I | T | P | S | S | G | S | T D | |
| 20.ABI46750 | 0.793 | 0.259 | 67.34 | A | S | I | T | P | S | S | G | S | T D | |
| 21.ABI46750 | 0.75 | 0.29 | 61.33 | A | S | I | T | P | S | S | G | S | T D | |
| 24.ABI46750 | 0.288 | 0.147 | 48.96 | A | S | I | T | P | S | S | G | S | T D | |
| 25.ABI46750 | 0.374 | 0.201 | 46.26 | A | S | I | T | P | S | S | G | S | T D | |
| 26.ABI46750 | 0.383 | 0.295 | 22.98 | A | S | I | T | P | S | S | G | S | T D | |
| 27.ABI46750 | 1.37 | 0.535 | 60.95 | A | S | I | T | P | S | S | G | S | T D | |
| 28.ABI46750 | 0.539 | 0.23 | 57.33 | A | S | I | T | P | S | S | G | S | T D | |
| 30.ABI46750 | 0.455 | 0.142 | 68.79 | A | S | I | T | P | S | S | G | S | T D | |
| 31.ABI46750 | 0.302 | 0.149 | 50.66 | A | S | I | T | P | S | S | G | S | T D | |
| 32.ABI46750 | 0.244 | 0.159 | 34.84 | A | S | I | T | P | S | S | G | S | T D | |

H3 NNK 3rd sort linear diUb selected clones

CDR H3

| | no diUb | 25 nM | % inhibition | 95<br>T | W | L | L | R | W | V | M | D | 102<br>Y | W | G | Q | G | T | L | V | T | V | 113<br>S | S | Well |
|---|---|---|---|---|---|---|---|---|---|---|---|---|---|---|---|---|---|---|---|---|---|---|---|---|---|
| 37.ABI46750 | 0.281 | 0.156 | 44.48 | S | W | L | L | R | W | V | M | D | Y | W | G | Q | G | T | L | V | T | V | S | S | |
| 81.ABI46750 | 0.175 | 0.061 | 65.14 | S | W | L | L | R | W | V | M | D | Y | W | G | Q | G | T | L | V | A | V | S | S | |
| 43.ABI46750 | 0.382 | 0.177 | 53.66 | T | W | Y | L | R | W | V | M | D | Y | W | G | Q | G | T | L | V | A | V | S | S | |
| 51.ABI46750 | 0.12 | 0.079 | 34.17 | T | W | Y | L | R | W | V | M | D | Y | W | G | Q | G | T | L | V | T | V | S | S | |
| 69.ABI46750 | 0.086 | 0.064 | 25.58 | T | W | Y | L | R | W | V | M | D | Y | W | G | Q | G | T | L | V | T | V | S | S | |
| 64.ABI46750 | 0.108 | 0.077 | 28.70 | T | W | L | I | R | W | V | M | D | Y | W | G | Q | G | T | L | V | T | V | S | S | |
| 82.ABI46750 | 0.388 | 0.106 | 72.68 | T | W | L | I | R | W | V | M | D | Y | W | G | Q | G | T | L | V | A | V | S | S | |
| 46.ABI46750 | 0.093 | 0.064 | 31.18 | T | W | L | V | R | W | V | M | D | Y | W | G | Q | G | T | L | V | T | V | S | S | |

TABLE 5-continued

| | | | | | |
|---|---|---|---|---|---|
| 34.ABI46750 | 0.366 | 0.187 | 48.91 | T W L L R W V F D Y W G Q G T L V A V S S | 4C10 |
| 38.ABI46750 | 1.464 | 1.273 | 13.05 | T W L L R W V F D Y W G Q G T L V A V S S | |
| 41.ABI46750 | 0.388 | 0.245 | 36.86 | T W L L R W V F D Y W G Q G T L V A V S S | |
| 47.ABI46750 | 0.272 | 0.155 | 43.01 | T W L L R W V F D Y W G Q G T L V A V S S | |
| 48.ABI46750 | 0.273 | 0.146 | 46.52 | T W L L R W V F D Y W G Q G T L V A V S S | |
| 50.ABI46750 | 0.319 | 0.091 | 71.47 | T W L L R W V F D Y W G Q G T L V A V S S | |
| 53.ABI46750 | 0.114 | 0.069 | 39.47 | T W L L R W V F D Y W G Q G T L V A V S S | |
| 55.ABI46750 | 0.403 | 0.131 | 67.49 | T W L L R W V F D Y W G Q G T L V A V S S | |
| 56.ABI46750 | 0.108 | 0.077 | 28.70 | T W L L R W V F D Y W G Q G T L V A V S S | |
| 59.ABI46750 | 0.134 | 0.076 | 43.28 | T W L L R W V F D Y W G Q G T L V A V S S | |
| 60.ABI46750 | 0.049 | 0.047 | 4.08 | T W L L R W V F D Y W G Q G T L V A V S S | |
| 61.ABI46750 | 0.059 | 0.053 | 10.17 | T W L L R W V F D Y W G Q G T L V A V S S | |
| 62.ABI46750 | 0.057 | 0.055 | 3.51 | T W L L R W V F D Y W G Q G T L V A V S S | |
| 66.ABI46750 | 0.117 | 0.087 | 25.64 | T W L L R W V F D Y W G Q G T L V A V S S | |
| 68.ABI46750 | 0.334 | 0.112 | 66.47 | T W L L R W V F D Y W G Q G T L V A V S S | |
| 70.ABI46750 | 0.237 | 0.109 | 54.01 | T W L L R W V F D Y W G Q G T L V A V S S | |
| 71.ABI46750 | 0.068 | 0.063 | 7.35 | T W L L R W V F D Y W G Q G T L V A V S S | |
| 74.ABI46750 | 0.127 | 0.075 | 40.94 | T W L L R W V F D Y W G Q G T L V A V S S | |
| 75.ABI46750 | 0.12 | 0.065 | 45.83 | T W L L R W V F D Y W G Q G T L V A V S S | |
| 78.ABI46750 | 0.103 | 0.07 | 32.04 | T W L L R W V F D Y W G Q G T L V A V S S | |
| 80.ABI46750 | 0.097 | 0.068 | 29.90 | T W L L R W V F D Y W G Q G T L V A V S S | |
| 83.ABI46750 | 0.127 | 0.072 | 43.31 | T W L L R W V F D Y W G Q G T L V A V S S | |
| 85.ABI46750 | 0.088 | 0.064 | 27.27 | T W L L R W V F D Y W G Q G T L V A V S S | |
| 86.ABI46750 | 0.058 | 0.049 | 15.52 | T W L L R W V F D Y W G Q G T L V A V S S | |
| 88.ABI46750 | 0.074 | 0.06 | 18.92 | T W L L R W V F D Y W G Q G T L V A V S S | |
| 92.ABI46750 | 0.112 | 0.077 | 31.25 | T W L L R W V F D Y W G Q G T L V A V S S | |
| 93.ABI46750 | 0.089 | 0.071 | 20.22 | T W L L R W V F D Y W G Q G T L V A V S S | |
| 94.ABI46750 | 0.062 | 0.05 | 19.35 | T W L L R W V F D Y W G Q G T L V A V S S | |
| 95.ABI46750 | 0.056 | 0.051 | 8.93 | T W L L R W V F D Y W G Q G T L V A V S S | |
| 96.ABI46750 | 0.083 | 0.074 | 10.84 | T W L L R W V F D Y W G Q G T L V A V S S | |
| 63.ABI46750 | 0.106 | 0.069 | 34.91 | T W L L R W V F D Y W G Q G T L V T V S S | 4F3 |
| 76.ABI46750 | 0.073 | 0.06 | 17.81 | T W L L R W V F D Y W G Q G T L V T V S S | |
| 89.ABI46750 | 0.136 | 0.101 | 25.74 | T W L L R W V F D Y W G Q G T L V T V S S | |
| 90.ABI46750 | 0.114 | 0.083 | 27.19 | T W L L R W V F D Y W G Q G T L V T V S S | |
| 91.ABI46750 | 0.096 | 0.071 | 26.04 | T W L L R W V L D Y W G Q G T L V T V S S | |
| 36.ABI46750 | 0.298 | 0.17 | 42.95 | T W L L R W V M D F W G Q G T L V A V S S | |
| 44.ABI46750 | 0.76 | 0.352 | 53.68 | T W L L R W V M D G W G Q G T L V A V S S | |
| 45.ABI46750 | 0.271 | 0.169 | 37.64 | T W L L R W V M D G W G Q G T L V T V S S | 4D9 |
| 42.ABI46750 | 0.384 | 0.224 | 41.67 | T W L L R W V M D G W G Q G T L V T V S S | |
| 67.ABI46750 | 0.211 | 0.1 | 52.61 | T W L L R W V M D G W G Q G T L V T V S S | |
| 77.ABI46750 | 0.109 | 0.082 | 24.77 | T W L L R W V M D G W G Q G T L V T V S S | |
| 79.ABI46750 | 0.111 | 0.072 | 35.14 | T W L L R W V M D G W G Q G T L V T V S S | 4G7 |
| 52.ABI46750 | 0.291 | 0.096 | 67.01 | T W L L R W V M D L W G Q G T L V A V S S | 4E4 |
| 39.ABI46750 | 0.75 | 0.376 | 49.87 | T W L L R W V M D L W G Q G T L V T V S S | |
| 33.ABI46750 | 0.458 | 0.201 | 56.11 | T W L L R W V M D M W G Q G T L V A V S S | 4C9 |
| 40.ABI46750 | 0.332 | 0.143 | 56.93 | T W L L R W V M D M W G Q G T L V A V S S | |
| 49.ABI46750 | 0.194 | 0.077 | 60.31 | T W L L R W V M D Y W G Q G T L V A V S S | 4E1 |
| 54.ABI46750 | 0.301 | 0.107 | 64.45 | T W L L R W V M D Y W G Q G T L V A V S S | |
| 57.ABI46750 | 0.111 | 0.067 | 39.64 | T W L L R W V M D Y W G Q G T L V A V S S | |
| 65.ABI46750 | 0.085 | 0.081 | 4.71 | T W L L R W V M D Y W G Q G T L V A V S S | |
| 01.ABI46750 | 0.475 | 0.315 | 33.68 | T W L L R W V M D Y W G Q G T L V T V S S | |
| 35.ABI46750 | 0.315 | 0.204 | 35.24 | T W L L R W V M D Y W G Q G T L V T V S S | |
| 58.ABI46750 | 0.116 | 0.075 | 35.34 | T W L L R W V M D Y W G Q G T L V T V S S | |
| 72.ABI46750 | 0.105 | 0.076 | 27.62 | T W L L R W V M D Y W G Q G T L V T V S S | |
| 73.ABI46750 | 0.123 | 0.091 | 26.02 | T W L L R W V M D Y W G Q G T L V T V S S | |
| 84.ABI46750 | 0.084 | 0.068 | 19.05 | T W L L R W V M D Y W G Q G T L V T V S S | |
| 87.ABI46750 | 0.108 | 0.07 | 35.19 | T W L L R W V M D Y W G Q G T L V T V S S | |

Table 6 discloses the CDR L1 sequences as SEQ ID NOS 1, 283, 50, 50, 50, 50, 50, 50, 50, 50, 50, 50, 50, 50, 50, 50, 50, 50, 50, 50, 50, 50, 284, 54, 285, 285-288, 55, 55, 55, 53, 289, 289, 290, 290, 290, 290, 290, 290-294, 327, 295, 295, 295, 295-297, 297, 1, 1, 1, 1, 1, 1 and 1, respectively, in order of appearance. Table 6 discloses the CDR L2 sequences as SEQ ID NOS 2, 298, 299, 60, 60, 300, 302-305, 305-307, 307, 307-309, 309, 309, 310, 310-314, 314, 314, 314, 314, 314, 314, 314, 314, 314, 314, 315, 2, 2, 2, 2, 2, 2, 2, 2, 2, 2, 2, 2, 2, 2 and 2, respectively, in order of appearance. Table 6 discloses the CDR L3 sequences as SEQ ID NOS 3, 6, 6, 6, 6, 6, 316-318, 318, 319, 66, 66, 320, 321, 321, 321, 321-324, 324, 324, 325, 301, 326, 301, 326, 382, 328, 328, 329, 64, 64, 330, 330, 331, 331, 331, 331, 331, 71, 71, 71, 71, 71, 71, 332, 69, 333, 333, 67, 67, 67, 67, 67, 334, 334, 334, 335, 335, 335, 3, 3, 3 and 3, respectively, in order of appearance. Table 6 discloses the CDR H1 sequences as SEQ ID NOS 255, 336, 337, 337, 337, 337, 337, 337, 337, 337, 337, 337, 337, 337-340, 340-343, 343, 343, 343, 343, 344, 344, 344, 344, 344, 344, 81, 81, 81, 81, 81, 81, 74, 74, 74, 74, 74, 74, 74, 74, 74, 74, 74, 74, 74, 74, 76, 76, 76, 76, 76, 76, 76, 76, 76, 76 and 255, respectively, in order of appearance. Table 6 discloses the CDR H2 sequences as SEQ ID NOS 8, 346, 347, 345, 348, 349, 349, 349, 349, 349, 349, 349, 349, 349, 349, 349, 349, 349-351, 351, 351, 351, 352, 352, 352, 353, 353, 353, 353, 353, 353, 353, 353, 353, 353, 353, 353, 353, 353, 353, 353, 353, 353, 353, 353, 353, 353, 353, 353, 353, 353, 353, 353, 353, 353, 353, 354, 8, 8, 8, 8, 8 and 8, respectively, in order of appearance. Table 6 discloses the CDR H3 sequences as SEQ ID NOS 355-358, 358, 359, 359-362, 362, 362, 362, 362, 362, 362, 362, 362, 362, 362, 362, 362, 362, 362, 362, 362, 362, 362, 362, 362, 362, 362, 362, 362, 362, 362, 362, 362, 362, 362-367, 355, 355, 355, 355, 355, 355, 355, 355, 355 and 355, respectively, in order of appearance. "0" is an ochre stop TAA and "q" is an amber stop TAG which can replaced by Gln (O) for example with the use of suppressor tRNA cell lines.

TABLE 6

L1 NNK 3rd sort K63 diUb selected clones

|  | 24 | | | | CDR L1 | | | | 34 | |
|---|---|---|---|---|---|---|---|---|---|---|
| 1E3 WT | R | A | S | Q | D | V | S | T | A | V | A |
| 26.ABI46771 | R | A | S | Q | K | V | S | T | A | V | A |
| 05.ABI46771 | R | A | S | Q | D | V | G | T | A | V | A |
| 07.ABI46771 | R | A | S | Q | D | V | G | T | A | V | A |
| 11.ABI46771 | R | A | S | Q | D | V | G | T | A | V | A |
| 22.ABI46771 | R | A | S | Q | D | V | G | T | A | V | A |
| 25.ABI46771 | R | A | S | Q | D | V | G | T | A | V | A |
| 28.ABI46771 | R | A | S | Q | D | V | G | T | A | V | A |
| 32.ABI46771 | R | A | S | Q | D | V | G | T | A | V | A |
| 36.ABI46771 | R | A | S | Q | D | V | G | T | A | V | A |
| 41.ABI46771 | R | A | S | Q | D | V | G | T | A | V | A |
| 48.ABI46771 | R | A | S | Q | D | V | G | T | A | V | A |
| 49.ABI46771 | R | A | S | Q | D | V | G | T | A | V | A |
| 50.ABI46771 | R | A | S | Q | D | V | G | T | A | V | A |
| 51.ABI46771 | R | A | S | Q | D | V | G | T | A | V | A |
| 52.ABI46771 | R | A | S | Q | D | V | G | T | A | V | A |
| 53.ABI46771 | R | A | S | Q | K | V | G | T | A | V | A |
| 54.ABI46771 | R | A | S | Q | D | V | G | T | A | V | A |
| 55.ABI46771 | R | A | S | Q | D | V | G | T | A | V | A |
| 57.ABI46771 | R | A | S | Q | D | V | G | T | A | V | A |
| 58.ABI46771 | R | A | S | Q | D | V | G | T | A | V | A |
| 62.ABI46771 | R | A | S | Q | D | V | G | T | A | V | A |
| 64.ABI46771 | R | A | S | Q | D | V | G | T | A | V | A |
| 42.ABI46771 | R | A | S | Q | D | V | H | T | A | V | A |
| 06.ABI46771 | R | A | S | Q | D | V | R | T | A | V | A |
| 18.ABI46771 | R | A | S | Q | D | V | V | T | A | V | A |
| 31.ABI46771 | R | A | S | Q | D | V | V | T | A | V | A |
| 20.ABI46771 | R | A | S | Q | D | V | Y | T | A | V | A |
| 16.ABI46771 | R | A | S | Q | D | V | S | A | A | V | A |
| 24.ABI46771 | R | A | S | Q | D | V | S | E | A | V | A |
| 39.ABI46771 | R | A | S | Q | D | V | S | G | A | V | A |
| 43.ABI46771 | R | A | S | Q | D | V | S | G | A | V | A |
| 47.ABI46771 | R | A | S | Q | D | V | S | G | A | V | A |
| 04.ABI46771 | R | A | S | Q | D | V | S | I | A | V | A |
| 34.ABI46771 | R | A | S | Q | D | V | S | K | A | V | A |
| 63.ABI46771 | R | A | S | Q | D | V | S | K | A | V | A |
| 09.ABI46771 | R | A | S | Q | D | V | S | O | A | V | A |
| 12.ABI46771 | R | A | S | Q | D | V | S | O | A | V | A |
| 27.ABI46771 | R | A | S | Q | D | V | S | O | A | V | A |
| 29.ABI46771 | R | A | S | Q | D | V | S | O | A | V | A |
| 35.ABI46771 | R | A | S | Q | D | V | S | O | A | V | A |
| 56.ABI46771 | R | A | S | Q | D | V | S | O | A | V | A |
| 33.ABI46771 | R | A | S | Q | D | V | S | P | A | V | A |
| 23.ABI46771 | R | A | S | Q | D | V | S | T | G | V | A |
| 30.ABI46771 | R | A | S | Q | D | V | S | T | K | V | A |
| 59.ABI46771 | R | A | S | Q | D | V | S | T | N | V | A |

TABLE 6-continued

| 08.ABI46771 | R | A | S | Q | D | V | S | T | q | V | A |
|---|---|---|---|---|---|---|---|---|---|---|---|
| 02.ABI46771 | R | A | S | Q | D | V | S | T | S | V | A |
| 10.ABI46771 | R | A | S | Q | D | V | S | T | S | V | A |
| 15.ABI46771 | R | A | S | Q | D | V | S | T | S | V | A |
| 40.ABI46771 | R | A | S | Q | D | V | S | T | S | V | A |
| 38.ABI46771 | R | A | S | Q | D | V | S | T | A | L | A |
| 17.ABI46771 | R | A | S | Q | D | V | S | T | A | S | A |
| 61.ABI46771 | R | A | S | Q | D | V | S | T | A | S | A |
| 03.ABI46771 | R | A | S | Q | D | V | S | T | A | V | A |
| 13.ABI46771 | R | A | S | Q | D | V | S | T | A | V | A |
| 14.ABI46771 | R | A | S | Q | D | V | S | T | A | V | A |
| 21.ABI46771 | R | A | S | Q | D | V | S | T | A | V | A |
| 45.ABI46771 | R | A | S | Q | D | V | S | T | A | V | A |
| 46.ABI46771 | R | A | S | Q | D | V | S | T | A | V | A |
| 60.ABI46771 | R | A | S | Q | D | V | S | T | A | V | A |

L2 NNK 3rd sort K63 diUb selected clones

|  | 50 | | CDR L2 | | | 56 |
|---|---|---|---|---|---|---|
| 1E3 WT | S | A | S | F | L | Y | S |
| 25.ABI46772 | S | K | S | F | L | Y | S |
| 81.ABI46771 | S | A | A | F | L | Y | S |
| 82.ABI46771 | S | A | R | F | L | Y | S |
| 17.ABI46772 | S | A | R | F | L | Y | S |
| 84.ABI46771 | S | A | S | G | L | Y | S |
| 72.ABI46771 | S | A | S | O | L | Y | S |
| 75.ABI46771 | S | A | S | O | L | Y | S |
| 77.ABI46771 | S | A | S | O | L | Y | S |
| 90.ABI46771 | S | A | S | O | L | Y | S |
| 03.ABI46772 | S | A | S | O | L | Y | S |
| 09.ABI46772 | S | A | S | O | L | Y | S |
| 20.ABI46772 | S | A | S | O | L | Y | S |
| 21.ABI46772 | S | A | S | O | L | Y | S |
| 24.ABI46772 | S | A | S | O | L | Y | S |
| 26.ABI46772 | S | A | S | O | L | Y | S |
| 30.ABI46772 | S | A | S | Y | L | Y | S |
| 83.ABI46771 | S | A | S | F | K | Y | S |
| 06.ABI46772 | S | A | S | F | M | Y | S |
| 79.ABI46771 | S | A | S | F | Q | Y | S |
| 18.ABI46772 | S | A | S | F | Q | Y | S |
| 78.ABI46771 | S | A | S | F | R | Y | S |
| 67.ABI46771 | S | A | S | F | V | Y | S |
| 14.ABI46772 | S | A | S | F | V | Y | S |
| 27.ABI46772 | S | A | S | F | V | Y | S |
| 28.ABI46772 | S | A | S | F | L | Y | A |
| 71.ABI46771 | S | A | S | F | L | Y | D |
| 73.ABI46771 | S | A | S | F | L | Y | D |
| 32.ABI46772 | S | A | S | F | L | Y | D |
| 68.ABI46771 | S | A | S | F | L | Y | E |
| 69.ABI46771 | S | A | S | F | L | Y | E |
| 10.ABI46772 | S | A | S | F | L | Y | N |
| 94.ABI46771 | S | A | S | F | L | Y | q |
| 11.ABI46772 | S | A | S | F | L | Y | R |
| 74.ABI46771 | S | A | S | F | L | Y | W |
| 80.ABI46771 | S | A | S | F | L | Y | W |
| 89.ABI46771 | S | A | S | F | L | Y | W |
| 91.ABI46771 | S | A | S | F | L | Y | W |
| 93.ABI46771 | S | A | S | F | L | Y | W |
| 96.ABI46771 | S | A | S | F | L | Y | W |
| 13.ABI46772 | S | A | S | F | L | Y | W |
| 15.ABI46772 | S | A | S | F | L | Y | W |
| 16.ABI46772 | S | A | S | F | L | Y | W |
| 23.ABI46772 | S | A | S | F | L | Y | W |
| 31.ABI46772 | S | A | S | F | L | Y | W |
| 19.ABI46772 | S | A | S | F | L | Y | Y |
| 65.ABI46771 | S | A | S | F | L | Y | S |

TABLE 6-continued

| | | | | | | | |
|---|---|---|---|---|---|---|---|
| 70.ABI46771 | S | A | S | F | L | Y | S |
| 76.ABI46771 | S | A | S | F | L | Y | S |
| 85.ABI46771 | S | A | S | F | L | Y | S |
| 86.ABI46771 | S | A | S | F | L | Y | S |
| 87.ABI46771 | S | A | S | F | L | Y | S |
| 88.ABI46771 | S | A | S | F | L | Y | S |
| 92.ABI46771 | S | A | S | F | L | Y | S |
| 95.ABI46771 | S | A | S | F | L | Y | S |
| 01.ABI46772 | S | A | S | F | L | Y | S |
| 02.ABI46772 | S | A | S | F | L | Y | S |
| 04.ABI46772 | S | A | S | F | L | Y | S |
| 07.ABI46772 | S | A | S | F | L | Y | S |
| 08.ABI46772 | S | A | S | F | L | Y | S |
| 12.ABI46772 | S | A | S | F | L | Y | S |
| 22.ABI46772 | S | A | S | F | L | Y | S |
| 29.ABI46772 | S | A | S | F | L | Y | S |

L3 NNK 3rd sort K63 diUb selected clones

| | 89 | | CDR | | L3 | | 97 | |
|---|---|---|---|---|---|---|---|---|
| 1E3 WT | Q | Q | S | Y | T | T | P | P | T |
| 46.ABI46772 | Q | Q | H | Y | T | T | P | P | T |
| 66.ABI46772 | Q | Q | H | Y | T | T | P | P | T |
| 71.ABI46772 | Q | Q | H | Y | T | T | P | P | T |
| 75.ABI46772 | Q | Q | H | Y | T | T | P | P | T |
| 76.ABI46772 | Q | Q | H | Y | T | T | P | P | T |
| 80.ABI46772 | Q | Q | P | Y | T | T | P | P | T |
| 90.ABI46772 | Q | Q | S | A | T | T | P | P | T |
| 41.ABI46772 | Q | Q | S | F | T | T | P | P | T |
| 70.ABI46772 | Q | Q | S | F | T | T | P | P | T |
| 85.ABI46772 | Q | Q | S | L | T | T | P | P | T |
| 33.ABI46772 | Q | Q | S | R | T | T | P | P | T |
| 58.ABI46772 | Q | Q | S | R | T | T | P | P | T |
| 45.ABI46772 | Q | Q | S | V | T | T | P | P | T |
| 49.ABI46772 | Q | Q | S | W | T | T | P | P | T |
| 50.ABI46772 | Q | Q | S | W | T | T | P | P | T |
| 61.ABI46772 | Q | Q | S | W | T | T | P | P | T |
| 65.ABI46772 | Q | Q | S | W | T | T | P | P | T |
| 48.ABI46772 | Q | Q | S | Y | E | T | P | P | T |
| 60.ABI46772 | Q | Q | S | Y | G | T | P | P | T |
| 55.ABI46772 | Q | Q | S | Y | I | T | P | P | T |
| 91.ABI46772 | Q | Q | S | Y | I | T | P | P | T |
| 94.ABI46772 | Q | Q | S | Y | I | T | P | P | T |
| 64.ABI46772 | Q | Q | S | Y | N | T | P | P | T |
| 39.ABI46772 | Q | Q | S | Y | O | T | P | P | T |
| 47.ABI46772 | Q | Q | S | Y | O | T | P | P | T |
| 83.ABI46772 | Q | Q | S | Y | q | T | P | P | T |
| 73.ABI46772 | Q | Q | S | Y | R | T | P | P | T |
| 86.ABI46772 | Q | Q | S | Y | R | T | P | P | T |
| 35.ABI46772 | Q | Q | S | Y | S | T | P | P | T |
| 63.ABI46772 | Q | Q | S | Y | T | A | P | P | T |
| 93.ABI46772 | Q | Q | S | Y | T | A | P | P | T |
| 68.ABI46772 | Q | Q | S | Y | T | D | P | P | T |
| 92.ABI46772 | Q | Q | S | Y | T | D | P | P | T |
| 37.ABI46772 | Q | Q | S | Y | T | E | P | P | T |
| 40.ABI46772 | Q | Q | S | Y | T | E | P | P | T |
| 43.ABI46772 | Q | Q | S | Y | T | E | P | P | T |
| 69.ABI46772 | Q | Q | S | Y | T | E | P | P | T |
| 96.ABI46772 | Q | Q | S | Y | T | E | P | P | T |
| 44.ABI46772 | Q | Q | S | Y | T | G | P | P | T |
| 59.ABI46772 | Q | Q | S | Y | T | G | P | P | T |
| 72.ABI46772 | Q | Q | S | Y | T | G | P | P | T |
| 81.ABI46772 | Q | Q | S | Y | T | G | P | P | T |
| 87.ABI46772 | Q | Q | S | Y | T | G | P | P | T |
| 95.ABI46772 | Q | Q | S | Y | T | G | P | P | T |
| 78.ABI46772 | Q | Q | S | Y | T | M | P | P | T |
| 62.ABI46772 | Q | Q | S | Y | T | P | P | P | T |
| 88.ABI46772 | Q | Q | S | Y | T | R | P | P | T |
| 89.ABI46772 | Q | Q | S | Y | T | R | P | P | T |
| 34.ABI46772 | Q | Q | S | Y | T | S | P | P | T |
| 38.ABI46772 | Q | Q | S | Y | T | S | P | P | T |
| 57.ABI46772 | Q | Q | S | Y | T | S | P | P | T |
| 74.ABI46772 | Q | Q | S | Y | T | S | P | P | T |
| 79.ABI46772 | Q | Q | S | Y | T | S | P | P | T |
| 42.ABI46772 | Q | Q | S | Y | T | V | P | P | T |
| 51.ABI46772 | Q | Q | S | Y | T | V | P | P | T |
| 84.ABI46772 | Q | Q | S | Y | T | V | P | P | T |
| 36.ABI46772 | Q | Q | S | Y | T | Y | P | P | T |
| 52.ABI46772 | Q | Q | S | Y | T | Y | P | P | T |
| 77.ABI46772 | Q | Q | S | Y | T | Y | P | P | T |
| 54.ABI46772 | Q | Q | S | Y | T | T | P | P | T |
| 56.ABI46772 | Q | Q | S | Y | T | T | P | P | T |
| 67.ABI46772 | Q | Q | S | Y | T | T | P | P | T |
| 82.ABI46772 | Q | Q | S | Y | T | T | P | P | T |

H1 NNK 3rd sort K63 diUb selected clones

| | 30 | | CDR | H1 | | 35 |
|---|---|---|---|---|---|---|
| 1E3 WT | S | N | T | Y | I | S |
| 40.ABI46773 | A | N | T | Y | I | S |
| 06.ABI46773 | E | N | T | Y | I | S |
| 09.ABI46773 | E | N | T | Y | I | S |
| 13.ABI46773 | E | N | T | Y | I | S |
| 14.ABI46773 | E | N | T | Y | I | S |
| 17.ABI46773 | E | N | T | Y | I | S |
| 22.ABI46773 | E | N | T | Y | I | S |
| 27.ABI46773 | E | N | T | Y | I | S |
| 29.ABI46773 | E | N | T | Y | I | S |
| 33.ABI46773 | E | N | T | Y | I | S |
| 35.ABI46773 | E | N | T | Y | I | S |
| 43.ABI46773 | E | N | T | Y | I | S |
| 52.ABI46773 | E | N | T | Y | I | S |
| 62.ABI46773 | E | N | T | Y | I | S |
| 19.ABI46773 | G | N | T | Y | I | S |
| 23.ABI46773 | H | N | T | Y | I | S |
| 05.ABI46773 | L | N | T | Y | I | S |
| 61.ABI46773 | L | N | T | Y | I | S |
| 47.ABI46773 | N | N | T | Y | I | S |
| 32.ABI46773 | S | Q | T | Y | I | S |
| 02.ABI46773 | S | W | T | Y | I | S |
| 03.ABI46773 | S | W | T | Y | I | S |
| 31.ABI46773 | S | W | T | Y | I | S |
| 36.ABI46773 | S | W | T | Y | I | S |
| 44.ABI46773 | S | W | T | Y | I | S |
| 48.ABI46773 | S | W | T | Y | I | S |
| 07.ABI46773 | S | Y | T | Y | I | S |
| 08.ABI46773 | S | Y | T | Y | I | S |
| 10.ABI46773 | S | Y | T | Y | I | S |
| 58.ABI46773 | S | Y | T | Y | I | S |
| 59.ABI46773 | S | Y | T | Y | I | S |
| 63.ABI46773 | S | Y | T | Y | I | S |
| 04.ABI46773 | S | N | I | Y | I | S |
| 12.ABI46773 | S | N | I | Y | I | S |
| 21.ABI46773 | S | N | I | Y | I | S |
| 51.ABI46773 | S | N | I | Y | I | S |
| 54.ABI46773 | S | N | I | Y | I | S |
| 60.ABI46773 | S | N | I | Y | I | S |

TABLE 6-continued

| | | | | | | |
|---|---|---|---|---|---|---|
| 11.ABI46773 | S | N | L | Y | I | S |
| 15.ABI46773 | S | N | L | Y | I | S |
| 16.ABI46773 | S | N | L | Y | I | S |
| 18.ABI46773 | S | N | L | Y | I | S |
| 20.ABI46773 | S | N | L | Y | I | S |
| 26.ABI46773 | S | N | L | Y | I | S |
| 38.ABI46773 | S | N | L | Y | I | S |
| 39.ABI46773 | S | N | L | Y | I | S |
| 41.ABI46773 | S | N | L | Y | I | S |
| 42.ABI46773 | S | N | L | Y | I | S |
| 46.ABI46773 | S | N | L | Y | I | S |
| 55.ABI46773 | S | N | L | Y | I | S |
| 56.ABI46773 | S | N | L | Y | I | S |
| 57.ABI46773 | S | N | L | Y | I | S |
| 50.ABI46773 | S | N | O | Y | I | S |
| 24.ABI46773 | S | N | V | Y | I | S |
| 25.ABI46773 | S | N | V | Y | I | S |
| 28.ABI46773 | S | N | V | Y | I | S |
| 30.ABI46773 | S | N | V | Y | I | S |
| 34.ABI46773 | S | N | V | Y | I | S |
| 37.ABI46773 | S | N | V | Y | I | S |
| 45.ABI46773 | S | N | V | Y | I | S |
| 49.ABI46773 | S | N | V | Y | I | S |
| 53.ABI46773 | S | N | V | Y | I | S |
| 64.ABI46773 | S | N | V | Y | I | S |
| 01.ABI46773 | S | N | T | Y | I | S |

H2 NNK 3rd sort K63 diUb selected clones

| | 49 | | | CDR | H2 | | | | | 58 |
|---|---|---|---|---|---|---|---|---|---|---|
| 1E3 WT | A | S | I | T | P | S | S | G | S | T | D |
| 09.ABI46774 | A | S | P | T | P | S | S | G | S | T | D |
| 74.ABI46773 | A | S | V | T | P | S | S | G | S | T | D |
| 13.ABI46774 | A | S | I | T | P | O | S | G | S | T | D |
| 65.ABI46773 | A | S | I | T | P | S | F | G | S | T | D |
| 78.ABI46773 | A | S | I | T | P | S | F | G | S | T | D |
| 81.ABI46773 | A | S | I | T | P | S | F | G | S | T | D |
| 84.ABI46773 | A | S | I | T | P | S | F | G | S | T | D |
| 86.ABI46773 | A | S | I | T | P | S | F | G | S | T | D |
| 06.ABI46774 | A | S | I | T | P | S | F | G | S | T | D |
| 08.ABI46774 | A | S | I | T | P | S | F | G | S | T | D |
| 10.ABI46774 | A | S | I | T | P | S | F | G | S | T | D |
| 16.ABI46774 | A | S | I | T | P | S | F | G | S | T | D |
| 20.ABI46774 | A | S | I | T | P | S | F | G | S | T | D |
| 26.ABI46774 | A | S | I | T | P | S | F | G | S | T | D |
| 28.ABI46774 | A | S | I | T | P | S | F | G | S | T | D |
| 29.ABI46774 | A | S | I | T | P | S | F | G | S | T | D |
| 12.ABI46774 | A | S | I | T | P | S | H | G | S | T | D |
| 71.ABI46773 | A | S | I | T | P | S | L | G | S | T | D |
| 72.ABI46773 | A | S | I | T | P | S | L | G | S | T | D |
| 88.ABI46773 | A | S | I | T | P | S | L | G | S | T | D |
| 32.ABI46774 | A | S | I | T | P | S | L | G | S | T | D |
| 14.ABI46774 | A | S | I | T | P | S | W | G | S | T | D |
| 24.ABI46774 | A | S | I | T | P | S | W | G | S | T | D |
| 31.ABI46774 | A | S | I | T | P | S | W | G | S | T | D |
| 66.ABI46773 | A | S | I | T | P | S | Y | G | S | T | D |
| 67.ABI46773 | A | S | I | T | P | S | Y | G | S | T | D |
| 69.ABI46773 | A | S | I | T | P | S | Y | G | S | T | D |
| 70.ABI46773 | A | S | I | T | P | S | Y | G | S | T | D |
| 73.ABI46773 | A | S | I | T | P | S | Y | G | S | T | D |
| 75.ABI46773 | A | S | I | T | P | S | Y | G | S | T | D |
| 76.ABI46773 | A | S | I | T | P | S | Y | G | S | T | D |
| 77.ABI46773 | A | S | I | T | P | S | Y | G | S | T | D |
| 79.ABI46773 | A | S | I | T | P | S | Y | G | S | T | D |
| 80.ABI46773 | A | S | I | T | P | S | Y | G | S | T | D |
| 82.ABI46773 | A | S | I | T | P | S | Y | G | S | T | D |
| 83.ABI46773 | A | S | I | T | P | S | Y | G | S | T | D |
| 85.ABI46773 | A | S | I | T | P | S | Y | G | S | T | D |
| 87.ABI46773 | A | S | I | T | P | S | Y | G | S | T | D |
| 90.ABI46773 | A | S | I | T | P | S | Y | G | S | T | D |
| 91.ABI46773 | A | S | I | T | P | S | Y | G | S | T | D |
| 92.ABI46773 | A | S | I | T | P | S | Y | G | S | T | D |
| 93.ABI46773 | A | S | I | T | P | S | Y | G | S | T | D |
| 94.ABI46773 | A | S | I | T | P | S | Y | G | S | T | D |
| 95.ABI46773 | A | S | I | T | P | S | Y | G | S | T | D |
| 02.ABI46774 | A | S | I | T | P | S | Y | G | S | T | D |
| 03.ABI46774 | A | S | I | T | P | S | Y | G | S | T | D |
| 04.ABI46774 | A | S | I | T | P | S | Y | G | S | T | D |
| 05.ABI46774 | A | S | I | T | P | S | Y | G | S | T | D |
| 07.ABI46774 | A | S | I | T | P | S | Y | G | S | T | D |
| 11.ABI46774 | A | S | I | T | P | S | Y | G | S | T | D |
| 15.ABI46774 | A | S | I | T | P | S | Y | G | S | T | D |
| 17.ABI46774 | A | S | I | T | P | S | Y | G | S | T | D |
| 19.ABI46774 | A | S | I | T | P | S | Y | G | S | T | D |
| 22.ABI46774 | A | S | I | T | P | S | Y | G | S | T | D |
| 23.ABI46774 | A | S | I | T | P | S | Y | G | S | T | D |
| 27.ABI46774 | A | S | I | T | P | S | Y | G | S | T | D |
| 30.ABI46774 | A | S | I | T | P | S | Y | G | S | T | D |
| 18.ABI46774 | A | S | I | T | P | S | S | G | Q | T | D |
| 68.ABI46773 | A | S | I | T | P | S | S | G | S | T | D |
| 89.ABI46773 | A | S | I | T | P | S | S | G | S | T | D |
| 96.ABI46773 | A | S | I | T | P | S | S | G | S | T | D |
| 01.ABI46774 | A | S | I | T | P | S | S | G | S | T | D |
| 21.ABI46774 | A | S | I | T | P | S | S | G | S | T | D |
| 25.ABI46774 | A | S | I | T | P | S | S | G | S | T | D |

H3 NNK 3rd sort K63 diUb selected clones

| | 95 | | | CDR | H3 | | | | 102 | | | | | | | 113 |
|---|---|---|---|---|---|---|---|---|---|---|---|---|---|---|---|---|
| 1E3 WT | T | W | L | L | R | W | V | M | D | Y | W | G | Q | G | T | L | V | T | V | S | S |
| 75.ABI46774 | T | I | L | L | R | W | V | M | D | Y | W | G | Q | G | T | L | V | T | V | S | S |
| 40.ABI46774 | T | W | Y | L | R | W | V | M | D | Y | W | G | Q | G | T | L | V | T | V | S | S |
| 54.ABI46774 | T | W | Y | L | R | W | V | M | D | Y | W | G | Q | G | T | L | V | A | V | S | S |
| 55.ABI46774 | T | W | Y | L | R | W | V | M | D | Y | W | G | Q | G | T | L | V | A | V | S | S |
| 47.ABI46774 | T | W | L | I | R | W | V | M | D | Y | W | G | Q | G | T | L | V | T | V | S | S |
| 88.ABI46774 | T | W | L | I | R | W | V | M | D | Y | W | G | Q | G | T | L | V | T | V | S | S |
| 89.ABI46774 | T | W | L | I | R | W | V | M | D | Y | W | G | Q | G | T | L | V | A | V | S | S |
| 57.ABI46774 | T | W | L | L | R | G | V | M | D | Y | W | G | Q | G | T | L | V | T | V | S | S |
| 33.ABI46774 | T | W | L | L | R | W | V | F | D | Y | W | G | Q | G | T | L | V | A | V | S | S |
| 34.ABI46774 | T | W | L | L | R | W | V | F | D | Y | W | G | Q | G | T | L | V | A | V | S | S |
| 35.ABI46774 | T | W | L | L | R | W | V | F | D | Y | W | G | Q | G | T | L | V | A | V | S | S |
| 36.ABI46774 | T | W | L | L | R | W | V | F | D | Y | W | G | Q | G | T | L | V | A | V | S | S |
| 37.ABI46774 | T | W | L | L | R | W | V | F | D | Y | W | G | Q | G | T | L | V | A | V | S | S |
| 42.ABI46774 | T | W | L | L | R | W | V | F | D | Y | W | G | Q | G | T | L | V | A | V | S | S |
| 43.ABI46774 | T | W | L | L | R | W | V | F | D | Y | W | G | Q | G | T | L | V | A | V | S | S |
| 44.ABI46774 | T | W | L | L | R | W | V | F | D | Y | W | G | Q | G | T | L | V | A | V | S | S |
| 45.ABI46774 | T | W | L | L | R | W | V | F | D | Y | W | G | Q | G | T | L | V | A | V | S | S |
| 46.ABI46774 | T | W | L | L | R | W | V | F | D | Y | W | G | Q | G | T | L | V | A | V | S | S |
| 48.ABI46774 | T | W | L | L | R | W | V | F | D | Y | W | G | Q | G | T | L | V | A | V | S | S |
| 49.ABI46774 | T | W | L | L | R | W | V | F | D | Y | W | G | Q | G | T | L | V | A | V | S | S |
| 51.ABI46774 | T | W | L | L | R | W | V | F | D | Y | W | G | Q | G | T | L | V | A | V | S | S |
| 53.ABI46774 | T | W | L | L | R | W | V | F | D | Y | W | G | Q | G | T | L | V | A | V | S | S |
| 56.ABI46774 | T | W | L | L | R | W | V | F | D | Y | W | G | Q | G | T | L | V | A | V | S | S |
| 59.ABI46774 | T | W | L | L | R | W | V | F | D | Y | W | G | Q | G | T | L | V | A | V | S | S |
| 61.ABI46774 | T | W | L | L | R | W | V | F | D | Y | W | G | Q | G | T | L | V | A | V | S | S |
| 62.ABI46774 | T | W | L | L | R | W | V | F | D | Y | W | G | Q | G | T | L | V | A | V | S | S |
| 64.ABI46774 | T | W | L | L | R | W | V | F | D | Y | W | G | Q | G | T | L | V | A | V | S | S |
| 65.ABI46774 | T | W | L | L | R | W | V | F | D | Y | W | G | Q | G | T | L | V | A | V | S | S |
| 66.ABI46774 | T | W | L | L | R | W | V | F | D | Y | W | G | Q | G | T | L | V | A | V | S | S |
| 68.ABI46774 | T | W | L | L | R | W | V | F | D | Y | W | G | Q | G | T | L | V | A | V | S | S |
| 69.ABI46774 | T | W | L | L | R | W | V | F | D | Y | W | G | Q | G | T | L | V | A | V | S | S |
| 70.ABI46774 | T | W | L | L | R | W | V | F | D | Y | W | G | Q | G | T | L | V | A | V | S | S |
| 72.ABI46774 | T | W | L | L | R | W | V | F | D | Y | W | G | Q | G | T | L | V | A | V | S | S |
| 73.ABI46774 | T | W | L | L | R | W | V | F | D | Y | W | G | Q | G | T | L | V | A | V | S | S |
| 76.ABI46774 | T | W | L | L | R | W | V | F | D | Y | W | G | Q | G | T | L | V | A | V | S | S |
| 78.ABI46774 | T | W | L | L | R | W | V | F | D | Y | W | G | Q | G | T | L | V | A | V | S | S |

TABLE 6-continued

```
80.ABI46774 T W L L R W V F D Y W G Q G T L V A V S S
81.ABI46774 T W L L R W V F D Y W G Q G T L V A V S S
82.ABI46774 T W L L R W V F D Y W G Q G T L V A V S S
83.ABI46774 T W L L R W V F D Y W G Q G T L V A V S S
85.ABI46774 T W L L R W V F D Y W G Q G T L V A V S S
87.ABI46774 T W L L R W V F D Y W G Q G T L V A V S S
90.ABI46774 T W L L R W V F D Y W G Q G T L V A V S S
92.ABI46774 T W L L R W V F D Y W G Q G T L V A V S S
95.ABI46774 T W L L R W V F D Y W G Q G T L V A V S S
96.ABI46774 T W L L R W V F D Y W G Q G T L V A V S S
93.ABI46774 T W L L R W V L D Y W G Q G T L V T V S S
58.ABI46774 T W L L R W V W D Y W G Q G T L V T V S S
39.ABI46774 T W L L R W V M D A W G Q G T L V T V S S
79.ABI46774 T W L L R W V M D Q W G Q G T L V A V S S
52.ABI46774 T W L L R W V M D Y W G Q G T L V A V S S
38.ABI46774 T W L L R W V M D Y W G Q G T L V T V S S
60.ABI46774 T W L L R W V M D Y W G Q G T L V A V S S
63.ABI46774 T W L L R W V M D Y W G Q G T L V A V S S
67.ABI46774 T W L L R W V M D Y W G Q G T L V T V S S
71.ABI46774 T W L L R W V M D Y W G Q G T L V T V S S
77.ABI46774 T W L L R W V M D Y W G Q G T L V T V S S
84.ABI46774 T W L L R W V M D Y W G Q G T L V T V S S
86.ABI46774 T W L L R W V M D Y W G Q G T L V T V S S
91.ABI46774 T W L L R W V M D Y W G Q G T L V T V S S
94.ABI46774 T W L L R W V M D Y W G Q G T L V T V S S
```

E) Phage $IC_{50}$ ELISA

Eight clones from the L1 library, six from the L2 library, nine from the L3 library, nine from the H1 library, five from the H2 library, and seven from the H3 library were tested in a phage $IC_{50}$ ELISA as described in example 1D. Eight three-fold serial dilutions of linear diubiquitin (Boston Biochem) from 500 nM to 0.23 nM were used. In each experiment the WT 1E3 clone was included for comparison. The $IC_{50}$ value for 1E3 varies between experiments, however clones which show higher affinity for linear diubiquitin than the parental clone can be identified. In an attempt to identify mutants with improved affinity for linear diubiquitin with minimal K63 diubiquitin binding, clones that were tested in the $IC_{50}$ ELISA were narrowed down by taking into account whether they had improved $IC_{50}$ values compared to the parental 1E3, whether they were isolated in the K63-linked diubiquitin sort (example 3C), as well as their signal for binding to K63-linked diubiquitin in the phage spot ELISA (example 3C). Clones with improved $IC_{50}$ values compared to 1E3 that were isolated multiple times in the linear diubiquitin sort but were not isolated in the K63-linked diubiquitin sort and demonstrated no K63-linked diubiquitin binding in the spot ELISA ($OD_{450}$ of less than 0.1) were selected for further analysis (1F11, 2A2, 2C11, 2H5, 3E4, 4C9, 4E4, and 4G7) (see Table 7). If a clone with an improved $IC_{50}$ that was isolated multiple times in the linear diubiquitin sort, was isolated only once in the K63-linked diubiquitin sort, and demonstrated no K63-linked diubiquitin binding in the phage spot ELISA, then it was considered for further analysis (3F5) (see Table 7). Clones 3A7 and 4C10 which were isolated multiple times in both the linear diubiquitin and the K63-linked diubiquitin sorts were chosen as negative controls. These 11 clones along with 1E3 were tested further in a phage specificity ELISA. Table 7 below shows the CDR L1, L2, L3, H1, H2 and H3 sequences of clones from the sorting of the 1E3 L1, L2, L3, H1, H2 and H3 NNK libraries, respectively, against linear diubiquitin that were further characterized by phage $IC_{50}$ ELISA. The $IC_{50}$ and the fold improvement over the parental 1E3 $IC_{50}$ is given. Binding to K63-linked diubiquitin is defined as having an $OD_{450}$ of greater than 0.1 in the phage spot ELISA. Also shown is the percent inhibition in binding in the presence of 25 nM soluble linear diubiquitin in the phage spot competition ELISA. The number of times each clone was isolated in the library sorts against linear diubiquitin or K63-linked diubiquitin is indicated.

Table 7 discloses the CDR L1 sequences as SEQ ID NOS 1, 1 and 50-57, respectively, in order of appearance. Table 7 discloses the CDR L2 sequences as SEQ ID NOS 2 and 58-63, respectively, in order of appearance. Table 7 discloses the CDR L3 sequences as SEQ ID NOS 3, 3, 64, 65, 3 and 66-72, respectively, in order of appearance. Table 7 discloses the CDR H1 sequences as SEQ ID NOS 255 and 73-81, respectively, in order of appearance. Table 7 discloses the CDR H2 sequences as SEQ ID NOS 8 and 82-86, respectively, in order of appearance. Table 7 discloses the CDR H3 sequences as SEQ ID NOS 368-372, 368 and 373-375, respectively, in order of appearance.

TABLE 7

CDR L1

| clone | CDR | IC50 (nm) | Fold improvement | 24 | | | | | | | | | 34 | K63 binding | % inhibition | # isolated linear | # isolated K63 |
|---|---|---|---|---|---|---|---|---|---|---|---|---|---|---|---|---|---|
| WT 1E3 | | 34 | | R | A | S | Q | D | V | S | T | A | V | A | | | | |
| WT 1E3 dup | | 40 | | R | A | S | Q | D | V | S | T | A | V | A | | | | |
| 1A5 | L1 | 30 | 1.2 | R | A | S | Q | D | V | G | T | A | V | A | yes | 43 | 3 | 21 |
| 1A7 | L1 | 24 | 1.5 | R | A | S | Q | D | V | S | T | Y | V | A | no | 63 | 3 | 0 |
| 1A8 | L1 | 33 | 1.1 | R | A | S | Q | D | V | S | T | Q | V | A | no | 61 | 2 | 0 |
| 1B3 | L1 | 25 | 1.5 | R | A | S | Q | D | V | S | I | A | V | A | no | 69 | 1 | 1 |
| 1D3 | L1 | 30 | 1.2 | R | A | S | Q | D | V | R | T | A | V | A | no | 72 | 4 | 1 |
| 1D7 | L1 | 58 | 0.6 | R | A | S | Q | D | V | S | G | A | V | A | yes | 77 | 2 | 3 |
| 1D10 | L1 | 39 | 0.9 | R | A | S | Q | A | V | S | T | A | V | A | no | 67 | 1 | 0 |
| 1E8 | L1 | 33 | 1.1 | R | A | S | Q | L | V | S | T | A | V | A | no | 61 | 1 | 0 |

TABLE 7-continued

CDR L2

| clone | CDR | IC50 (nm) | Fold improvement | 50 | | | | | | 56 | K63 binding | % inhibition | # isolated linear | # isolated K63 |
|---|---|---|---|---|---|---|---|---|---|---|---|---|---|---|
| WT 1E3 | L2 | 49 | | S | A | S | F | L | Y | S | | | | |
| 1F11 | L2 | 15 | 3.3 | S | A | K | F | L | Y | S | no | 49 | 3 | 0 |
| 1H5 | L2 | 30 | 1.6 | S | R | S | F | L | Y | S | no | 62 | 2 | 0 |
| 2A2 | L2 | 15 | 3.3 | S | A | R | F | L | Y | S | no | 67 | 10 | 2 |
| 2A9 | L2 | 121 | 0.4 | S | A | S | F | S | Y | S | no | 62 | 2 | 0 |
| 2C1 | L2 | 42 | 1.2 | S | A | S | F | M | Y | S | no | 64 | 1 | 1 |
| 2C4 | L2 | 92 | 0.5 | S | A | S | F | N | Y | S | no | 64 | 1 | 0 |

CDR L3

| clone | CDR | IC50 (nm) | Fold improvement | 89 | | | | | | | | 97 | K63 binding | % inhibition | # isolated linear | # isolated K63 |
|---|---|---|---|---|---|---|---|---|---|---|---|---|---|---|---|---|
| WT 1E3 | | 32 | | Q | Q | S | Y | T | T | P | P | T | | | | |
| WT 1E3 dup | | 40 | | Q | Q | S | Y | T | T | P | P | T | | | | |
| 2C9 | L3 | 11 | 3.4 | Q | Q | S | Y | T | A | P | P | T | yes | 65 | 4 | 2 |
| 2C11 | L3 | 26 | 1.4 | Q | Q | S | Y | T | Q | P | P | T | no | 72 | 3 | 0 |
| WT 1E3 dup | L3 | 26 | | Q | Q | S | Y | T | T | P | P | T | | | | |
| 2D2 | L3 | 20 | 1.3 | Q | Q | S | R | T | T | P | P | T | no | 63 | 4 | 2 |
| 2E1 | L3 | 16 | 1.6 | Q | Q | S | Y | T | S | P | P | T | yes | 71 | 8 | 5 |
| 2E2 | L3 | 56 | 0.5 | Q | Q | S | V | T | T | P | P | T | no | 72 | 1 | 1 |
| 2F8 | L3 | 15 | 1.7 | Q | Q | S | Y | T | P | P | P | T | yes | 66 | 1 | 1 |
| 2F10 | L3 | 29 | 0.9 | Q | Q | S | Y | V | T | P | P | T | no | 69 | 1 | 0 |
| 2G11 | L3 | 14 | 1.9 | Q | Q | S | Y | T | G | P | P | T | yes | 61 | 2 | 6 |
| 2H5 | L3 | 15 | 1.7 | Q | Q | S | Y | T | N | P | P | T | no | 77 | 7 | 0 |

CDR H1

| clone | CDR | IC50 (nm) | Fold improvement | 30 | | | | | 35 | K63 binding | % inhibition | # isolated linear | # isolated K63 |
|---|---|---|---|---|---|---|---|---|---|---|---|---|---|
| WT 1E3 | H1 | 43 | | S | N | T | Y | I | S | | | | |
| 3A5 | H1 | 73 | 0.6 | F | N | T | Y | I | S | no | 69 | 1 | 0 |
| 3A7 | H1 | 15 | 2.9 | S | N | L | Y | I | S | yes | 77 | 14 | 14 |
| 3B7 | H1 | 33 | 1.3 | Q | N | T | Y | I | S | no | 68 | 4 | 0 |
| 3B11 | H1 | 18 | 2.4 | S | N | V | Y | I | S | yes | 70 | 10 | 10 |
| 3C9 | H1 | 53 | 0.8 | R | N | T | Y | I | S | no | 66 | 7 | 0 |
| 3D2 | H1 | 50 | 0.9 | S | N | M | Y | I | S | no | 70 | 1 | 0 |
| 3D6 | H1 | 56 | 0.8 | K | N | T | Y | I | S | no | 68 | 2 | 0 |
| 3E4 | H1 | 21 | 2.0 | S | N | T | Y | M | S | no | 72 | 3 | 0 |
| 3F1 | H1 | 30 | 1.4 | S | N | I | Y | I | S | no | 62 | 1 | 6 |

CDR H2

| clone | CDR | IC50 (nm) | Fold improvement | 49 | | | | | | | | 58 | K63 binding | % inhibition | # isolated linear | # isolated K63 |
|---|---|---|---|---|---|---|---|---|---|---|---|---|---|---|---|---|
| WT 1E3 | | 49 | | A | S | I | T | P | S | S | G | S | T | D | | | |
| 3F5 | H2 | 19 | 2.6 | A | S | I | T | P | S | S | G | Q | T | D | no | 59 | 11 | 1 |
| 3H9 | H2 | 44 | 1.1 | A | S | I | T | P | S | S | G | L | T | D | no | 61 | 2 | 0 |
| 3H10 | H2 | 33 | 1.5 | A | S | S | T | P | S | S | G | S | T | D | no | 67 | 1 | 0 |
| 4B2 | H2 | 92 | 0.5 | A | S | I | T | P | S | S | G | I | T | D | no | 61 | 1 | 0 |
| 4C5 | H2 | 80 | 0.6 | A | S | I | T | P | S | S | G | S | T | N | no | 66 | 1 | 0 |

TABLE 7-continued

| clone | CDR | IC50 (nm) | Fold improvement | CDR H3 92 | | | | | | | | | 102 | | | | | | | | | 113 | K63 binding | % inhibition | # isolated linear | # isolated K63 |
|---|---|---|---|---|---|---|---|---|---|---|---|---|---|---|---|---|---|---|---|---|---|---|---|---|---|---|
| WT 1E3 | L3 | 26 | | C | A | R | T | W | L | L | R | W | V | M | D | Y | W | G | Q | G | T | L | V T V S | S | | | |
| 4C9 | H3 | 10 | 2.6 | C | A | R | T | W | L | L | R | W | V | M | D | M | W | G | Q | G | T | L | V A V S | S | no | 57 | 2 | 0 |
| 4C10 | H3 | 10 | 2.6 | C | A | R | T | W | L | L | R | W | V | F | D | Y | W | G | Q | G | T | L | V A V S | S | no | 71 | 30 | 38 |
| 4E4 | H3 | 4 | 6.5 | C | A | R | T | W | L | L | R | W | V | M | D | L | W | G | Q | G | T | L | V A V S | S | no | 67 | 1 | 0 |
| 4G7 | H3 | 15 | 1.7 | C | A | R | T | W | L | L | R | W | V | M | D | G | W | G | Q | G | T | L | V T V S | S | no | 52 | 4 | 0 |
| WT2 | H3 | 31 | | C | A | R | T | W | L | Y | R | W | V | M | D | Y | W | G | Q | G | T | L | V T V S | S | | | | |
| 4D9 | H3 | 26 | 1.2 | C | A | R | T | W | L | L | R | W | V | M | D | G | W | G | Q | G | T | L | V A V S | S | no | 38 | 1 | 0 |
| 4E1 | H3 | 38 | 0.8 | C | A | R | T | W | L | L | R | W | V | M | D | Y | W | G | Q | G | T | L | V A V S | S | no | 64 | 4 | 1 |
| 4F3 | H3 | 22 | 1.4 | C | A | R | T | W | L | L | R | W | V | F | D | Y | W | G | Q | G | T | L | V T V S | S | no | 35 | 5 | 0 |

F) Phage Specificity ELISA

Figure 7A:
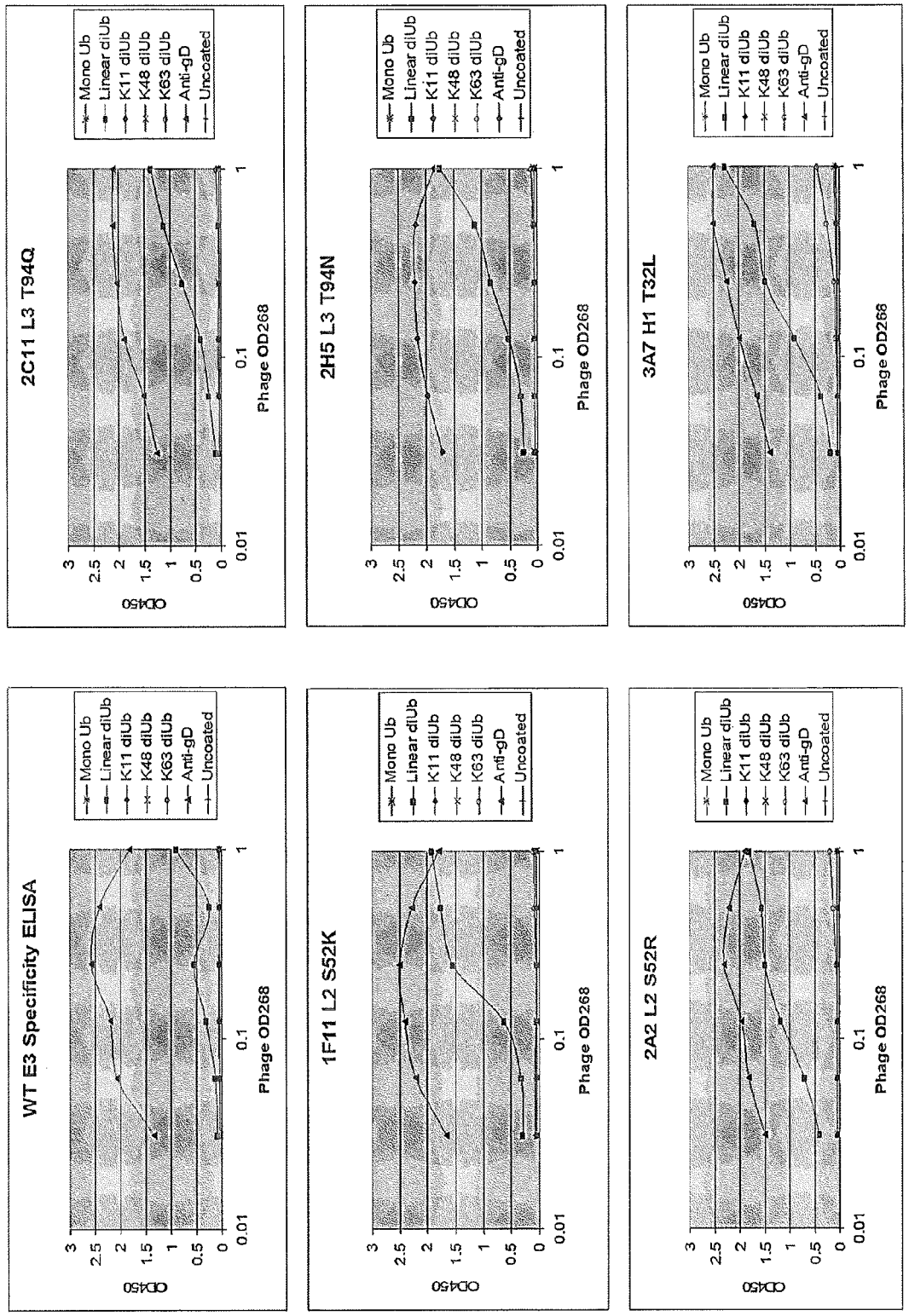
FIGS. 7A and B depict the results of studies assessing the binding specificity characteristics of the mutant affinity matured variants in comparison to the parental 1E3 clone and controls. The binding of the parental 1E3 clone and 11 single mutant affinity matured variants displayed on phage were tested for binding to a panel of ubiquitin proteins in an ELISA. Binding to an anti-gD antibody was used to assess Fab display on phage and uncoated wells were used as a negative control.
Figure 7B:
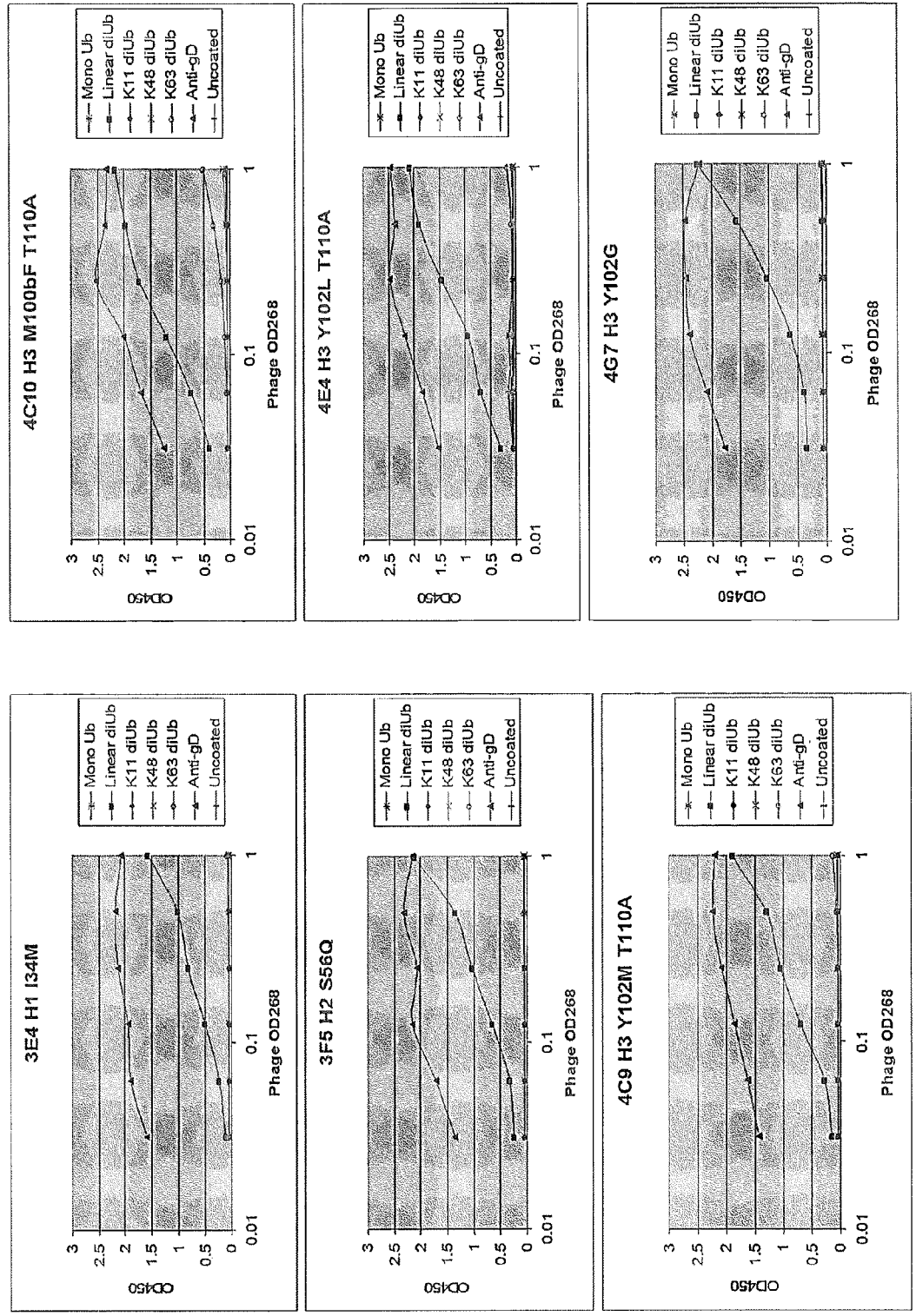

1F11, 2A2, 2C11, 2H5, 3E4, 4C9, 4E4, 4G7, 3F5, 3A7, and 4C10 along with the parental clone 1E3 were tested in a phage specificity ELISA against monoubiquitin (Boston Biochem), linear diubiquitin (Boston Biochem), K11-linked diubiquitin (Genentech), K48-linked diubiquitin (Boston Biochem), K63-linked diubiquitin (Boston Biochem), an anti-gD antibody (Genentech), or an uncoated well. The panel of ubiquitin proteins was immobilized on 96-well Maxisorb immunoplates (NUNC) (see FIGS. 7A and 7B). Plates were coated at 4° C. overnight with 1 µg/mL of each protein in 50 mM sodium carbonate buffer, pH 9.6. The coated plates were blocked with 200 µL/well of 2.5% milk in PBST for one hour at 25° C. with shaking. Six two-fold serial dilutions of phage from $OD_{268}=1.0$ to $OD_{268}=0.03$ were made in 2.5% milk in PBST. After one hour, the blocking buffer was dumped off of the plate and 100 µL of the phage serial dilutions was added. Plates were incubated at 25° C. for one hour with shaking. The plate was then washed six times with PBST using a plate washer. A 1:5,000 dilution of an anti-M13 horseradish peroxidase (HRP)-conjugated secondary antibody (GE Healthcare) in PBST was used for detection of phage binding. 100 µL/well of the secondary dilution was added and the plate was incubated at 25° C. for 1.25 hours with shaking. The plate was then washed six times with PBST using a plate washer and twice manually with PBS. Bound secondary antibody was detected using a TMB substrate (KPL) followed by quenching with an equal volume of 1 M phosphoric acid. The absorbance was read at 450 nm.

Clones 3A7 and 4C10 which were isolated multiple times in both the linear diubiquitin and the K63-linked diubiquitin sorts were used as negative controls. Both demonstrated significant K63-linked binding at a phage $OD_{268}=1.0$ ($OD_{450}=0.44$ and $OD_{450}=0.5$ for 3A7 and 4C10, respectively) (see FIGS. 7A and 7B). 2A2 which was isolated twice in the K63-linked diubiquitin sort showed intermediate levels of K63-linked binding ($OD_{450}=0.2$ at a phage $OD_{268}=1.0$). All other clones demonstrated negligible K63-linked diubiquitin binding ($OD_{450}<0.16$ at a phage $OD_{268}=1.0$).

G) Cloning Light Chain/Heavy Chain Double Mutants

Clones which demonstrated improved $IC_{50}$s over the parental 1E3 (example 3E) and showed negligible K63-linked diubiquitin binding in the phage specificity ELISA (example 3F) were chosen for further consideration. These included light chain mutants 1F11, 2C11, and 2H5 and heavy chain mutants 3E4, 3F5, and 4G7. To see whether there was an additive effect in affinity improvement double mutants were constructed combining different combinations of light and heavy chain mutations. Light chain variable domains were removed by digesting the phagemids with EcoRV and KpnI and were then cloned into the various heavy chain mutant phagemids using the same sites.

H) Double Mutant Phage $IC_{50}$ ELISA

Double mutants 1F11/3E4, 1F11/3F5; 1F11/4G7, 2C11/3E4, 2C11/3F5, 2C11/4G7, 2H5/3E4, 2H5/3F5, and 2H5/4G7 were compared to their respective single mutants and parental 1E3 in a phage $IC_{50}$ ELISA as previously described (examples 1D and 3E). Double mutants 1F11/3F5 and 2H5/3F5 demonstrated an additive improvement in affinity over their individual single mutants (see Table 8). 2C11/3F5 was border line additive. The single mutant 3F5 in this particular assay gave a lower $IC_{50}$ (9 nM) than in the other two experiments (12 or 13 nM) which could make 2C11/3F5 ($IC_{50}$ of 10 nM) appear not to be additive. Therefore 2C11/3F5 was also chosen for further consideration.

TABLE 8

| | IC50 (nM) | CDR | mutation |
|---|---|---|---|
| WT | 29 | | |
| 1F11 | 14 | L2 | S52K |
| 3E4 | 44 | H1 | I34M |
| 3F5 | 12 | H2 | S56Q |
| 4G7 | 23 | H3 | Y102G |
| 1F11/3E4 | 12 | L2/H1 | S52K I34M |
| 1F11/3F5 | 5 | L2/H2 | S52K S56Q |
| 1F11/4G7 | 13 | L2/H3 | S52K Y102G |
| WT | 24 | | |
| 2C11 | 20 | L3 | T94Q |
| 3E4 | 33 | H1 | I34M |
| 3F5 | 9 | H2 | S56Q |
| 4G7 | 16 | H3 | Y102G |
| 2C11/3E4 | 24 | L3/H1 | T94Q I34M |
| 2C11/3F5 | 10 | L3/H2 | T94Q S56Q |
| 2C11/4G7 | 31 | L3/H3 | T94Q Y102G |
| WT | 25 | | |
| 2H5 | 17 | L3 | T94N |
| 3E4 | 26 | H1 | I34M |
| 3F5 | 13 | H2 | S56Q |
| 4G7 | 19 | H3 | Y102G |
| 2H5/3E4 | 26 | L3/H1 | T94N I34M |
| 2H5/3F5 | 8 | L3/H2 | T94N S56Q |
| 2H5/4G7 | 23 | L3/H3 | T94N Y102G |

I) Double Mutant Phage Specificity ELISA

Figure 8A:
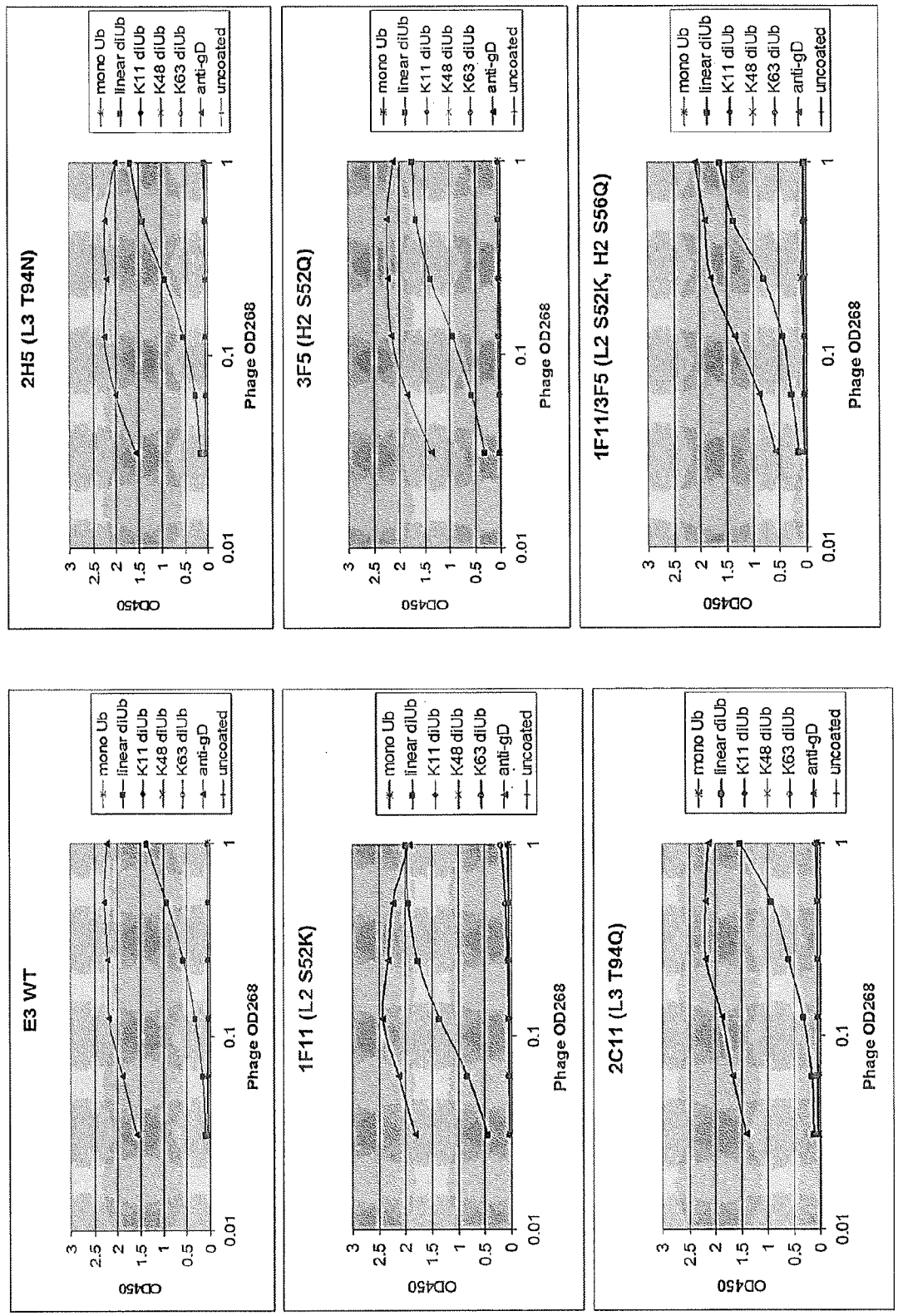
FIGS. 8A and B depict the results of studies assessing the binding specificity characteristics of single mutant and double mutant variants in comparison to the parental 1E3 clone and controls, as described in Example 3. The binding of the parental 1E3 clone, 4 single mutant affinity matured variants and 3 double mutant affinity matured variants, displayed on phage, were tested for binding to a panel of ubiquitin proteins in an ELISA. Binding to an anti-gD antibody was used to assess Fab display on phage and uncoated wells were used as a negative control.
Figure 8B:
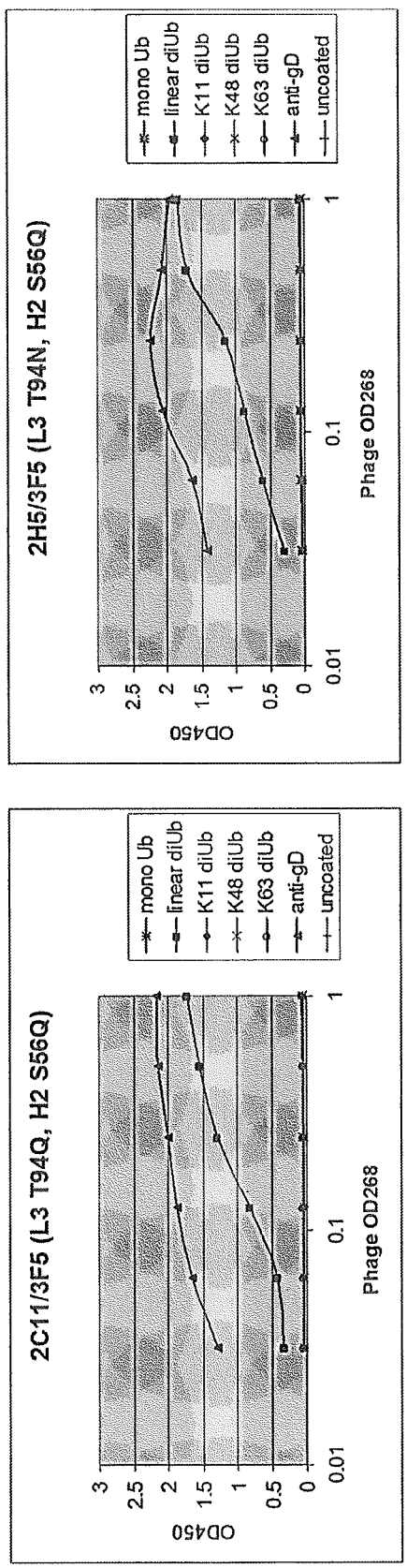

Double mutants 1F11/3F5, 2C11/3F5, and 2H5/3F5 were compared to their respective single mutants and parental 1E3 in a phage specificity ELISA as in example 3F. All double mutants showed negligible K63-linked diubiquitin binding ($OD_{450}<0.1$ at phage $OD_{268}=1.0$) (see FIGS. 8A and 8B).

J) Double Mutant Fab Production

The parental clone (1E3), single mutants (1F11, 2C11, 2H5, 3F5) and double mutants (1F11/3F5, 2C11/3F5, 2H5/

3F5) were cloned as Fab expression constructs by inserting a TAA stop codon into the phagemids at the end of the CH1 domain as described in example 1E. These Fabs were expressed in E. coli and purified as described in example 1E.

K) Conversion to IgG Format

The parental clone (1E3), single mutants (1F11, 2C11, 2H5, 3F5) and double mutants (1F11/3F5, 2C11/3F5, 2H5/3F5) were also expressed in HEK293 cells as human immunoglobulins (IgGs). Expression constructs were generated by cloning the Fab variable domains into pRK mammalian expression constructs encoding the heavy and light chains of human kappa IgG1 (Gorman et al., DNA Prot. Eng. Tech. 2:3-10 (1990)). IgGs were purified by affinity chromatography on protein A-sepharose columns by standard methodologies as described for the Fab purification in Example 1E.

L) Double Mutant Biacore

The affinity of the double mutant Fabs (from Example 3J) was analyzed by surface plasmon resonance (SPR) using a BIACORE™ 3000 (GE Healthcare) and direct binding as described in example 1G. Approximately 150 resonance units (RUs) of linear diubiquitin (Boston Biochem), K48-linked diubiquitin (Boston Biochem), and K63-linked diubiquitin (Boston Biochem) were immobilized on flow cell two, flow cell three, and flow cell four, respectively, of a CM5 chip using the amine coupling protocol supplied by the manufacturer. Flow cell one was activated and ethanolamine blocked without immobilizing protein, to be used for reference subtraction. Even with 10 mM glycine, pH 1.7 the chip surface could not be regenerated back to baseline and an increase in RUs was seen suggesting that the chip surface was altered.

An alternative approach was tested using an IgG capture method with the IgGs from example 3K on a BIACORE™ 3000 (GE Healthcare). Approximately 8,000 resonance units (RUs) of an anti-human Fc capture antibody (GE Healthcare) were immobilized on flow cells one and two of a CM5 chip using the amine coupling protocol supplied by the manufacturer. 60 µL of 1 µg/mL IgG in 10 mM Hepes, pH 7.2, 150 mM NaCl, and 0.01% Tween 20 (HBST) was injected at a flow rate of 30 µL/minute over flow cell two, resulting in capture of approximately 750 RUs of IgG. Flow cell one had only the capture antibody on it to serve as a reference subtraction. Two-fold serial dilutions (3.9-500 nM) of linear diubiquitin (Boston Biochem) or K63-linked diubiquitin (Boston Biochem) in HBST were injected (60 µL total at a flow rate of 30 µL/minute) over flow cells one and two. The signal for each flow cell was recorded and the reference signal was subtracted. Following a dissociation period of four minutes, the chip surface was regenerated with one injection of 15 µL of 3M MgCl$_2$ at a flow rate of 30 µL/minute. Much like the Fab capture Biacore experiment (see example 1G), data were difficult to fit to any binding model because the diubiquitin did not fully dissociate from the chip. In addition the association rates were very fast and binding did not reach a plateau even at the highest concentration of diubiquitin used. Therefore it is difficult to estimate a KD for these IgGs.

M) Western Blots of Purified Diubiquitin with Double Mutants

To rank the affinity and specificity of the double mutants the IgGs described in example 3K were tested in a western blot for binding to linear diubiquitin (Boston Biochem) and K63-linked diubiquitin (Boston Biochem). 1 µg of K63-linked diubiquitin and five three-fold serial dilutions of linear diubiquitin (1000, 333, 111, 37, 12 ng) in 1×LDS buffer (Invitrogen) with reducing agent was heated at 70° C. for ten minutes and run on 4-12% NuPAGE Bis Tris 1.0 mm gels in MES buffer (Invitrogen). Gels were transferred at 30 V constant for 1 hour by wet transfer in 10% methanol and 1× NuPAGE transfer buffer (Invitrogen) to 0.2 µm nitrocellulose (Invitrogen). Non-specific binding sites on the membranes were blocked by incubation in 5% milk in PBST for 1 hour at 25° C. with shaking. The membranes were then incubated in 1 µg/mL of 1E3, 1F11, 2C11, 2H5, 3F5, 1F11/3F5, 2C11/3F5, or 2H5/3F5 IgG in 5% milk in PBST for one hour at 25° C. with shaking. The membranes were washed three times in PBST with shaking. The IgGs were detected by incubating the membrane in a 1:10,000 dilution of a goat anti-human Fc fragment-specific IR Dye 800CW-conjugated secondary antibody (Rockland Immunochemicals) in 5% milk in PBST for 30 minutes at 25° C. with shaking. The membranes were then washed three times in PBST followed by one wash in PBS. The secondary antibody was detected and quantified using the LI-COR Odyssey infrared imaging system (LI-COR Biosciences).

Figure 10:
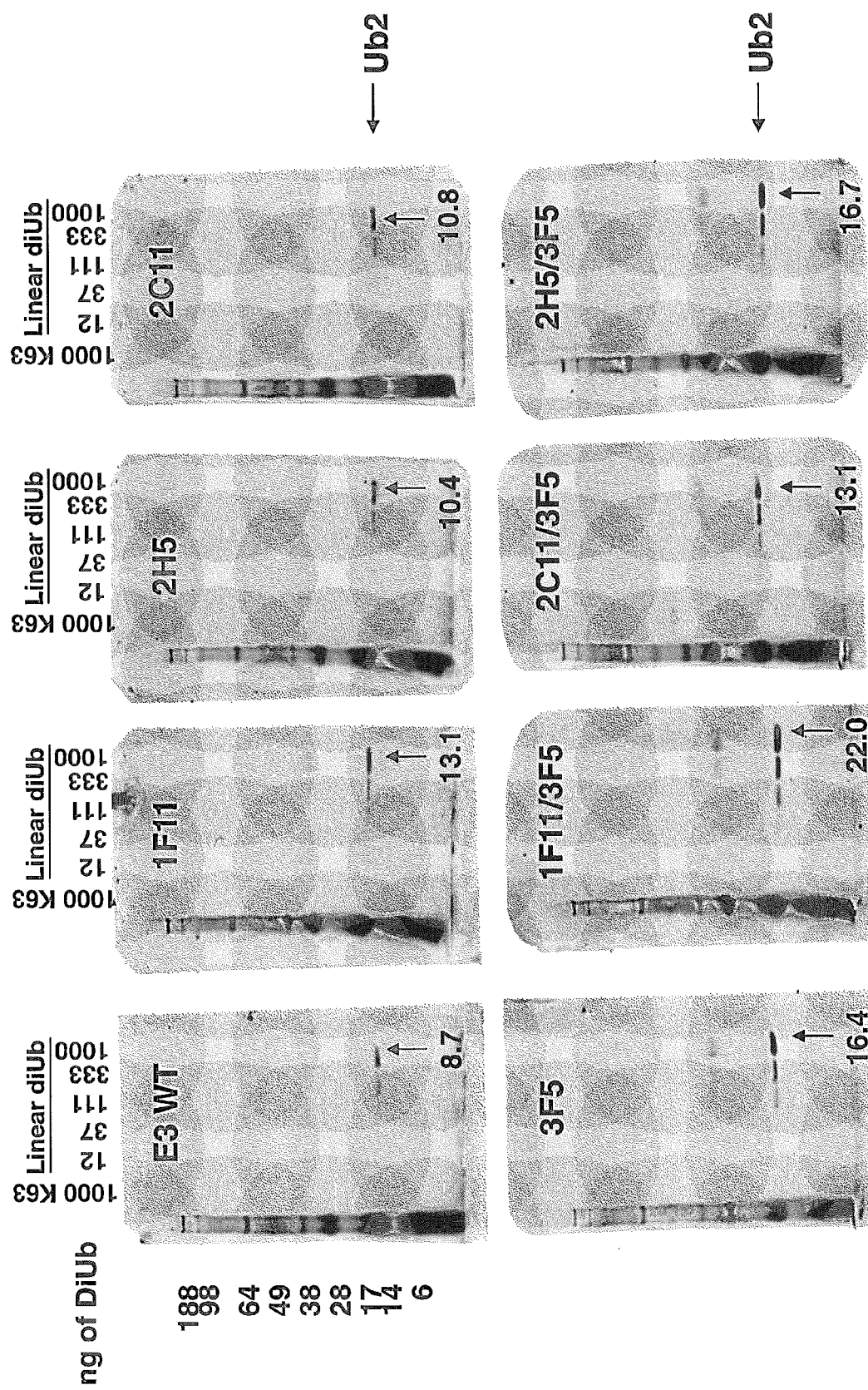
FIG. 10 provides western blot analyses of binding of parental 1E3, single, and double mutant IgGs to linear diubiquitin (serial dilutions of 1000, 333, 111, 37 and 12 ng per lane) and K63-linked diubiquitin (1000 ng per lane).

Single mutants 1F11 and 3F5 were considerably more sensitive than the parental 1E3, whereas single mutants 2C11 and 2H5 were only slightly improved (see FIG. 10). The double mutant 1F11/3F5 had an additive improvement in sensitivity over the respective single mutants, whereas 2C11/3F5 and 2H5/3F5 were not any better than 3F5 alone.

N) Cloning Triple Mutants

To see whether a further improvement in affinity could be achieved by combining three mutations, the 1F11/2C11/3F5 and 1F11/2H5/3F5 triple mutants were generated. Mutagenic oligonucleotides 5'-1F11 S52K (CCGAAGCTTCTGATT-TACTCGGCAAAGTTCCTCTA CTCTGGAGTCCC) (SEQ ID NO:187) and 3'-1F11 S52K (GGGACTCCAGAG-TAG AGGAACTTTGCCGAGTAAATCAGAAGCTTCGG) (SEQ ID NO:188) were combined with either the 2C11 or 2H5 pRK light chain constructs from example 3K and the QuikChange® Lightning Site-Directed Mutagenesis kit (Agilent) was used to generate the double mutant light chains. Triple mutants were then generated by combining the double mutant light chain pRK constructs with the 3F5 heavy chain pRK construct and IgGs were expressed in HEK293 cells and purified as described in example 3K.

O) Western Blots of Purified Diubiquitin with Triple Mutants

Figure 11:
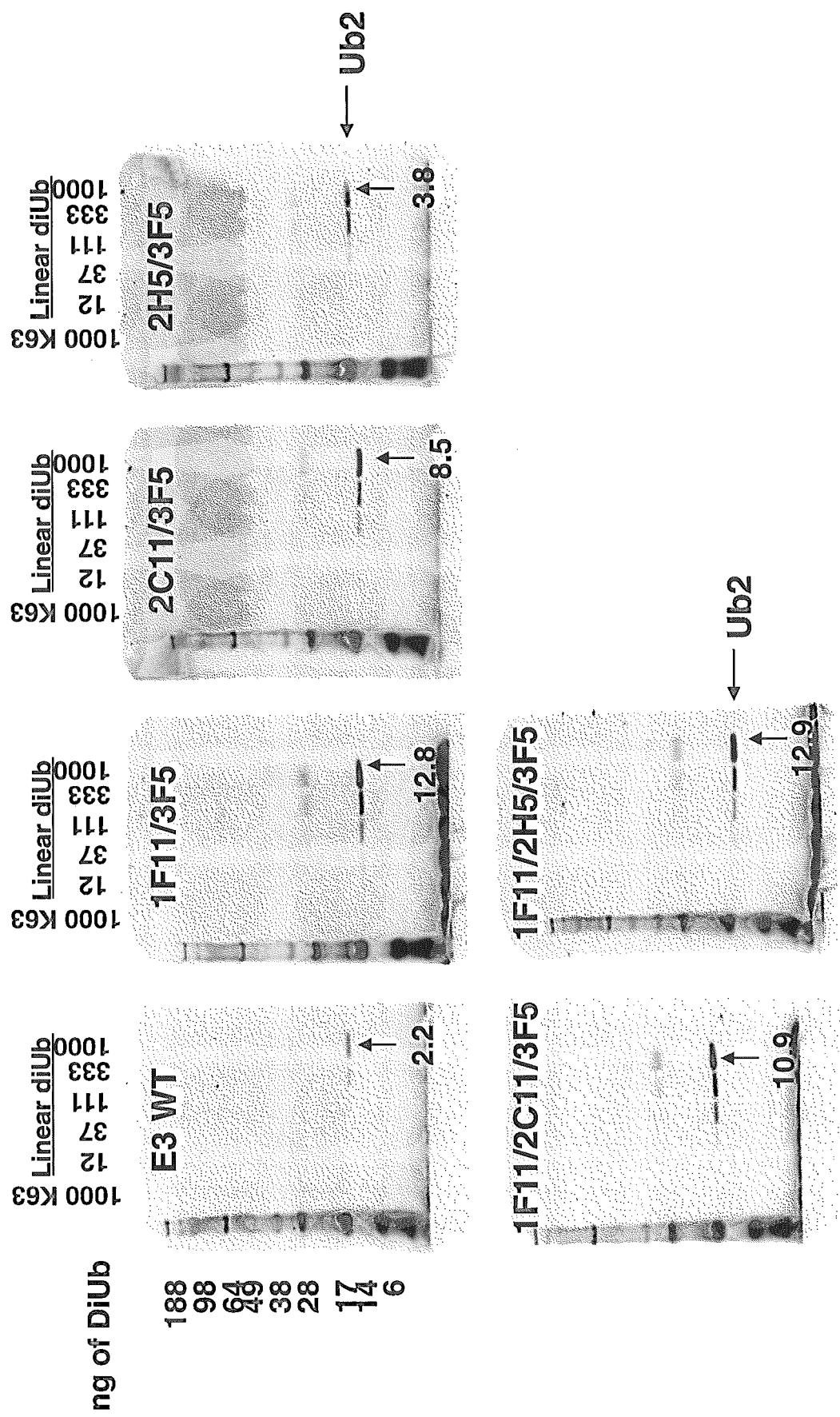
FIG. 11 provides western blot analysis of binding of parental 1E3, double, and triple mutant IgGs to linear diubiquitin (serial dilutions of 1000, 333, 111, 37 and 12 ng per lane) and K63-linked diubiquitin (1000 ng per lane).

To rank the affinity and specificity of the triple mutants 1F11/2C11/3F5 and 1F11/2H5/3F5 the IgGs described in example 3N were tested in a western blot for binding to linear diubiquitin (Boston Biochem) and K63-linked diubiquitin (Boston Biochem) as described in example 3M. Neither 1F11/2C11/3F5 nor 1F11/2H5/3F5 was more sensitive than the double mutant 1F11/3F5 (see FIG. 11).

P) Cloning Additional Triple Mutants

One H3 mutant, 4E4 that demonstrated an improved IC$_{50}$ value over the parental 1E3 in example 3E was not originally considered when making double mutants because it had a small amount of K63-linked diubiquitin binding in the specificity ELISA (OD$_{450}$=0.16 at a phage OD$_{268}$=1.0, see example 3F). Since none of the IgG mutants tested so far demonstrated any K63-linked diubiquitin binding in the western blots, the 4E4 clone was analyzed further. 4E4 was an H3 clone that actually contained two mutations, Y102L immediately adjacent to CDR H3 and T110A in framework 4. To determine whether the unintentional T110A mutation had any affect on affinity, both the Y102L single mutant and the Y102L T110A double mutant heavy chain was made in the context of the 1E3 parental heavy chain or the mutant 3F5 heavy chain. To insert the Y102L mutation mutagenic oligonucleotides 5'-Y102L (CGGTGGGTTATGGACCT-GTGGGGTCAAGGAACCCTGGTC ACCGTCTCCTCG-GCCTCC) (SEQ ID NO:189) and 3'-Y102L (GGAGGCCGAGGAGA CGGTGACCAGGGTTCCT-TGACCCCACAGGTCCATAACCCACCG) (SEQ ID NO:190) were combined with either the 1E3 or 3F5 IgG heavy chain pRK expression construct and the mutants were synthesized using the QuikChange® Lightning Site-Directed Mutagenesis kit (Agilent). To insert the Y102L T110A mutations mutagenic oligonucleotides 5'-Y102L T110A (CG- GTGGGTTATGGACCTGTGGGGTCAAG-
GAACCCTGGTCGCGGTCTCCTCGGCCTCC) (SEQ ID NO:191) and 3'-Y102L T110A (GGAGGCCGAGGGAGAC-CGCGACCAGG GTTCCTTGACCCCACAGGTCCAT-AACCCACCG) (SEQ ID NO:192) were combined with either the 1E3 or 3F5 IgG heavy chain pRK expression construct and the mutants were synthesized using the QuikChange® Lightning Site-Directed Mutagenesis kit (Agilent). The resulting heavy chain IgG pRK constructs were combined with either the parental 1E3 or the mutant 1F11 light chain IgG pRK constructs and the resulting IgGs were expressed in HEK293 cells and purified as described in example 3K.

Figure 12:
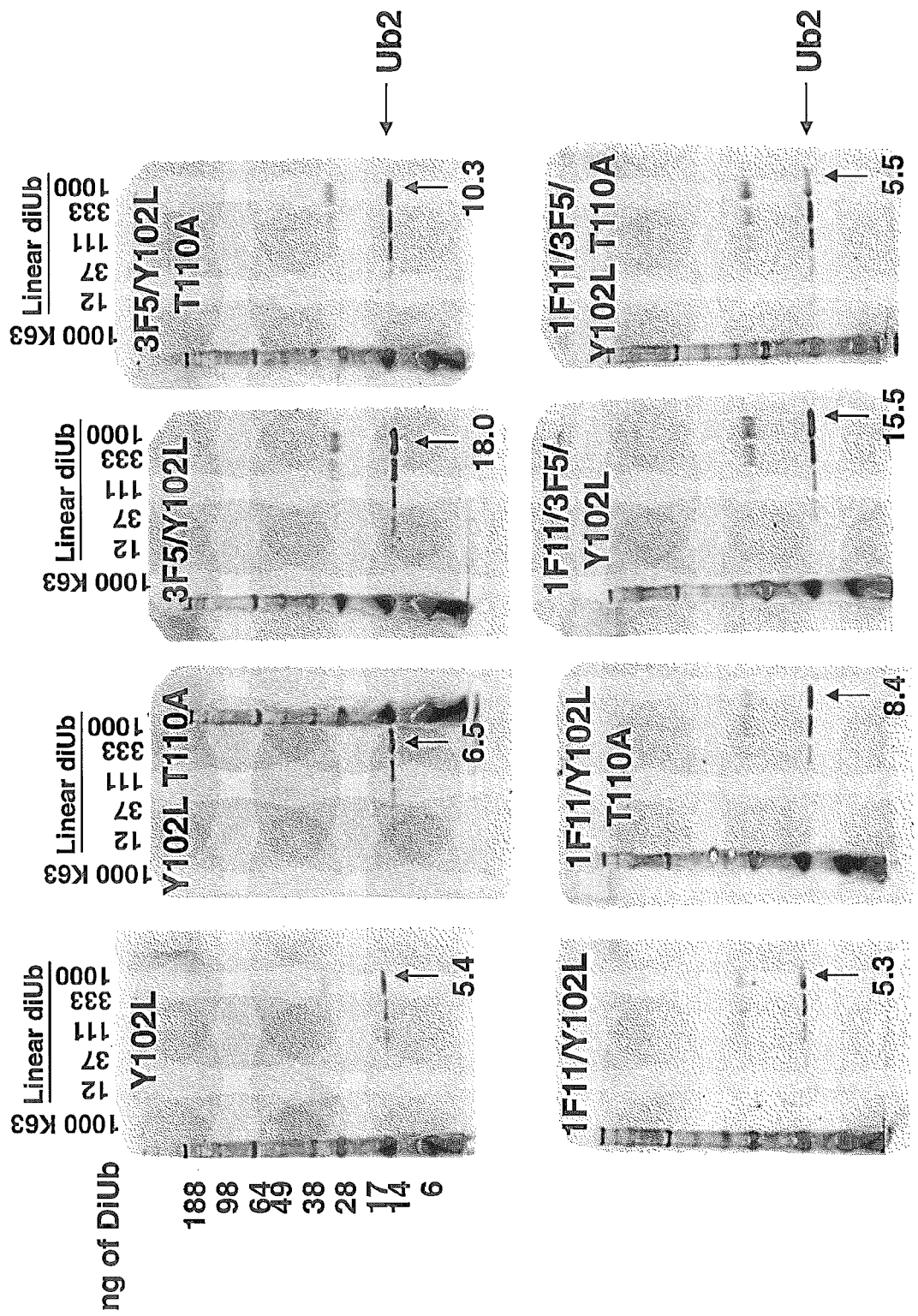
FIG. 12 provides western blot analysis of binding of Y102L, Y1012L T110A mutant and various mutant combinations of Y102L, T110A, 3F5 and 1F11 IgGs to linear diubiquitin (serial dilutions of 1000, 333, 111, 37 and 12 ng per lane) and K63-linked diubiquitin (1000 ng per lane).

These mutants (Y012L vs. Y102L T110A, 3F5/Y102L vs. 3F5/Y102L T110A, 1F11/Y102L vs. 1F11/Y102L T110A, and 1F11/3F5/Y102L vs. 1F11/3F5/Y102L T110A) were then compared side by side in a western blot for binding linear or K63-linked diubiquitin as described in example 3M. Generally, having the T110A mutation in combination with Y102L did not significantly improve sensitivity compared to Y102L alone (see FIG. 12). Also from the phage IC$_{50}$s it is known that T110A alone (clone 4E1) does not improve affinity compared to the parental 1E3 (see Table 7). Therefore the Y102L mutation alone was considered for further analysis.

Figure 13:
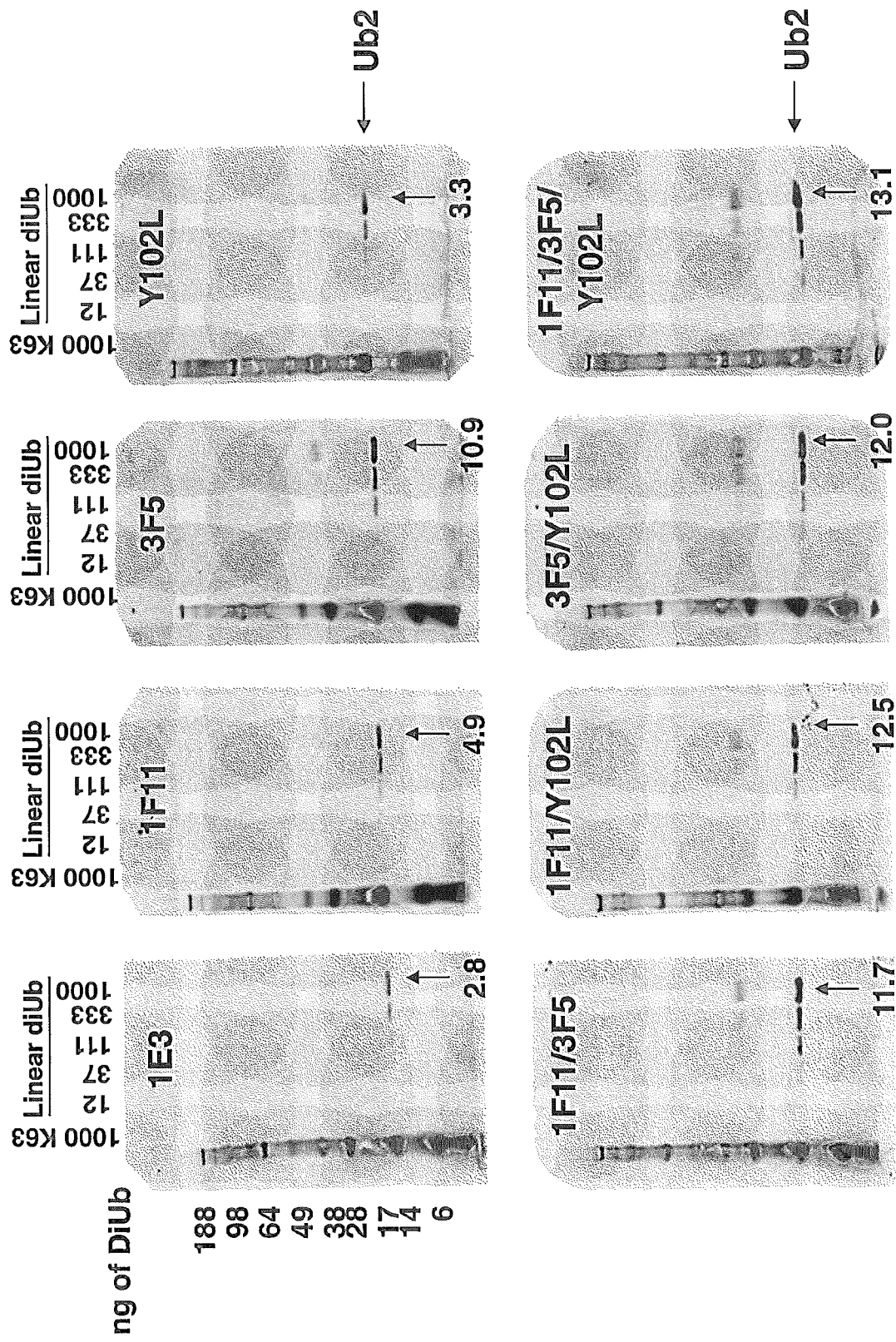
FIG. 13 provides western blot analysis of binding of parental 1E3, single, double, and triple mutant IgGs, as described in Example 3M, to linear diubiquitin (serial dilutions of 1000, 333, 111, 37 and 12 ng per lane) and K63-linked diubiquitin (1000 ng per lane).

The triple mutant 1F11/3F5/Y102L was then compared to the parental 1E3, each of the single mutants (1F11, 3F5, Y102L), as well as the double mutants (1F11/3F5, 1F11/Y102L, 3F5/Y102L) side by side in a western blot for binding linear or K63-linked diubiquitin as described in example 3M. The triple mutant was more sensitive than the parental clone 1E3, all of the single mutants, and all of the double mutants for binding linear diubiquitin (see FIG. 13). In addition it showed no binding to K63-linked diubiquitin indicating that the specificity is maintained.

Example 4

Characterization of the Affinity Matured Anti-Linear Polyubiquitin Antibody

A) IgG Western Blot of Purified Diubiquitin Chains

The 1E3 parental and 1F11/3F5/Y102L IgGs were tested for their ability to detect pure diubiquitin chains in a western blot. Seven two-fold serial dilutions of linear diubiquitin (Boston Biochem) from 1 μg to 16 ng and 1 μg each of monoubiquitin (Boston Biochem), K11-linked diubiquitin (Genentech), K48-linked diubiquitin (Boston Biochem), and K63-linked diubiquitin (Boston Biochem) in 1×LDS buffer (Invitrogen) with reducing agent (Invitrogen) were heated at 70° C. for ten minutes and run on 4-12% Bis Tris NuPAGE 1.0 mm gels (Invitrogen) in MES buffer (Invitrogen) in triplicate. One gel was stained by SimplyBlue Coomassie stain (Invitrogen) to detect all proteins. For comparison to get an idea of affinity, a second western blot was done with the anti-K63 antibody, Apu3.A8 which has a known KD of 8.7 nM for K63-linked diubiquitin (see Newton, K. et al. (2008) Cell 134:668-678). For this western, seven two-fold serial dilutions of K63-linked diubiquitin (Boston Biochem) from 1 μg to 16 ng and 1 μg each of monoubiquitin (Boston Biochem), linear diubiquitin (Boston Biochem), K11-linked diubiquitin (Genentech), and K48-linked diubiquitin (Boston Biochem) were run on the gel as described above. The three gels were transferred individually at 30 V constant for one hour by wet transfer in 10% methanol and 1× NuPAGE transfer buffer (Invitrogen) to 0.2 μM nitrocellulose (Invitrogen). Non-specific binding sites on the membranes were blocked by incubation in 5% milk in PBST for one hour at 25° C. with shaking. The membranes were then incubated in 1 μg/mL of 1E3, 1F11/3F5/Y102L, or Apu3.A8 in 5% milk in PBST for one hour at 25° C. with shaking. The membranes were washed three times in PBST with shaking. The IgGs were detected by incubating the membranes in a 1:10000 dilution of a goat anti-human Fcγ-specific HRP-conjugated F(ab')2 secondary antibody (Jackson Immunoresearch) in 5% milk in PBST for one hour at 25° C. with shaking. The membranes were then washed three times in PBST followed by one wash in PBS. The secondary antibody was detected using Super Signal West Pico chemiluminescent substrate (Thermo Scientific) followed by exposure of the blots to film.

Figure 14:
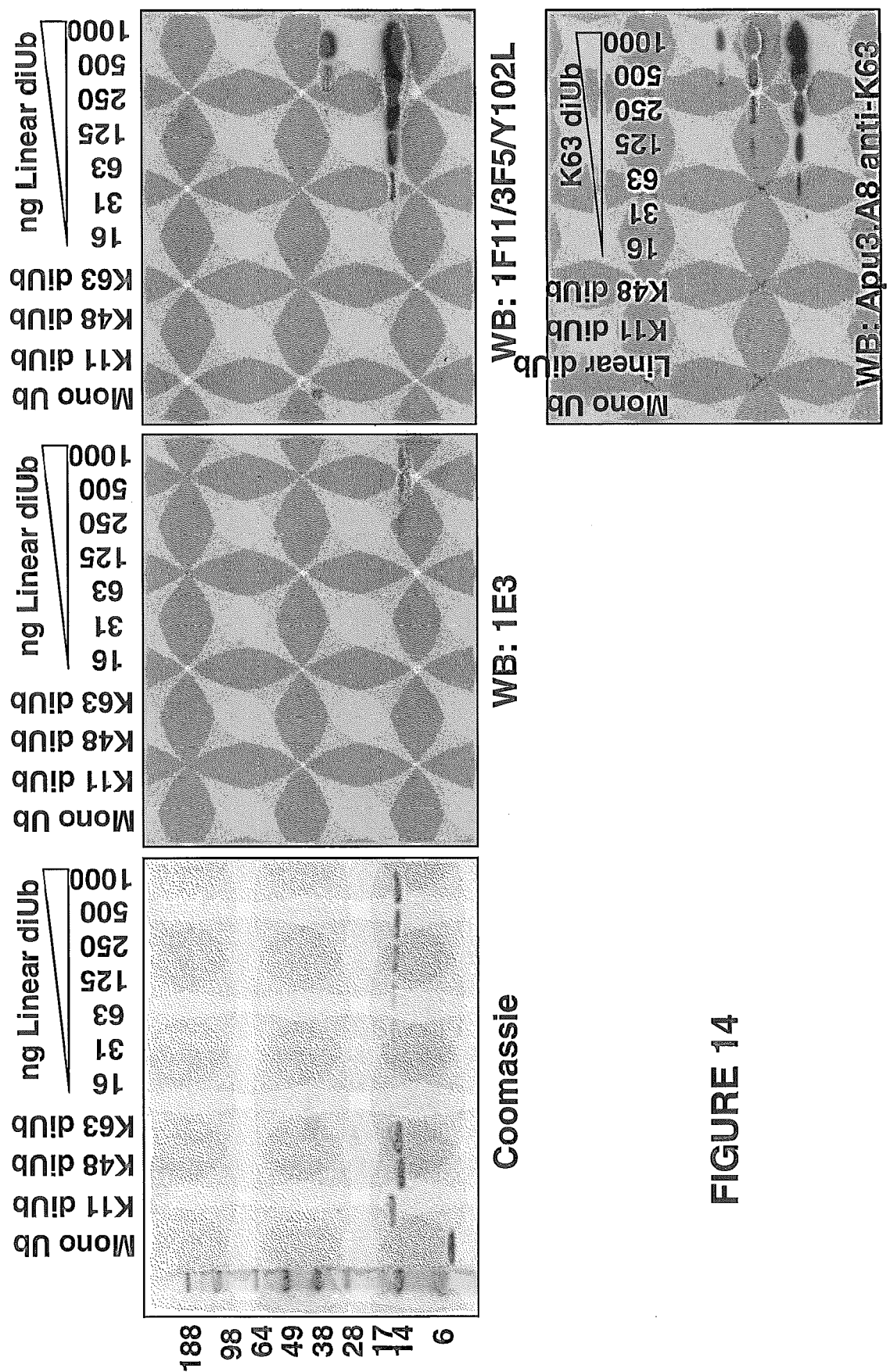
FIG. 14 provides western blot analyses of binding of 1E3 and 1F11/3F5/Y102L IgGs to two-fold serial dilutions of linear diubiquitin (1000, 500, 250, 125, 63, 31, and 16 ng/lane where gradient is indicated) or monoubiquitin, K11-linked diubiquitin, K48-linked diubiquitin, and K63-linked diubiquitin (1 µg/lane). As a control the anti-K63 IgG, Apu3.A8 was analyzed for binding to two-fold serial dilutions of K63-linked diubiquitin (1000, 500, 250, 125, 63, 31, and 16 ng/lane where gradient is indicated) or monoubiquitin, linear diubiquitin, K11-lined diubiquitin, and K48-linked diubiquitin (1 µg/lane). The Coomassie stained gel (upper left panel) provides an indication of where each of the tested ubiquitin migrates in the gels.

The 1E3 limit of detection was ~250 ng of linear diubiquitin (see FIG. 14). In contrast, 1F11/3F5/Y102L was much more sensitive and could detect as little as 31 ng of linear diubiquitin. In addition 1F11/3F5/Y102L was highly specific, demonstrating no binding to any of the other forms of ubiquitin tested. For comparison the limit of detection of Apu3.A8, which has a K$_D$ of 8.7 nM, was ~62 ng. The K$_D$ of 1F11/3F5/Y102L for linear diubiquitin is therefore likely in the low nM range.

B) IgG Western Blot of Purified Polyubiquitin Chains

Figure 15:
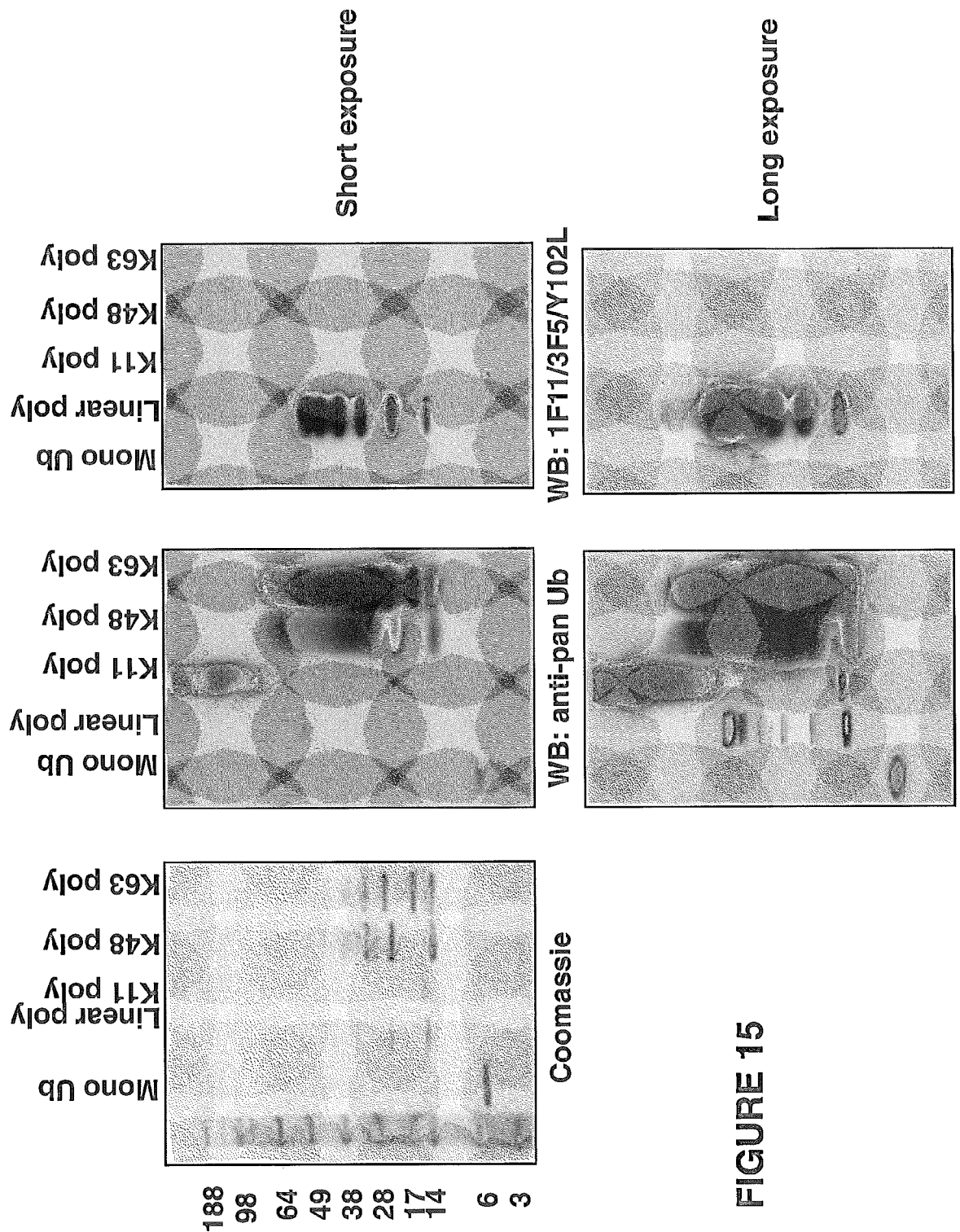
FIG. 15 depicts the results of experiments in which monoubiquitin, linear polyubiquitin 2-7 (two to seven ubiquitin subunits in length), K48-linked polyubiquitin 2-7 (two to seven ubiquitin subunits in length), K63-linked polyubiquitin 2-7 (two to seven ubiquitin subunits in length), and K11-linked polyubiquitin (1 µg each per lane) were immunoblotted with a pan-ubiquitin antibody P4D1 (middle panel) or the 1F11/3F5/Y102L IgG (right panel). Coomassie staining revealed the composition of the samples (left panel). A long and short exposure of the western blots is shown.

The linear-specific antibodies were generated against a linear diubiquitin antigen so they presumably recognize either the linkage itself or the surrounding surface residues on the proximal and distal ubiquitins that are placed in close proximity due to the conformation of diubiquitin which results from the linear linkage. Since diubiquitin is the smallest recognition unit of antigen and linear polyubiquitin is a polymeric chain with diubiquitin as the repeating "monomer" unit, the antibodies should also bind the polyubiquitin form. To examine this, the 1F11/3F5/Y102L IgG was tested for its ability to detect pure polyubiquitin chains in a western blot. 1 μg each of monoubiquitin (Boston Biochem), linear polyubiquitin 2-7 (Enzo Lifesciences), K11-linked polyubiquitin (Genentech), K48-linked polyubiquitin 2-7 (Boston Biochem), and K63-linked polyubiquitin 2-7 (Boston Biochem) in 1×LDS buffer (Invitrogen) with reducing agent (Invitrogen) was heated at 70° C. for ten minutes and run on 4-12% Bis Tris NuPAGE 1.0 mm gels (Invitrogen) in MES buffer (Invitrogen) in triplicate. One gel was stained by SimplyBlue Coomassie stain (Invitrogen) to detect all proteins. The other two gels were transferred separately at 30 V constant for one hour by wet transfer in 10% methanol and 1× NuPAGE transfer buffer (Invitrogen) to 0.2 μm nitrocellulose (Invitrogen). Non-specific binding sites on the membranes were blocked by incubation in 5% milk in PBST for one hour at 25° C. with shaking. The membranes were then incubated in 1 μg/mL of 1F11/3F5/Y102L IgG or a 1:200 dilution of a mouse pan-ubiquitin antibody, P4D1 (non-linkage specific, Santa Cruz Biotechnology) in 5% milk in PBST for one hour at 25° C. with shaking. The membranes were washed three times in PBST with shaking. The 1F11/3F5/Y102L IgG was detected by incubating the membrane in a 1:10000 dilution of a goat anti-human Fcγ-specific HRP-conjugated F(ab')2 secondary antibody (Jackson Immunoresearch) in 5% milk in PBST for one hour at 25° C. with shaking. The P4D1 IgG was detected by incubating the membrane in a 1:10,000 dilution of a goat anti-mouse Fcγ-specific HRP-conjugated F(ab')2 secondary antibody (Jackson Immunoresearch) in 5% milk in PBST for one hour at 25° C. with shaking. The membranes were then washed three times in PBST followed by one wash in PBS. The secondary antibodies were detected using Super Signal West Pico chemiluminescent substrate (Thermo Scientific) followed by exposure of the blots to film. Whereas the control pan-ubiquitin antibody, P4D1 recognizes monoubiquitin, linear polyubiquitin 2-7 (albeit poorly), K11-linked polyubiquitin, K48-linked polyubiquitin 2-7, and K63-linked polyubiquitin 2-7, the 1F11/3F5/Y102L IgG recognizes only linear polyubiquitin (see FIG. 15). Thus, just as with linear diubiquitin, the 1F11/3F5/Y102L antibody can detect polyubiquitin chains containing the linear linkage, but does not recognize polyubiquitin chains of other linkages.

C) IgG Western Blot of TNFα-Treated Cell Lysates

HeLa S3 cells were grown in suspension culture in 50:50 F-12: Dulbecco's Modified Eagle Media (DMEM) supplemented with 10% fetal bovine serum (FBS), 2 mM L-glutamine, 1% glycine/hypoxanthine/thymidine (GHT) solution, and 1% penicillin/streptomycin. The day before the experiment the cells were split 1:2. The cells were grown overnight until reaching a density of $0.38 \times 10^6$ cells/mL (98% viable). The cells were divided into three flasks of 1.5 L of cells each. Flask 1 was pretreated with 5.8 μM MG132 (Cayman Chemicals) for 10 minutes. Flask 2 and 3 received no pretreatment. At time zero flasks 2 and 3 also were treated with 5.8 μM MG132. In addition at time zero, flasks 1 and 3 were treated with 100 ng/mL TNFα (Shenandoah Biotechnology) and flask 2 was treated with 500 ng/mL TNFα. At time zero, five minutes, and 20 minutes 444 mL of cells were removed from each flask, spun down at 800 rpm for five minutes at 4° C., and the supernatants were aspirated. Cells were immediately washed with 40 mL of cold PBS, pelleted at 800 rpm for five minutes at 4° C., and the supernatants were aspirated. Each pellet was lysed in 13 mL of cold lysis buffer (20 mM Tris pH 7.5, 150 mM NaCl, 1 mM EDTA, 1% Triton X-100, 10 mM N-ethylmaleimide (NEM), 25 μM MG132, 50 mM NaF, Complete protease inhibitor cocktail tablets (Roche), and PhosSTOP phosphatase inhibitor cocktail tablets (Roche)) for 10 minutes at 4° C. with rocking. Debris was pelleted by spinning at 10,000×g for five minutes at 4° C. Lysates were precleared with 133 μL of Protein A Dynabeads (Invitrogen) for 1 hour at 4° C. with rocking. Beads were pelleted by spinning at 2000 rpm for five minutes. The supernatant was removed and stored at −80° C.

Linear polyubiquitin chains have been suggested to play a signaling role in the NFκB pathway. Therefore the above lysates were probed with 1F11/3F5/Y102L in a western blot. Thirteen μL of each lysate in 1×LDS sample buffer (Invitrogen) with reducing agent (Invitrogen) was heated at 70° C. for ten minutes and run on 4-12% Bis Tris NuPAGE 1.0 mm gels (Invitrogen) in MES buffer (Invitrogen) in duplicate. As specificity controls 250 ng of purified linear (Enzo Lifesciences) and K63-linked polyubiquitin chains (Boston Biochem) were run on the gel. The gels were transferred individually at 30 V constant for one hour by wet transfer in 10% methanol and 1× NuPAGE transfer buffer (Invitrogen) to 0.45 μm nitrocellulose (Invitrogen). Non-specific binding sites on the membranes were blocked by incubation in 5% milk in PBST for one hour at 25° C. with shaking. The membranes were then incubated in 1 μg/mL of 1F11/3F5/Y102L or Apu3.A8 anti-K63 in 5% milk in PBST for one hour at 25° C. with shaking. The membranes were washed three times in PBST with shaking. The IgGs were detected by incubating the membranes in a 1:10,000 dilution of a goat anti-human Fcγ-specific HRP-conjugated F(ab')2 secondary antibody (Jackson Immunoresearch) in 5% milk in PBST for one hour at 25° C. with shaking. The membranes were then washed three times in PBST followed by one wash in PBS. The secondary antibody was detected using Super Signal West Pico chemiluminescent substrate (Thermo Scientific) followed by exposure of the blots to film. An additional western blot was done to assess activation of the NFκB pathway by probing for IκBα levels. Upon TNFα signaling this leads to ubiquitination and degradation of the inhibitor of NFκB, IκBα. Five μL of the above lysates in 1×LDS sample buffer (Invitrogen) with reducing agent (Invitrogen) was heated at 70° C. for ten minutes and run on a 4-12% Bis Tris NuPAGE 1.0 mm gel (Invitrogen) in MES buffer (Invitrogen) in duplicate. The gel was transferred at 30 V constant for two hours by wet transfer in 20% methanol and 1× NuPAGE transfer buffer (Invitrogen) to Invitrolon PVDF (Invitrogen). The membrane was blocked in 5% milk in PBST for one hour at 25° C. with shaking and then probed with 1:1000 dilutions of an anti-IκBα (Cell Signaling) and an anti-β-tubulin (Cell Signaling) antibody as a loading control at 4° C. overnight with shaking. The following day the blots were washed three times in PBST with shaking. The IgGs were detected by incubating the membranes in a 1:10,000 dilution of a goat anti-rabbit Fcγ-specific HRP-conjugated F(ab')2 secondary antibody (Jackson Immunoresearch) in 5% milk in PBST for one hour at 25° C. with shaking. The membranes were then washed three times in PBST followed by one wash in PBS. The secondary antibody was detected using Super Signal West Pico chemiluminescent substrate (Thermo Scientific) followed by exposure of the blots to film.

Figure 16A:
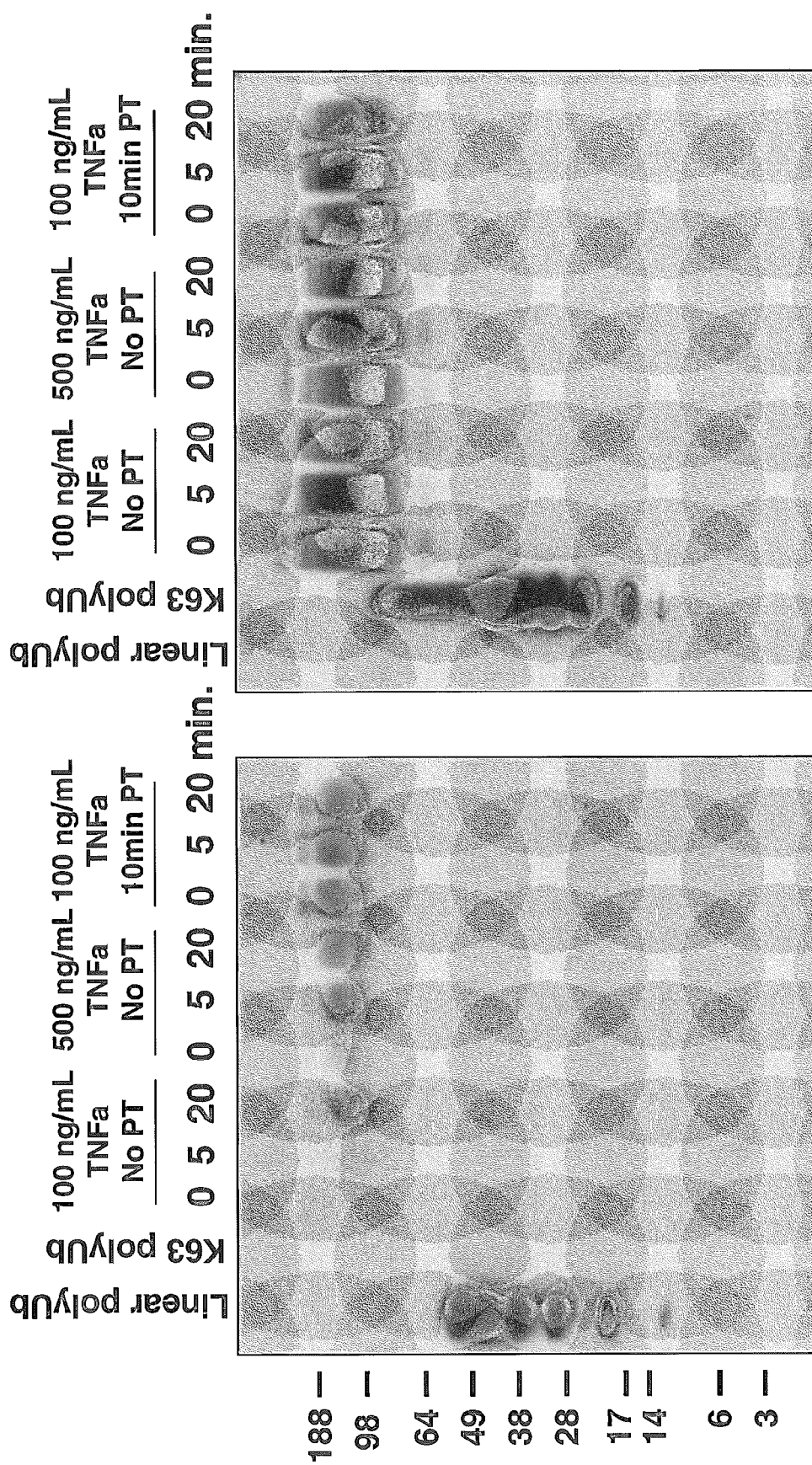
FIGS. 16A and B depict the results of experiments in which lysates of HeLa S3 cells treated with varying concentrations of TNFα and for varying amounts of time with 5.8 µM MG132 were immunoblotted for linear ubiquitin chains with the hybrid antibody 1F11/3F5/Y102L or for K63-linked ubiquitin chains with the Apu3.A8 antibody. As a control 250 ng each of purified linear polyubiquitin 2-7 and K63-linked polyubiquitin 2-7 was run on each gel (FIG. 16A). To assess the level of NFκB pathway activation the lysates were blotted for IκBα levels (FIG. 16B). As a loading control the lysates were blotted for β-tubulin.
Figure 16B:
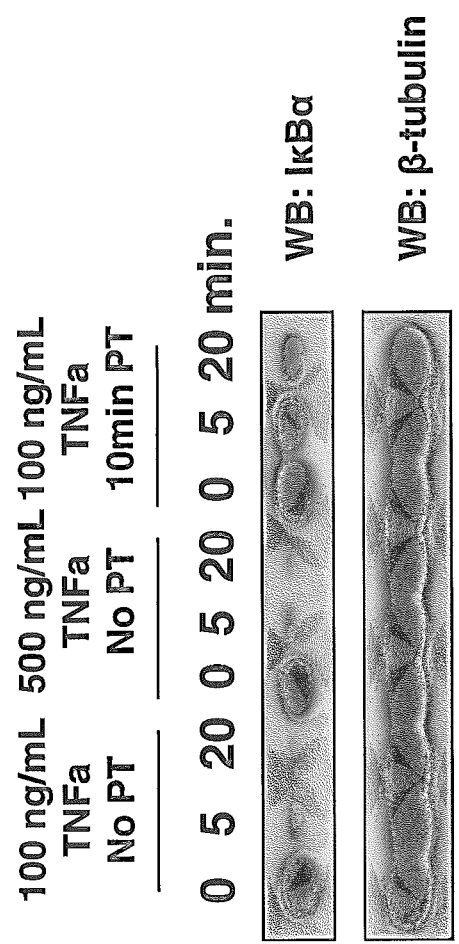

In cells which were stimulated with 100 ng/mL TNFα and no pretreatment with MG132, the amount of linear polyubiquitin chains increases from time zero to five minutes to 20 minutes (see FIG. 16A). In contrast, K63-linked polyubiquitin chains which were much more abundant at all three time points showed an increase from zero to five minutes and then a decrease back down to the starting levels at 20 minutes. In cells which were stimulated with 500 ng/mL TNFα and no pretreatment with MG132, the linear polyubiquitin chains demonstrated the same pattern of increasing from zero to 20 minutes, however the abundance of the linear chains at each time point was increased compared to the cells treated with 100 ng/mL TNFα. In contrast, the K63-linked chains demonstrated the same pattern and abundance as compared to the cells treated with 100 ng/mL TNFα. In cells which were pretreated for 10 minutes with 5.8 μM MG132 and then 100 ng/mL TNFα, the levels of both linear and K63-linked chains remained fairly constant over the three time points. The blot for IκBα demonstrates that under all three experimental conditions the NFκB pathway is activated as evidenced by degradation of IκBα upon TNFα treatment over time, however the extent of activation in greater in the absence of MG132 pretreatment (see FIG. 16B). This demonstrates that 1F11/3F5/Y102L can recognize endogenous linear polyubiquitin chains and suggests that these chains are up regulated in HeLa S3 cells upon TNFα, stimulation.

D) Immunoprecipitation of Linear Polyubiquitin Chains

Figure 17:
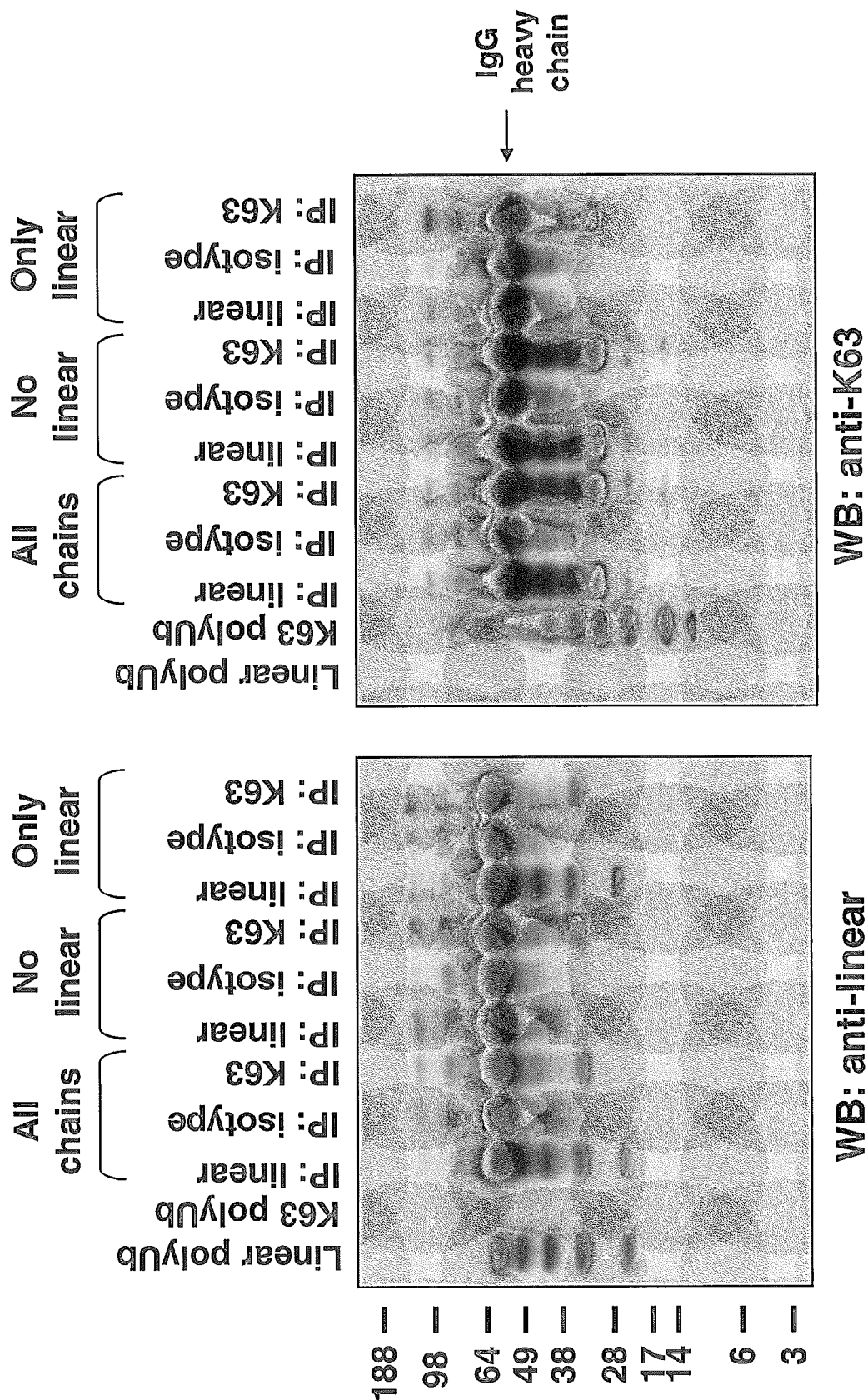
FIG. 17 depicts the results of immunoprecipitation experiments with the hybrid anti-linear polyubiquitin antibody 1F11/3F5/Y102L, an isotype control, or an anti-K63 antibody Apu3.A8. The IP experiments were performed in 4 M urea IP buffer under three conditions (a mixture of all ubiquitin chains, no linear ubiquitin chains, or only linear ubiquitin chains). As a control 1 µg each of purified linear polyubiquitin 2-7 and K63-linked polyubiquitin 2-7 was run on each gel.

The 1F11/3F5/Y102L IgG was tested to see whether it is capable of immunoprecipitating linear polyubiquitin chains. As a positive control the Apu3.A8 anti-K63 antibody was also used to monitor immunoprecipitation of K63-linked chains. As a negative control an unrelated human kappa IgG1 antibody was used as an isotype control. Three immunoprecipitation (IP) conditions were tested. In reaction 1 which contained all chains, 2 μg each of monoubiquitin (Boston Biochem), linear polyubiquitin 2-7 (Enzo Lifesciences), K11-linked polyubiquitin (Genentech), K48-linked polyubiquitin 2-7 (Boston Biochem), and K63-linked polyubiquitin 2-7 (Boston Biochem) were mixed. In reaction 2 which lacked linear chains, 2 μg each of monoubiquitin, K11-linked polyubiquitin, K48-linked polyubiquitin 2-7, and K63-linked polyubiquitin 2-7 were mixed. Reaction 3 consisted of 2 μg of linear polyubiquitin 2-7 chains alone. Each reaction was diluted in 500 μL of 4 M urea IP buffer (4 M urea, 20 mM Tris, pH 7.5, 135 mM NaCl, 1% Triton X-100, 10% glycerol, 1 mM EDTA, 1.5 mM MgCl$_2$). The reactions were precleared with 50 μL of Protein A Dynabeads (Invitrogen) for three hours at 25° C. with rotation. The beads were then captured on a magnetic stand and the supernatants were transferred to new tubes. Twenty μg of 1F11/3F5/Y102L anti-linear, Apu3.A8 anti-K63, or an isotype control IgG was added to each IP reaction and incubated overnight at 25° C. with rotation. The following day 100 μL of Protein A Dynabeads were added to each reaction and the IgGs were captured for 15 minutes at 25° C. with rotation. The beads were then washed three times with 1 mL each of 4M urea IP buffer followed by two washes with 1 mL each of PBS. During the final wash the beads were transferred to new tubes to avoid eluting any proteins bound to the tube walls. The beads were resuspended in 30 μL of 1×LDS sample buffer (Invitrogen) with reducing agent (Invitrogen) and heated at 70° C. for 10 minutes to elute the immunoprecipitated proteins. The beads were then captured on a magnetic stand and the supernatant was split in half and loaded in duplicate onto two 4-12% Bis Tris NuPAGE 1.0 mm gels (Invitrogen). As positive and negative controls 1 μg each of purified linear polyubiquitin 2-7 (Enzo Lifesciences) and K63-linked polyubiquitin 2-7 (Boston Biochem) were also run on the gels. The gels were run in MES buffer (Invitrogen) and were then transferred individually at 30 V constant for one hour by wet transfer in 10% methanol and 1× NuPAGE transfer buffer (Invitrogen) to 0.2 μm nitrocellulose (Invitrogen). Non-specific binding sites on the membranes were blocked by incubation in 5% milk in PBST for one hour at 25° C. with shaking. The membranes were then incubated in 1 μg/mL of 1F11/3F5/Y102L or Apu3.A8 anti-K63 in 5% milk in PBST for 1.5 hours at 25° C. with shaking. The membranes were washed three times in PBST with shaking. The IgGs were detected by incubating the membranes in a 1:10,000 dilution of a goat anti-human Fcγ-specific HRP-conjugated F(ab')2 secondary antibody (Jackson Immunoresearch) in 5% milk in PBST for one hour at 25° C. with shaking. The membranes were then washed three times in PBST followed by one wash in PBS. The secondary antibody was detected using Super Signal West Pico chemiluminescent substrate (Thermo Scientific) followed by exposure of the blots to film. 1F11/3F5/Y102L is able to immunoprecipitate linear polyubiquitin chains in 4M urea however it is not specific under these conditions as it is also able to pull down K63-linked chains (see FIG. 17).

Figure 18A:
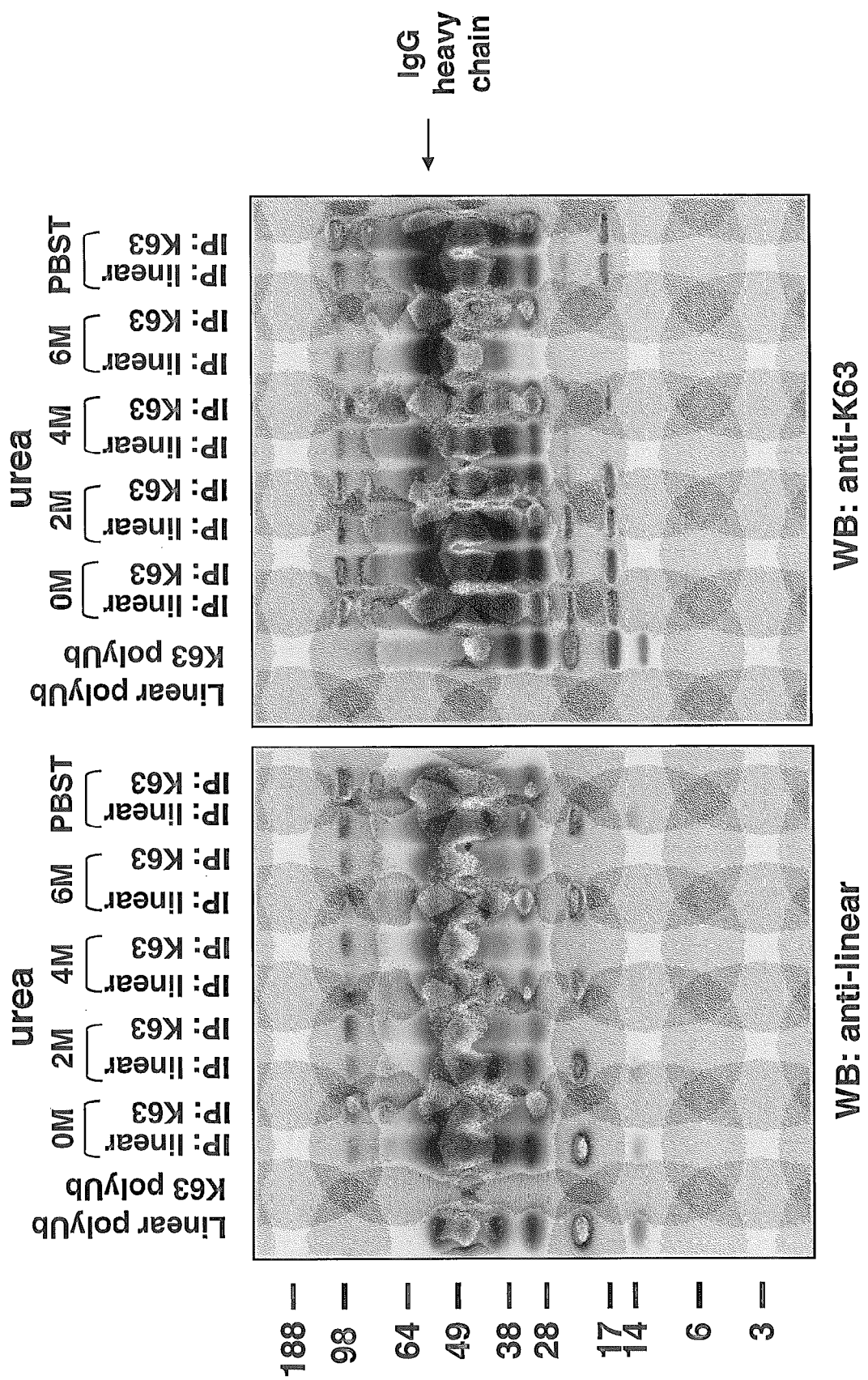
FIGS. 18A and B depict the results of immunoprecipitation experiments using a 1:1 mixture of linear polyubiquitin 2-7 and K63-linked polyubiquitin 2-7 with the anti-linear polyubiquitin antibody 1F11/3F5/Y102L or the anti-K63 antibody Apu3.A8 in varying concentrations of urea or PBST which were immunoblotted with either IF11/3F5/Y102L (anti-linear) or Apu3.A8 (anti-K63). As a control 1 µg each of purified linear polyubiquitin 2-7 and K63-linked polyubiquitin 2-7 was run on each gel.

To determine whether different concentrations of urea could help improve specificity, immunoprecipitations were carried out under different buffer conditions. Two μg each of linear polyubiquitin 2-7 and K63-linked polyubiquitin 2-7 were mixed and diluted with 500 μl of IP buffer (20 mM Tris, pH 7.5, 135 mM NaCl, 1% Triton X-100, 10% glycerol, 1 mM EDTA, 1.5 mM $MgCl_2$) containing 0, 2, 4, or 6 M urea. An additional IP was done using 500 μL of PBST. The reactions were precleared with 50 μL of Protein A Dynabeads (Invitrogen) for 30 minutes at 25° C. with rotation. The beads were then captured on a magnetic stand and the supernatants were transferred to new tubes. Twenty μg of 1F11/3F5/Y102L anti-linear or Apu3.A8 anti-K63 IgG was added to each IP reaction and incubated at 25° C. with rotation for one hour. Next 100 μL of Protein A Dynabeads were added to each reaction and the IgGs were captured for 15 minutes at 25° C. with rotation. The beads were then washed three times with 1 mL each of the corresponding buffer used in the IP (0, 2, 4, or 6 M urea FP buffer or PBST) followed by two washes with 1 mL each of PBS. During the final wash the beads were transferred to new tubes to avoid eluting any proteins bound to the tube walls. The beads were resuspended in 20 μL at of 1×LDS sample buffer (Invitrogen) with reducing agent (Invitrogen) and heated at 70° C. for 10 minutes to elute the immunoprecipitated proteins. The beads were then captured on a magnetic stand and the supernatant was split in half and loaded in duplicate onto two 4-12% Bis Tris NuPAGE 1.0 mm gels (Invitrogen). As positive and negative controls 1 μg each of purified linear polyubiquitin 2-7 and K63-linked polyubiquitin 2-7 were also run on the gels. The gels were run in MES buffer (Invitrogen) and were then transferred individually at 30 V constant for one hour by wet transfer in 10% methanol and 1× NuPAGE transfer buffer (Invitrogen) to 0.2 μm nitrocellulose (Invitrogen). Non-specific binding sites on the membranes were blocked by incubation in 5% milk in PBST for one hour at 25° C. with shaking. The membranes were then incubated in 1 μg/mL of 1F11/3F5/Y102L or Apu3.A8 anti-K63 in 5% milk in PBST for one hour at 25° C. with shaking. The membranes were washed three times in PBST with shaking. The IgGs were detected by incubating the membranes in a 1:10,000 dilution of a goat anti-human Fcγ-specific HRP-conjugated F(ab')2 secondary antibody (Jackson Immunoresearch) in 5% milk in PBST for one hour at 25° C. with shaking. The membranes were then washed three times in PBST followed by one wash in PBS. The secondary antibody was detected using Super Signal West Pico chemiluminescent substrate (Thermo Scientific) followed by exposure of the blots to film. As the concentration of urea is increased in the IP buffer, the 1F11/3F5/Y102L IP becomes more specific (see FIG. 18A). At 6 M urea very little K63-linked polyubiquitin is pulled down by the 1F11/3F5/Y102L IgG and yet it is still able to pull down a significant amount of linear polyubiquitin.

Figure 18B:
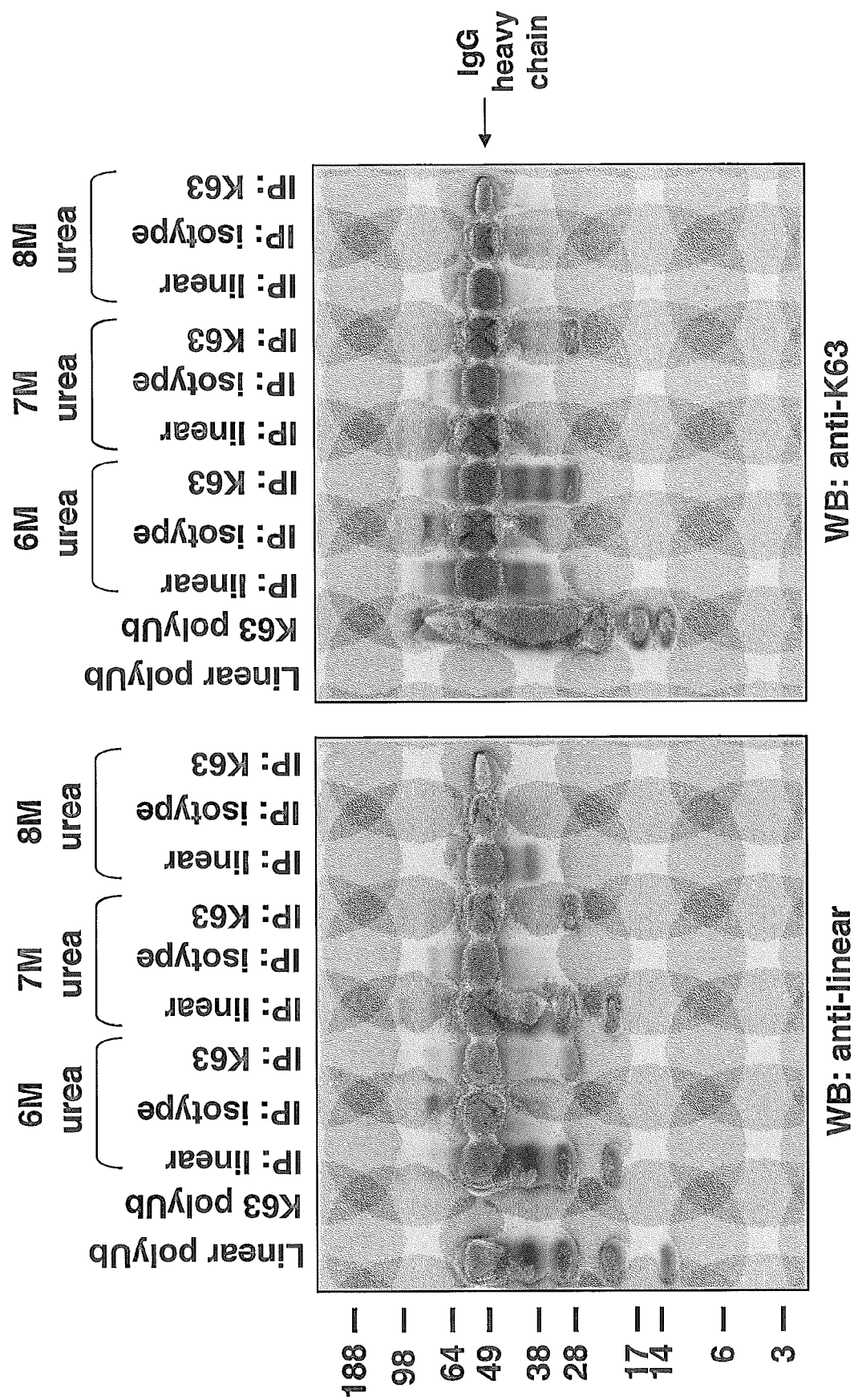
FIG. 18B shows the results of IP experiments in 6M, 7M, and 8M urea.

To see whether even higher concentrations of urea could further improve specificity the IPs were repeated using 6, 7, or 8 M urea IP buffer. Two μg each of linear polyubiquitin 2-7 and K63-linked polyubiquitin 2-7 were mixed and diluted with 500 of IP buffer (20 mM Tris, pH 7.5, 135 mM NaCl, 1% Triton X-100, 10% glycerol, 1 mM EDTA, 1.5 mM $MgCl_2$) containing 6, 7, or 8 M urea. The reactions were precleared with 50 μL of Protein A Dynabeads (Invitrogen) for 15 minutes at 25° C. with rotation. The beads were then captured on a magnetic stand and the supernatants were transferred to new tubes. Twenty μg of 1F11/3F5/Y102L anti-linear, Apu3.A8 anti-K63, or an isotype control IgG was added to each IP reaction and incubated at 25° C. with rotation for one hour. Next 100 μL of Protein A Dynabeads were added to each reaction and the IgGs were captured for 15 minutes at 25° C. with rotation. The beads were then washed three times with 1 mL each of the corresponding buffer used in the IP (6, 7, or 8 M urea IP buffer) followed by two washes with 1 mL each of PBS. During the final wash the beads were transferred to new tubes to avoid eluting any proteins bound to the tube walls. The beads were resuspended in 30 μL of 1×LDS sample buffer (Invitrogen) with reducing agent (Invitrogen) and heated at 70° C. for 10 minutes to elute the immunoprecipitated proteins. The beads were then captured on a magnetic stand and the supernatant was split in half and loaded in duplicate onto two 4-12% Bis Tris NuPAGE 1.0 mm gels (Invitrogen). As positive and negative controls 1 μg each of purified linear polyubiquitin 2-7 and K63-linked polyubiquitin 2-7 were also run on the gels. The gels were run in MES buffer (Invitrogen) and the western blots were performed as described in the preceding paragraph. One blot was probed with 1F11/3F5/Y102L to detect linear chains and the other was probed with Apu3.A8 anti-K63 to detect K63-linked chains. In 6 M urea there is a small amount of K63-linked chains pulled down by 1F11/3F5/Y102L as seen in the previous IPs (see FIG. 18B). In 7 M urea 1F11/3F5/Y102L behaves just like the isotype control and does not pull down any K63-linked chains however it still retains the ability to IP a significant amount of linear polyubiquitin when compared to what was present in the starting material. In 8 M urea, however the amount of linear chains pulled down by 1F11/3F5/Y102L is dramatically reduced. Thus, 7 M urea is the most specific condition which strikes a balance between pulling down a significant amount of linear chains without bringing down K63-linked chains.

Figure 19:
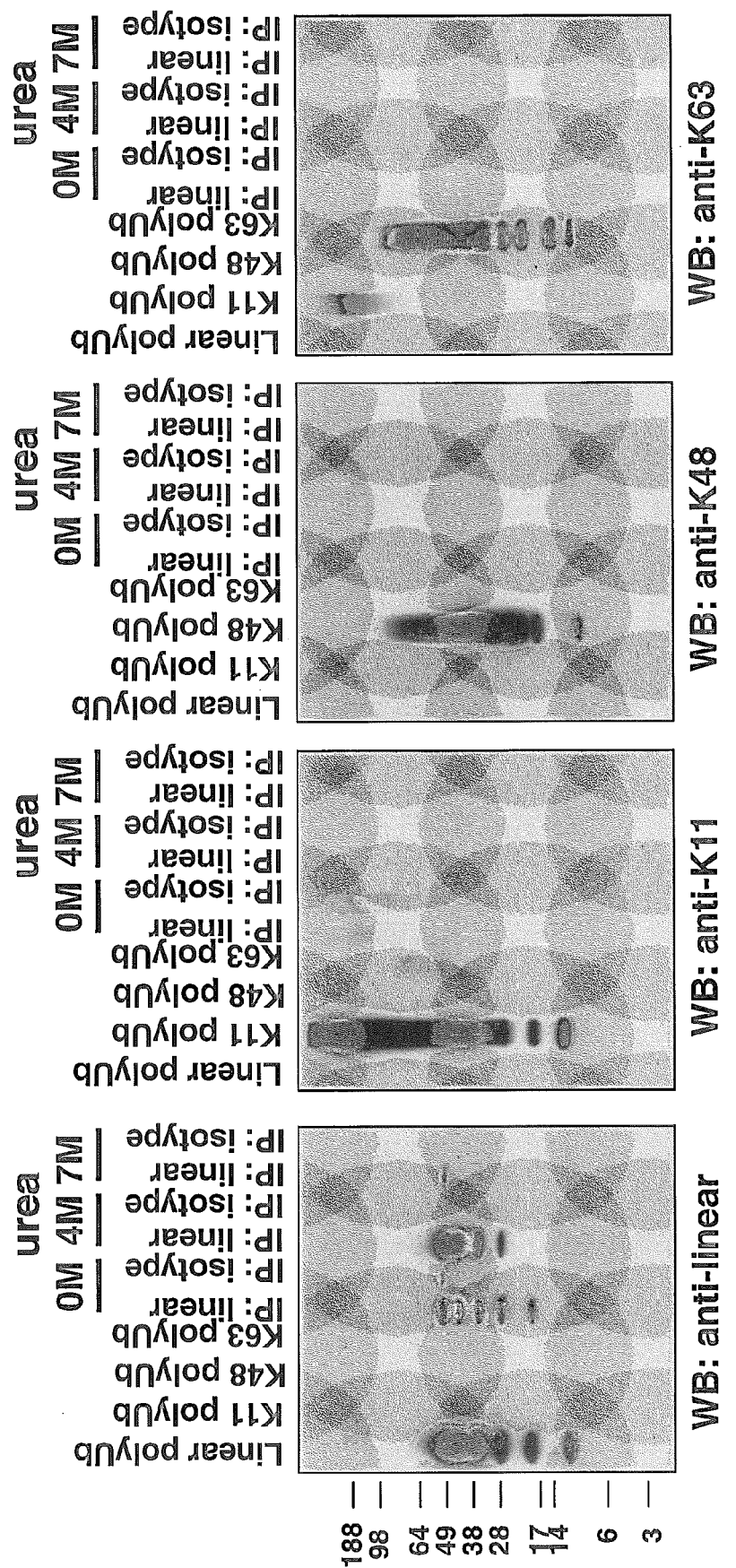
FIG. 19 shows the results of immunoprecipitation and immunoblotting experiments using a 1:1:1:1 mixture of linear polyubiquitin 2-7, K11-linked polyubiquitin, K48-linked polyubiquitin, and K63-linked polyubiquitin 2-7 with the anti-linear polyubiquitin antibody 1F11/3F5/Y102L, an isotype control, or the anti-K63 polyubiquitin antibody Apu3.A8 crosslinked to Protein A beads in varying concentrations of urea. Antibodies used in the immunoblotting were 1F11/3F5/Y102L (anti-linear), 2A3/2E6 (anti-K11), Apu2.07 (anti-K48), or Apu3.A8 (anti-K63) IgG. As a control 1 µg each of purified linear polyubiquitin 2-7, K11-linked polyubiquitin, K48-linked polyubiquitin 2-7, and K63-linked polyubiquitin 2-7 was run on each gel.

In the previous IPs the heavy chain of the IgGs used in the pull down is eluted from the beads and detected by the secondary antibody used in the western blots. This band can often obscure bands of the pull down material. To make the blots cleaner and to be absolutely sure no K63-linked chains were being pulled down the IgGs were crosslinked to the beads before the IPs. Twenty μg of either 1F11/3F5/Y102L or an isotype control IgG were incubated with 200 μL of Protein A Dynabeads in PBST for 30 minutes at 25° C. with rotation. The beads were captured on a magnetic stand and washed twice with 800 μL of conjugation buffer (20 mM sodium phosphate pH 7.5, 150 mM NaCl). The IgG-coupled beads were resuspended in 1 mL of 5 mM Bis(sulfosuccinimidyl) suberate (BS3) in conjugation buffer and incubated at 25° C. with rotation for 30 minutes to crosslink. While crosslinking the IgGs to the beads the IP reactions were set up. Four µg each of linear polyubiquitin 2-7, K11-linked polyubiquitin, K48-linked polyubiquitin 2-7, and K63-linked polyubiquitin 2-7 were mixed and diluted with 500 µL of IP buffer (20 mM Tris, pH 7.5, 135 mM NaCl, 1% Triton X-100, 10% glycerol, 1 mM EDTA, 1.5 mM $MgCl_2$) containing 0, 4, or 7 M urea. The mixtures were precleared with 50 µL of Protein A Dynabeads for 45 minutes at 25° C. with rotation. After 30 minutes the crosslinking reaction was quenched by the addition of 48 µL of 1 M Tris pH 7.5 and incubation at 25° C. with rotation for 15 minutes. The crosslinked beads were washed three times with 800 µL of IP buffer containing the corresponding amount of urea to be used in the IP (i.e. 0, 4, or 7 M urea). After washing the IgG-crosslinked beads were resuspended in the precleared IP reactions and incubated at 25° C. with rotation for one hour. The IgG-crosslinked beads were then washed three times with 1 mL of IP buffer containing the corresponding amount of urea followed by two washes with 1 mL of PBS. During the final wash the beads were transferred to new tubes to avoid eluting any proteins bound to the tube walls. The beads were resuspended in 50 µL of 1×LDS sample buffer (Invitrogen) with reducing agent (Invitrogen) and heated at 70° C. for 10 minutes to elute the immunoprecipitated proteins. The beads were then captured on a magnetic stand and the supernatant was split and loaded in quadruplicate onto 4-12% Bis Tris NuPAGE 1.0 mm gels (Invitrogen). As positive and negative controls 1 µg each of purified linear polyubiquitin 2-7, K11-linked polyubiquitin, K48-linked polyubiquitin and K63-linked polyubiquitin 2-7 were also run on the gels. The gels were run in MES buffer (Invitrogen) and the western blots were performed as described above in this example. One blot was probed with 1F11/3F5/Y102L to detect linear chains, one blot was probed with 2A3/2E6 anti-K11 to detect K11-linked chains, one blot was probed with Apu2.07 anti-K48 to detect K48-linked chains, and one blot was probed with Apu3.A8 anti-K63 to detect K63-linked chains. When comparing the amount of material in the IPs with the amount of material present in the starting inputs, overall much less linear polyubiquitin was pulled down in each IP with 1F11/3F5/Y102L compared to the IPs done with free IgG that was subsequently captured on the beads in the previous paragraphs (see FIG. 19). This could be due to the fact that 1F11/3F5/Y102L is a member of the human IgG1 VH3 subgroup which contains a second Protein A binding site in the heavy chain variable domain, in addition to the usual binding site in the Fc domain. Therefore, precoupling and crosslinking of the IgGs to Protein A beads before antigen binding could diminish the binding capacity of this antibody. Under these precoupling and crosslinking conditions 4 M urea is the most specific condition where 1F11/3F5/Y102L is able to pull down linear chains without bringing down any K11-, K48-, or K63-linked chains.

Figure 20:
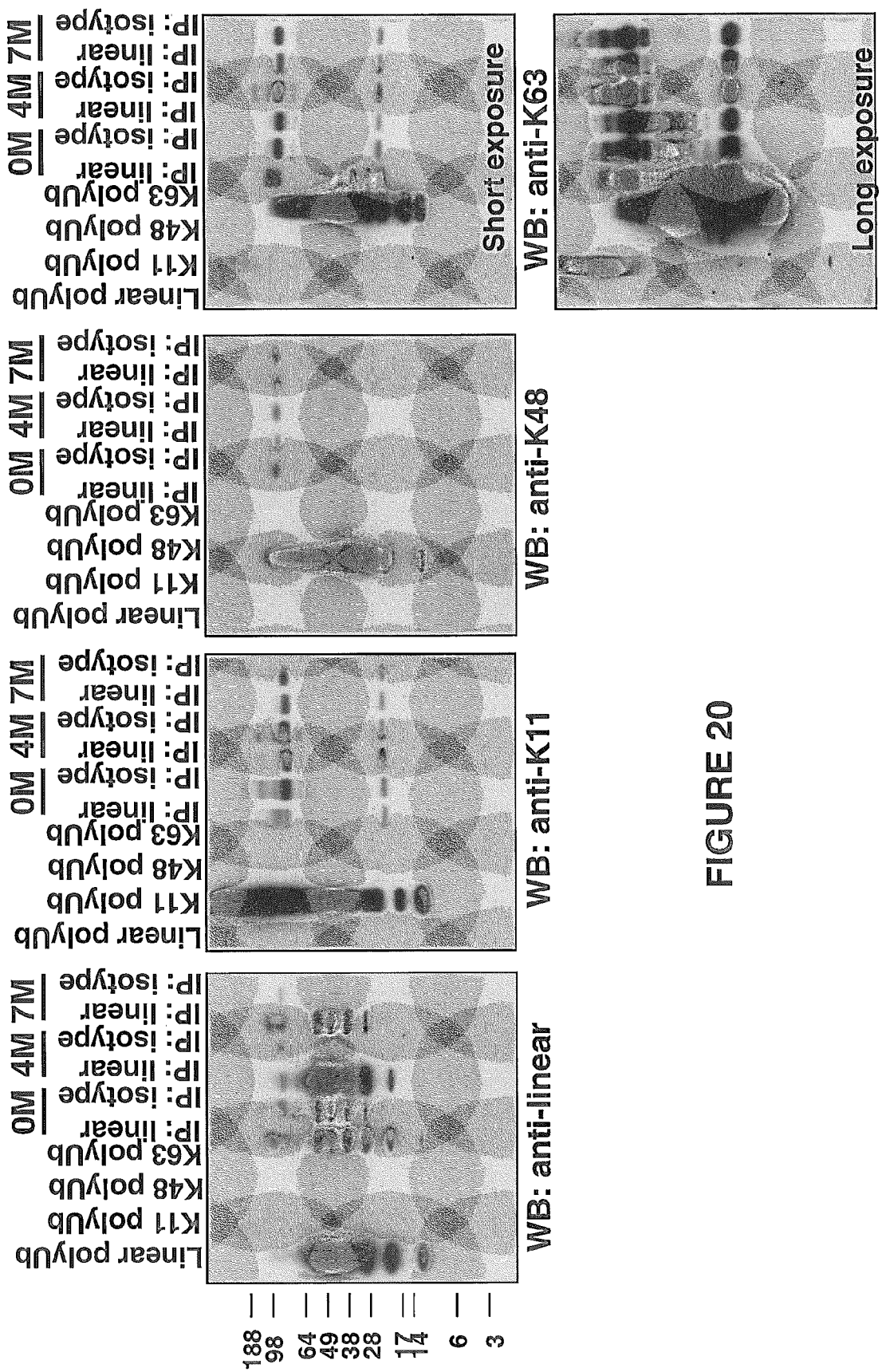
FIG. 20 shows the results of immunoprecipitation and immunoblotting experiments using a 1:1:1:1 mixture of linear polyubiquitin 2-7, K11-linked polyubiquitin, K48-linked polyubiquitin, and K63-linked polyubiquitin 2-7 with the hybrid anti-linear polyubiquitin antibody 1F11/3F5/Y102L, an isotype control, or the anti-K63 polyubiquitin IgG antibody Apu3.A8 crosslinked to Protein G beads in varying concentrations of urea. Antibodies used in immunoblotting were 1F11/3F5/Y102L (anti-linear), 2A3/2E6 (anti-K11), Apu2.07 (anti-K48), or Apu3.A8 (anti-K63) IgG. As a control 1 µg each of purified linear polyubiquitin 2-7, K11-linked polyubiquitin, K48-linked polyubiquitin 2-7, and K63-linked polyubiquitin 2-7 was run on each gel.

To see whether the reduction in linear chains pulled down was due to the additional Protein A binding site in the heavy chain variable domain, the IPs were done using IgGs crosslinked to Protein G beads. Protein G also has two binding sites on human IgG1 but both are in the constant domains (CH1 and Fc). The IPs were repeated as described above except Protein G Dynabeads (Invitrogen) were used for precoupling and crosslinking the IgGs. Much more linear polyubiquitin chains were pulled down in each condition by 1F11/3F5/Y102L compared to the experiments with the IgGs crosslinked to Protein A (see FIG. 20). Upon over-exposure of the anti-K63 blot at 4 M urea there is a small amount of K63-linked chains pulled down by 1F11/3F5/Y102L. Thus 7 M urea seems to be the most specific condition when 1F11/ 3F5/Y102L is precoupled to Protein G beads however this comes at the expense of pulling down less linear polyubiquitin compared to when the IPs are done with free IgG that is subsequently captured on beads (compare to FIG. 18B). It is possible that precoupling and crosslinking of Protein G beads to the CH1 domain may also diminish binding to linear polyubiquitin through steric hindrance of the neighboring VH domain, although less significantly than precoupling and crosslinking of Protein A beads to the VH domain.

Figure 21A:
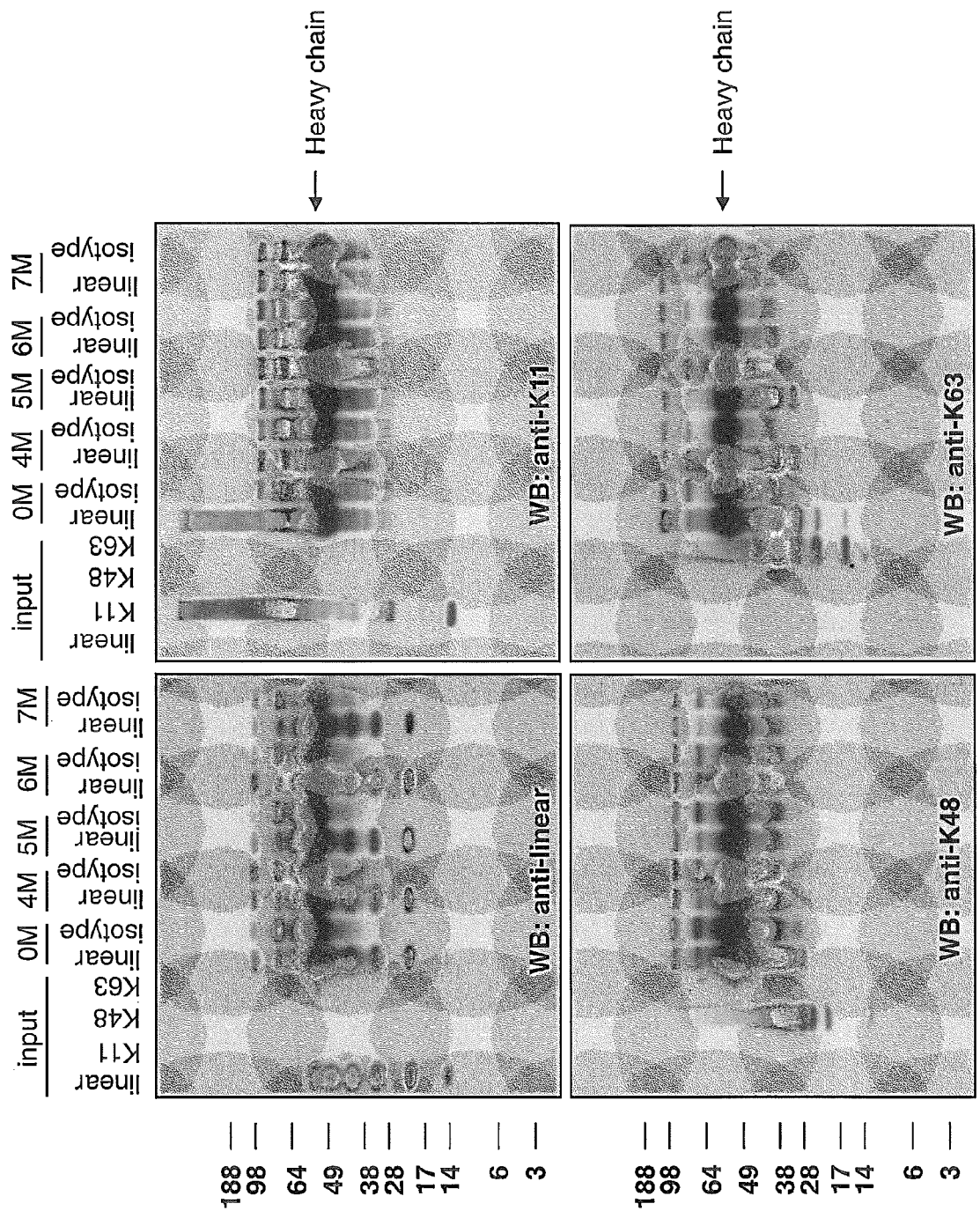
FIG. 21A depicts the results of immunoprecipitation and immunoblotting experiments from a 1:1:1:1 mixture of linear polyubiquitin 2-7, K11-linked polyubiquitin, K48-linked polyubiquitin, and K63-linked polyubiquitin 2-7 with the anti-linear polyubiquitin antibody 1F11/3F5/Y102L, an isotype control, or the anti-K63 polyubiquitin antibody Apu3.A8 in varying concentrations of urea. Antibodies used in immunoblotting were 1F11/3F5/Y102L (anti-linear), 2A3/2E6 (anti-K11), Apu2.07 (anti-K48), or Apu3.A8 (anti-K63) IgG. As a control 500 ng each of purified linear polyubiquitin 2-7, K11-linked polyubiquitin, K48-linked polyubiquitin 2-7, and K63-linked polyubiquitin 2-7 was run on each gel.

The IPs using free IgG followed by subsequent capture with Protein A beads were repeated using a mixture of polyubiquitin chains of different linkages as the substrate and were analyzed more extensively by western blot and mass spectrometry. Two µg each of linear polyubiquitin 2-7 (Boston Biochem), K11-linked polyubiquitin (Genentech), K48-linked polyubiquitin 2-7 (Boston Biochem), and K63-linked polyubiquitin 2-7 (Boston Biochem) were mixed and diluted with 500 µL of IP buffer (20 mM Tris, pH 7.5, 135 mM NaCl, 1% Triton X-100, 10% glycerol, 1 mM EDTA, 1.5 mM $MgCl_2$) containing 0, 4, 5, 6 or 7 M urea. Each IP was done in duplicate, one for western blots and the other for mass spectrometry analysis. The reactions were precleared with 50 µL of Protein A Dynabeads (Invitrogen) for 15 minutes at 25° C. with rotation. The beads were then captured on a magnetic stand and the supernatants were transferred to new tubes. Twenty µg of 1F11/3F5/Y102L anti-linear or an isotype control IgG was added to each IP reaction and incubated at 25° C. with rotation for one hour. Next 100 µL of Protein A Dynabeads were added to each reaction and the IgGs were captured for 15 minutes at 25° C. with rotation. The beads were then washed three times with 1 mL each of the corresponding buffer used in the IP (0, 4, 5, 6, or 7 M urea IP buffer) followed by two washes with 1 mL each of PBS. During the final wash the beads were transferred to new tubes to avoid eluting any proteins bound to the tube walls. The beads were resuspended in 50 µL of 1×LDS sample buffer (Invitrogen) with reducing agent (Invitrogen) and heated at 70° C. for 10 minutes to elute the immunoprecipitated proteins. The beads were then captured on a magnetic stand and the supernatant was split and loaded in quadruplicate onto 4-12% Bis Tris NuPAGE 1.0 mm gels (Invitrogen) for western blots. As positive and negative controls 500 ng each of purified linear polyubiquitin 2-7, K11-linked polyubiquitin, K48-linked polyubiquitin 2-7, and K63-linked polyubiquitin 2-7 were also run on the gels. The other set of IPs were run on 4-12% Bis Tris NuPAGE 1.0 mm gels (Invitrogen) for mass spectrometry AQUA analysis. The gels were run in MES buffer (Invitrogen) and the western blots were performed as described above in this example. The blots were probed with 1F11/3F5/Y102L anti-linear polyubiquitin, 2A3/2E6 anti-K11-linked polyubiquitin, Apu2.07 anti-K48-linked polyubiquitin, and Apu3.A8 anti-K63 polyubiquitin antibodies (see FIG. 21A). The other gels for mass spectrometry AQUA were stained with SimplyBlue Coomasie Safe stain (Invitrogen) (see FIG. 21B). In the absence of urea, F11/3F5/Y102L is able to IP chains of all linkages (see FIG. 21A). As the concentration of urea is increased in the IP buffer, the 1F11/3F5/Y102L IP becomes more specific. At 7 M urea no K11-linked, K48-linked, or K63-linked polyubiquitin is pulled down by the 1F11/3F5/Y102L IgG and yet it is still able to pull down a significant amount of linear polyubiquitin relative to the starting input.

Figure 21B:
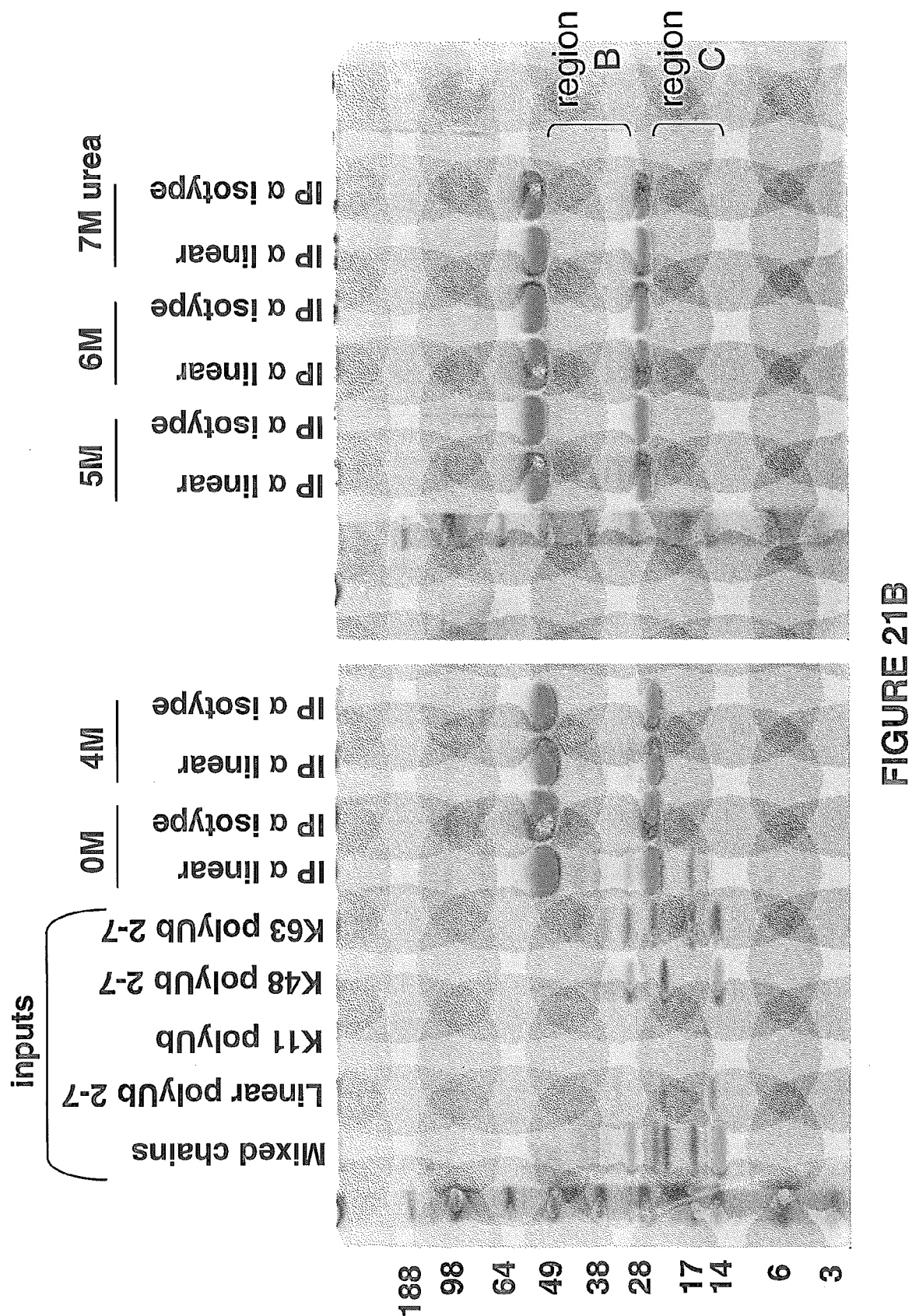
FIG. 21B depicts the results of immunoprecipitation experiments from a 1:1:1:1 mixture of linear polyubiquitin 2-7, K11-linked polyubiquitin, K48-linked polyubiquitin, and K63-linked polyubiquitin 2-7 with the hybrid anti-linear polyubiquitin antibody 1F11/3F5/Y102L, an isotype control, or the anti-K63 polyubiquitin antibody Apu3.A8 in varying concentrations of urea and separated by SDS-PAGE gel and Coomassie stained. Regions excised for mass spec AQUA are indicated.
Figure 21C:
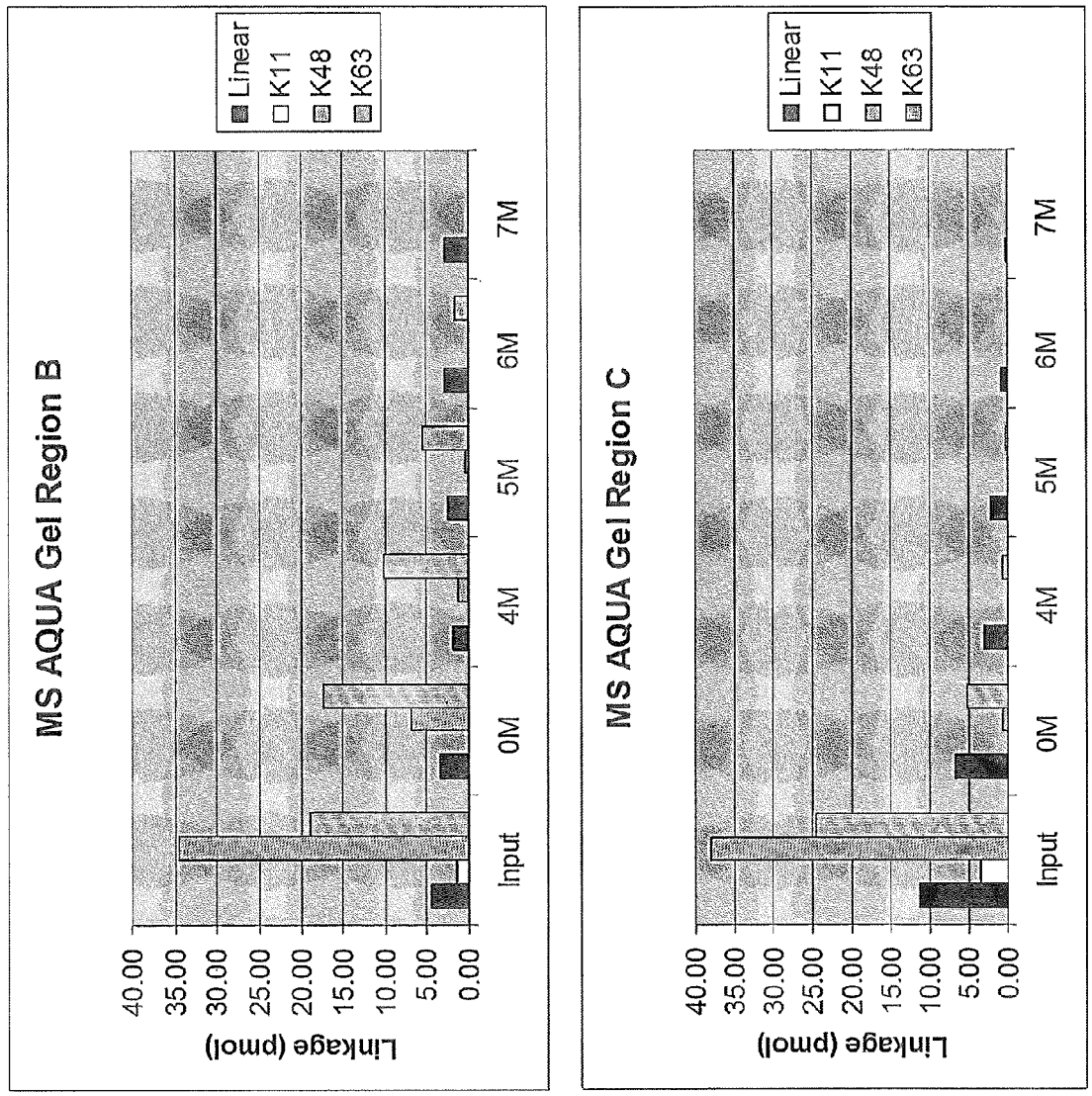
FIG. 21C is a graph which indicates the amount in picomoles of polyubiquitin linkages identified by mass spec AQUA from the 1F11/3F5/Y102L immunoprecipitations as shown in FIG. 24B (region B and region C) and described in Example 4D.
Figure 21D:
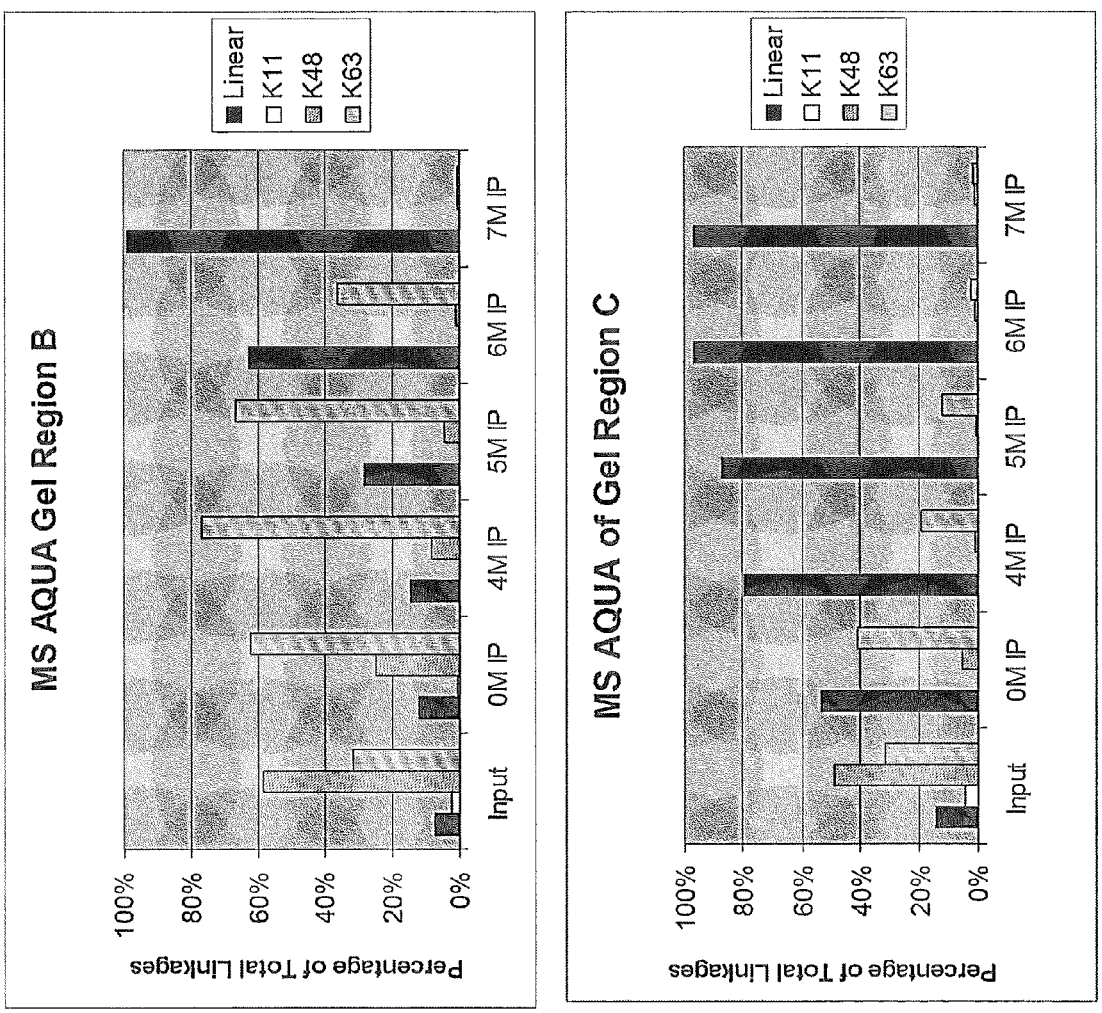
FIG. 21D is a graph which indicates the linkage composition of polyubiquitin chains identified by mass spec AQUA from the 1F11/3F5/Y102L immunoprecipitations as shown in FIG. 24B (region B and region C).
Figure 21E:
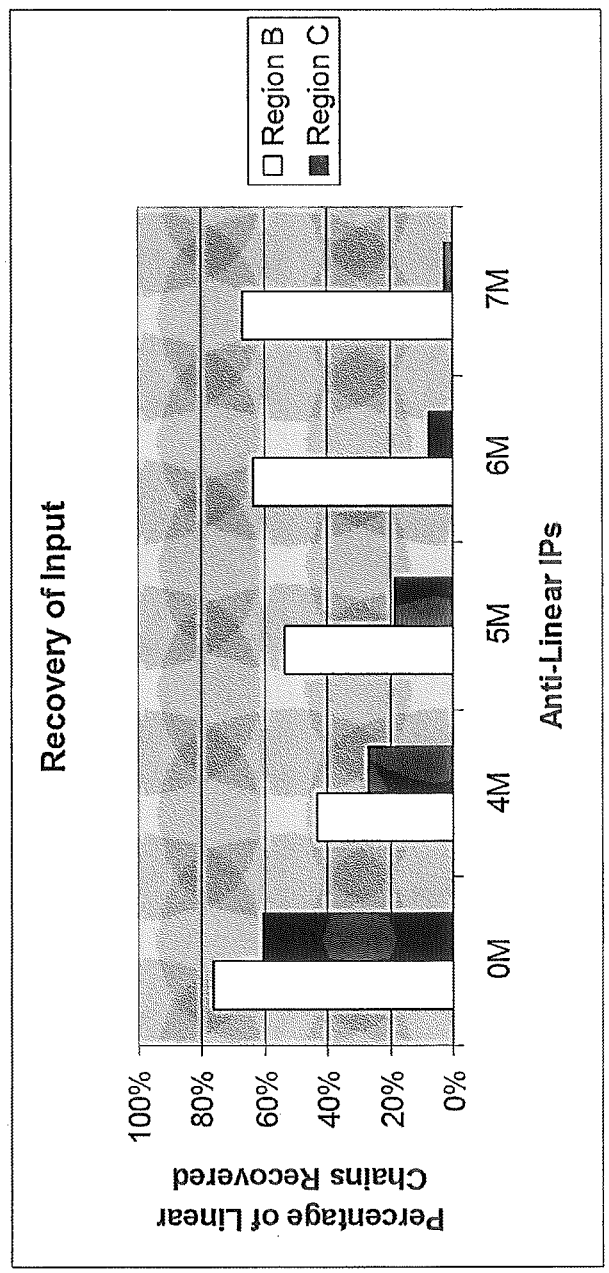
FIG. 21E is a graph which indicates the percent of linear chains recovered in the 1F11/3F5/Y102L immunoprecipitations as identified by mass spec AQUA.

Regions B and C of the Coomassie stained gel were excised, subjected to in-gel tryptic digestion, and analyzed by mass spectrometry AQUA (see FIG. 21B). Gel pieces were destained using 50 mM ammonium bicarbonate/50% methanol and then desiccated with acetonitrile (ACN). To permit effective uptake of trypsin, gel pieces were incubated on ice for 2 hr with 20 ng/µL modified sequencing grade trypsin (Promega, Madison Wis.) diluted in 50 mM ammonium bicarbonate/5% ACN. Digests were performed overnight at 37° C. and stopped by the addition of 50% ACN/5% formic acid (FA). Isotope labeled internal standard peptides (1 pmol) were added to each sample prior to two rounds of extraction (1st—50% ACN/5% FA 2nd—100% ACN). Extracted peptides were dried completely, and resuspended in 10% ACN/5% FA/0.01% $H_2O_2$ at least 30 minutes prior to mass spectrometric analysis. Samples were loaded directly onto a Thermo AQUASIL C18 column (2.1×150 mm) and separated using an Agilent 1200 capillary LC at a flow rate of 200 μl/min over a 26 minute gradient of 5% to 90% buffer B (98% ACN/0.1% FA). Mass spectrometric detection was performed on an ABI 4000 QTRAP using a segmented multiple reaction monitoring (MRM) method for detecting both labeled and unlabeled peptides covering the sequence of ubiquitin. Quantitation was performed by comparing peak areas between labeled and unlabeled versions of each peptide using ABI Multiquant 1.1 software. By measuring the abundances of the -GG signature peptides corresponding to modification of the seven lysines of ubiquitin and the amino terminus, 7M urea was confirmed to be the most specific condition for immunoprecipitation of linear polyubiquitin chains (see FIGS. 21C and 21D). In 7M urea the antibody is able to recover 67% of the linear chains present in the input from region B which contains the longer chains (tetraubiquitin through heptaubiquitin) however it is less efficient at recovering the short chains found in region C (diubiquitin and triubiquitin), with only 2% of linear chains recovered (see FIG. 21E). This is likely due to avidity from the bivalent antibody and the multiple linkages found in longer chains.

E) Overexpression of LUBAC

Figure 22A:
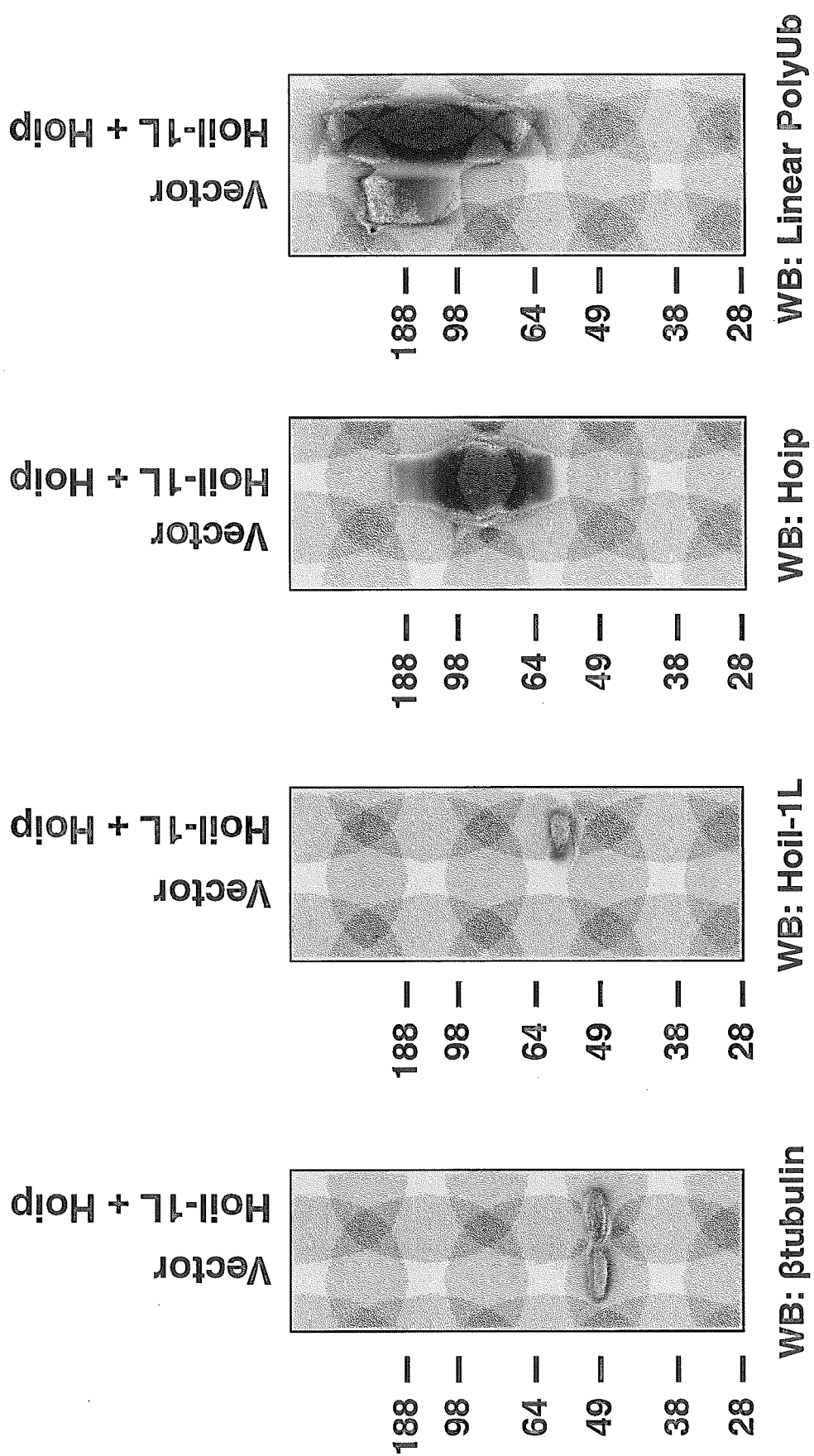
FIG. 22A depicts immunoblots with lysates from 293T cells transfected with a plasmid over-expressing Hoil-1L and Hoip or an empty vector. The blots were probed for linear polyubiquitin, Hoil-1L, Hoip, and β-tubulin as described in Example 4E.

The Linear Ubiquitin Assembly Complex (LUBAC) is an E3 ligase has been demonstrated to assemble linear polyubiquitin chains (Kirisako, T. et al. (2006) *EMBO J.* 25:4877-4887). The open reading frames (ORFs) of two of the members of this complex, Hoil-1L and Hoip, were synthesized (Blue Heron Biotechnology) and cloned into the pBI-CMV1 mammalian expression vector (Clonetech) containing a bidirectional CMV promoter. Hod-1L was cloned into multiple cloning site (MCS) 1 using restriction enzyme sites MluI and EcoRV and Hoip was cloned into the MCS2 using restriction enzyme sites EcoRI and PstI. The construct was verified by sequencing the ORFs. The resulting construct, pBI-CMV1-Hoil1L-Hoip, or the empty vector was transfected into 293T cells. 293T cells were split 1:20 into 20 ten cm plates two days before transfection and grown at 37° C. in 5% CO2. On the day of transfection 150 μL of Lipofectamine 2000 was diluted into 2.5 mL of Opti-MEM media lacking serum for each plasmid to be transfected. Also 50 μg of either pBI-CMV1 empty vector or pBI-CMV1-Hoil1L-Hoip was diluted into 2.5 mL of Opti-MEM media lacking serum. These dilutions were incubated at 25° C. for five minutes. The diluted Lipofectamine and the diluted DNA were combined, mixed gently by inversion, and incubated 25° C. for 30 minutes. 500 μL of the DNA/Lipofectamine mixture was then added to each ten cm plate (ten plates per plasmid). Forty-eight hours after transfection the media was collected and the cells were scraped off the plates. The cells were spun down at 10,000 rpm for ten minutes at 4° C. The supernatants were removed and the cells were washed in 40 mL of cold PBS. The cells were spun down at 10,000 rpm for ten minutes at 4° C. The supernatants were removed and the cells were resuspended in 4 mL of lysis buffer containing 8M urea, 50 mM Tris pH 7.5, 25 mM NaCl, 10 μL/mL HALT protease and phosphatase inhibitors (Thermo Scientific), 5 mM EDTA, and 2 mM NEM. Lysates were sonicated briefly to reduce viscosity and then frozen at −80° C. To determine whether Hoil-1L and Hoip were overexpressed and whether this leads to an increase in linear polyubiquitin chain assembly, the lysates were analyzed by western blot. One μL of each lysate was mixed with LDS sample buffer containing reducing reagent and then loaded onto a 4-12% NuPAGE Bis Tris 1.0 mm gel (Invitrogen) and run in MES buffer (Invitrogen) in quadruplicate. The gels were transferred individually at 30V for two hours in 1× NuPAGE transfer buffer containing 10% methanol to 0.45 μm nitrocellulose. The membranes were blocked in 5% milk in PBST for one hour at 25° C. with shaking and then incubated in the primary antibody. The first blot was probed with 1 t/mL 1F11/3F5/Y102L anti-linear polyUb IgG in 5% milk in PBST. The second blot was probed with a 1:500 dilution of an anti-Hoil-1L/RBCK antibody (Abcam ab38540) in 5% milk in PBST. The third blot was probed with 1 μg/mL anti-Hoip/RNF31 antibody (Abcam ab85294) in 5% milk in PBST. The fourth blot was probed with a 1:1000 dilution of an anti-β-tubulin antibody (Cell Signaling 9F3 #2128) in 5% milk in PBST. Blots one, two and three were incubated in their respective primary antibodies for one hour at 25° C. with shaking. The anti-β-tubulin blot was incubated overnight at 4° C. with rotation. Blots were then washed three times in PBST0.05 and then incubated in a 1:10,000 dilution of secondary antibody in 5% milk in PBST for one hour at 25° C. with shaking. The anti-linear polyUb blot was probed with a goat anti-human F(ab)'2-HRP secondary (Jackson Immunoresearch) and the other three blots were probed with a goat anti-rabbit F(ab)'2-HRP secondary (Jackson Immunoresearch). The blots were then washed three times with PBST and then once with PBS. The secondary antibody was detected using Super Signal West Pico chemiluminescent substrate (Thermo Scientific) followed by exposure of the blots to film. The anti-β-tubulin blot demonstrates that equal amounts of cells were used in the transfections and that equivalent amounts of lysate were loaded on the gel (see FIG. 22A). The anti-Hoil-1L and anti-Hoip blots show that when pBI-CMV1-Hoil1L-Hoip is transfected both Hoil-1L and Hoip are overexpressed relative to endogenous levels of the two proteins. Finally overexpression of Hoil-1L and Hoip leads to a dramatic increase in the levels of linear polyUb chains as expected. Given that these are detected by the 1F11/3F5/Y102L IgG indicates that this antibody can recognize endogenous, enzymatically synthesized, linear polyUb chains.

Figure 22B:
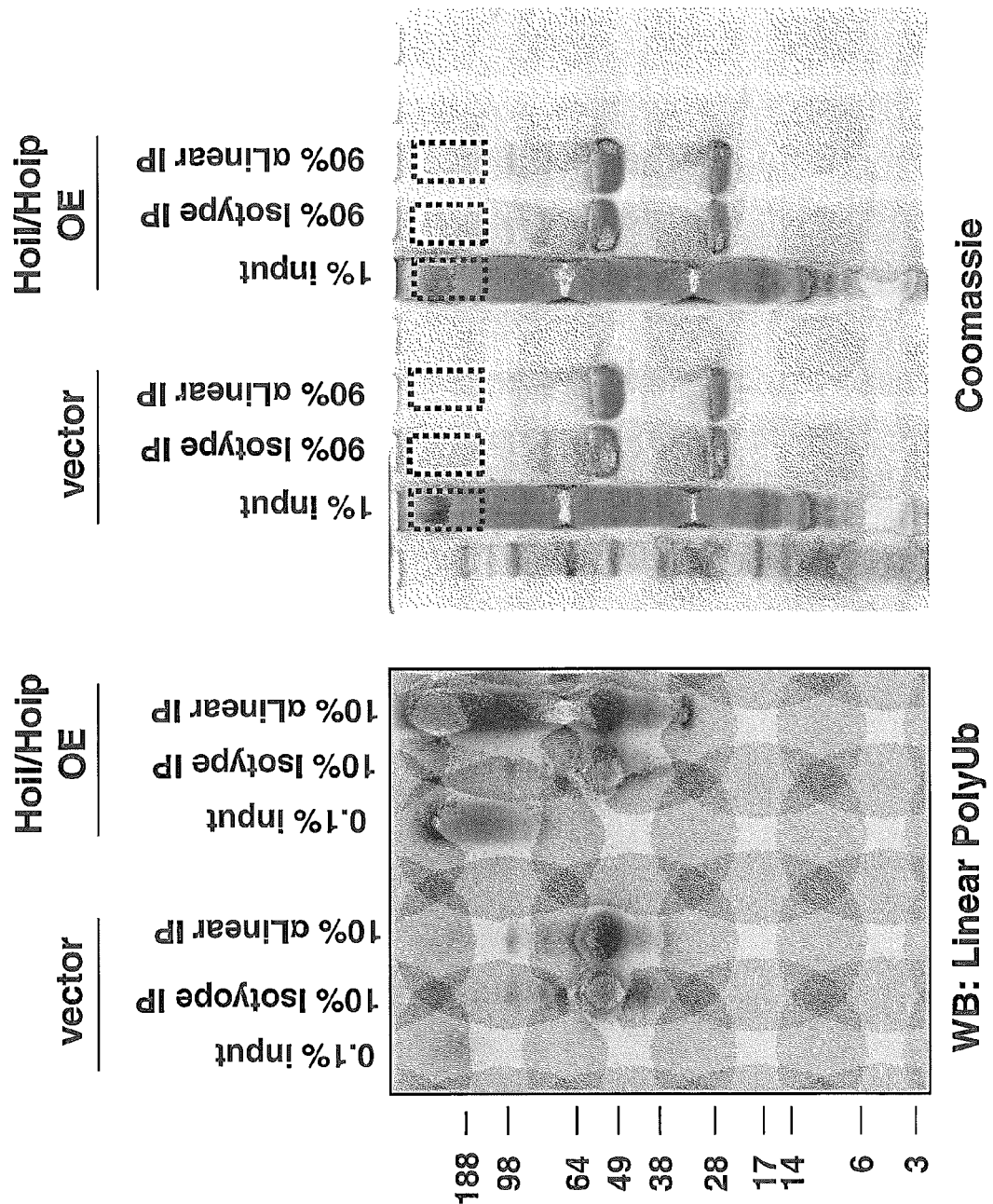
FIG. 22B depicts the results of immunoprecipitation experiments from lysates of 293T cells transfected with a plasmid over-expressing Hoil-1L and Hoip or an empty vector. Immunoblots were probed for linear polyubiquitin or Coomassie stained. The indicated regions on the Coomassie-stained gel were excised for mass spec AQUA.

In addition to probing these lysates by western blot, immunoprecipitations of linear polyUb was also performed. 500 μL of the above lysates were diluted to 7M urea with 71 μL of 50 mM Tris pH 7.5, 25 mM NaCl. The lysates were then precleared with 200 μl of Protein A Dynabeads (Invitrogen) in 7M urea, 50 mM Tris pH 7.5, 25 mM NaCl for one hour at 25° C. with rotation. The beads were captured with a magnetic stand and the supernatants were transferred to new tubes. The precleared lysates were then spun at 14,000 rpm for five minutes to pellet any precipitation. The supernatants were transferred to new tubes and 40 μg of 1F11/3F5/Y102L IgG or an isotype control IgG were added. The immunoprecipitations were then incubated overnight at 25° C. with rotation. The following day the IgGs were captured by the addition of 200 μL of Protein A Dynabeads in 7M urea, 50 mM Tris pH 7.5, 25 mM NaCl for 15 minutes at 25° C. with rotation. The beads were captured on a magnetic stand and washed five times with 1 mL of 7M urea, 50 mM Tris pH 7.5, 25 mM NaCl and then three times with 1 mL of PBS. After the final wash the beads were transferred to new tubes to avoid eluting any protein sticking to the tube walls. The beads were then resuspended in 30 μl of 1×LDS sample buffer with reducing agent (Invitrogen) and eluted at 70° C. for ten minutes. Two 4-12% NuPAGE Bis Tris 1.0 mm gels were run: one for western blot and the other for Coomassie staining for mass spec AQUA analysis. For western blot 10% of each IP was run along with 0.1% of each lysate. For mass spec 90% of each IP was run along with 1% of each lysate. The western blot with 1F11/3F5/Y102L was done as described in the above paragraph except the transfer done for one hour. The gel for mass spec AQUA analysis was stained with Simply Blue Safe Stain (Invitrogen). The western blot shows that the 1F11/3F5/Y102L IgG can immunoprecipitate linear polyUb chains from cells lysates (see FIG. 22B). More chains are pulled down from the LUBAC overexpression lysates than from the vector alone consistent with the much higher levels of linear chains present when LUBAC is overexpressed.

The high molecular weight regions of the gel indicated were excised (see FIG. 22B) and subjected to mass spectrometry AQUA as described above in Example 4D. In the vector control samples no linear polyubiquitin linkages were identified in the input samples (see Table 9). The majority of the polyubiquitin chains identified were of the K48 and K63 linkages.

TABLE 9

|  | Vector Input | Vector Isotype IP | Vector Linear IP | LUBAC OE Input | LUBAC OE Isotype IP | LUBAC OE Linear IP |
|---|---|---|---|---|---|---|
| Linear | 0 | 0 | 0 | 4808 | 0 | 598 |
| K11 | 1085 | 0 | 0 | 700 | 0 | 12 |
| K48 | 15680 | 2 | 7 | 12420 | 1 | 111 |
| K63 | 5128 | 0 | 4 | 5075 | 0 | 76 |

Figure 22C:
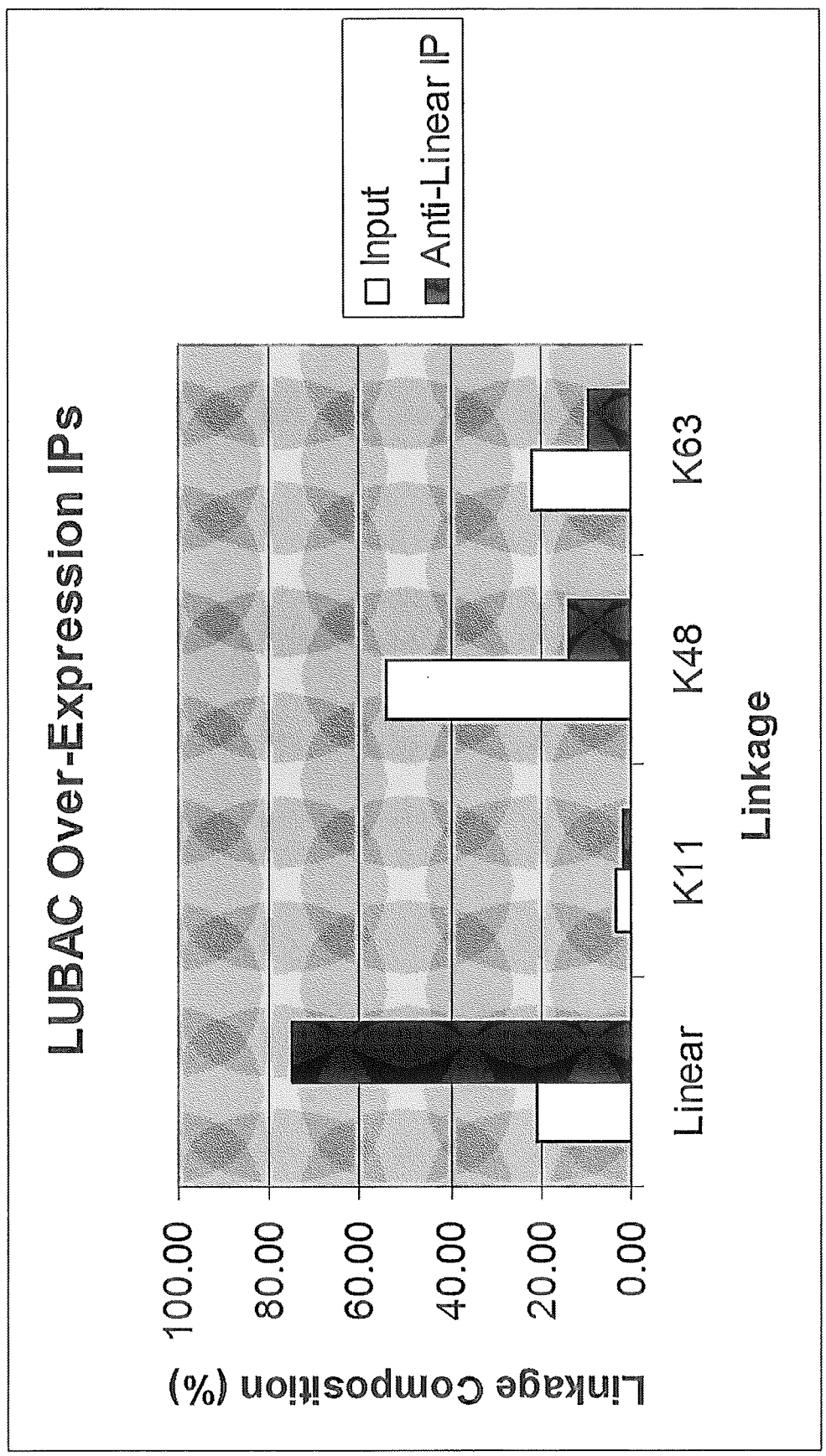
FIG. 22C is a graph which indicates the polyubiquitin linkage composition, identified by mass spec AQUA, in the 1F11/3F5/Y102L immunoprecipitations from Hoil-1L/Hoip over-expressing cells as shown in FIG. 22B.

Consistent with this, no linear polyubiquitin was pulled down in the IP with either the anti-linear antibody or the isotype control antibody. In LUBAC over-expressed cells the levels of linear polyubiquitin linkages reaches 4808 pmols, which is similar in abundance to K63 linkages (5075 pmols). When the anti-linear antibody is used for IP it significantly enriches for linear linkages with some additional K11, K48, and K63 linkages being pulled down (see FIG. 22C). This is likely due to the presence of mixed linkage chains or substrates modified with multiple homogenous chains of different linkages since only 7 and 4 pmols of K48 and K63 linkages, respectively, were pulled down by the anti-linear antibody from the vector control cells (see Table 9). Additionally, only 1 pmol of K48 linkages and no K68 linkages were identified in the IP with the isotype control antibody from LUBAC over-expressed cells indicating that these linkages are simply not sticky. This demonstrates that the anti-linear antibody is able to enrich for endogenous linear polyubiquitin chains (see FIG. 22C).

Figure 22D:
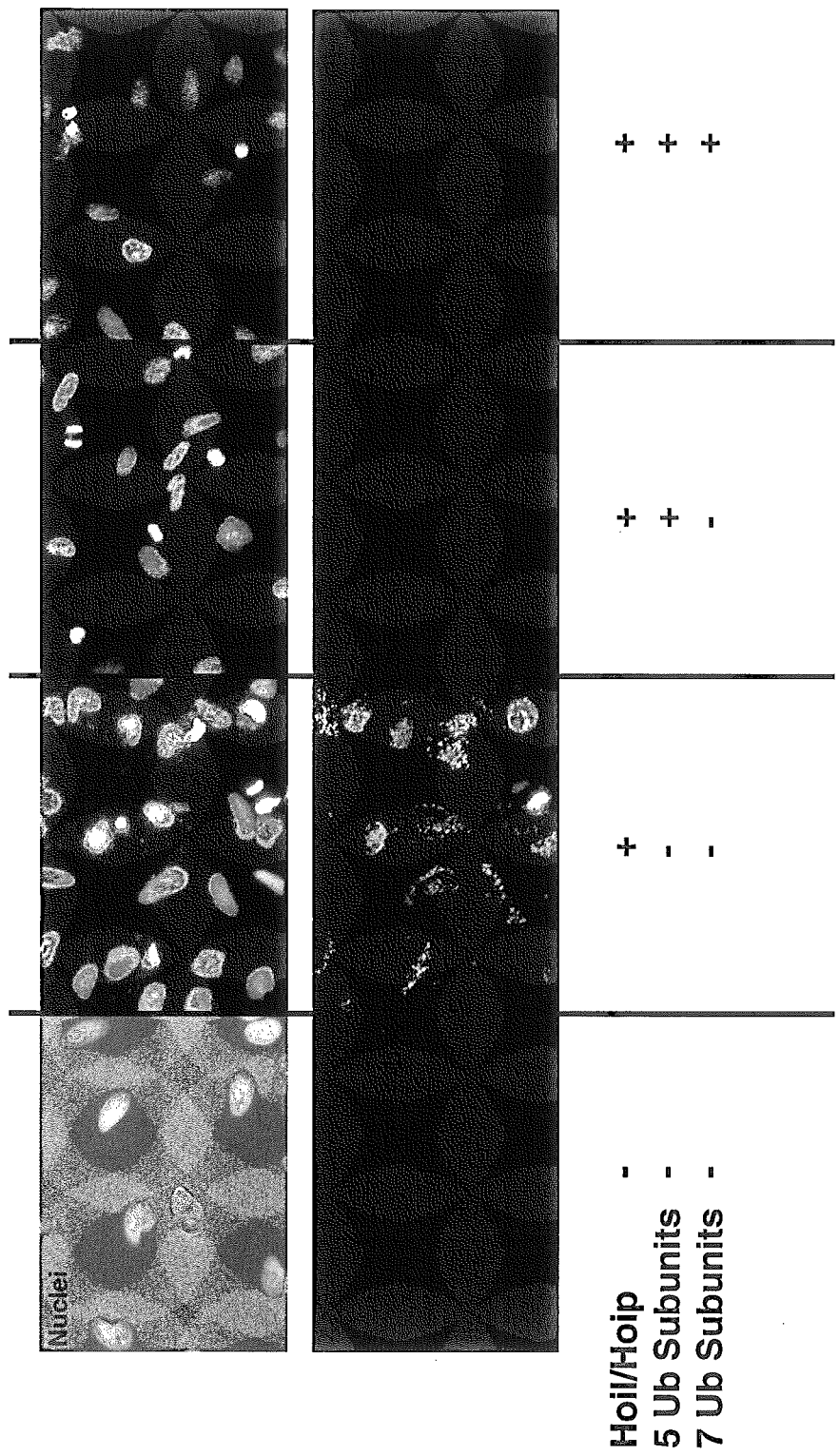
FIG. 22D depicts the immunofluorescence of HeLa S3 cells transfected with a plasmid over-expressing Hoil-1L and Hoip or an empty vector and stained with the anti-linear polyubiquitin antibody 1F11/3F5/Y102L. Addition of recombinant linear polyubiquitin of five or seven subunits (+) competes for binding of the anti-linear polyubiquitin antibody.

To determine whether 1F11/3F5/Y102L is functional for immunofluorescence, HeLa cells over-expressing Hoil-1L and Hoip were stained with the antibody. HeLa cells (5,000 cells/100 μl/well) were seeded in a clear bottomed, black walled 96-well plate and grown for 24 h. The cells were transfected with Hoil/Hoip plasmids for 18 hours using lipofectamine 2000 according to manufacturer's protocols. The cells were rinsed with PBS, fixed with ice cold methanol at −20° C. for 10 minutes, permeabilized with PBS/0.1% Triton X-100 at room temperature for 5 min, then blocked with PBS/0.3% Triton X-100/5% BSA at room temperature for 1 hour. The linear ubiquitin antibody (1 μg/ml) was incubated with or without poly-ubiquitin chains (5 μg/ml) at room temperature for 1 hour and then used to label cells at room temperature for 1 hour. After 6 washes (10 min each) with PBS/0.05% Triton X-100, the cells were stained with DyLight488-conjugated donkey anti-human antibody (1:500, Jackson ImmunoResearch Laboratories) at room temperature for 1 hour. The cells then were washed 6 times (10 minutes each) with PBS containing 0.05% Triton X-100, stained with Hoechst (1:10,000) at room temperature for 10 min and washed with PBS. The plate was covered with black seals and imaged using ImageXpress Micro imaging system. Untransfected cells did not show any signal when stained with 1F11/3F5/Y102L but cells over-expressing Hoil-1L and Hoip demonstrated a cytoplasmic punctate staining pattern (see FIG. 22D). This staining was specific for linear polyubiquitin chains as it could be blocked by the addition of recombinant linear polyubiquitin.

Example 5

Structural Analysis of Fab Binding to Linear Diubiquitin

To better understand the interaction of the anti-linear Fab with linear polyubiquitin the 1F11/3F5/Y102L Fab was co-crystallized with linear diubiquitin. The Fab fragment of 1F11/3F5/Y102L was expressed in *E. coli* and purified over a Protein A column as described above in Example 1E. The Fab was further purified over a 5 mL SP HiTrap column (GE Healthcare) in 20 mM 2-(N-morpholino)ethanesulfonic acid (MES), pH 5.5 with a 0-100% linear gradient of 20 mM MES, pH 5.5, 0.5 M NaCl. Fractions containing the Fab fragment were pooled and run over a 320 mL S75 sizing column (GE Healthcare) in 25 mM Tris, pH 7.5, 150 mM NaCl. Fractions containing the Fab fragment were pooled and concentrated to 22 mg/mL.

A head-to-tail fusion of two ubiquitin subunits through a canonical peptide bond (linear diubiquitin) was also expressed in *E. coli*. BL21-Gold (Agilent Technologies) cells were transformed with a linear diubiquitin expression plasmid constructed in a pET15b vector (Novagen). This construct has an N-terminal $His_6$ tag (SEQ ID NO: 376) followed by a thrombin cleavage site under the control of the T7 promoter and lac operator. An overnight culture of BL21-Gold transformed with the pET15b-linear diubiquitin expression plasmid grown in LB media was diluted 50-fold into 1 L of warmed Terrific Broth containing 1% glycerol, 0.1 M MOPS, pH 7.3, and 50 μg/mL carbenicilin. The culture was grown at 37° C. with shaking at 250 rpms in a 2.5 L ultra-yield flask (Thomson) to an $OD_{600}$=1.64. Expression was induced by adding 0.5 mM IPTG and the culture was grown overnight at 16° C. with shaking at 250 rpms. Next day the cells were pelleted by spinning at 8K rpm for 10 minutes and the pellets were frozen in liquid nitrogen. Cells were resuspended and lysed in 40 mM Tris, pH 8.0, 0.3 M NaCl, and Complete EDTA-free protease inhibitor tablets (Roche) by microfluidizing three times. Cell debris was pelleted by spinning at 10K rpm for 1 hour and the supernatant was filtered through a 0.45 μM low protein-binding filter. The $His_6$-diUb ('$His_6$' disclosed as SEQ ID NO: 376) was purified over a 5 mL Ni-NTA agarose (Qiagen) column. The column was washed with 12 column volumes of Buffer A (20 mM Tris, pH 8.0, 1 M NaCl, 20 mM imidazole) and eluted with four column volumes of Buffer B (20 mM Tris, pH 8.0, 1 M NaCl, 250 mM imidazole). The expression of the diubiquitin was high such that it exceeded the binding capacity of the column and some diubiquitin was eluted in the wash with Buffer A. Thus the wash material was run over a second 5 mL Ni-NTA agarose column and purified as described above. The $His_6$ tag (SEQ ID NO: 376) was removed by cleaving with 1800 units of Thrombin (GE Healthcare) at 4° C. for 3 days while dialyzing into 25 mM Tris, pH 8.0, 150 mM NaCl, 2 mM $CaCl_2$ using a 3500 MWCO dialysis tubing (Spectrum Medical). The dialyzed and cleaved material was split in half and the free diubiquitin was separated from the $His_6$ tag (SEQ ID NO: 376) using two 5 mL Ni-NTA agarose columns. The flow through and all washes were collected. The columns were washed with four column volumes of Buffer C (25 mM Tris, pH 8.0, 0.5 M NaCl), four column volumes of Buffer D (25 mM Tris, pH 8.0, 0.5 M NaCl, 20 mM imidazole), and then one column volume of Buffer E (25 mM Tris, pH 8.0, 0.5 M NaCl, 250 mM imidazole). The presence of detagged diubiquitin was monitored by running samples from the flow through and each wash on an 18% Novex tris-glycine gel (Invitrogen) and staining with Simply Blue Safe Stain (Invitrogen). The majority of the detagged diubiquitin was present in the flow through, wash with Buffer C, and wash with Buffer D. These were pooled, concentrated and purified further over a 320 mL S75 sizing column (GE Healthcare) in 25 mM Tris, pH 7.5, 150 mM NaCl. Fractions containing the diubiquitin were pooled and concentrated to 15.3 mg/mL.

The Fab/diubiquitin complex was set up using a three-fold molar excess of linear diubiquitin to Fab and was incubated at 4° C. overnight. The complex was then purified over a 320 mL S75 sizing column (GE Healthcare) in 25 mM Tris, pH 7.5, 150 mM NaCl. Fractions containing the complex were pooled and concentrated to 20 mg/mL.

Figure 23:
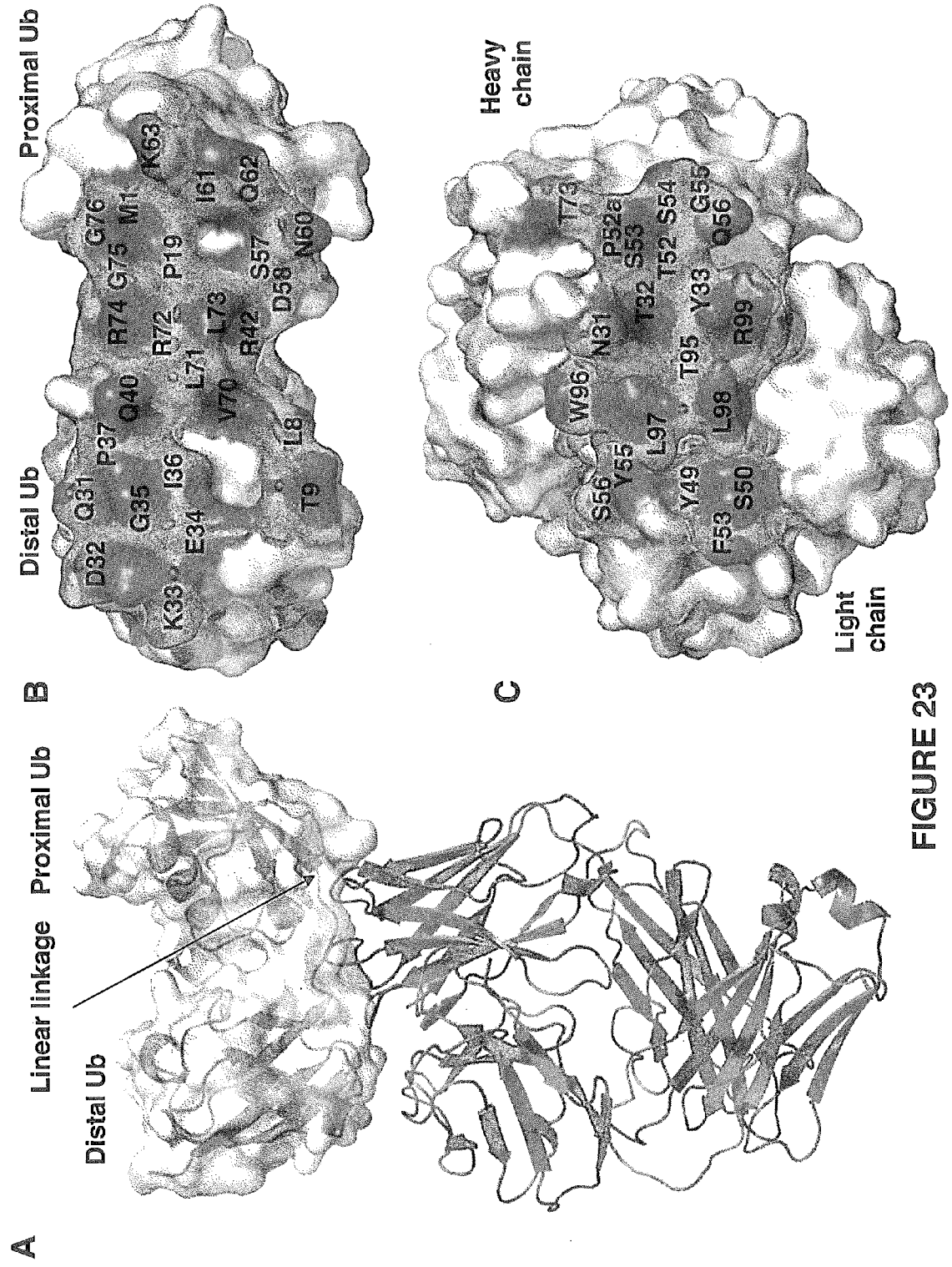
FIG. 23 depicts various views of the co-crystal structure of the complex formed between the 1F11/3F5/Y102L Fab fragment and linear diubiquitin. A) 1F11/3F5/Y102L is shown as a cartoon diagram at the bottom of the figure and linear diubiquitin is depicted as a cartoon diagram inside the space-filled model at the top. The proximal and distal ubiquitin subunits and the linear linkage are indicated. B) The epitope on linear diubiquitin is shown in dark gray on the surface of the diubiquitin that interacts with 1F11/3F5/Y102L. Residues which have at least 25% of their solvent accessible surface area buried at the interface of linear diubiquitin and 1F11/3F5/Y102L and/or are within 4.5 Å of the Fab are indicated by single letter amino acid code and residue number.

Crystals were grown using the sitting drop vapor diffusion method in drops containing 0.2 μL of 1F11/3F5/Y102L Fab/linear diubiquitin complex (20 mg/mL complex in 25 mM Tris, pH 7.5, 150 mM NaCl) and 0.2 μL of mother liquor (20% isopropanol, 0.1 M MES, pH 6.0, 20% polyethylene glycol (PEG) 2K monomethylether (MME)). Initial crystals grew under these conditions at 19° C. over 27 days. Crystals were optimized in sitting drops using a microbridge with 2 μL of 1F11/3F5/Y102L Fab/linear diubiquitin complex (20 mg/mL complex in 25 mM Tris, pH 7.5, 150 mM NaCl) and 3 μL of mother liquor (18% isopropanol, 0.09 M MES, pH 6.0, 19.8% PEG 2K MME, 10 mM sodium bromide). Crystals grew at 19° C. over five days and could be manipulated to obtain single, diffracting crystals. Crystals were cryoprotected using 20% isopropanol, 0.1 M MES, pH 6.0, 20% PEG 2K MME with an additional 25-30% PEG 2K MME. Crystallographic data was collected at Berkeley Advanced Light Source beamline 5.0.2 and was processed using HKL2000. Crystals belonged to the P1 space group with unit cell dimensions a=53 Å, b=60 Å, c=96 Å, α=87°, β=77°, and γ=72°, with two complexes in the asymmetric unit. The structure was solved by molecular replacement using the program Phaser and the coordinates of a variant of the humanized 4D5 Fab fragment (PDB code for 4D5: 1FVE) and of human monoubiquitin (PDB code: 1UBQ). Model building was carried out in Coot and the structure was refined using Phenix. The resolution of the structure is 2.43 Å and the complex has been refined to an R of 22.8% and Rfree of 25.0% (see FIG. 23. Panel A).

Analysis of the structure indicates that the majority of the binding to diubiquitin is mediated through contacts with the heavy chain CDRs. Between the heavy chain and diubiquitin there is 785 Å² of buried surface area, in contrast to no buried surface area between the light chain and diubiquitin. The structural epitope and paratope is defined as residues which bury at least 25% of their solvent accessible surface area upon binding (see FIG. 23 Panels B and C) and/or have at least one atom within 4.5 Å of the interacting chain (see Tables 10 and 11).

TABLE 10

Residues with at least 25% of solvent accessible surface area buried at the interface (Table 10 discloses residues 52-57 and 96-100 as SEQ ID NOS 377 and 378, respectively.)

| Fab HC (chain C) | DiUb (chain A) | |
|---|---|---|
| N31 | L8 | Nterm Ub |
| T32 | T9 | Nterm Ub |
| Y33 | E34 | Nterm Ub |
| T52 | I36 | Nterm Ub |
| P53 (Kabat# P52a) | P37 | Nterm Ub |
| S54 (S53) | Q40 | Nterm Ub |
| S55 (S54) | R42 | Nterm Ub |
| G56 (G55) | V70 | Nterm Ub |
| Q57 (Q56) | L71 | Nterm Ub |
| T74 (T73) | L73 | Nterm Ub |
| T96 (T95) | R74 | Nterm Ub |
| W97 (W96) | G75 | Nterm Ub |

TABLE 10-continued

Residues with at least 25% of solvent accessible surface area buried at the interface (Table 10 discloses residues 52-57 and 96-100 as SEQ ID NOS 377 and 378, respectively.)

| Fab HC (chain C) | DiUb (chain A) | |
|---|---|---|
| L98 (L97) | M1 | Cterm Ub |
| L99 (L98) | P19 | Cterm Ub |
| R100 (R99) | S57 | Cterm Ub |
| | D58 | Cterm Ub |
| | N60 | Cterm Ub |
| | I61 | Cterm Ub |
| | Q62 | Cterm Ub |
| | K63 | Cterm Ub |

TABLE 11

Residues with at least 1 atom within 4.5 Å of Fab or diUb (Table 11 discloses residues 52-57, 96-100, 31-37, 70-76 and 60-63 as SEQ ID NOS 377-381, respectively.)

| Fab HC (chain C) | Fab LC (chain B) | DiUb (chain A) | |
|---|---|---|---|
| N31 | Y49 | L8 | Nterm Ub |
| T32 | S50 | T9 | Nterm Ub |
| Y33 | F53 | Q31 | Nterm Ub |
| T52 | Y55 | D32 | Nterm Ub |
| P53 (Kabat# P52a) | S56 | K33 | Nterm Ub |
| S54 (S53) | | E34 | Nterm Ub |
| S55 (S54) | | G35 | Nterm Ub |
| G56 (G55) | | I36 | Nterm Ub |
| Q57 (Q56) | | P37 | Nterm Ub |
| T74 (T73) | | Q40 | Nterm Ub |
| T96 (T95) | | R42 | Nterm Ub |
| W97 (W96) | | V70 | Nterm Ub |
| L98 (L97) | | L71 | Nterm Ub |
| L99 (L98) | | R72 | Nterm Ub |
| R100 (R99) | | L73 | Nterm Ub |
| | | R74 | Nterm Ub |
| | | G75 | Nterm Ub |
| | | G76 | Nterm Ub |
| | | M1 | Cterm Ub |
| | | P19 | Cterm Ub |
| | | S57 | Cterm Ub |
| | | D58 | Cterm Ub |
| | | N60 | Cterm Ub |
| | | I61 | Cterm Ub |
| | | Q62 | Cterm Ub |
| | | K63 | Cterm Ub |

There are 15 heavy chain residues and only five light chain residues which make up the Fab paratope. The diubiquitin epitope consists of 18 residues from the distal Ub (C-terminus involved in the linkage) and eight residues from the proximal ubiquitin (N-terminus involved in the linkage). The contact interface also consists of nine hydrogen bonds between the heavy chain and diubiquitin and three hydrogen bonds between the light chain and diubiquitin (see Table 12). Rather than making exclusive contact with the linear linkage itself, the specificity appears to be derived from multiple interactions with surface residues from both the proximal and distal ubiquitins.

TABLE 12

Summary of H-bonds between Fab and diUb

| diUb (chain A) | | Fab LC (chain B) |
|---|---|---|
| Nterm Ub | E34 O | Y49 OH |
| Nterm Ub | E34 OE2 | Y49 OH |
| Nterm Ub | G35 O | S50 OG |

TABLE 12-continued

Summary of H-bonds between Fab and diUb

| diUb (chain A) | | Fab HC (chain C) |
|---|---|---|
| Nterm Ub | Q40 NE2 | R100 N (Kabat# R99) |
| Nterm Ub | R42 NH1 | N31 ND2 |
| Nterm Ub | R74 N | Y33 OH |
| Nterm Ub | R74 O | R100 NH2 (R99) |
| Nterm Ub | G75 O | Q57 NE2 (Q56) |
| Nterm Ub | G76 O | Q57 NE2 (Q56) |
| Cterm Ub | Q62 NE2 | P53 O (P52a) |
| Cterm Ub | Q62 OE2 | G56 N (G55) |
| Cterm Ub | K63 N | S55 O (S54) |

Despite free linear polyubiquitin and free K63-linked polyubiquitin chains adopting similar structures due to Lys63 and the free amino-terminus situated only ~6 Å apart in the monoubiquitin structure (PDB code 1UBQ), this antibody preferentially binds linear chains. This specificity is achieved through the dual recognition of the relative orientations of both the proximal and distal ubiquitin subunits. Recognition of the proximal ubiquitin is achieved through interaction of CDR H2 residues with the 60 s loop of the proximal subunit. In particular, two hydrogen bonds are made with the side-chain of Gln62 of the proximal ubiquitin, both involving residues of CDR H2. One is between the main-chain carbonyl oxygen of Pro52a and the side-chain amine of Gln62. The other is between the main-chain amide of Gly55 and the side-chain carbonyl of Gln62. There is also a third hydrogen bond between the main-chain carbonyl of Ser54 and the main-chain amide of Lys63. In addition to these three hydrogen bonds, numerous Van der Waals interactions also occur between CDR H2 and the proximal ubiquitin. Although the distal ubiquitin of K63-linked diubiquitin could theoretically bind in the same orientation to the antibody, the proximal ubiquitin would be rotated slightly due to the ~6 Å difference in position of Met1 and Lys63. This rotation would likely disrupt the hydrogen bonds and Van der Waals interactions between CDR H2 and the 60's loop. Therefore specificity is encoded by recognition of the relative spatial orientations of the proximal and distal ubiquitins resulting from the linear linkage.

The structure also illustrates why the particular mutations selected in the affinity maturation help increase affinity. In CDR H2 the mutation that made the most significant improvement in sensitivity in western blots was S56Q (see FIG. 13, clone 3F5). The structure shows that Gln56 makes two hydrogen bonds: one with the carbonyl oxygen of Gly75 of the distal ubiquitin and the second with the carbonyl oxygen of Gly76 of the distal ubiquitin, which participates in the linear linkage between the distal and proximal ubiquitins (see FIG. 24, Panel A). The shorter side chain of Ser likely would not reach these residues to make the hydrogen bonds. The mutation which made the second largest improvement in sensitivity in western blots was S52K in CDR L2 (see FIG. 13, clone 1F11). Lys52 is placed in proximity to Asp32 found at the carboxy-terminal end of the alpha helix of the distal ubiquitin. Although Lys52 is too far away to make a salt bridge with the side chain of Asp32 it may make a favorable electrostatic interaction given that it is also oriented towards the negative end of the helix dipole (see FIG. 24, Panel B). The third mutation which improved sensitivity of the antibody was Y102L in CDR H3 (see FIG. 13, clone Y102L). Although this residue does not contact the diubiquitin it may help stabilize a favorable conformation of CDR H3 for improved binding. Leu102 intercalates between Val2 and Leu4 of framework 1 of the heavy chain (see FIG. 24, Panel C). The more hydrophobic side chain of Leu could provide a more favorable interaction with Val2 and Leu4 than Tyr and might help position the rest of CDR H3 to make contacts with the diubiquitin.

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

What is claimed is:

1. An isolated antibody that specifically binds C- to N-terminal-linked polyubiquitin, wherein the antibody comprises:
   (a) a hypervariable (HVR)-L1 comprising the sequence of SEQ ID NO: 1, a HVR-L2 sequence comprising the sequence of SEQ ID NO: 58, a HVR-L3 sequence comprising the sequence of SEQ ID NO: 3, a HVR-H1 sequence comprising the sequence of SEQ ID NO: 7, a HVR-H2 sequence comprising the sequence of SEQ ID NO: 82, and a HVR-H3 sequence comprising the sequence of SEQ ID NO: 9;
   (b) a HVR-L1 comprising the sequence of SEQ ID NO: 1, a HVR-L2 sequence comprising the sequence of SEQ ID NO: 2, a HVR-L3 sequence comprising the sequence of SEQ ID NO: 65 or 72, a HVR-H1 sequence comprising the sequence of SEQ ID NO: 7, a HVR-H2 sequence comprising the sequence of SEQ ID NO: 82, and a HVR-H3 sequence comprising the sequence of SEQ ID NO: 9; or
   (c) a HVR-L1 comprising the sequence of SEQ ID NO: 1, a HVR-L2 sequence comprising the sequence of SEQ ID NO:58, a HVR-L3 sequence comprising the sequence of SEQ ID NO: 65 or 72, a HVR-H1 sequence comprising the sequence of SEQ ID NO: 7, a HVR-H2 sequence comprising the sequence of SEQ ID NO: 82, and a HVR-H3 sequence comprising the sequence of SEQ ID NO: 9.

2. The isolated antibody of claim 1, wherein the antibody comprises a HVR-L1 comprising the sequence of SEQ ID NO: 1, a HVR-L2 sequence comprising the sequence of SEQ ID NO: 58, a HVR-L3 sequence comprising the sequence of SEQ ID NO: 3, a HVR-H1 sequence comprising the sequence of SEQ ID NO: 7, a HVR-H2 sequence comprising the sequence of SEQ ID NO: 82 and a HVR-H3 sequence comprising the sequence of SEQ ID NO: 9.

3. The antibody of claim 2, wherein the first amino acid after the C-terminus of HVR-H3 is a leucine.

4. The isolated antibody of claim 1, wherein the antibody comprises a HVR-L1 comprising the sequence of SEQ ID NO: 1, a HVR-L2 sequence comprising the sequence of SEQ ID NO: 2, a HVR-L3 sequence comprising the sequence of SEQ ID NO: 65, a HVR-H1 sequence comprising the sequence of SEQ ID NO: 7, a HVR-H2 sequence comprising the sequence of SEQ ID NO: 82 and a HVR-H3 sequence comprising the sequence of SEQ ID NO: 9.

5. The isolated antibody of claim 1, wherein the antibody comprises a HVR-L1 comprising the sequence of SEQ ID NO: 1, a HVR-L2 sequence comprising the sequence of SEQ ID NO: 2, a HVR-L3 sequence comprising the sequence of SEQ ID NO: 72, a HVR-H1 sequence comprising the sequence of SEQ ID NO: 7, a HVR-H2 sequence comprising the sequence of SEQ ID NO: 82 and a HVR-H3 sequence comprising the sequence of SEQ ID NO: 9.

6. The isolated antibody of claim 1, wherein the antibody comprises a HVR-L1 comprising the sequence of SEQ ID NO: 1, a HVR-L2 sequence comprising the sequence of SEQ ID NO: 58, a HVR-L3 sequence comprising the sequence of SEQ ID NO: 65, a HVR-H1 sequence comprising the sequence of SEQ ID NO: 7, a HVR-H2 sequence comprising the sequence of SEQ ID NO: 82 and a HVR-H3 sequence comprising the sequence of SEQ ID NO: 9.

7. The isolated antibody of claim 1, wherein the antibody comprises a HVR-L1 comprising the sequence of SEQ ID NO: 1, a HVR-L2 sequence comprising the sequence of SEQ ID NO: 58, a HVR-L3 sequence comprising the sequence of SEQ ID NO: 72, a HVR-H1 sequence comprising the sequence of SEQ ID NO: 7, a HVR-H2 sequence comprising the sequence of SEQ ID NO: 82 and a HVR-H3 sequence comprising the sequence of SEQ ID NO: 9.

8. The isolated antibody of claim 1, wherein the antibody comprises a light chain comprising a sequence that is at least 95% identical to a sequence selected from SEQ ID NOs: 25, 193, 194, 195 and 94.

9. The isolated antibody of claim 1, wherein the antibody comprises a heavy chain comprising a sequence that is at least 95% identical to a sequence selected from SEQ ID NOs: 29, 196, 197, 198 and 95.

10. The isolated antibody of claim 1, wherein the antibody comprises a light chain comprising a sequence that is at least 95% identical to a sequence selected from SEQ ID NOs: 25, 193, 194, 195 and 94 and a heavy chain comprising a sequence that is at least 95% identical to a sequence selected from SEQ ID NOs: 29, 196, 197, 198 and 95.

11. The isolated antibody of claim 1, wherein the antibody comprises a light chain comprising the sequence of SEQ ID NO: 94 and a heavy chain comprising the sequence of SEQ ID NO: 95.

12. The isolated antibody of claim 1, wherein the antibody does not specifically bind monoubiquitin.

13. The isolated antibody of claim 1, wherein the antibody does not bind a second polyubiquitin comprising a lysine linkage.

14. The isolated antibody of claim 1, wherein the antibody modulates at least one polyubiquitin-mediated signaling pathway.

15. The isolated antibody of claim 1, wherein the antibody is a monoclonal antibody, a human antibody, a humanized antibody, a chimeric antibody, or an antibody fragment that binds C- to N-terminal-linked polyubiquitin.

16. An immunoconjugate comprising the antibody of claim 1 and a cytotoxic agent.

17. A pharmaceutical formulation comprising the antibody of claim 1 and a pharmaceutically acceptable carrier.

* * * * *

SEQUENCE LISTING

```
<160> NUMBER OF SEQ ID NOS: 382

<210> SEQ ID NO 1
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Arg Ala Ser Gln Asp Val Ser Thr Ala Val Ala
1               5                   10

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Ser Ala Ser Phe Leu Tyr Ser
1               5
```

```
<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gln Gln Ser Tyr Thr Thr Pro Pro Thr
1               5

<210> SEQ ID NO 4
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Arg Ala Ser Gln Ser Val Ser Ser Ala Val Ala
1               5                   10

<210> SEQ ID NO 5
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gln Gln Tyr Tyr Tyr Tyr Ser Pro Leu Thr
1               5                   10

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gln Gln His Tyr Thr Thr Pro Pro Thr
1               5

<210> SEQ ID NO 7
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Thr Phe Ser Asn Thr Tyr Ile Ser
1               5

<210> SEQ ID NO 8
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 8

Ala Ser Ile Thr Pro Ser Ser Gly Ser Thr Asp
1               5                   10

<210> SEQ ID NO 9
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Arg Thr Trp Leu Leu Arg Trp Val Met Asp
1               5                   10

<210> SEQ ID NO 10
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Thr Phe Thr Asp Tyr Asp Ile His
1               5

<210> SEQ ID NO 11
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Ala Gly Ile Ser Pro Tyr Gly Gly Tyr Thr Asp
1               5                   10

<210> SEQ ID NO 12
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Arg Glu Ala Gly Ser Arg Leu Leu Ser Val Met Asp
1               5                   10

<210> SEQ ID NO 13
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Asn Phe Tyr Ser Tyr Tyr Met His
1               5

<210> SEQ ID NO 14
<211> LENGTH: 11
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 14

Ala Ser Ile Tyr Ser Tyr Tyr Ser Tyr Thr Ser
1               5                   10

<210> SEQ ID NO 15
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Arg Gly Tyr Val Trp Lys Gly Ala Met Asp
1               5                   10

<210> SEQ ID NO 16
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Asn Ile Tyr Tyr Ser Ser Ile His
1               5

<210> SEQ ID NO 17
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Ala Ser Ile Tyr Pro Tyr Tyr Gly Tyr Thr Ser
1               5                   10

<210> SEQ ID NO 18
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Arg Gly Tyr Ser Trp Tyr Tyr Gly Ser Pro Ala Phe Asp
1               5                   10

<210> SEQ ID NO 19
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Arg Ala Ser Gln Gly Val Asp Asn Ser Val Ala
1               5                   10
```

<210> SEQ ID NO 20
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Gln Gln Ser Tyr Ala Ser Pro Pro Thr
1               5

<210> SEQ ID NO 21
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Gln Gln Ser Phe Thr Thr Pro Pro Thr
1               5

<210> SEQ ID NO 22
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Thr Phe Thr Asp Asp Asp Ile His
1               5

<210> SEQ ID NO 23
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Ala Trp Ile Ser Pro Tyr Ser Gly Tyr Thr Asp
1               5                   10

<210> SEQ ID NO 24
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Ala Glu Ile Ser Pro Tyr Gly Gly Tyr Thr Asp
1               5                   10

<210> SEQ ID NO 25
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide -continued

<400> SEQUENCE: 25

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Thr Thr Pro Pro
                85                  90                  95

Thr Phe Gly Gln Gly Thr Lys Val Glu Ile Lys
            100                 105

<210> SEQ ID NO 26
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Thr Thr Pro Pro
                85                  90                  95

Thr Phe Gly Gln Gly Thr Lys Val Glu Ile Lys
            100                 105

<210> SEQ ID NO 27
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60

```
Ser Arg Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Tyr Tyr Tyr Ser Pro
                 85                  90                  95

Leu Thr Phe Gly Gln Gly Thr Lys Val Glu Ile Lys
            100                 105

<210> SEQ ID NO 28
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Ser Val Ser Ser Ala
                 20                  25                  30

Val Ala Trp Tyr Gln Gln Lys Pro Gly Lys Ala Pro Lys Leu Leu Ile
             35                  40                  45

Tyr Ser Ala Ser Ser Leu Tyr Ser Gly Val Pro Ser Arg Phe Ser Gly
 50                  55                  60

Ser Arg Ser Gly Thr Asp Phe Thr Leu Thr Ile Ser Ser Leu Gln Pro
 65                  70                  75                  80

Glu Asp Phe Ala Thr Tyr Tyr Cys Gln Gln His Tyr Thr Thr Pro Pro
                 85                  90                  95

Thr Phe Gly Gln Gly Thr Lys Val Glu Ile Lys
            100                 105

<210> SEQ ID NO 29
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Asn Thr
                 20                  25                  30

Tyr Ile Ser Trp Val Arg Gln Ala Pro Gly Lys Gly Leu Glu Trp Val
             35                  40                  45

Ala Ser Ile Thr Pro Ser Ser Gly Ser Thr Asp Tyr Ala Asp Ser Val
 50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Arg Thr Trp Leu Leu Arg Trp Val Met Asp Tyr Trp Gly Gln Gly
            100                 105                 110

Thr Leu Val Thr Val Ser Ser
            115

<210> SEQ ID NO 30
<211> LENGTH: 121
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Asp Ile His Trp Val Arg Gln Ala Pro Gly Lys Gly Leu Glu Trp Val
        35                  40                  45

Ala Gly Ile Ser Pro Tyr Gly Gly Tyr Thr Asp Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Glu Ala Gly Ser Arg Leu Leu Ser Val Met Asp Tyr Trp Gly
            100                 105                 110

Gln Gly Thr Leu Val Thr Val Ser Ser
        115                 120

<210> SEQ ID NO 31
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Glu Ile Ser Glu Val Gln Leu Val Glu Ser Gly Gly Gly Leu Val Gln
1               5                   10                  15

Pro Gly Gly Ser Leu Arg Leu Ser Cys Ala Ala Ser Gly Phe Asn Phe
            20                  25                  30

Tyr Ser Tyr Tyr Met His Trp Val Arg Gln Ala Pro Gly Lys Gly Leu
        35                  40                  45

Glu Trp Val Ala Ser Ile Tyr Ser Tyr Tyr Ser Tyr Thr Ser Tyr Ala
    50                  55                  60

Asp Ser Val Lys Gly Arg Phe Thr Ile Ser Ala Asp Thr Ser Lys Asn
65                  70                  75                  80

Thr Ala Tyr Leu Gln Met Asn Ser Leu Arg Ala Glu Asp Thr Ala Val
                85                  90                  95

Tyr Tyr Cys Ala Arg Gly Tyr Val Trp Lys Gly Ala Met Asp Tyr Trp
            100                 105                 110

Gly Gln Gly Thr Leu Val Thr Val Ser Ser
        115                 120

<210> SEQ ID NO 32
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Glu Ile Ser Glu Val Gln Leu Val Glu Ser Gly Gly Gly Leu Val Gln
```

```
                1               5                   10                  15
Pro Gly Gly Ser Leu Arg Leu Ser Cys Ala Ala Ser Gly Phe Asn Ile
                20                  25                  30

Tyr Tyr Ser Ser Ile His Trp Val Arg Gln Ala Pro Gly Lys Gly Leu
            35                  40                  45

Glu Trp Val Ala Ser Ile Tyr Pro Tyr Tyr Gly Tyr Thr Ser Tyr Ala
    50                  55                  60

Asp Ser Val Lys Gly Arg Phe Thr Ile Ser Ala Asp Thr Ser Lys Asn
65                  70                  75                  80

Thr Ala Tyr Leu Gln Met Asn Ser Leu Arg Ala Glu Asp Thr Ala Val
                85                  90                  95

Tyr Tyr Cys Ala Arg Gly Tyr Ser Trp Tyr Tyr Gly Ser Pro Ala Phe
                100                 105                 110

Asp Tyr Trp Gly Gln Gly Thr Leu Val Thr Val Ser Ser
                115                 120                 125
```

<210> SEQ ID NO 33
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Val Asp Asn Ser
                20                  25                  30

Val Ala Trp Tyr Gln Gln Lys Pro Gly Lys Ala Pro Lys Leu Leu Ile
            35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Thr Thr Pro Pro
                85                  90                  95

Thr Phe Gly Gln Gly Thr Lys Val Glu Ile Lys
                100                 105
```

<210> SEQ ID NO 34
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
                20                  25                  30

Val Ala Trp Tyr Gln Gln Lys Pro Gly Lys Ala Pro Lys Leu Leu Ile
            35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
```

```
                65                  70                  75                  80
Glu Asp Phe Ala Thr Tyr Tyr Cys Gln Gln Ser Tyr Ala Ser Pro Pro
                    85                  90                  95

Thr Phe Gly Gln Gly Thr Lys Val Glu Ile Lys
                100                 105

<210> SEQ ID NO 35
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
                20                  25                  30

Val Ala Trp Tyr Gln Gln Lys Pro Gly Lys Ala Pro Lys Leu Leu Ile
            35                  40                  45

Tyr Ser Ala Ser Phe Leu Tyr Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Phe Thr Pro Pro
                    85                  90                  95

Thr Phe Gly Gln Gly Thr Lys Val Glu Ile Lys
                100                 105

<210> SEQ ID NO 36
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
                20                  25                  30

Asp Ile His Trp Val Arg Gln Ala Pro Gly Lys Gly Leu Glu Trp Val
            35                  40                  45

Ala Trp Ile Ser Pro Tyr Ser Gly Tyr Thr Asp Tyr Ala Asp Ser Val
        50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                    85                  90                  95

Ala Arg Glu Ala Gly Ser Arg Leu Leu Ser Val Met Asp Tyr Trp Gly
                100                 105                 110

Gln Gly Thr Leu Val Thr Val Ser Ser
            115                 120

<210> SEQ ID NO 37
<211> LENGTH: 121
<212> TYPE: PRT
```

```
<213> ORGANISM: Artificial Sequence
<220> FEATURE:
<223> OTHER INFORMATION: Description of Artificial Sequence: Synthetic
      polypeptide

<400> SEQUENCE: 37

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Asp Ile His Trp Val Arg Gln Ala Pro Gly Lys Gly Leu Glu Trp Val
        35                  40                  45

Ala Gly Ile Ser Pro Tyr Gly Gly Tyr Thr Asp Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Glu Ala Gly Ser Arg Leu Leu Ser Val Met Asp Tyr Trp Gly
            100                 105                 110

Gln Gly Thr Leu Val Thr Val Ser Ser
        115                 120

<210> SEQ ID NO 38
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Asp
            20                  25                  30

Asp Ile His Trp Val Arg Gln Ala Pro Gly Lys Gly Leu Glu Trp Val
        35                  40                  45

Ala Glu Ile Ser Pro Tyr Gly Gly Tyr Thr Asp Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Glu Ala Gly Ser Arg Leu Leu Ser Val Met Asp Tyr Trp Gly
            100                 105                 110

Gln Gly Thr Leu Val Thr Val Ser Ser
        115                 120

<210> SEQ ID NO 39
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Asp, Ser or Gly
<220> FEATURE:
```

```
<221> NAME/KEY: MOD_RES
<222> LOCATION: (7)..(7)
<223> OTHER INFORMATION: Ser or Asp
<220> FEATURE:
<221> NAME/KEY: MOD_RES
<222> LOCATION: (8)..(8)
<223> OTHER INFORMATION: Ser, Thr or Asn
<220> FEATURE:
<221> NAME/KEY: MOD_RES
<222> LOCATION: (9)..(9)
<223> OTHER INFORMATION: Ala or Ser

<400> SEQUENCE: 39

Arg Ala Ser Gln Xaa Val Xaa Xaa Xaa Val Ala
1               5                   10

<210> SEQ ID NO 40
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Ser, Tyr or His
<220> FEATURE:
<221> NAME/KEY: MOD_RES
<222> LOCATION: (4)..(4)
<223> OTHER INFORMATION: Tyr or Phe
<220> FEATURE:
<221> NAME/KEY: MOD_RES
<222> LOCATION: (5)..(5)
<223> OTHER INFORMATION: Thr, Tyr or Ala
<220> FEATURE:
<221> NAME/KEY: MOD_RES
<222> LOCATION: (6)..(6)
<223> OTHER INFORMATION: Thr, Tyr or Ser
<220> FEATURE:
<221> NAME/KEY: MOD_RES
<222> LOCATION: (7)..(7)
<223> OTHER INFORMATION: May or may not be present
<220> FEATURE:
<221> NAME/KEY: MOD_RES
<222> LOCATION: (9)..(9)
<223> OTHER INFORMATION: Pro or Leu

<400> SEQUENCE: 40

Gln Gln Xaa Xaa Xaa Xaa Ser Pro Xaa Thr
1               5                   10

<210> SEQ ID NO 41
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Thr or Asn
<220> FEATURE:
<221> NAME/KEY: MOD_RES
<222> LOCATION: (2)..(2)
<223> OTHER INFORMATION: Phe or Ile
<220> FEATURE:
<221> NAME/KEY: MOD_RES
<222> LOCATION: (3)..(3)
<223> OTHER INFORMATION: Ser, Thr or Tyr
<220> FEATURE:
<221> NAME/KEY: MOD_RES
<222> LOCATION: (4)..(4)
<223> OTHER INFORMATION: Asn, Asp, Ser or Tyr
```

```
<220> FEATURE:
<221> NAME/KEY: MOD_RES
<222> LOCATION: (5)..(5)
<223> OTHER INFORMATION: Thr, Tyr, Ser or Asp
<220> FEATURE:
<221> NAME/KEY: MOD_RES
<222> LOCATION: (6)..(6)
<223> OTHER INFORMATION: Tyr, Asp or Ser
<220> FEATURE:
<221> NAME/KEY: MOD_RES
<222> LOCATION: (7)..(7)
<223> OTHER INFORMATION: Ile or Met
<220> FEATURE:
<221> NAME/KEY: MOD_RES
<222> LOCATION: (8)..(8)
<223> OTHER INFORMATION: Ser or His

<400> SEQUENCE: 41

Xaa Xaa Xaa Xaa Xaa Xaa Xaa Xaa
1               5

<210> SEQ ID NO 42
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Ser, Gly, Trp or Glu
<220> FEATURE:
<221> NAME/KEY: MOD_RES
<222> LOCATION: (4)..(4)
<223> OTHER INFORMATION: Thr, Ser or Tyr
<220> FEATURE:
<221> NAME/KEY: MOD_RES
<222> LOCATION: (5)..(5)
<223> OTHER INFORMATION: Pro or Ser
<220> FEATURE:
<221> NAME/KEY: MOD_RES
<222> LOCATION: (6)..(6)
<223> OTHER INFORMATION: Ser or Tyr
<220> FEATURE:
<221> NAME/KEY: MOD_RES
<222> LOCATION: (7)..(7)
<223> OTHER INFORMATION: Gly, Ser or Tyr
<220> FEATURE:
<221> NAME/KEY: MOD_RES
<222> LOCATION: (8)..(8)
<223> OTHER INFORMATION: Gly or Ser
<220> FEATURE:
<221> NAME/KEY: MOD_RES
<222> LOCATION: (9)..(9)
<223> OTHER INFORMATION: Ser or Tyr
<220> FEATURE:
<221> NAME/KEY: MOD_RES
<222> LOCATION: (11)..(11)
<223> OTHER INFORMATION: Asp or Ser

<400> SEQUENCE: 42

Ala Xaa Ile Xaa Xaa Xaa Xaa Xaa Xaa Thr Xaa
1               5                   10

<210> SEQ ID NO 43
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
```

```
<223> OTHER INFORMATION: Thr, Glu or Gly
<220> FEATURE:
<221> NAME/KEY: MOD_RES
<222> LOCATION: (3)..(3)
<223> OTHER INFORMATION: Trp, Ala or Tyr
<220> FEATURE:
<221> NAME/KEY: MOD_RES
<222> LOCATION: (4)..(4)
<223> OTHER INFORMATION: Leu, Gly, Val or Ser
<220> FEATURE:
<221> NAME/KEY: MOD_RES
<222> LOCATION: (5)..(5)
<223> OTHER INFORMATION: Leu, Ser or Trp
<220> FEATURE:
<221> NAME/KEY: MOD_RES
<222> LOCATION: (6)..(6)
<223> OTHER INFORMATION: Arg, Lys or Tyr
<220> FEATURE:
<221> NAME/KEY: MOD_RES
<222> LOCATION: (7)..(7)
<223> OTHER INFORMATION: Trp, Leu, Gly or Tyr
<220> FEATURE:
<221> NAME/KEY: MOD_RES
<222> LOCATION: (8)..(8)
<223> OTHER INFORMATION: Val, Leu, Ala or Gly
<220> FEATURE:
<221> NAME/KEY: MOD_RES
<222> LOCATION: (9)..(9)
<223> OTHER INFORMATION: May or may not be present
<220> FEATURE:
<221> NAME/KEY: MOD_RES
<222> LOCATION: (10)..(10)
<223> OTHER INFORMATION: Val, Pro or not present
<220> FEATURE:
<221> NAME/KEY: MOD_RES
<222> LOCATION: (11)..(11)
<223> OTHER INFORMATION: May or may not be present
<220> FEATURE:
<221> NAME/KEY: MOD_RES
<222> LOCATION: (12)..(12)
<223> OTHER INFORMATION: Met or Phe

<400> SEQUENCE: 43

Arg Xaa Xaa Xaa Xaa Xaa Xaa Xaa Ser Xaa Ala Xaa Asp
1               5                   10

<210> SEQ ID NO 44
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Asp, Ala, Glu, Gly, Leu, Asn, Ser, Thr or Val
<220> FEATURE:
<221> NAME/KEY: MOD_RES
<222> LOCATION: (6)..(6)
<223> OTHER INFORMATION: Val, Ala, Leu or Ser
<220> FEATURE:
<221> NAME/KEY: MOD_RES
<222> LOCATION: (7)..(7)
<223> OTHER INFORMATION: Ser, Phe, Gly, Leu, Arg or Val
<220> FEATURE:
<221> NAME/KEY: MOD_RES
<222> LOCATION: (8)..(8)
<223> OTHER INFORMATION: Thr, Gly, Ile, Asn, Ser or Val
<220> FEATURE:
<221> NAME/KEY: MOD_RES
<222> LOCATION: (9)..(9)
<223> OTHER INFORMATION: Ala, His, Gln, Arg, Ser or Tyr
<220> FEATURE:
<221> NAME/KEY: MOD_RES
<222> LOCATION: (10)..(10)
<223> OTHER INFORMATION: Val or Leu
```

```
<400> SEQUENCE: 44

Arg Ala Ser Gln Xaa Xaa Xaa Xaa Xaa Xaa Ala
1               5                   10

<210> SEQ ID NO 45
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Ala or Arg
<220> FEATURE:
<221> NAME/KEY: MOD_RES
<222> LOCATION: (3)..(3)
<223> OTHER INFORMATION: Ser, Lys, Gln or Arg
<220> FEATURE:
<221> NAME/KEY: MOD_RES
<222> LOCATION: (4)..(4)
<223> OTHER INFORMATION: Phe or Tyr
<220> FEATURE:
<221> NAME/KEY: MOD_RES
<222> LOCATION: (5)..(5)
<223> OTHER INFORMATION: Leu, Ala, Phe, Gly, His, Ile, Lys, Met, Asn,
      Pro, Arg, Ser, Val or Tyr
<220> FEATURE:
<221> NAME/KEY: MOD_RES
<222> LOCATION: (7)..(7)
<223> OTHER INFORMATION: Ser, Ala, Asp, Phe, Gly, His, Val, Trp or Tyr

<400> SEQUENCE: 45

Ser Xaa Xaa Xaa Xaa Tyr Xaa
1               5

<210> SEQ ID NO 46
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: His or Ser
<220> FEATURE:
<221> NAME/KEY: MOD_RES
<222> LOCATION: (4)..(4)
<223> OTHER INFORMATION: Tyr, Lys, Asn, Gln, Arg, Ser, Val or Trp
<220> FEATURE:
<221> NAME/KEY: MOD_RES
<222> LOCATION: (5)..(5)
<223> OTHER INFORMATION: Thr, Ile, Gln, Arg, Ser or Val
<220> FEATURE:
<221> NAME/KEY: MOD_RES
<222> LOCATION: (6)..(6)
<223> OTHER INFORMATION: Thr, Ala, Asp, Phe, Gly, Lys, Asn, Pro, Gln,
      Arg, Ser or Val

<400> SEQUENCE: 46

Gln Gln Xaa Xaa Xaa Xaa Pro Pro Thr
1               5

<210> SEQ ID NO 47
<211> LENGTH: 6
<212> TYPE: PRT
<213> ORGANISM: Artificial Sequence
<220> FEATURE:
<223> OTHER INFORMATION: Description of Artificial Sequence: Synthetic
```

```
            peptide
<220> FEATURE:
<221> NAME/KEY: MOD_RES
<222> LOCATION: (1)..(1)
<223> OTHER INFORMATION: Ala, Phe, Lys, Met, Gln, Arg or Ser
<220> FEATURE:
<221> NAME/KEY: MOD_RES
<222> LOCATION: (2)..(2)
<223> OTHER INFORMATION: Asn or Trp
<220> FEATURE:
<221> NAME/KEY: MOD_RES
<222> LOCATION: (3)..(3)
<223> OTHER INFORMATION: Thr, Ala, Ile, Leu, Met or Val
<220> FEATURE:
<221> NAME/KEY: MOD_RES
<222> LOCATION: (5)..(5)
<223> OTHER INFORMATION: Ile, Met or Val

<400> SEQUENCE: 47

Xaa Xaa Xaa Tyr Xaa Ser
1               5

<210> SEQ ID NO 48
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Thr or Ser
<220> FEATURE:
<221> NAME/KEY: MOD_RES
<222> LOCATION: (3)..(3)
<223> OTHER INFORMATION: Ile, Ser or Val
<220> FEATURE:
<221> NAME/KEY: MOD_RES
<222> LOCATION: (6)..(6)
<223> OTHER INFORMATION: Ser or Ala
<220> FEATURE:
<221> NAME/KEY: MOD_RES
<222> LOCATION: (9)..(9)
<223> OTHER INFORMATION: Ser, His, Ile, Leu, Met or Gln
<220> FEATURE:
<221> NAME/KEY: MOD_RES
<222> LOCATION: (11)..(11)
<223> OTHER INFORMATION: Asp or Asn

<400> SEQUENCE: 48

Ala Xaa Xaa Thr Pro Xaa Ser Gly Xaa Thr Xaa
1               5                   10

<210> SEQ ID NO 49
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ser or Thr
<220> FEATURE:
<221> NAME/KEY: MOD_RES
<222> LOCATION: (3)..(3)
<223> OTHER INFORMATION: Leu or Tyr
<220> FEATURE:
<221> NAME/KEY: MOD_RES
<222> LOCATION: (4)..(4)
<223> OTHER INFORMATION: Leu, Ile or Val
<220> FEATURE:
<221> NAME/KEY: MOD_RES
```

```
<222> LOCATION: (8)..(8)
<223> OTHER INFORMATION: Met or Phe

<400> SEQUENCE: 49

Xaa Trp Xaa Xaa Arg Trp Val Xaa Asp
1               5

<210> SEQ ID NO 50
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Arg Ala Ser Gln Asp Val Gly Thr Ala Val Ala
1               5                   10

<210> SEQ ID NO 51
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Arg Ala Ser Gln Asp Val Ser Thr Tyr Val Ala
1               5                   10

<210> SEQ ID NO 52
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Arg Ala Ser Gln Asp Val Ser Thr Gln Val Ala
1               5                   10

<210> SEQ ID NO 53
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Arg Ala Ser Gln Asp Val Ser Ile Ala Val Ala
1               5                   10

<210> SEQ ID NO 54
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Arg Ala Ser Gln Asp Val Arg Thr Ala Val Ala
1               5                   10
```

```
<210> SEQ ID NO 55
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Arg Ala Ser Gln Asp Val Ser Gly Ala Val Ala
1               5                   10

<210> SEQ ID NO 56
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Arg Ala Ser Gln Ala Val Ser Thr Ala Val Ala
1               5                   10

<210> SEQ ID NO 57
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Arg Ala Ser Gln Leu Val Ser Thr Ala Val Ala
1               5                   10

<210> SEQ ID NO 58
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Ser Ala Lys Phe Leu Tyr Ser
1               5

<210> SEQ ID NO 59
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Ser Arg Ser Phe Leu Tyr Ser
1               5

<210> SEQ ID NO 60
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60
```

```
Ser Ala Arg Phe Leu Tyr Ser
1               5

<210> SEQ ID NO 61
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Ser Ala Ser Phe Ser Tyr Ser
1               5

<210> SEQ ID NO 62
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Ser Ala Ser Phe Met Tyr Ser
1               5

<210> SEQ ID NO 63
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Ser Ala Ser Phe Asn Tyr Ser
1               5

<210> SEQ ID NO 64
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Gln Gln Ser Tyr Thr Ala Pro Pro Thr
1               5

<210> SEQ ID NO 65
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Gln Gln Ser Tyr Thr Gln Pro Pro Thr
1               5

<210> SEQ ID NO 66
<211> LENGTH: 9
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 66

Gln Gln Ser Arg Thr Thr Pro Pro Thr
1               5

<210> SEQ ID NO 67
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Gln Gln Ser Tyr Thr Ser Pro Pro Thr
1               5

<210> SEQ ID NO 68
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Gln Gln Ser Val Thr Thr Pro Pro Thr
1               5

<210> SEQ ID NO 69
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Gln Gln Ser Tyr Thr Pro Pro Pro Thr
1               5

<210> SEQ ID NO 70
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Gln Gln Ser Tyr Val Thr Pro Pro Thr
1               5

<210> SEQ ID NO 71
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Gln Gln Ser Tyr Thr Gly Pro Pro Thr
1               5
```

```
<210> SEQ ID NO 72
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Gln Gln Ser Tyr Thr Asn Pro Pro Thr
1               5

<210> SEQ ID NO 73
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Phe Asn Thr Tyr Ile Ser
1               5

<210> SEQ ID NO 74
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Ser Asn Leu Tyr Ile Ser
1               5

<210> SEQ ID NO 75
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Gln Asn Thr Tyr Ile Ser
1               5

<210> SEQ ID NO 76
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Ser Asn Val Tyr Ile Ser
1               5

<210> SEQ ID NO 77
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 77

Arg Asn Thr Tyr Ile Ser
1               5

<210> SEQ ID NO 78
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Ser Asn Met Tyr Ile Ser
1               5

<210> SEQ ID NO 79
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Lys Asn Thr Tyr Ile Ser
1               5

<210> SEQ ID NO 80
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Ser Asn Thr Tyr Met Ser
1               5

<210> SEQ ID NO 81
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Ser Asn Ile Tyr Ile Ser
1               5

<210> SEQ ID NO 82
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Ala Ser Ile Thr Pro Ser Ser Gly Gln Thr Asp
1               5                   10

<210> SEQ ID NO 83
<211> LENGTH: 11
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 83

Ala Ser Ile Thr Pro Ser Ser Gly Leu Thr Asp
1               5                   10

<210> SEQ ID NO 84
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Ala Ser Ser Thr Pro Ser Ser Gly Ser Thr Asp
1               5                   10

<210> SEQ ID NO 85
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Ala Ser Ile Thr Pro Ser Ser Gly Ile Thr Asp
1               5                   10

<210> SEQ ID NO 86
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Ala Ser Ile Thr Pro Ser Ser Gly Ser Thr Asn
1               5                   10

<210> SEQ ID NO 87
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Thr Trp Leu Leu Arg Trp Val Met Asp
1               5

<210> SEQ ID NO 88
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Thr Trp Leu Leu Arg Trp Val Phe Asp
1               5
```

```
<210> SEQ ID NO 89
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Thr Trp Leu Leu Arg Trp Val Met Asp
1               5

<210> SEQ ID NO 90
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Thr Trp Leu Leu Arg Trp Val Met Asp
1               5

<210> SEQ ID NO 91
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Thr Trp Leu Leu Arg Trp Val Met Asp
1               5

<210> SEQ ID NO 92
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Thr Trp Leu Leu Arg Trp Val Met Asp
1               5

<210> SEQ ID NO 93
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Thr Trp Leu Leu Arg Trp Val Phe Asp
1               5

<210> SEQ ID NO 94
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 94

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Lys Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Thr Thr Pro Pro
                85                  90                  95

Thr Phe Gly Gln Gly Thr Lys Val Glu Ile Lys
            100                 105

<210> SEQ ID NO 95
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 95

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Thr
            20                  25                  30

Tyr Ile Ser Trp Val Arg Gln Ala Pro Gly Lys Gly Leu Glu Trp Val
        35                  40                  45

Ala Ser Ile Thr Pro Ser Ser Gly Gln Thr Asp Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Thr Trp Leu Leu Arg Val Met Asp Leu Trp Gly Gln Gly
            100                 105                 110

Thr Leu Val Thr Val Ser Ser
        115

<210> SEQ ID NO 96
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Thr Trp Leu Leu Arg Val Met Asp Leu
1               5

<210> SEQ ID NO 97
<211> LENGTH: 76
<212> TYPE: PRT
<213> ORGANISM: Homo sapiens

```
<400> SEQUENCE: 97

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly
65                  70                  75

<210> SEQ ID NO 98
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 98

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105

<210> SEQ ID NO 99
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 99

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Thr Thr Pro Pro
                85                  90                  95

Thr Phe Gly Gln Gly Thr Lys Val Glu Ile Lys
```

<210> SEQ ID NO 100
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 100
tcttgtgaca aaactcacag tggcggtggc tctggt                                 36

<210> SEQ ID NO 101
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 101
tgtgacaaaa ctcacctcag tggcggtggc tctggttccg gtgattttga ttatgaaaag       60

<210> SEQ ID NO 102
<211> LENGTH: 55
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 102
cccaaatctt gtgacaaaac tcacacataa agtggcggtg gctctggttc cggtg            55

<210> SEQ ID NO 103
<211> LENGTH: 55
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 103
caccggaacc agagccaccg ccactttatg tgtgagtttt gtcacaagat ttggg            55

<210> SEQ ID NO 104
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 104
gtcaccatca cctgctaagc cagtcaggat gtg                                    33

<210> SEQ ID NO 105
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 105
gaagcttctg atttactaag catccttcct ctac                                   34

<210> SEQ ID NO 106
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 106
gcaacttatt actgttaaca atcttatact actc                                34

<210> SEQ ID NO 107
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 107
gccgtctatt attgtgctcg ttaagccggg tcccgcttgt tgtcg                    45

<210> SEQ ID NO 108
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 108
gaggacactg ccgtctatta ttgtgctcgt gaggcctcgt aactgccccc ctacgttatg    60
gactactggg gtcaaggaac actagtc                                        87

<210> SEQ ID NO 109
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 109
catcacctgc cgtgccagtt aatccgtgtc cagcgctgta g                        41

<210> SEQ ID NO 110
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 110
cttctgattt actcggcata aagcctctac tctggagtc                           39

<210> SEQ ID NO 111
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 111
gcaacttatt actgtcagta atattattat tattctccg          39

<210> SEQ ID NO 112
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 112
gccgtctatt attgtgctta aggttacgtt tggaaaggtg          40

<210> SEQ ID NO 113
<211> LENGTH: 55
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (29)..(29)
<223> OTHER INFORMATION: a, c, t or g

<400> SEQUENCE: 113
acctgccgtg ccagtcagrd trktrvwanw thtgtagcct ggtatcaaca gaaac          55

<210> SEQ ID NO 114
<211> LENGTH: 55
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (29)..(29)
<223> OTHER INFORMATION: a, c, t or g

<400> SEQUENCE: 114
acctgccgtg ccagtcagrd trktrvwanw thtctggcct ggtatcaaca gaaac          55

<210> SEQ ID NO 115
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 115
ccgaagcttc tgatttackb ggcatccavc ctctactctg gagtccct          48

<210> SEQ ID NO 116
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 116
ccgaagcttc tgatttackb ggcatccavc ctcgmatctg gagtcccttc tcgc          54

<210> SEQ ID NO 117
<211> LENGTH: 57
<212> TYPE: DNA

```
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (31)..(31)
<223> OTHER INFORMATION: a, c, t or g

<400> SEQUENCE: 117
gcaacttatt actgtcagca atmtdmcrvt nhtcctykga cgttcggaca gggtacc        57

<210> SEQ ID NO 118
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (31)..(31)
<223> OTHER INFORMATION: a, c, t or g

<400> SEQUENCE: 118
gcaacttatt actgtcagca atmtdmcrvt nhtccttwta cgttcggaca gggtacc        57

<210> SEQ ID NO 119
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (31)..(31)
<223> OTHER INFORMATION: a, c, t or g

<400> SEQUENCE: 119
gcaacttatt actgtcagca asrtdmcrvt nhtcctykga cgttcggaca gggtacc        57

<210> SEQ ID NO 120
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (31)..(31)
<223> OTHER INFORMATION: a, c, t or g

<400> SEQUENCE: 120
gcaacttatt actgtcagca asrtdmcrvt nhtccttwta cgttcggaca gggtacc        57

<210> SEQ ID NO 121
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (19)..(30)
<223> OTHER INFORMATION: a, c, t or g
<220> FEATURE:
<221> NAME/KEY: modified_base
<222> LOCATION: (34)..(36)
```

<223> OTHER INFORMATION: a, c, t or g

<400> SEQUENCE: 121
acttattact gtcagcaann nnnnnnnnnn cctnnnacgt tcggacaggg tacc        54

<210> SEQ ID NO 122
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (19)..(30)
<223> OTHER INFORMATION: a, c, t or g

<400> SEQUENCE: 122
acttattact gtcagcaann nnnnnnnnnn ccttwtacgt tcggacaggg tacc        54

<210> SEQ ID NO 123
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (19)..(30)
<223> OTHER INFORMATION: a, c, t or g

<400> SEQUENCE: 123
acttattact gtcagcaann nnnnnnnnnn cctykgacgt tcggacaggg tacc        54

<210> SEQ ID NO 124
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (22)..(36)
<223> OTHER INFORMATION: a, c, t or g
<220> FEATURE:
<221> NAME/KEY: modified_base
<222> LOCATION: (40)..(42)
<223> OTHER INFORMATION: a, c, t or g

<400> SEQUENCE: 124
gcaacttatt actgtcagca annnnnnnnn nnnnnnccgn nnacgttcgg acagggtacc  60
aag                                                                63

<210> SEQ ID NO 125
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (28)..(30)
<223> OTHER INFORMATION: a, c, t or g
<220> FEATURE:
<221> NAME/KEY: modified_base
<222> LOCATION: (34)..(36)
<223> OTHER INFORMATION: a, c, t or g

```
<220> FEATURE:
<221> NAME/KEY: modified_base
<222> LOCATION: (40)..(48)
<223> OTHER INFORMATION: a, c, t or g

<400> SEQUENCE: 125
gacactgccg tctattattg tgctcgcnnn tacnnntggn nnnnnnnnat ggactactgg    60
ggtcaaggaa cc                                                       72

<210> SEQ ID NO 126
<211> LENGTH: 77
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (25)..(27)
<223> OTHER INFORMATION: a, c, t or g
<220> FEATURE:
<221> NAME/KEY: modified_base
<222> LOCATION: (31)..(33)
<223> OTHER INFORMATION: a, c, t or g
<220> FEATURE:
<221> NAME/KEY: modified_base
<222> LOCATION: (37)..(42)
<223> OTHER INFORMATION: a, c, t or g
<220> FEATURE:
<221> NAME/KEY: modified_base
<222> LOCATION: (52)..(54)
<223> OTHER INFORMATION: a, c, t or g

<400> SEQUENCE: 126
ggtaagggcc tggaatgggt tgcannnatt nnntctnnnn nnagctatac tnnntatgcc    60
gatagcgtca agggccg                                                  77

<210> SEQ ID NO 127
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (22)..(33)
<223> OTHER INFORMATION: a, c, t or g

<400> SEQUENCE: 127
gcagcttctg gcttcaactt tnnnnnnnnn nnnatgcact gggtgcgtca ggcc          54

<210> SEQ ID NO 128
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (25)..(48)
<223> OTHER INFORMATION: a, c, t or g

<400> SEQUENCE: 128
gccgtctatt attgtgctcg tgagnnnnnn nnnnnnnnnn nnnnnnnnat ggactactgg    60
ggtcaaggaa cc                                                       72
```

-continued

```
<210> SEQ ID NO 129
<211> LENGTH: 77
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (25)..(27)
<223> OTHER INFORMATION: a, c, t or g
<220> FEATURE:
<221> NAME/KEY: modified_base
<222> LOCATION: (31)..(33)
<223> OTHER INFORMATION: a, c, t or g
<220> FEATURE:
<221> NAME/KEY: modified_base
<222> LOCATION: (37)..(42)
<223> OTHER INFORMATION: a, c, t or g
<220> FEATURE:
<221> NAME/KEY: modified_base
<222> LOCATION: (52)..(54)
<223> OTHER INFORMATION: a, c, t or g

<400> SEQUENCE: 129
ggtaagggcc tggaatgggt tgctnnnatt nnncctnnnn nnggttatac tnnntatgcc      60
gatagcgtca agggccg                                                    77

<210> SEQ ID NO 130
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (22)..(33)
<223> OTHER INFORMATION: a, c, t or g

<400> SEQUENCE: 130
gcagcttctg gcttcacctt cnnnnnnnnn nnnattcact gggtgcgtca ggcc            54

<210> SEQ ID NO 131
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (28)..(30)
<223> OTHER INFORMATION: a, c, t or g
<220> FEATURE:
<221> NAME/KEY: modified_base
<222> LOCATION: (34)..(42)
<223> OTHER INFORMATION: a, c, t or g
<220> FEATURE:
<221> NAME/KEY: modified_base
<222> LOCATION: (46)..(48)
<223> OTHER INFORMATION: a, c, t or g

<400> SEQUENCE: 131
gacactgccg tctattattg tgctcgtnnn tggnnnnnnn nntggnnnat ggactactgg      60
ggtcaaggaa ccctg                                                      75

<210> SEQ ID NO 132
<211> LENGTH: 77
<212> TYPE: DNA
<213> ORGANISM: Artificial Sequence
```

```
<220> FEATURE:
<223> OTHER INFORMATION: Description of Artificial Sequence: Synthetic
      oligonucleotide
<220> FEATURE:
<221> NAME/KEY: modified_base
<222> LOCATION: (25)..(27)
<223> OTHER INFORMATION: a, c, t or g
<220> FEATURE:
<221> NAME/KEY: modified_base
<222> LOCATION: (31)..(33)
<223> OTHER INFORMATION: a, c, t or g
<220> FEATURE:
<221> NAME/KEY: modified_base
<222> LOCATION: (37)..(42)
<223> OTHER INFORMATION: a, c, t or g
<220> FEATURE:
<221> NAME/KEY: modified_base
<222> LOCATION: (52)..(54)
<223> OTHER INFORMATION: a, c, t or g

<400> SEQUENCE: 132
ggtaagggcc tggaatgggt tgctnnnatt nnncctnnnn nnggttctac tnnntatgcc    60
gatagcgtca agggccg                                                  77

<210> SEQ ID NO 133
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (22)..(33)
<223> OTHER INFORMATION: a, c, t or g

<400> SEQUENCE: 133
gcagcttctg gcttcacctt cnnnnnnnnn nnnattagct gggtgcgtca ggcc          54

<210> SEQ ID NO 134
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 134
gccagtcagg atgtgtccta agctgtagcc tggtatcaac                         40

<210> SEQ ID NO 135
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 135
ctgatttact cggcatccta actctactct ggagtccctt c                        41

<210> SEQ ID NO 136
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 136
```
cttattactg tcagcaatct tattaaactc ctcccacgtt cggacag      47

<210> SEQ ID NO 137
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 137
ggcttcacct tcagtaatta atatattagc tgggtgcgtc      40

<210> SEQ ID NO 138
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 138
gttgcttcta ttactcctta aagcggttct actgactatg      40

<210> SEQ ID NO 139
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 139
gctcgtacct ggttgctcta atgggttatg gactactgg      39

<210> SEQ ID NO 140
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (23)..(24)
<223> OTHER INFORMATION: a, c, t, g, unknown or other

<400> SEQUENCE: 140
catcacctgc cgtgccagtc agnnkgtgtc cactgctgta gcctggtatc aacagaaacc      60
agg      63

<210> SEQ ID NO 141
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (26)..(27)
<223> OTHER INFORMATION: a, c, t, g, unknown or other

<400> SEQUENCE: 141
catcacctgc cgtgccagtc aggatnnktc cactgctgta gcctggtatc aacagaaacc      60
agg      63

<210> SEQ ID NO 142
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (29)..(30)
<223> OTHER INFORMATION: a, c, t, g, unknown or other

<400> SEQUENCE: 142
catcacctgc cgtgccagtc aggatgtgnn kactgctgta gcctggtatc aacagaaacc    60
agg                                                                  63

<210> SEQ ID NO 143
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (32)..(33)
<223> OTHER INFORMATION: a, c, t, g, unknown or other

<400> SEQUENCE: 143
catcacctgc cgtgccagtc aggatgtgtc cnnkgctgta gcctggtatc aacagaaacc    60
agg                                                                  63

<210> SEQ ID NO 144
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (35)..(36)
<223> OTHER INFORMATION: a, c, t, g, unknown or other

<400> SEQUENCE: 144
catcacctgc cgtgccagtc aggatgtgtc cactnnkgta gcctggtatc aacagaaacc    60
agg                                                                  63

<210> SEQ ID NO 145
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (38)..(39)
<223> OTHER INFORMATION: a, c, t, g, unknown or other

<400> SEQUENCE: 145
catcacctgc cgtgccagtc aggatgtgtc cactgctnnk gcctggtatc aacagaaacc    60
agg                                                                  63

<210> SEQ ID NO 146

```
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (41)..(42)
<223> OTHER INFORMATION: a, c, t, g, unknown or other

<400> SEQUENCE: 146
catcacctgc cgtgccagtc aggatgtgtc cactgctgta nnktggtatc aacagaaacc    60
agg                                                                  63

<210> SEQ ID NO 147
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (22)..(23)
<223> OTHER INFORMATION: a, c, t, g, unknown or other

<400> SEQUENCE: 147
gctccgaagc ttctgattta cnnkgcatcc ttcctctact ctggagtccc ttctcgcttc    60
tctg                                                                 64

<210> SEQ ID NO 148
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (25)..(26)
<223> OTHER INFORMATION: a, c, t, g, unknown or other

<400> SEQUENCE: 148
gctccgaagc ttctgattta ctcgnnktcc ttcctctact ctggagtccc ttctcgcttc    60
tctg                                                                 64

<210> SEQ ID NO 149
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (28)..(29)
<223> OTHER INFORMATION: a, c, t, g, unknown or other

<400> SEQUENCE: 149
gctccgaagc ttctgattta ctcggcannk ttcctctact ctggagtccc ttctcgcttc    60
tctg                                                                 64

<210> SEQ ID NO 150
<211> LENGTH: 64
<212> TYPE: DNA
<213> ORGANISM: Artificial Sequence
```

<220> FEATURE:
<223> OTHER INFORMATION: Description of Artificial Sequence: Synthetic
      oligonucleotide
<220> FEATURE:
<221> NAME/KEY: modified_base
<222> LOCATION: (31)..(32)
<223> OTHER INFORMATION: a, c, t, g, unknown or other

<400> SEQUENCE: 150
gctccgaagc ttctgattta ctcggcatcc nnkctctact ctggagtccc ttctcgcttc    60
tctg                                                                 64

<210> SEQ ID NO 151
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (34)..(35)
<223> OTHER INFORMATION: a, c, t, g, unknown or other

<400> SEQUENCE: 151
gctccgaagc ttctgattta ctcggcatcc ttcnnktact ctggagtccc ttctcgcttc    60
tctg                                                                 64

<210> SEQ ID NO 152
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (37)..(38)
<223> OTHER INFORMATION: a, c, t, g, unknown or other

<400> SEQUENCE: 152
gctccgaagc ttctgattta ctcggcatcc ttcctcnnkt ctggagtccc ttctcgcttc    60
tctg                                                                 64

<210> SEQ ID NO 153
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (40)..(41)
<223> OTHER INFORMATION: a, c, t, g, unknown or other

<400> SEQUENCE: 153
gctccgaagc ttctgattta ctcggcatcc ttcctctacn nkggagtccc ttctcgcttc    60
tctg                                                                 64

<210> SEQ ID NO 154
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide -continued

```
<220> FEATURE:
<221> NAME/KEY: modified_base
<222> LOCATION: (22)..(23)
<223> OTHER INFORMATION: a, c, t, g, unknown or other

<400> SEQUENCE: 154
gcaacttatt actgtcagca annktatact actcctccca cgttcggaca gggtaccaag      60

<210> SEQ ID NO 155
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (25)..(26)
<223> OTHER INFORMATION: a, c, t, g, unknown or other

<400> SEQUENCE: 155
gcaacttatt actgtcagca atctnnkact actcctccca cgttcggaca gggtaccaag      60

<210> SEQ ID NO 156
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (28)..(29)
<223> OTHER INFORMATION: a, c, t, g, unknown or other

<400> SEQUENCE: 156
gcaacttatt actgtcagca atcttatnnk actcctccca cgttcggaca gggtaccaag      60

<210> SEQ ID NO 157
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (31)..(32)
<223> OTHER INFORMATION: a, c, t, g, unknown or other

<400> SEQUENCE: 157
gcaacttatt actgtcagca atcttatact nnkcctccca cgttcggaca gggtaccaag      60

<210> SEQ ID NO 158
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (34)..(35)
<223> OTHER INFORMATION: a, c, t, g, unknown or other

<400> SEQUENCE: 158
gcaacttatt actgtcagca atcttatact actnnkccca cgttcggaca gggtaccaag      60

<210> SEQ ID NO 159
```

```
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (37)..(38)
<223> OTHER INFORMATION: a, c, t, g, unknown or other

<400> SEQUENCE: 159
gcaacttatt actgtcagca atcttatact actcctnnka cgttcggaca gggtaccaag        60

<210> SEQ ID NO 160
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (22)..(23)
<223> OTHER INFORMATION: a, c, t, g, unknown or other

<400> SEQUENCE: 160
gcagcttctg gcttcacctt cnnkaatact tatattagct gggtgcgtca ggccccg           57

<210> SEQ ID NO 161
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (25)..(26)
<223> OTHER INFORMATION: a, c, t, g, unknown or other

<400> SEQUENCE: 161
gcagcttctg gcttcacctt cagtnnkact tatattagct gggtgcgtca ggccccg           57

<210> SEQ ID NO 162
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (28)..(29)
<223> OTHER INFORMATION: a, c, t, g, unknown or other

<400> SEQUENCE: 162
gcagcttctg gcttcacctt cagtaatnnk tatattagct gggtgcgtca ggccccg           57

<210> SEQ ID NO 163
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (31)..(32)
<223> OTHER INFORMATION: a, c, t, g, unknown or other
```

<400> SEQUENCE: 163
gcagcttctg gcttcacctt cagtaatact nnkattagct gggtgcgtca ggccccg    57

<210> SEQ ID NO 164
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (34)..(35)
<223> OTHER INFORMATION: a, c, t, g, unknown or other

<400> SEQUENCE: 164
gcagcttctg gcttcacctt cagtaatact tatnnkagct gggtgcgtca ggccccg    57

<210> SEQ ID NO 165
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (37)..(38)
<223> OTHER INFORMATION: a, c, t, g, unknown or other

<400> SEQUENCE: 165
gcagcttctg gcttcacctt cagtaatact tatattnnkt gggtgcgtca ggccccg    57

<210> SEQ ID NO 166
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (22)..(23)
<223> OTHER INFORMATION: a, c, t, g, unknown or other

<400> SEQUENCE: 166
ggtaagggcc tggaatgggt tnnktctatt actccttcta gcggttctac tgactatgcc    60
gatagcgtca agggc    75

<210> SEQ ID NO 167
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (25)..(26)
<223> OTHER INFORMATION: a, c, t, g, unknown or other

<400> SEQUENCE: 167
ggtaagggcc tggaatgggt tgctnnkatt actccttcta gcggttctac tgactatgcc    60
gatagcgtca agggc    75

<210> SEQ ID NO 168
<211> LENGTH: 75

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (28)..(29)
<223> OTHER INFORMATION: a, c, t, g, unknown or other

<400> SEQUENCE: 168
ggtaagggcc tggaatgggt tgcttctnnk actccttcta gcggttctac tgactatgcc      60
gatagcgtca agggc                                                      75

<210> SEQ ID NO 169
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (31)..(32)
<223> OTHER INFORMATION: a, c, t, g, unknown or other

<400> SEQUENCE: 169
ggtaagggcc tggaatgggt tgcttctatt nnkccttcta gcggttctac tgactatgcc      60
gatagcgtca agggc                                                      75

<210> SEQ ID NO 170
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (34)..(35)
<223> OTHER INFORMATION: a, c, t, g, unknown or other

<400> SEQUENCE: 170
ggtaagggcc tggaatgggt tgcttctatt actnnktcta gcggttctac tgactatgcc      60
gatagcgtca agggc                                                      75

<210> SEQ ID NO 171
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (37)..(38)
<223> OTHER INFORMATION: a, c, t, g, unknown or other

<400> SEQUENCE: 171
ggtaagggcc tggaatgggt tgcttctatt actcctnnka gcggttctac tgactatgcc      60
gatagcgtca agggc                                                      75

<210> SEQ ID NO 172
<211> LENGTH: 75
<212> TYPE: DNA
<213> ORGANISM: Artificial Sequence
<220> FEATURE:
```

```
<223> OTHER INFORMATION: Description of Artificial Sequence: Synthetic
      oligonucleotide
<220> FEATURE:
<221> NAME/KEY: modified_base
<222> LOCATION: (40)..(41)
<223> OTHER INFORMATION: a, c, t, g, unknown or other

<400> SEQUENCE: 172
ggtaagggcc tggaatgggt tgcttctatt actccttctn nkggttctac tgactatgcc    60
gatagcgtca agggc                                                     75

<210> SEQ ID NO 173
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (43)..(44)
<223> OTHER INFORMATION: a, c, t, g, unknown or other

<400> SEQUENCE: 173
ggtaagggcc tggaatgggt tgcttctatt actccttcta gcnnktctac tgactatgcc    60
gatagcgtca agggc                                                     75

<210> SEQ ID NO 174
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (46)..(47)
<223> OTHER INFORMATION: a, c, t, g, unknown or other

<400> SEQUENCE: 174
ggtaagggcc tggaatgggt tgcttctatt actccttcta gcggtnnkac tgactatgcc    60
gatagcgtca agggc                                                     75

<210> SEQ ID NO 175
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (49)..(50)
<223> OTHER INFORMATION: a, c, t, g, unknown or other

<400> SEQUENCE: 175
ggtaagggcc tggaatgggt tgcttctatt actccttcta gcggttctnn kgactatgcc    60
gatagcgtca agggc                                                     75

<210> SEQ ID NO 176
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
```

<221> NAME/KEY: modified_base
<222> LOCATION: (52)..(53)
<223> OTHER INFORMATION: a, c, t, g, unknown or other

<400> SEQUENCE: 176
ggtaagggcc tggaatgggt tgcttctatt actccttcta gcggttctac tnnktatgcc    60
gatagcgtca agggc    75

<210> SEQ ID NO 177
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (22)..(23)
<223> OTHER INFORMATION: a, c, t, g, unknown or other

<400> SEQUENCE: 177
gccgtctatt attgtgctcg tnnktggttg ctccggtggg ttatggacta ctggggtcaa    60
ggaaccctgg tc    72

<210> SEQ ID NO 178
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (25)..(26)
<223> OTHER INFORMATION: a, c, t, g, unknown or other

<400> SEQUENCE: 178
gccgtctatt attgtgctcg taccnnkttg ctccggtggg ttatggacta ctggggtcaa    60
ggaaccctgg tc    72

<210> SEQ ID NO 179
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (28)..(29)
<223> OTHER INFORMATION: a, c, t, g, unknown or other

<400> SEQUENCE: 179
gccgtctatt attgtgctcg tacctggnnk ctccggtggg ttatggacta ctggggtcaa    60
ggaaccctgg tc    72

<210> SEQ ID NO 180
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (31)..(32)
<223> OTHER INFORMATION: a, c, t, g, unknown or other

<400> SEQUENCE: 180
gccgtctatt attgtgctcg tacctggttg nnkcggtggg ttatggacta ctggggtcaa    60
ggaaccctgg tc                                                        72

<210> SEQ ID NO 181
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (34)..(35)
<223> OTHER INFORMATION: a, c, t, g, unknown or other

<400> SEQUENCE: 181
gccgtctatt attgtgctcg tacctggttg ctcnnktggg ttatggacta ctggggtcaa    60
ggaaccctgg tc                                                        72

<210> SEQ ID NO 182
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (37)..(38)
<223> OTHER INFORMATION: a, c, t, g, unknown or other

<400> SEQUENCE: 182
gccgtctatt attgtgctcg tacctggttg ctccggnnkg ttatggacta ctggggtcaa    60
ggaaccctgg tc                                                        72

<210> SEQ ID NO 183
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (40)..(41)
<223> OTHER INFORMATION: a, c, t, g, unknown or other

<400> SEQUENCE: 183
gccgtctatt attgtgctcg tacctggttg ctccggtggn nkatggacta ctggggtcaa    60
ggaaccctgg tc                                                        72

<210> SEQ ID NO 184
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (43)..(44)
<223> OTHER INFORMATION: a, c, t, g, unknown or other

<400> SEQUENCE: 184
gccgtctatt attgtgctcg tacctggttg ctccggtggg ttnnkgacta ctggggtcaa    60
ggaaccctgg tc    72

<210> SEQ ID NO 185
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (46)..(47)
<223> OTHER INFORMATION: a, c, t, g, unknown or other

<400> SEQUENCE: 185
gccgtctatt attgtgctcg tacctggttg ctccggtggg ttatgnnkta ctggggtcaa    60
ggaaccctgg tc    72

<210> SEQ ID NO 186
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (49)..(50)
<223> OTHER INFORMATION: a, c, t, g, unknown or other

<400> SEQUENCE: 186
gccgtctatt attgtgctcg tacctggttg ctccggtggg ttatggacnn ktggggtcaa    60
ggaaccctgg tc    72

<210> SEQ ID NO 187
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 187
ccgaagcttc tgatttactc ggcaaagttc ctctactctg gagtccc    47

<210> SEQ ID NO 188
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 188
gggactccag agtagaggaa ctttgccgag taaatcagaa gcttcgg    47

<210> SEQ ID NO 189
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 189
cggtgggtta tggacctgtg gggtcaagga accctggtca ccgtctcctc ggcctcc        57

<210> SEQ ID NO 190
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 190
ggaggccgag gagacggtga ccagggttcc ttgaccccac aggtccataa cccaccg        57

<210> SEQ ID NO 191
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 191
cggtgggtta tggacctgtg gggtcaagga accctggtcg cggtctcctc ggcctcc        57

<210> SEQ ID NO 192
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 192
ggaggccgag gagaccgcga ccagggttcc ttgaccccac aggtccataa cccaccg        57

<210> SEQ ID NO 193
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 193

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Lys Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Thr Thr Pro Pro
                85                  90                  95

Thr Phe Gly Gln Gly Thr Lys Val Glu Ile Lys
            100                 105

<210> SEQ ID NO 194
<211> LENGTH: 107
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 194

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Thr Thr Pro Pro
                85                  90                  95

Thr Phe Gly Gln Gly Thr Lys Val Glu Ile Lys
            100                 105

<210> SEQ ID NO 195
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 195

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Thr Thr Pro Pro
                85                  90                  95

Thr Phe Gly Gln Gly Thr Lys Val Glu Ile Lys
            100                 105

<210> SEQ ID NO 196
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 196

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Thr
            20                  25                  30

Tyr Ile Ser Trp Val Arg Gln Ala Pro Gly Lys Gly Leu Glu Trp Val
        35                  40                  45

Ala Ser Ile Thr Pro Ser Ser Gly Ser Thr Asp Tyr Ala Asp Ser Val

```
            50                  55                  60
Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Arg Thr Trp Leu Leu Arg Trp Val Met Asp Tyr Trp Gly Gln Gly
                100                 105                 110

Thr Leu Val Thr Val Ser Ser
            115

<210> SEQ ID NO 197
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 197

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Asn Thr
             20                  25                  30

Tyr Ile Ser Trp Val Arg Gln Ala Pro Gly Lys Gly Leu Glu Trp Val
         35                  40                  45

Ala Ser Ile Thr Pro Ser Ser Gly Gln Thr Asp Tyr Ala Asp Ser Val
     50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Arg Thr Trp Leu Leu Arg Trp Val Met Asp Tyr Trp Gly Gln Gly
                100                 105                 110

Thr Leu Val Thr Val Ser Ser
            115

<210> SEQ ID NO 198
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 198

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Asn Thr
             20                  25                  30

Tyr Ile Ser Trp Val Arg Gln Ala Pro Gly Lys Gly Leu Glu Trp Val
         35                  40                  45

Ala Ser Ile Thr Pro Ser Ser Gly Ser Thr Asp Tyr Ala Asp Ser Val
     50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Arg Thr Trp Leu Leu Arg Trp Val Met Asp Leu Trp Gly Gln Gly
```

```
                   100                 105                 110
Thr Leu Val Thr Val Ser Ser
        115

<210> SEQ ID NO 199
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 199

Arg Ala Ser Gln Glu Val Ser Thr Ala Val Ala
1               5                   10

<210> SEQ ID NO 200
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 200

Arg Ala Ser Gln Gly Val Ser Thr Ala Val Ala
1               5                   10

<210> SEQ ID NO 201
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 201

Arg Ala Ser Gln Asn Val Ser Thr Ala Val Ala
1               5                   10

<210> SEQ ID NO 202
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 202

Arg Ala Ser Gln Ser Val Ser Thr Ala Val Ala
1               5                   10

<210> SEQ ID NO 203
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 203

Arg Ala Ser Gln Thr Val Ser Thr Ala Val Ala
1               5                   10

<210> SEQ ID NO 204
<211> LENGTH: 11
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 204

Arg Ala Ser Gln Val Val Ser Thr Ala Val Ala
1               5                   10

<210> SEQ ID NO 205
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 205

Arg Ala Ser Gln Asp Ala Ser Thr Ala Val Ala
1               5                   10

<210> SEQ ID NO 206
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 206

Arg Ala Ser Gln Asp Leu Ser Thr Ala Val Ala
1               5                   10

<210> SEQ ID NO 207
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 207

Arg Ala Ser Gln Asp Ser Ser Thr Ala Val Ala
1               5                   10

<210> SEQ ID NO 208
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 208

Arg Ala Ser Gln Asp Val Phe Thr Ala Val Ala
1               5                   10

<210> SEQ ID NO 209
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 209

Arg Ala Ser Gln Asp Val Leu Thr Ala Val Ala
1               5                   10
```

<210> SEQ ID NO 210
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 210

Arg Ala Ser Gln Asp Val Val Thr Ala Val Ala
1               5                   10

<210> SEQ ID NO 211
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 211

Arg Ala Ser Gln Asp Val Ser Asn Ala Val Ala
1               5                   10

<210> SEQ ID NO 212
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 212

Arg Ala Ser Gln Asp Val Ser Ser Ala Val Ala
1               5                   10

<210> SEQ ID NO 213
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 213

Arg Ala Ser Gln Asp Val Ser Val Ala Val Ala
1               5                   10

<210> SEQ ID NO 214
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 214

Arg Ala Ser Gln Asp Val Ser Thr His Val Ala
1               5                   10

<210> SEQ ID NO 215
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 215

Arg Ala Ser Gln Asp Val Ser Thr Arg Val Ala
1               5                   10

<210> SEQ ID NO 216
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 216

Arg Ala Ser Gln Asp Val Ser Thr Ser Val Ala
1               5                   10

<210> SEQ ID NO 217
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 217

Arg Ala Ser Gln Asp Val Ser Thr Tyr Val Ala
1               5                   10

<210> SEQ ID NO 218
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 218

Arg Ala Ser Gln Asp Val Ser Thr Ala Leu Ala
1               5                   10

<210> SEQ ID NO 219
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 219

Ser Ala Gln Phe Leu Tyr Ser
1               5

<210> SEQ ID NO 220
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 220

Ser Ala Ser Tyr Leu Tyr Ser
1               5

<210> SEQ ID NO 221
<211> LENGTH: 7

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 221

Ser Ala Ser Phe Ala Tyr Ser
1               5

<210> SEQ ID NO 222
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 222

Ser Ala Ser Phe Phe Tyr Ser
1               5

<210> SEQ ID NO 223
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 223

Ser Ala Ser Phe Gly Tyr Ser
1               5

<210> SEQ ID NO 224
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 224

Ser Ala Ser Phe His Tyr Ser
1               5

<210> SEQ ID NO 225
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 225

Ser Ala Ser Phe Ile Tyr Ser
1               5

<210> SEQ ID NO 226
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 226

Ser Ala Ser Phe Lys Tyr Ser
```

```
1               5

<210> SEQ ID NO 227
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 227

Ser Ala Ser Phe Asn Tyr Ser
1               5

<210> SEQ ID NO 228
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 228

Ser Ala Ser Phe Pro Tyr Ser
1               5

<210> SEQ ID NO 229
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 229

Ser Ala Ser Phe Arg Tyr Ser
1               5

<210> SEQ ID NO 230
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 230

Ser Ala Ser Phe Val Tyr Ser
1               5

<210> SEQ ID NO 231
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 231

Ser Ala Ser Phe Tyr Tyr Ser
1               5

<210> SEQ ID NO 232
<211> LENGTH: 7
<212> TYPE: PRT
<213> ORGANISM: Artificial Sequence
<220> FEATURE:
<223> OTHER INFORMATION: Description of Artificial Sequence: Synthetic
```

```
              peptide

<400> SEQUENCE: 232

Ser Ala Ser Phe Leu Tyr Ala
1               5

<210> SEQ ID NO 233
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 233

Ser Ala Ser Phe Leu Tyr Asp
1               5

<210> SEQ ID NO 234
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 234

Ser Ala Ser Phe Leu Tyr Phe
1               5

<210> SEQ ID NO 235
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 235

Ser Ala Ser Phe Leu Tyr Gly
1               5

<210> SEQ ID NO 236
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 236

Ser Ala Ser Phe Leu Tyr His
1               5

<210> SEQ ID NO 237
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 237

Ser Ala Ser Phe Leu Tyr Val
1               5

<210> SEQ ID NO 238
```

```
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 238

Ser Ala Ser Phe Leu Tyr Trp
1               5

<210> SEQ ID NO 239
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 239

Ser Ala Ser Phe Leu Tyr Tyr
1               5

<210> SEQ ID NO 240
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 240

Gln Gln Ser Lys Thr Thr Pro Pro Thr
1               5

<210> SEQ ID NO 241
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 241

Gln Gln Ser Asn Thr Thr Pro Pro Thr
1               5

<210> SEQ ID NO 242
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 242

Gln Gln Ser Gln Thr Thr Pro Pro Thr
1               5

<210> SEQ ID NO 243
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 243
```

```
Gln Gln Ser Ser Thr Thr Pro Pro Thr
1               5

<210> SEQ ID NO 244
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 244

Gln Gln Ser Trp Thr Thr Pro Pro Thr
1               5

<210> SEQ ID NO 245
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 245

Gln Gln Ser Tyr Ile Thr Pro Pro Thr
1               5

<210> SEQ ID NO 246
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 246

Gln Gln Ser Tyr Gln Thr Pro Pro Thr
1               5

<210> SEQ ID NO 247
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 247

Gln Gln Ser Tyr Arg Thr Pro Pro Thr
1               5

<210> SEQ ID NO 248
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 248

Gln Gln Ser Tyr Ser Thr Pro Pro Thr
1               5

<210> SEQ ID NO 249
<211> LENGTH: 9
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 249

Gln Gln Ser Tyr Thr Asp Pro Pro Thr
1               5

<210> SEQ ID NO 250
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 250

Gln Gln Ser Tyr Thr Phe Pro Pro Thr
1               5

<210> SEQ ID NO 251
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 251

Gln Gln Ser Tyr Thr Lys Pro Pro Thr
1               5

<210> SEQ ID NO 252
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 252

Gln Gln Ser Tyr Thr Arg Pro Pro Thr
1               5

<210> SEQ ID NO 253
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 253

Gln Gln Ser Tyr Thr Val Pro Pro Thr
1               5

<210> SEQ ID NO 254
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 254

Gln Gln Ser Tyr Thr Thr Pro Thr Thr
1               5
```

```
<210> SEQ ID NO 255
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 255

Ser Asn Thr Tyr Ile Ser
1               5

<210> SEQ ID NO 256
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 256

Ala Asn Thr Tyr Ile Ser
1               5

<210> SEQ ID NO 257
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 257

Met Asn Thr Tyr Ile Ser
1               5

<210> SEQ ID NO 258
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 258

Ser Trp Thr Tyr Ile Ser
1               5

<210> SEQ ID NO 259
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 259

Ser Asn Ala Tyr Ile Ser
1               5

<210> SEQ ID NO 260
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 260
```

```
Ser Asn Thr Tyr Val Ser
1               5
```

<210> SEQ ID NO 261
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 261

```
Ala Ser Val Thr Pro Ser Ser Gly Ser Thr Asp
1               5                   10
```

<210> SEQ ID NO 262
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 262

```
Ala Ser Ile Thr Pro Ala Ser Gly Ser Thr Asp
1               5                   10
```

<210> SEQ ID NO 263
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 263

```
Ala Ser Ile Thr Pro Ser Ser Gly His Thr Asp
1               5                   10
```

<210> SEQ ID NO 264
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 264

```
Ala Ser Ile Thr Pro Ser Ser Gly Met Thr Asp
1               5                   10
```

<210> SEQ ID NO 265
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 265

```
Thr Trp Leu Leu Arg Trp Val Met Asp Tyr Trp Gly Gln Gly Thr Leu
1               5                   10                  15

Val Thr Val Ser Ser
            20
```

<210> SEQ ID NO 266

```
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 266

Ser Trp Leu Leu Arg Trp Val Met Asp Tyr Trp Gly Gln Gly Thr Leu
1               5                   10                  15

Val Thr Val Ser Ser
            20

<210> SEQ ID NO 267
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 267

Ser Trp Leu Leu Arg Trp Val Met Asp Tyr Trp Gly Gln Gly Thr Leu
1               5                   10                  15

Val Ala Val Ser Ser
            20

<210> SEQ ID NO 268
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 268

Thr Trp Tyr Leu Arg Trp Val Met Asp Tyr Trp Gly Gln Gly Thr Leu
1               5                   10                  15

Val Ala Val Ser Ser
            20

<210> SEQ ID NO 269
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 269

Thr Trp Tyr Leu Arg Trp Val Met Asp Tyr Trp Gly Gln Gly Thr Leu
1               5                   10                  15

Val Thr Val Ser Ser
            20

<210> SEQ ID NO 270
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 270

Thr Trp Leu Ile Arg Trp Val Met Asp Tyr Trp Gly Gln Gly Thr Leu
1               5                   10                  15
```

```
Val Thr Val Ser Ser
            20

<210> SEQ ID NO 271
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 271

Thr Trp Leu Ile Arg Trp Val Met Asp Tyr Trp Gly Gln Gly Thr Leu
1               5                   10                  15

Val Ala Val Ser Ser
            20

<210> SEQ ID NO 272
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 272

Thr Trp Leu Val Arg Trp Val Met Asp Tyr Trp Gly Gln Gly Thr Leu
1               5                   10                  15

Val Thr Val Ser Ser
            20

<210> SEQ ID NO 273
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 273

Thr Trp Leu Leu Arg Trp Val Phe Asp Tyr Trp Gly Gln Gly Thr Leu
1               5                   10                  15

Val Ala Val Ser Ser
            20

<210> SEQ ID NO 274
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 274

Thr Trp Leu Leu Arg Trp Val Phe Asp Tyr Trp Gly Gln Gly Thr Leu
1               5                   10                  15

Val Thr Val Ser Ser
            20

<210> SEQ ID NO 275
<211> LENGTH: 21
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 275

Thr Trp Leu Leu Arg Trp Val Leu Asp Tyr Trp Gly Gln Gly Thr Leu
1               5                   10                  15

Val Thr Val Ser Ser
            20

<210> SEQ ID NO 276
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 276

Thr Trp Leu Leu Arg Trp Val Met Asp Phe Trp Gly Gln Gly Thr Leu
1               5                   10                  15

Val Ala Val Ser Ser
            20

<210> SEQ ID NO 277
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 277

Thr Trp Leu Leu Arg Trp Val Met Asp Gly Trp Gly Gln Gly Thr Leu
1               5                   10                  15

Val Ala Val Ser Ser
            20

<210> SEQ ID NO 278
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 278

Thr Trp Leu Leu Arg Trp Val Met Asp Gly Trp Gly Gln Gly Thr Leu
1               5                   10                  15

Val Thr Val Ser Ser
            20

<210> SEQ ID NO 279
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 279

Thr Trp Leu Leu Arg Trp Val Met Asp Leu Trp Gly Gln Gly Thr Leu
1               5                   10                  15

Val Ala Val Ser Ser
            20

```
<210> SEQ ID NO 280
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 280

Thr Trp Leu Leu Arg Trp Val Met Asp Leu Trp Gly Gln Gly Thr Leu
1               5                   10                  15

Val Thr Val Ser Ser
            20

<210> SEQ ID NO 281
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 281

Thr Trp Leu Leu Arg Trp Val Met Asp Met Trp Gly Gln Gly Thr Leu
1               5                   10                  15

Val Ala Val Ser Ser
            20

<210> SEQ ID NO 282
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 282

Thr Trp Leu Leu Arg Trp Val Met Asp Tyr Trp Gly Gln Gly Thr Leu
1               5                   10                  15

Val Ala Val Ser Ser
            20

<210> SEQ ID NO 283
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 283

Arg Ala Ser Gln Lys Val Ser Thr Ala Val Ala
1               5                   10

<210> SEQ ID NO 284
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 284

Arg Ala Ser Gln Asp Val His Thr Ala Val Ala
1               5                   10
```

```
<210> SEQ ID NO 285
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 285

Arg Ala Ser Gln Asp Val Val Thr Ala Val Ala
1               5                   10

<210> SEQ ID NO 286
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 286

Arg Ala Ser Gln Asp Val Tyr Thr Ala Val Ala
1               5                   10

<210> SEQ ID NO 287
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 287

Arg Ala Ser Gln Asp Val Ser Ala Ala Val Ala
1               5                   10

<210> SEQ ID NO 288
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 288

Arg Ala Ser Gln Asp Val Ser Glu Ala Val Ala
1               5                   10

<210> SEQ ID NO 289
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 289

Arg Ala Ser Gln Asp Val Ser Lys Ala Val Ala
1               5                   10

<210> SEQ ID NO 290
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 290
```

```
Arg Ala Ser Gln Asp Val Ser
1               5

<210> SEQ ID NO 291
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 291

Arg Ala Ser Gln Asp Val Ser Pro Ala Val Ala
1               5                   10

<210> SEQ ID NO 292
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 292

Arg Ala Ser Gln Asp Val Ser Thr Gly Val Ala
1               5                   10

<210> SEQ ID NO 293
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 293

Arg Ala Ser Gln Asp Val Ser Thr Lys Val Ala
1               5                   10

<210> SEQ ID NO 294
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 294

Arg Ala Ser Gln Asp Val Ser Thr Asn Val Ala
1               5                   10

<210> SEQ ID NO 295
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 295

Arg Ala Ser Gln Asp Val Ser Thr Ser Val Ala
1               5                   10

<210> SEQ ID NO 296
<211> LENGTH: 11
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 296

Arg Ala Ser Gln Asp Val Ser Thr Ala Leu Ala
1               5                   10

<210> SEQ ID NO 297
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 297

Arg Ala Ser Gln Asp Val Ser Thr Ala Ser Ala
1               5                   10

<210> SEQ ID NO 298
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 298

Ser Lys Ser Phe Leu Tyr Ser
1               5

<210> SEQ ID NO 299
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 299

Ser Ala Ala Phe Leu Tyr Ser
1               5

<210> SEQ ID NO 300
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 300

Ser Ala Ser Gly Leu Tyr Ser
1               5

<210> SEQ ID NO 301
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 301

Gln Gln Ser Tyr
1
```

<210> SEQ ID NO 302
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 302

Ser Ala Ser Tyr Leu Tyr Ser
1               5

<210> SEQ ID NO 303
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 303

Ser Ala Ser Phe Lys Tyr Ser
1               5

<210> SEQ ID NO 304
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 304

Ser Ala Ser Phe Met Tyr Ser
1               5

<210> SEQ ID NO 305
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 305

Ser Ala Ser Phe Gln Tyr Ser
1               5

<210> SEQ ID NO 306
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 306

Ser Ala Ser Phe Arg Tyr Ser
1               5

<210> SEQ ID NO 307
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 307

Ser Ala Ser Phe Val Tyr Ser
1               5

<210> SEQ ID NO 308
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 308

Ser Ala Ser Phe Leu Tyr Ala
1               5

<210> SEQ ID NO 309
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 309

Ser Ala Ser Phe Leu Tyr Asp
1               5

<210> SEQ ID NO 310
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 310

Ser Ala Ser Phe Leu Tyr Glu
1               5

<210> SEQ ID NO 311
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 311

Ser Ala Ser Phe Leu Tyr Asn
1               5

<210> SEQ ID NO 312
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (7)..(7)
<223> OTHER INFORMATION: May or may not be present

<400> SEQUENCE: 312

Ser Ala Ser Phe Leu Tyr Gln
1               5
```

<210> SEQ ID NO 313
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 313

Ser Ala Ser Phe Leu Tyr Arg
1               5

<210> SEQ ID NO 314
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 314

Ser Ala Ser Phe Leu Tyr Trp
1               5

<210> SEQ ID NO 315
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 315

Ser Ala Ser Phe Leu Tyr Tyr
1               5

<210> SEQ ID NO 316
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 316

Gln Gln Pro Tyr Thr Thr Pro Pro Thr
1               5

<210> SEQ ID NO 317
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 317

Gln Gln Ser Ala Thr Thr Pro Pro Thr
1               5

<210> SEQ ID NO 318
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 318

Gln Gln Ser Phe Thr Thr Pro Pro Thr
1               5

<210> SEQ ID NO 319
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 319

Gln Gln Ser Leu Thr Thr Pro Pro Thr
1               5

<210> SEQ ID NO 320
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 320

Gln Gln Ser Val Thr Thr Pro Pro Thr
1               5

<210> SEQ ID NO 321
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 321

Gln Gln Ser Trp Thr Thr Pro Pro Thr
1               5

<210> SEQ ID NO 322
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 322

Gln Gln Ser Tyr Glu Thr Pro Pro Thr
1               5

<210> SEQ ID NO 323
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 323

Gln Gln Ser Tyr Gly Thr Pro Pro Thr
1               5

<210> SEQ ID NO 324
<211> LENGTH: 9
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 324

Gln Gln Ser Tyr Ile Thr Pro Pro Thr
1               5

<210> SEQ ID NO 325
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 325

Gln Gln Ser Tyr Asn Thr Pro Pro Thr
1               5

<210> SEQ ID NO 326
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 326

Thr Pro Pro Thr
1

<210> SEQ ID NO 327
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (9)..(11)
<223> OTHER INFORMATION: This region may or may not be present in its
      entirety

<400> SEQUENCE: 327

Arg Ala Ser Gln Asp Val Ser Thr Gln Val Ala
1               5                   10

<210> SEQ ID NO 328
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 328

Gln Gln Ser Tyr Arg Thr Pro Pro Thr
1               5

<210> SEQ ID NO 329
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 329

Gln Gln Ser Tyr Ser Thr Pro Pro Thr
1               5

<210> SEQ ID NO 330
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 330

Gln Gln Ser Tyr Thr Asp Pro Pro Thr
1               5

<210> SEQ ID NO 331
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 331

Gln Gln Ser Tyr Thr Glu Pro Pro Thr
1               5

<210> SEQ ID NO 332
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 332

Gln Gln Ser Tyr Thr Met Pro Pro Thr
1               5

<210> SEQ ID NO 333
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 333

Gln Gln Ser Tyr Thr Arg Pro Pro Thr
1               5

<210> SEQ ID NO 334
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 334

Gln Gln Ser Tyr Thr Val Pro Pro Thr
1               5

<210> SEQ ID NO 335
<211> LENGTH: 9
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 335

Gln Gln Ser Tyr Thr Tyr Pro Pro Thr
1               5

<210> SEQ ID NO 336
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 336

Ala Asn Thr Tyr Ile Ser
1               5

<210> SEQ ID NO 337
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 337

Glu Asn Thr Tyr Ile Ser
1               5

<210> SEQ ID NO 338
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 338

Gly Asn Thr Tyr Ile Ser
1               5

<210> SEQ ID NO 339
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 339

His Asn Thr Tyr Ile Ser
1               5

<210> SEQ ID NO 340
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 340

Leu Asn Thr Tyr Ile Ser
```

```
<210> SEQ ID NO 341
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 341

Asn Asn Thr Tyr Ile Ser
1               5

<210> SEQ ID NO 342
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 342

Ser Gln Thr Tyr Ile Ser
1               5

<210> SEQ ID NO 343
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 343

Ser Trp Thr Tyr Ile Ser
1               5

<210> SEQ ID NO 344
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 344

Ser Tyr Thr Tyr Ile Ser
1               5

<210> SEQ ID NO 345
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 345

Ala Ser Ile Thr Pro
1               5

<210> SEQ ID NO 346
<211> LENGTH: 11
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 346

Ala Ser Pro Thr Pro Ser Ser Gly Ser Thr Asp
1               5                   10

<210> SEQ ID NO 347
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 347

Ala Ser Val Thr Pro Ser Ser Gly Ser Thr Asp
1               5                   10

<210> SEQ ID NO 348
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 348

Ser Gly Ser Thr Asp
1               5

<210> SEQ ID NO 349
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 349

Ala Ser Ile Thr Pro Ser Phe Gly Ser Thr Asp
1               5                   10

<210> SEQ ID NO 350
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 350

Ala Ser Ile Thr Pro Ser His Gly Ser Thr Asp
1               5                   10

<210> SEQ ID NO 351
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 351

Ala Ser Ile Thr Pro Ser Leu Gly Ser Thr Asp
1               5                   10

<210> SEQ ID NO 352

```
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 352

Ala Ser Ile Thr Pro Ser Trp Gly Ser Thr Asp
1               5                   10

<210> SEQ ID NO 353
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 353

Ala Ser Ile Thr Pro Ser Tyr Gly Ser Thr Asp
1               5                   10

<210> SEQ ID NO 354
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 354

Ala Ser Ile Thr Pro Ser Ser Gly Gln Thr Asp
1               5                   10

<210> SEQ ID NO 355
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 355

Thr Trp Leu Leu Arg Trp Val Met Asp Tyr Trp Gly Gln Gly Thr Leu
1               5                   10                  15

Val Thr Val Ser Ser
            20

<210> SEQ ID NO 356
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 356

Thr Ile Leu Leu Arg Trp Val Met Asp Tyr Trp Gly Gln Gly Thr Leu
1               5                   10                  15

Val Thr Val Ser Ser
            20

<210> SEQ ID NO 357
<211> LENGTH: 21
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 357

Thr Trp Tyr Leu Arg Trp Val Met Asp Tyr Trp Gly Gln Gly Thr Leu
1               5                   10                  15

Val Thr Val Ser Ser
            20

<210> SEQ ID NO 358
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 358

Thr Trp Tyr Leu Arg Trp Val Met Asp Tyr Trp Gly Gln Gly Thr Leu
1               5                   10                  15

Val Ala Val Ser Ser
            20

<210> SEQ ID NO 359
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 359

Thr Trp Leu Ile Arg Trp Val Met Asp Tyr Trp Gly Gln Gly Thr Leu
1               5                   10                  15

Val Thr Val Ser Ser
            20

<210> SEQ ID NO 360
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 360

Thr Trp Leu Ile Arg Trp Val Met Asp Tyr Trp Gly Gln Gly Thr Leu
1               5                   10                  15

Val Ala Val Ser Ser
            20

<210> SEQ ID NO 361
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 361

Thr Trp Leu Leu Arg Gly Val Met Asp Tyr Trp Gly Gln Gly Thr Leu
1               5                   10                  15

Val Thr Val Ser Ser
            20
```

```
<210> SEQ ID NO 362
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 362

Thr Trp Leu Leu Arg Trp Val Phe Asp Tyr Trp Gly Gln Gly Thr Leu
1               5                   10                  15

Val Ala Val Ser Ser
            20

<210> SEQ ID NO 363
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 363

Thr Trp Leu Leu Arg Trp Val Leu Asp Tyr Trp Gly Gln Gly Thr Leu
1               5                   10                  15

Val Thr Val Ser Ser
            20

<210> SEQ ID NO 364
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 364

Thr Trp Leu Leu Arg Trp Val Trp Asp Tyr Trp Gly Gln Gly Thr Leu
1               5                   10                  15

Val Thr Val Ser Ser
            20

<210> SEQ ID NO 365
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 365

Thr Trp Leu Leu Arg Trp Val Met Asp Ala Trp Gly Gln Gly Thr Leu
1               5                   10                  15

Val Thr Val Ser Ser
            20

<210> SEQ ID NO 366
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 366
```

```
Thr Trp Leu Leu Arg Trp Val Met Asp Gln Trp Gly Gln Gly Thr Leu
1               5                   10                  15

Val Ala Val Ser Ser
            20

<210> SEQ ID NO 367
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 367

Thr Trp Leu Leu Arg Trp Val Met Asp Tyr Trp Gly Gln Gly Thr Leu
1               5                   10                  15

Val Ala Val Ser Ser
            20

<210> SEQ ID NO 368
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 368

Cys Ala Arg Thr Trp Leu Leu Arg Trp Val Met Asp Tyr Trp Gly Gln
1               5                   10                  15

Gly Thr Leu Val Thr Val Ser Ser
            20

<210> SEQ ID NO 369
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 369

Cys Ala Arg Thr Trp Leu Leu Arg Trp Val Met Asp Met Trp Gly Gln
1               5                   10                  15

Gly Thr Leu Val Ala Val Ser Ser
            20

<210> SEQ ID NO 370
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 370

Cys Ala Arg Thr Trp Leu Leu Arg Trp Val Phe Asp Tyr Trp Gly Gln
1               5                   10                  15

Gly Thr Leu Val Ala Val Ser Ser
            20

<210> SEQ ID NO 371
<211> LENGTH: 24
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 371

Cys Ala Arg Thr Trp Leu Leu Arg Trp Val Met Asp Leu Trp Gly Gln
1               5                   10                  15

Gly Thr Leu Val Ala Val Ser Ser
            20

<210> SEQ ID NO 372
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 372

Cys Ala Arg Thr Trp Leu Leu Arg Trp Val Met Asp Gly Trp Gly Gln
1               5                   10                  15

Gly Thr Leu Val Thr Val Ser Ser
            20

<210> SEQ ID NO 373
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 373

Cys Ala Arg Thr Trp Leu Leu Arg Trp Val Met Asp Gly Trp Gly Gln
1               5                   10                  15

Gly Thr Leu Val Ala Val Ser Ser
            20

<210> SEQ ID NO 374
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 374

Cys Ala Arg Thr Trp Leu Leu Arg Trp Val Met Asp Tyr Trp Gly Gln
1               5                   10                  15

Gly Thr Leu Val Ala Val Ser Ser
            20

<210> SEQ ID NO 375
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 375

Cys Ala Arg Thr Trp Leu Leu Arg Trp Val Phe Asp Tyr Trp Gly Gln
1               5                   10                  15

Gly Thr Leu Val Thr Val Ser Ser
```

<210> SEQ ID NO 376
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 376

His His His His His His
1               5

<210> SEQ ID NO 377
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 377

Thr Pro Ser Ser Gly Gln
1               5

<210> SEQ ID NO 378
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 378

Thr Trp Leu Leu Arg
1               5

<210> SEQ ID NO 379
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 379

Gln Asp Lys Glu Gly Ile Pro
1               5

<210> SEQ ID NO 380
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 380

Val Leu Arg Leu Arg Gly Gly
1               5

<210> SEQ ID NO 381
<211> LENGTH: 4
<212> TYPE: PRT
<213> ORGANISM: Artificial Sequence
<220> FEATURE:
<223> OTHER INFORMATION: Description of Artificial Sequence: Synthetic

```
      peptide

<400> SEQUENCE: 381

Asn Ile Gln Lys
1

<210> SEQ ID NO 382
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (5)..(9)
<223> OTHER INFORMATION: This region may or may not be present in its
      entirety

<400> SEQUENCE: 382

Gln Gln Ser Tyr Gln Thr Pro Pro Thr
1               5
```